US007273966B2

(12) United States Patent
Voelker et al.

(10) Patent No.: US 7,273,966 B2
(45) Date of Patent: Sep. 25, 2007

(54) ELEVATION OF FATTY ACID SYNTHASE LEVELS IN PLANTS

(75) Inventors: Toni A. Voelker, Davis, CA (US); Dale L. Val, Woodland, CA (US); Thomas J. Savage, Sacramento, CA (US)

(73) Assignee: Monsanto Technology LLC, St. Louis, MI (US)

( * ) Notice: Subject to any disclaimer, the term of this patent is extended or adjusted under 35 U.S.C. 154(b) by 274 days.

(21) Appl. No.: 10/741,191

(22) Filed: Dec. 19, 2003

(65) Prior Publication Data

US 2004/0121467 A1 Jun. 24, 2004

Related U.S. Application Data

(60) Provisional application No. 60/435,197, filed on Dec. 19, 2002.

(51) Int. Cl.
*A01H 1/00* (2006.01)
*C12N 15/00* (2006.01)
*C12N 5/14* (2006.01)
*C12N 15/82* (2006.01)

(52) U.S. Cl. .................. 800/281; 800/288; 435/320.1; 435/419; 435/468

(58) Field of Classification Search ..................... None
See application file for complete search history.

(56) References Cited

U.S. PATENT DOCUMENTS 5,510,255 A 4/1996 Knauf et al. ............. 435/172.3
5,925,805 A 7/1999 Ohlrogge et al. ........... 800/295
6,268,550 B1 7/2001 Gengenbach et al. ....... 800/298

OTHER PUBLICATIONS

Falcon-Perez JM et al. 1999, J Biol Chem. 274:23584-90.*
Lazar et al. 1988, Mol. Cell. Biol. 8:1247-1252.*
Hill et al 1998, Biochem. Biophys. Res. Comm. 244:573-577.*
Stuible et al. 1996, Journal of Bacteriology 178:4787-4793.*
Kawaguchi et al., "Fatty Acid Synthase from *Brevibacterium ammoniagenes*", Methods in Enzymology, 71:120-127 (1981).
Lambalot et al., "A New Enzyme Superfamily—the Phosphopantetheinyl Transferases", Chem. Biol., 3:923-936 (1996).
Mootz et al., "4'-Phosphopantetheine Transfer in Primary and Secondary Metabolism of *Bacillus subtilis*", J. Biol.Chem., 276:37289:37298 (2001).
Sanchez et al., "Cloning and Characterization of a Phosphopantetheinyl Transferase from *Streptomyces verticillus* ATCC15003, the Producer of the Hybrid Peptide—Polyketide Antitumor Drug Bleomycin", Chem. Biol., 8:725-728 (2001).
Stuible et al., "Identification, Isolation and Biochemical Characterization of a Phosphopantetheine:Protein Transferase that Activates the Two Type-I Fatty.Acid Synthases of *Brevibacterium ammoniagenes*", Eur. J. Biochem., 248:481-487 (1997).
Stuible et al., "Identification and Functional Differentiation of Two Type I Fatty Acid Synthases in *Brevibacterium ammoniagenes*", J. Bacteriol., 178:4787-4793 (1996).
Borchert et al., NCBI General Identifier No. 474184, Accession No. X76434 (Apr. 1994).
Cole et al., NCBI General Identifier No. 3261686, Accession No. CAB06201 (Jun. 2004).
Eiglmeier et al., NCBI General Identifier No. 4539127, Accession No. CAB39571 (Aug. 1999).
Fernandes et al., NCBI General Identifier No. 1036834, Accession No. U36763 (Aug. 2001).
Fraser et al., NCBI General Identifier No. 17507093, Accession No. NP_492417 (Nov. 2003).
Miller et al., NCBI General Identifier No. 929999, Accession No. U32586 (Oct. 1996).
Nakano et al., NCBI General Identifier No. 40138, Accession No. X63158 (Apr. 1992).
Oshima et al., NCBI General Identifier No. 1651238, Accession No. D90700 (Dec. 2002).
Saitoh et al., NCBI General Identifier No. 1199959, Accession No. D83412 (Feb. 1999).
Sanchez et al., NCBI General Identifier No. 12003273, Accession No. AF210311 (Nov. 2002).
Schweizer et al., NCBI General Identifier No. 56132, Accession No. X13415 (Sep. 1993).
Sofia et al., NCBI General Identifier No. 466582, Accession No. U00039 (Nov. 1996).
Southard et al., NCBI General Identifier No. 456442, Accession No. L29063 (Feb. 1994).
Urrestarazu et al., NCBI General Identifier No. 1370478, Accession No. CAA97948 (Aug. 1997).
Wieman et al., NCBI General Identifier No. 486321, Accession No. CAA82025 (Aug. 1997).
Yuan et al., NCBI General Identifier No. 211766, Accession No. J03860 (Apr. 1993).
Zhao et al., NCBI General Identifier No. 402177, Accession No. CAA52907 (Dec. 1994).

* cited by examiner

*Primary Examiner*—Ashwin Mehta
*Assistant Examiner*—Li Zheng
(74) *Attorney, Agent, or Firm*—Fulbright & Jaworski L.L.P.

(57) ABSTRACT

This present invention provides a method for increasing fatty acid synthase activity in a plant by expressing a transgenic multifunctional fatty acid synthase (mfFAS) within the plant, wherein the plant is not of the *Brassica* species. In one embodiment, the present invention provides isolated nucleic acid molecules encoding mfFAS proteins from various sources for this purpose, and vectors containing same.

4 Claims, 20 Drawing Sheets

```
FASA pMON70058.SEQ  ATGTCGTTGACCCCCTTGCATACCTTGTCTAATGACAGCA  40
X87822 orf.SEQ      ATGTCGTTGACCCCCTTGCATACCTTGTCTAATGACAGCA  40

FASA pMON70058.SEQ  CTGCTCCCGCGGTGCTGTTTGCGGGTCAGGGTTCTGCATG  80
X87822 orf.SEQ      CTGCTCCCGCGGTGCTGTTTGCGGGTCAGGGTTCTGCATG  80

FASA pMON70058.SEQ  GCAAAAGGCCATCGCTGATGCCGCAGCCAGCCCTCACCAG  120
X87822 orf.SEQ      GCAAAAGGCCATCGCTGATGCCGCAGCCAGCCCTCACCAG  120

FASA pMON70058.SEQ  GGCGCACAATTGCGCGACATCCTAAAAGAAGTTCGCACGA  160
X87822 orf.SEQ      GGCGCACAATTGCGCGACATCCTAAAAGAAGTTCGCACGA  160

FASA pMON70058.SEQ  CCACCGGCCCAGTAGCACGCATCATTGCGTCGTCGTGCCC  200
X87822 orf.SEQ      CCACCGGCCCAGTAGCACGCATCATTGCGTCGTCGTGCCC  200

FASA pMON70058.SEQ  TGGCGTTTATGAACGCTTGGAAGAACTTGCTCAGACCCCC  240
X87822 orf.SEQ      TGGCGTTTATGAACGCTTGGAAGAACTTGCTCAGACCCCC  240

FASA pMON70058.SEQ  GCTGACCAAGCACCGGTGGCCAAGGAATATGACGCGTACC  280
X87822 orf.SEQ      GCTGACCAAGCACCGGTGGCCAAGGAATATGACGCGTACC  280

FASA pMON70058.SEQ  CGGCTTACTCCATCCCCGGCATCGTCCTGGGACAAATTGG  320
X87822 orf.SEQ      CGGCTTACTCCATCCCCGGCATCGTCCTGGGACAAATTGG  320

FASA pMON70058.SEQ  TGCCATTGAGCACCTGCGCGAGCTGGGCATCGATGTCGAT  360
X87822 orf.SEQ      TGCCATTGAGCACCT[CGCGC]AGCTGGGCATCGATGTCGAT  360

FASA pMON70058.SEQ  TCCGCGCAGTTAGCAGGCCACTCCCAGGGTTCATTAGGTG  400
X87822 orf.SEQ      TCCGCGCAGTTAGCAGGCCACTCCCAGGGTTCATTAGGTG  400

FASA pMON70058.SEQ  TTGCAGCCGTTAAGGATGCACGCCAGGCCCTGGCTATTGC  440
X87822 orf.SEQ      TTGCAGCCGTTAAGGATGCACGCCAGGCCCTGGCTATTGC  440

FASA pMON70058.SEQ  TGTTTTGATGGGTACTGCAGCAGCGGTGACCCAGGGCGCG  480
X87822 orf.SEQ      TGTTTTGATGGGTACTGCAGCAGCGGTGACCCAGGGCGCG  480

FASA pMON70058.SEQ  AATGATTCCCGCTCCCACATGCTGTCCGTGCGTGGCGTAC  520
X87822 orf.SEQ      AATGATTCCCGC[A]CCCACATGCTGTCCGTGCGTGGCGTAC  520

FASA pMON70058.SEQ  CACGTGAGATGGTCGAAGAATACCTCGCTGGTGACGCTGC  560
X87822 orf.SEQ      CACGTGAGATGGTCGAAGAATACCTCGCTGGTGACGCTGC  560

FASA pMON70058.SEQ  GATTGCCGTGGTCAACGGCCGCGTGCACTTTGCACTGTCG  600
X87822 orf.SEQ      GATTGCCGTGGTCAACGGCCGCGTGCACTTTGCACTGTCG  600

FASA pMON70058.SEQ  GGTACCCCAGAGGATCTGGCTAAGACCGAGTCCAACCTCA  640
X87822 orf.SEQ      GGTACCCCAGAGGATCTGGCTAAGACCGAGTCCAACCTCA  640

FASA pMON70058.SEQ  CCCAGGCTGCCGAGTCCTACAACGACGCGCTGGAAGAACG  680
X87822 orf.SEQ      CCCAGGCTGCCGAGTCCTACAACGACGCGCTGGAAGAACG  680

FASA pMON70058.SEQ  CCGCATCGGCGGCTCCGAAATTAACCCAGTCTTCGACGTA  720
X87822 orf.SEQ      CCGCATCGGCGGCTCCGAAATTAACCCAGTCTTCGACGTA  720

FASA pMON70058.SEQ  TTGGCCGTGGCACTTCCTTTCCACCACGCATCACTGCAGG  760
X87822 orf.SEQ      TTGGCCGTGGCACTTCCTTTCCACCACGCATCACTGCAGG  760

FASA pMON70058.SEQ  ATGCAGCGGATCTGACCGTGGACTACGCCACCCAGTGTGG  800
X87822 orf.SEQ      ATGCAGCGGATCTGACCGTGGACTACGCCACCCAGTGTGG  800

FASA pMON70058.SEQ  CCTGGACGCTGAGCTTGCACGCGAGCTGGCAGATTCCATC  840
X87822 orf.SEQ      CCTGGACGCTGAGCTTGCACGCGAGCTGGCAGATTCCATC  840

FASA pMON70058.SEQ  CTGGTTCAGCCACATAGCTGGGTTGAGACCGTGGCCGGTC  880
X87822 orf.SEQ      CTGGTTCAGCCACATAGCTGGGTTGAGACCGTGGCCGGTC  880

FASA pMON70058.SEQ  TCAACTCCACCTACCTGCTCTCCTTAGACCGTGGTCTGTC  920
X87822 orf.SEQ      TCAACTCCACCTACCTGCTCTCCTTAGACCGTGGTCTGTC  920

FASA pMON70058.SEQ  TTCGTTGACTACACCTTTGA                      940
X87822 orf.SEQ      TTCGTTGACTACACCTTTGA                      940
```

Boxed Residues Differ from pMON70058

FIG. 2A

```
FASA pMON70058.SEQ  T T G C C G G C A C C G G C A A G G T T G T G G T T C C A G C T G C T A C G C C  980
X87822 orf.SEQ      T T G C C G G C A C C G G C A A G G T T G T G G T T C C A G C T G C T A C G C C  980

FASA pMON70058.SEQ  A G C G G A G C G C G A T A A C C T G G C T A C C C C A G G C A C T G A G C T G  1020
X87822 orf.SEQ      A G C G G A G C G C G A T A A C C T G G C T A C C C C A G G C A C T G A G C T G  1020

FASA pMON70058.SEQ  C C T A C C G C G G T G A A C T A C G A G A A G T T C T C A C C A A A G C T C A  1060
X87822 orf.SEQ      C C T A C C G C G G T G A A C T A C G A G A A G T T C T C A C C A A A G C T C A  1060

FASA pMON70058.SEQ  T C T C C T T G C C C A A C G G C A A G T C C T A C A C T C A G A C T C G T T T  1100
X87822 orf.SEQ      T C T C C T T G C C C A A C G G C A A G T C C T A C A C T C A G A C T C G T T T  1100

FASA pMON70058.SEQ  C T C C G A G T G G A C C G G C A T G T C C C C A T C A T T T T G G G C G G C  1140
X87822 orf.SEQ      C T C C G A G T G G A C C G G C A T G T C C C C A T C A T T T T G G G C G G C  1140

FASA pMON70058.SEQ  A T G A C G C C G A C C A C G A T G G A T C C G G G C A T C G T T G C C G C A G  1180
X87822 orf.SEQ      A T G A C G C C G A C C A C G A T G G A T C C G G G C A T C G T T G C C G C A G  1180

FASA pMON70058.SEQ  C G G C C A A C G G T G G C T A C T G G T C A G A G A T G G C C G G T G G C G G  1220
X87822 orf.SEQ      C G G C C A A C G G T G G C T A C T G G T C A G A G A T G G C C G G T G G C G G  1220

FASA pMON70058.SEQ  T C A G T A C T C C G A T G A A G C T T T T A C C A T C A A C A A A G A C G G C  1260
X87822 orf.SEQ      T C A G T A C T C C G A T G A A G C T T T T A C C A T C A A C A A A G A C G G C  1260

FASA pMON70058.SEQ  A T G A T G G A G C T G C T G G A G C C A G G T C G C A C C G C A G C A T T T A  1300
X87822 orf.SEQ      A T G A T G G A G C T G C T G G A G C C A G G T C G C A C C G C A G C A T T T A  1300

FASA pMON70058.SEQ  A C A C C A T G T T C T T T G A C C G C T A C C T G T G G A A C C T A C A G T T  1340
X87822 orf.SEQ      A C A C C A T G T T C T T T G A C C G C T A C C T G T G G A A C C T A C A G T T  1340

FASA pMON70058.SEQ  C G G T G T C A C C C G C A T T G T T C C C A A G G C A C G C G C T A A T G G T  1380
X87822 orf.SEQ      C G G T G T C A C C C G C A T T [T] [G] [T] C C A A G G C A C G C G C T A A T G G T  1380

FASA pMON70058.SEQ  G C T G C G T T T A C C G G C G T G A C C A T C T C C G C T G G T A T C C C A G  1420
X87822 orf.SEQ      G C T G C G T T T A C C G G C G T G A C C A T C T [G] C G C T G G T A T C C C A G  1420

FASA pMON70058.SEQ  A G C T G G A T G A A G C C A A G G A A T T G C T G G A C C A G C T C A C C T C  1460
X87822 orf.SEQ      A G C T G G A T G A A G C C A A G G A A T T G C T G G A C C A G C T C A C C T C  1460

FASA pMON70058.SEQ  C G A T G G C T T C C C A T A C A T C T C T T T C A A G C C G G G C A C C A C C  1500
X87822 orf.SEQ      C G A T G G C T T [T] C C A T A C A T C T C T T T C A A G C C G G G C A C C A C C  1500

FASA pMON70058.SEQ  A A G C A G A T T C A A G A C T G C A T C G C T A T C G C A G C G G A T A A C C  1540
X87822 orf.SEQ      A A G C A G A T T C A A G A C T G C [G] T C G C T A T C G C A G C G G A T A A C C  1540

FASA pMON70058.SEQ  C C A C C C A C C G C G T C A T C A T C C A A A T T G A A G A C G G C C A C G C  1580
X87822 orf.SEQ      C C A C C C A C C G C G T C A T C A T C C A A A T T G A A G A C G [C] C C A C G C  1580

FASA pMON70058.SEQ  T G G T G G C C A C C A C T C C T G G G T G G A T C T G G A T G A A A T G C T G  1620
X87822 orf.SEQ      T G G T G G C C A C C A C T C C T G G G T G G A T C T G G A T G A A A T G C T G  1620

FASA pMON70058.SEQ  C T G G C T A C C T A C G C A T C T G C C C G T G A G C A C G A C A A C C T G G  1660
X87822 orf.SEQ      C T G G C T A C C T A C G C A T [G] T G C C C G T G A G C A C G A C A A C C T G G  1660

FASA pMON70058.SEQ  C C A T C A C T G T T G G T G G C G G C A T C C A C T C C C C A G A C C G C G C  1700
X87822 orf.SEQ      C C A T C A C T G T T G G T G G C G G C A T C C A C T C C C C A G A C C G C G C  1700

FASA pMON70058.SEQ  A T C G G A A T A C C T G A C C G G T A C C T G G T C C A C C A A G T A C G G T  1740
X87822 orf.SEQ      A T C G G A A T A C C T G A C C G G T A C C T G G T C C A C C A A G T A C G G T  1740

FASA pMON70058.SEQ  T T G C C C A T C A T G C C G G T T G A T G G T G T C T T C T T G G G C A C C G  1780
X87822 orf.SEQ      T T G C C C A T C A T G C C G G T T G A T G G T G T C T T C T T G G G C A C C G  1780

FASA pMON70058.SEQ  T A G C C A T G G C G A C C A A G G A A G C A A C G G C T A A T G A T G A C G T  1820
X87822 orf.SEQ      T A G C C A T G G C G A C C A A G G A A G C A A C G G C T A A T G A T G A C G T  1820

FASA pMON70058.SEQ  T A A G C A G T T G C T A G T T G A T A C C C C A G G T A T T T C C C C A G A G  1860
X87822 orf.SEQ      T A A G C A G T T G C T A G T T G A T A C C C C A G G T A T T T C C C C A G A G  1860

FASA pMON70058.SEQ  A C C A A T G G C G G T T G G G T A G G C C G A C T A G A T G C C G A C G G C G  1900
X87822 orf.SEQ      A C C A A T G G C G G T T G G G T A G G C C G A C T A G A T G C C G A C G G C G  1900
```

Boxed Residues Differ from pMON70058

FIG. 2B

```
FASA pMON70058.SEQ   G C G T C T C C T C C T C C C A G T C C C A C C T G T T G G C T G A C T T G C A   1940
X87822 orf.SEQ       G C G T[G]T C C T C C T C C C A G T C C C A C C T G T T G G C T G A C T T G C A   1940

FASA pMON70058.SEQ   C G A G A T T G A T A A C T C G T T T G C C A A G G C C T C G C G C A T G A T C   1980
X87822 orf.SEQ       C G A G A T T G A T A A C T C G T T T G C C A A G G C C T C G C G C A T G A T C   1980

FASA pMON70058.SEQ   A C C T C G A T C C C G A T C G A G G A G T A T G A C G A G C G T C G C G A C G   2020
X87822 orf.SEQ       A C C T C G A T C C C G A T C G A G G A G T A T G A C G A G C G T C G C G A C G   2020

FASA pMON70058.SEQ   A G A T C A T T G C T G C T C T G G A C A A G A C C T C C A A G C C A T A C T T   2060
X87822 orf.SEQ       A G A T C A T T G C T G C T C T G G A C A A G A C C T C C A A G C C A T A C T T   2060

FASA pMON70058.SEQ   C G G T G A C C T G T C G G A G A T G A C C T A C G A G G A T T G G G T C G C T   2100
X87822 orf.SEQ       C G G T G A C C T G T C G G A G A T G A C C T A C G A G G A T T G G G T C G C T   2100

FASA pMON70058.SEQ   C G T T T C G C A G A G C G C G C C T A C C C T T G G G T G G A T C C A A C C T   2140
X87822 orf.SEQ       C G T T T C G C A G A G C G C G C C T A C C C T T G G G T G G A T C C A A C C T   2140

FASA pMON70058.SEQ   G G C A C G A T C G T T T C C A C G A T C T G C T C C A G C G C G T A G A A G C   2180
X87822 orf.SEQ       G G C A C G A T C G T T T C C A C G A T C T G C T C C A G C G C G T A G A A G C   2180

FASA pMON70058.SEQ   G C G T C T C A A T G A C G C T G A C C A C G G C G A C A T C G A G A C C C T A   2220
X87822 orf.SEQ       G C G T C T C A A T G A C G C T G A C C A C G G C G A C A T C G A G A C C C T A   2220

FASA pMON70058.SEQ   T T C C C C A C A C T C G A C G A C T C C G A G A A C G C A C C A G A G G C A G   2260
X87822 orf.SEQ       T T C C C C A C A C T C G A C G A C T C C G A G A A C G C A C C A G A G G C A G   2260

FASA pMON70058.SEQ   T A G C C A A G C T G C T G G C T G C C T A C C C G A A T G C A A A G A C C A C   2300
X87822 orf.SEQ       T A G C C A A G C T G C T G G C T G C C T A C C C G A A T G C A A A G A C C A C   2300

FASA pMON70058.SEQ   C A A G G T C A A C A C C C G C G A T G A G G C A T G G T T C C C T A C C C T T   2340
X87822 orf.SEQ       C A A G G T C A A C A C C C G C G A T G A G G C A T G G T T C C C T A C C C T T   2340

FASA pMON70058.SEQ   A T C C G C A A G C A C G T C A A G C C A A T G C C G T G G A C C A C C G C T A   2380
X87822 orf.SEQ       A T C C G C A A G C A C G T C A A G C C A A T G C C G T G G A C C A C C G C T A   2380

FASA pMON70058.SEQ   T T G A C G G T G A C C T G A A G G A A T G G T T T G C C A A G G A C A C C C T   2420
X87822 orf.SEQ       T T G A C G G T G A C C T G A A G G A A T G G T T T G C C A A G G A C A C C C T   2420

FASA pMON70058.SEQ   G T G G C A G G C C C A G G A C C C A C G C T A C G A C G C A G A C G G C G T A   2460
X87822 orf.SEQ       G T G G C A G G C C C A G G A C C C A C G C T A C G A C G C A G A C G G C G T A   2460

FASA pMON70058.SEQ   C G C A T C A T T C C A G G A C C G G T T T C G G T T G C T G G T A T C A C C A   2500
X87822 orf.SEQ       C G C A T C A T T C C A G G A C C G G T T T C G G T T G C T G G T A T C A C C A   2500

FASA pMON70058.SEQ   A G A A G A A T G A G C C C G T C G C A A A C C T G C T C G G T C G C T T C G A   2540
X87822 orf.SEQ       A G A A G A A T G A G C C C G T C G C A A A C C T G C T C G G T C G C T T C G A   2540

FASA pMON70058.SEQ   A G A C G C C A C C A C C G C A G C G C T T A A C G A T G C C G G C G T G G C A   2580
X87822 orf.SEQ       A G A C G C C A C C A C C G C A G C G C T T A A C G A T G C C G G C G T G G C A   2580

FASA pMON70058.SEQ   C C A G T T G A G C T C T A C T C C C G C T T G G C T T C T G C C A A G A A T G   2620
X87822 orf.SEQ       C C A G T T G A G C T C T A C T C C C G C T T G G C T T C T G C C A A G A A T G   2620

FASA pMON70058.SEQ   C A G A A G A G T T C C T G C G C A A T G C A C C A A C C A T C A T G T G G C A   2660
X87822 orf.SEQ       C A G A A G A G T T C C T G C G C A A T G C A C C A A C C A T C A T G T G G C A   2660

FASA pMON70058.SEQ   C G G T C A C C T C A T T G C C A A C C C G G C G T A T G A G C T G C C A G A A   2700
X87822 orf.SEQ       C G G T C A C C T C A T T G C C A A C C C G G C G T A T G A G C T G C C A G A A   2700

FASA pMON70058.SEQ   G A A G C T T T T G A C A T C G T C G A T G A C G G C G A A G G C T T T G C T A   2740
X87822 orf.SEQ       G A A G C T T T T G A C A T C G T C G A T G A C G G C G A A G G C T T T G C T A   2740

FASA pMON70058.SEQ   T T C G C A T C A A C T C T G A C T C C T A C T G G G A T A A C C T C C C A G A   2780
X87822 orf.SEQ       T T C G C A T C A A C T C T G A C T C C T A C[A]G G G A T A A C C T C C C A G A   2780

FASA pMON70058.SEQ   A G A G C A G C G T C C G T T C T A C G T C A A G C A C G T T G A T A T C C C C   2820
X87822 orf.SEQ       A G A G C A G C G T C C G T T C T A C G T C A A G C A C G T T G A T A T C C C C   2820

FASA pMON70058.SEQ   G T T G C G C T G T C G G A A G C C G T A G C A A C C G G T G C C T C C C C T G   2860
X87822 orf.SEQ       G T T G C G C T G T C G G A A G C C G T A G C A A C C G G T G C C T C C C C T G   2860
```

Boxed Residues Differ from pMON70058

FIG. 2C

```
FASA pMON70058.SEQ   T T G T T G A T G A C G C G C G T T T G C C A A A G G C A G T C T T C G A C C T   2900
X87822 orf.SEQ       T T G T T G A T G A C G C G C G T T T G C C A A A G G C A G T C T T C G A C C T   2900

FASA pMON70058.SEQ   G C T C G C A G G C G T T G C T G G T G T C G G G T C T A T C T C T G A G A C C   2940
X87822 orf.SEQ       G C T C G C A G G C G T T G C T G G T G T C G G G T C T A T C T C T G A G A C C   2940

FASA pMON70058.SEQ   G G C G A T A A G A T C A C C G A A C T G C C G A A G G T C A T C G A A G G C T   2980
X87822 orf.SEQ       G G C G A T A A G A T C A C C G A A C T G C C G A A G G T C A T C G A A G G C T   2980

FASA pMON70058.SEQ   C T G T C T C C G A A G A A A A C C C T T A C G G C C T G G T G G A A T A C T C   3020
X87822 orf.SEQ       C T G T C T C C G A A G A A A A C C C T T A C G G C C T G G T G G A A T A C T C   3020

FASA pMON70058.SEQ   C T T T A C C T T G C C T T C T A C C C T G C T G A C C G C A C A C A C C G C G   3060
X87822 orf.SEQ       C T T T A C C T T G C C T T C T A C C C T G C T G A C C G C A C A C A C C G C G   3060

FASA pMON70058.SEQ   G T A A C C G G C G C T G C C T T G G G C A C C G C C A A C G C A G G C A C C C   3100
X87822 orf.SEQ       G T A A C C G G C G C T G C C T T G G G C A C C G C C A A C G C A G G C A C C C   3100

FASA pMON70058.SEQ   C A G A T G C G C T G G T T G G C C C C T G C T G G C C A G C A A T T T A C A C   3140
X87822 orf.SEQ       C A G A T G C G C T G G T T G G C C C C T G C T G G C C A G C A A T T T A C A C   3140

FASA pMON70058.SEQ   C G C G C T G G G C A C C G G T C G A T T G A C C G A A G A A C A C G G T G A G   3180
X87822 orf.SEQ       C G C G C T G G G C A C C G G T C G A T T G A C C G A A G A A C A C G G T G A G   3180

FASA pMON70058.SEQ   C C A G C C G G C A C C G A C T T C C C G G T C A T T G A A G G C C T G C T C A   3220
X87822 orf.SEQ       C C A G C C G G C A C C G A C T T C C C G G T C A T T G A A G G C C T G C T C A   3220

FASA pMON70058.SEQ   A C G C A G T C C A C C T C G A C C A C G T C G T C G A T G T G C G T G T T C C   3260
X87822 orf.SEQ       A C G C A G T C C A C C T C G A C C A C G T C G T C G A T G T G C G T G T T C C   3260

FASA pMON70058.SEQ   T C T T C A C G A A C T C G C A A A G G G T G A A A A G G G C G A A G G C C G T   3300
X87822 orf.SEQ       T C T T C A C G A A C T C G C A A A G G G T G A A A A G G G C G A A G G C[G]G T   3300

FASA pMON70058.SEQ   C G C A T T G A C G T C A C C T C C C G C T G T G C A T C C A T C G C G G A A T   3340
X87822 orf.SEQ       C G C A T T G A C G T C A C C T C C C G C T G T G C A T C C A T C G C G G A A T   3340

FASA pMON70058.SEQ   C C A A C T C C G G T C G C A T T G T C A C C G T G G A A C T T G A G T T G T G   3380
X87822 orf.SEQ       C C A A C T C C G G T C G C A T T G T C A C C G T G G A A C T T G A G T T G T G   3380

FASA pMON70058.SEQ   G G A T G C C G C A A C T C A A G A A G T T G T G G C G A C G C A G A T G C A G   3420
X87822 orf.SEQ       G G A T G C C G C A A C T C A A G A A G T T G T G G C G A C G C A G A T G C A G   3420

FASA pMON70058.SEQ   C G C T T T G C C A T C C G T G G C C G C G C T A C C G G C A C C T C C G T T C   3460
X87822 orf.SEQ       C G C T T T G C C A T C C G T G G C C G C G C T A C C G G C A C C T C C G T T C   3460

FASA pMON70058.SEQ   C G G T T T C T G C A C C A T C C T G G G G C G G C G G C A A G T C T C A G G A   3500
X87822 orf.SEQ       C G G T T T C T G C A C C A T C C T G G G G C G G C G G C A A G T C T C A G G A   3500

FASA pMON70058.SEQ   C A A G A T T G A G A C C A C C C C A C G T T C C T T C G T G G A T C G C G C C   3540
X87822 orf.SEQ       C A A G A T T G A G A C C A C C C C A C G T T C C T T C G T G G A T C G C G C C   3540

FASA pMON70058.SEQ   A T T G T C A C C G C G C C A T C G G A T A T G A C C C C A T T C G C G C T G G   3580
X87822 orf.SEQ       A T T G T C A C C G C G C C A T C G G A T A T G A C C C C A T T C G C G C T G G   3580

FASA pMON70058.SEQ   T C T C C G G T G A C T A C A A C C C A A T T C A C A C C T C C A C C A A C G C   3620
X87822 orf.SEQ       T C T C C G G T G A C T A C A A C C C A A T T C A C A C C T C C A C C A A C G C   3620

FASA pMON70058.SEQ   C G C G C G C T T G G T C A A C C T C G A C G C C C C A C T G G T G C A C G G C   3660
X87822 orf.SEQ       C G C G C G C T T G G T C A A C C T C G A C G C C C C A C T G G T G C A C G G C   3660

FASA pMON70058.SEQ   A T G T G G C T A T C T G C C A C C G C G C A G C A C C T A G C T G G C A A C C   3700
X87822 orf.SEQ       A T G T G G C T A T C T G C C A C C G C G C A G C A C C T A G C T G G C A A C C   3700

FASA pMON70058.SEQ   A C G G C A C C G T G G T G G G T T G G A C C T A T T C C A T G T A C G G C A T   3740
X87822 orf.SEQ       A C G G C A C C G T G G T G G G T T G G A C C T A T T C C A T G T A C G G C A T   3740

FASA pMON70058.SEQ   G G T C C A G C T C A A C G A T G A A G T A G A A A T C A C C G T C G A A C G C   3780
X87822 orf.SEQ       G G T C C A G C T C A A C G A T G A A G T A G A A A T C A C C G T C G A A C G C   3780

FASA pMON70058.SEQ   G T A G G C C G C A A G G G C A T T C A C G C A G C A T T C G A G G T C A C C T   3820
X87822 orf.SEQ       G T A G G C C G C A A G G G C A T T C A C G C A G C A T T C G A G G T C A C C T   3820
```

Boxed Residues Differ from pMON70058

FIG. 2D

```
FASA pMON70058.SEQ  G C C G C A T C G A C G G C G A A G T A G T C T C C C G C G G C C A G G C G C T  3860
X87822 orf.SEQ      G C C G C A T C G A C G G C G A A G T A G T C T C C C G C G G C C A G G C G C T  3860

FASA pMON70058.SEQ  C A T G G C A C A G C C A C G C A C C G C T T A T G T C T A C C C A G G C C A G  3900
X87822 orf.SEQ      C A T G G C A C A G C C A C G C A C C G C T T A T G T C T A C C C A G G C C A G  3900

FASA pMON70058.SEQ  G G C A T C C A G G C C G A G G G C A T G G G C C G T G G T G A C C G C G A T G  3940
X87822 orf.SEQ      G G C A T C C A G G C C G A G G G C A T G G G C C G T G G T G A C C G C G A T G  3940

FASA pMON70058.SEQ  C T T C G G C A G C A G C G C G T G A G G T A T G G C G T C G T G C A G A C C G  3980
X87822 orf.SEQ      C T T C G G C A G C A G C G C G T G A G G T A T G G C G T C G T G C A G A C C G  3980

FASA pMON70058.SEQ  C C A C A C C C G C A C C G C A A T G G G C T T T T C T A T T C G C C A G A T C  4020
X87822 orf.SEQ      C C A C A C C C G C A C C G C A C T G G G C T T T T C T A T T C G C C A G A T C  4020

FASA pMON70058.SEQ  A T C G A T G A C A A C C C C A C C G A G C T C G T C G T T C G C G G C A C C A  4060
X87822 orf.SEQ      A T C G A T G A C A A C C C C A C C G A G C T C G T C G T T C G C G G C A C C A  4060

FASA pMON70058.SEQ  A G T T C G T C C A C C C C A A T G G C G T G C T G C A C T T A A C G C A G T T  4100
X87822 orf.SEQ      A G T T C G T C C A C C C C A A T G G C G T G C T G C A C T T A A C G C A G T T  4100

FASA pMON70058.SEQ  C A C T C A G G T T G C C C T C G C A G T C G T T G C T T A T G C A C A A A C C  4140
X87822 orf.SEQ      C A C T C A G G T T G C C C T C G C A G T C G T T G C T T A T G C A C A A A C C  4140

FASA pMON70058.SEQ  G A G C G C C T G C G C G A A G C A G A T G C T C T G G G C A C C A A C T C C A  4180
X87822 orf.SEQ      G A G C G C C T G C G C G A A G C A G A T G C T C T G G G C A C C A A C T C C A  4180

FASA pMON70058.SEQ  T G T A C G C C G G T C A C T C A C T G G G T G A G T A C A C C G C G C T G G C  4220
X87822 orf.SEQ      T G T A C G C C G G T C A C T C A C T G G G T G A G T A C A C C G C G C T G G C  4220

FASA pMON70058.SEQ  A T C G T T G G C G A A T A T C T T T G A C C T C G A A G C G G T T A T C G A C  4260
X87822 orf.SEQ      A T C G T T G G C G A A T A T C T T T G A C C T C G A A G C G G T T A T C G A C  4260

FASA pMON70058.SEQ  A T C G T C T A C T C C C G T G G C T C T G C C A T G G G C A C C T T G G T C G  4300
X87822 orf.SEQ      A T C G T C T A C T C C C G T G G C T C T G C C A T G G G C A C C T T G G T C G  4300

FASA pMON70058.SEQ  A A C G T G A T G A A A A C G G T A A C T C C A A C T A C G G C A T G G G C G C  4340
X87822 orf.SEQ      A A C G T G A T G A A A A C G G T A A C T C C A A C T A C G G C A T G G G C G C  4340

FASA pMON70058.SEQ  G C T G C G T C C A A A C A T G A T T G G T G T T C C C G C A G A C C A G G T T  4380
X87822 orf.SEQ      G C T G C G T C C A A A C A T G A T T G G T G T T C C C G C A G A C C A G G T T  4380

FASA pMON70058.SEQ  G A G G C C T A C A T C G C G C A G A C C G C G G A A G A A A C T G G C G A A T  4420
X87822 orf.SEQ      G A G G C C T A C A T C G C G C A G A C C G C G G A A G A A A C T G G C G A A T  4420

FASA pMON70058.SEQ  T C C T C G A A A T C G T C A A C T A C A A C A T C G C T G G T C A G C A G T A  4460
X87822 orf.SEQ      T C C T C G A A A T C G T C A A C T A C A A C A T C G C T G G T C A G C A G T A  4460

FASA pMON70058.SEQ  C T C C A T C G C G G G T A C C A A G G C T G G T T T G G C C G C C C T G A A G  4500
X87822 orf.SEQ      C T C C A T C G C G G G T A C C A A G G C T G G T T T G G C C G C C C T G A A G  4500

FASA pMON70058.SEQ  A A A A A G G C C A A C T C C G T C A A G G A C C G T G C T T A T G T C A C G G  4540
X87822 orf.SEQ      A A A A A G G C C A A C T C C G T C A A G G A C C G T G C T T A T G T C A C G G  4540

FASA pMON70058.SEQ  T T C C A G G C A T C G A T G T A C C T T T C C A C T C C C A G G T A C T G C G  4580
X87822 orf.SEQ      T T C C A G G C A T C G A T G T A C C T T T C C A C T C C C A G G T A C T G C G  4580

FASA pMON70058.SEQ  C G A C G G C G T T C C T G C T T T C G C A G A A A A G C T C G A T G A A C T G  4620
X87822 orf.SEQ      C G A C G G C G T T C C T G C T T T C G C A G A A A A G C T C G A T G A A C T G  4620

FASA pMON70058.SEQ  T T G C C A G A A A C C T T G G A C C T G G A C G C C C T G G T C G G C C G C T  4660
X87822 orf.SEQ      T T G C C A G A A A C C T T G G A C C T G G A C G C C C T G G T C G G C C G C T  4660

FASA pMON70058.SEQ  A C G T G C C G A A C C T G G T G G C G C T G C C A T T C G A G C T G A C C C A  4700
X87822 orf.SEQ      A C G T G C C G A A C C T G G T G G C G C T G C C A T T C G A G C T G A C C C A  4700

FASA pMON70058.SEQ  G G A A T T T G T C G A T A A G G T C A A G C C T T T G G C T C C T T C C G G C  4740
X87822 orf.SEQ      G G A A T T T G T C G A T A A G G T C A A G C C T T T G G C T C C T T C C G G C  4740

FASA pMON70058.SEQ  A A G C T G G A T A A C C T C A A G G T C G A A G A C A C C G A T G A G C A A G  4780
X87822 orf.SEQ      A A G C T G G A T A A C C T C A A G G T C G A A G A C A C C G A T G A G C A A G  4780
```

Boxed Residues Differ from pMON70058

FIG. 2E

| | | |
|---|---|---|
| FASA pMON70058.SEQ | CCCTTGCTCGCCTGCTCATGATTGAGCTATTGTCCTGGCA | 4820 |
| X87822 orf.SEQ | CCCCTTCTCGCCTGCTCATGATTGAGCTATTGTCCTGGCA | 4820 |
| FASA pMON70058.SEQ | GTTCGCATCACCTGTGCGCTGGATTGAAACCCAGCAGCTG | 4860 |
| X87822 orf.SEQ | GTTCGCATCACCTGTGCGCTGGATTGAAACCCAGCAGCTG | 4860 |
| FASA pMON70058.SEQ | CTCTTTGAAGAAGTAGACCAGATCATCGAAGTCGGTCTCG | 4900 |
| X87822 orf.SEQ | CTCTTTGAAGAAGTAGACCAGATCATCGAAGTCGGTCTCG | 4900 |
| FASA pMON70058.SEQ | CGGCATCCCCAACGCTGACCAACTTGGCCAAGCGCTCCAT | 4940 |
| X87822 orf.SEQ | CTTCATCCCCAACGCTGACCAACTTGGCCAAGCGCTCCAT | 4940 |
| FASA pMON70058.SEQ | GGATATCGCCGGCGTGGACCTCCCGGTCTTCAACGTCGAA | 4980 |
| X87822 orf.SEQ | GGATATCGCCGGCGTGGACCTCCCGGTCTTCAACGTCGAA | 4980 |
| FASA pMON70058.SEQ | CGCGACCAAGACCAGGTCATGCTCCAAGACGTTCAGGAAG | 5020 |
| X87822 orf.SEQ | CGCGACCAAGACCAGGTCATGCTCCAAGACGTTCAGGAAG | 5020 |
| FASA pMON70058.SEQ | CACCAGCTGCCTCCTTCGACGTCGAGGAAGGAGAGGCCAC | 5060 |
| X87822 orf.SEQ | CACCAGCTGCCTCCTTCGACGTCGAGGAAGGAGAGGCCAC | 5060 |
| FASA pMON70058.SEQ | CTCTTCGACCGCAGCGTCTGAAACCCCAGGTGAATCCGCT | 5100 |
| X87822 orf.SEQ | CTCTTCGACCGCAGCGTCTGAAACCCCAGGTGAATCCGCT | 5100 |
| FASA pMON70058.SEQ | GCGGCGGCCTCGGATAATACCCAGGCCATCCCATCGGCTG | 5140 |
| X87822 orf.SEQ | GCGGCGGCCTCGGATAATACCCAGGCCATCCCATCGGCTG | 5140 |
| FASA pMON70058.SEQ | AGCCACAAACGGTGGCAGAGGCACCAGCACCATCCGCCGC | 5180 |
| X87822 orf.SEQ | AGCCACAAACGGTGGCAGAGGCACCAGCACCATCCGCCGC | 5180 |
| FASA pMON70058.SEQ | ACCAGCTGGCGGCACCGCTGCCGCAGATGCTCCTGACCTG | 5220 |
| X87822 orf.SEQ | ACCAGCTGGCGGCACCCGTGCCGCAGATGCTCCTGACCTG | 5220 |
| FASA pMON70058.SEQ | CCATTTACCGCAGCAGAAGCCATCATGGTTCTGTTCGCTT | 5260 |
| X87822 orf.SEQ | CCATTTACCGCAGCAGAAGCCATCATGGTTCTGTTCGCTT | 5260 |
| FASA pMON70058.SEQ | TCCAGAACAAGATCCGCCAGGACCAGATCAATGACTCGGA | 5300 |
| X87822 orf.SEQ | TCCAGAACAAGATCCGCCAGGACCAGATCAATGACTCGGA | 5300 |
| FASA pMON70058.SEQ | TACGGTCGAAGAGCTCACCAACGGTGTCTCCTCCCGCCGT | 5340 |
| X87822 orf.SEQ | TACGGTCGAAGAGCTCACCAACGGTGTCTCCTCCCGCCGT | 5340 |
| FASA pMON70058.SEQ | AACCAACTGTTGATGGATATGTCCGCAGAAATCGGCGTGC | 5380 |
| X87822 orf.SEQ | AACCAACTGTTGATGGATATGTCCGCAGAAAATCGCGTGC | 5380 |
| FASA pMON70058.SEQ | CCGCCATTGACGGTGCAGCCGATGCTGACGTGGCAACCTT | 5420 |
| X87822 orf.SEQ | CCGCCATTGACGGTGCAGCCGATGCTGACGTGGCAACCTT | 5420 |
| FASA pMON70058.SEQ | GCGTGAGCGCGTCAAGACTGCCGCTCCGGGCTACTCGCCA | 5460 |
| X87822 orf.SEQ | GCGTGAGCGCGTCAAGACTGCCGCTCCGGGCTACTCGCCA | 5460 |
| FASA pMON70058.SEQ | TTCGGCACCGTCTTGTCTGAGGCTATTACCGCTCGTCTGC | 5500 |
| X87822 orf.SEQ | TTCGGCACCGTCTTGTCTGAGGCTATTACCGCTCGTCTGC | 5500 |
| FASA pMON70058.SEQ | GCCAGCTCACTGGTGCAGCAGGCGTCAAGCCGGCCTACAT | 5540 |
| X87822 orf.SEQ | GCCAGCTCACTGGTGCAGCAGGCGTCAAGCCGGCCTACAT | 5540 |
| FASA pMON70058.SEQ | TTCAGAGCGCGTGACCGGAACTTGGGGCTTGCCTATGTCC | 5580 |
| X87822 orf.SEQ | TTCAGAGCGCGTGACCGGAACTTGGGGGCTGCCTATGTCC | 5580 |
| FASA pMON70058.SEQ | TGGGCAGCCCACGTTGAGGCTGAAATCTTGCTCGGCTCCC | 5620 |
| X87822 orf.SEQ | TGGGCAGCCCACGTTGAGGCTGAAATCTTGCTCGGCTCCC | 5620 |
| FASA pMON70058.SEQ | GTGAAGAAGACTCCGTGCGCGGTGGCTCCTTGTCCACCGT | 5660 |
| X87822 orf.SEQ | GTGAAGAAGACTCAGTGCGCGGTGGCTCCTTGTCCACCGT | 5660 |
| FASA pMON70058.SEQ | TCCTTCCGCGGCGTCGTCGAAGGCCGATGTCGATGCGCTT | 5700 |
| X87822 orf.SEQ | TCCTTCCGCGGCGTCGTCGAAGGCCGATGTCGATGCGCTT | 5700 |
| FASA pMON70058.SEQ | GTCGATGCCGCCGTCCAGGCCGTAGCCGCAGCACACGGCA | 5740 |
| X87822 orf.SEQ | GTCGATGCCGCGGTCCAGGCCGTAGCCGCAGCACACGGCA | 5740 |

Boxed Residues Differ from pMON70058

FIG. 2F

| | | |
|---|---|---|
| FASA pMON70058.SEQ | C C T C G G T A T C C A T G G G T G C T G C G A G T G G C G C C G G C G G C G G | 5780 |
| X87822 orf.SEQ | C C T C G G T A T C C [C A T] G G T G C T G C G A G T G G C G C C G G C G G C G G | 5780 |
| FASA pMON70058.SEQ | T G G A G T C G T C G A C T C C G C A G C C T T G G A T G C T T A C G C A G A T | 5820 |
| X87822 orf.SEQ | T G G A G T C G T C G A C T C C G C A G C C T T G G A T G C T T A C G C A G A T | 5820 |
| FASA pMON70058.SEQ | A T C G T C A C C G G T G A A A A C G G T G T C C T C G C T A C T G C T G C T C | 5860 |
| X87822 orf.SEQ | A T C G T C A C C G G T G A A A A C G G T G T C C T C G C T A C T G C T G C T C | 5860 |
| FASA pMON70058.SEQ | G C C A G G T T C T G G C T C A G C T G G G C T T G G T C G A G G A A G C C C C | 5900 |
| X87822 orf.SEQ | G C C A G G T T C T G G C T C A G C T G G G C T T G G T C G A G G A A G C C C C | 5900 |
| FASA pMON70058.SEQ | T G A G A C C C C T G A G A C C G A T A A C A C C T T G T T C G A G A C C G T C | 5940 |
| X87822 orf.SEQ | T G A G A C C C C T G A G A C C G A T A A C A C C T T G T T C G [C] G A C C G T C | 5940 |
| FASA pMON70058.SEQ | G A G G C C G A G C T G G G T T C C G G T T G G G A A A A G A C C G T T A C C C | 5980 |
| X87822 orf.SEQ | G A G G C C G A G C T G G G T T C C G G T T G G G A A A A G A C C G T T A C C C | 5980 |
| FASA pMON70058.SEQ | C A T C C T T T G A C G C C A A G C G C G C A G T G C T T T T C G A T G A C C G | 6020 |
| X87822 orf.SEQ | C A T C C T T T G A C G C C A A G C G C G C A G T G C T T T T C G A T G A C C G | 6020 |
| FASA pMON70058.SEQ | C T G G G C G T C T G C T C G C G A A G A T C T C G C C C G C G T G G C A C T C | 6060 |
| X87822 orf.SEQ | C T G G G C G T C T G C T C G C G A A G A T C T C G C C C G C G T G G C A C T C | 6060 |
| FASA pMON70058.SEQ | G G C G A G A T C G A C T T G C C A G T C A A G C G T T T C C A G G G A A C C G | 6100 |
| X87822 orf.SEQ | G G C G A G A T C G A C T T G C C A G T C A A G C G T T T C C A G G G A A C C G | 6100 |
| FASA pMON70058.SEQ | G A G A G A C C A T C G C C A A G C A A G C G G A A T G G T G G G C G G A G A A | 6140 |
| X87822 orf.SEQ | G A G A G A C C A T C G C C A A G C A A G C G G A A T G G T G G G C G G A G A A | 6140 |
| FASA pMON70058.SEQ | C A C C G C T G C T T C C A C T G G T G C G C A C G C G A A G G C A A C C T C T | 6180 |
| X87822 orf.SEQ | C A C C G C T G C T T C C A C T G G T G C G C A C G C G A A G G C A A C C [G] C T | 6180 |
| FASA pMON70058.SEQ | G C C G A G A C C C T G C A T G C T A T T G C T G C C G C A G C G C G C G A A G | 6220 |
| X87822 orf.SEQ | G C C G A G A C C C T G C A T G C T A T T G C T G C C G C A G C G C G C G A A G | 6220 |
| FASA pMON70058.SEQ | A A C T C G A C G G C G A A T T C G C T G G C G A T G T C G C G T T G G T C A C | 6260 |
| X87822 orf.SEQ | A A C T C G A C G G C G A A T T C G C T G G C G A T G T C G C G T T G G T C A C | 6260 |
| FASA pMON70058.SEQ | C G G T G C A G C C C C A G G C T C C A T T G C T A C C G C T C T C G T A G A A | 6300 |
| X87822 orf.SEQ | C G G T G C A G C C C C A G G C T C C A T T G C T A C C G C T C T C G T A G A A | 6300 |
| FASA pMON70058.SEQ | C G C C T G C T G G A A G G C G G C G C G A C C G T C A T C A T G A C T G C G T | 6340 |
| X87822 orf.SEQ | C G C C T G C T G G A A G G C G G C G C G A C C G T C A T C A T G A C T G C G T | 6340 |
| FASA pMON70058.SEQ | C A C G T G T C A G C C A G T C C C G T A A G G A A T T T G C A C G C A A G C T | 6380 |
| X87822 orf.SEQ | C A C G T G T C A G C C A G T C C C G T A A G G A A T T T G C A C G C A A G C T | 6380 |
| FASA pMON70058.SEQ | C T A C G C T G C A C A C G C G A T T C C T G G C G C T G C C C T G T G G G T T | 6420 |
| X87822 orf.SEQ | C T A C G C T G C A C A C G C G A T T C C T G G C G C T G C C C T G T G G G T T | 6420 |
| FASA pMON70058.SEQ | G T T C C T G C G A A C T T G A G C T C C T A C C G C G A T G T T G A T G C T C | 6460 |
| X87822 orf.SEQ | G T T C C T G C G A A C T T G [C] G C T C C T A C C G C G A T G T T G A T G C T C | 6460 |
| FASA pMON70058.SEQ | T C A T T G A C T G G A T T G G T A A T G A G C A G C G T G A A T C T G T C G G | 6500 |
| X87822 orf.SEQ | T C A T T G A C T G G A T T G G T A A T G A G C A G C G T G [C C] T C T G T C G G | 6500 |
| FASA pMON70058.SEQ | C A A C G A A G T C A A G A T C A C C A A G C C A G C G T T G A C C C C A A C C | 6540 |
| X87822 orf.SEQ | C A A C G A A G T C A A G A T C A C C A A G C C A G C G T T G A C C C C A A C C | 6540 |
| FASA pMON70058.SEQ | T T G G C C T T C C C A T T C G C G G C A C C T T C C G T G T C C G G T T C T G | 6580 |
| X87822 orf.SEQ | T T G G C C T T C C C A T T C G C G G C A C C T T C C G T G T C C G G T T C T G | 6580 |
| FASA pMON70058.SEQ | T G G C C G A T G C C G G C C C A C A G G C T G A A A A C C A G A C T C G C C T | 6620 |
| X87822 orf.SEQ | T G G C C G A T G C C G G C C C A C A G G C T G A A A A C C A G A C T C G C C T | 6620 |
| FASA pMON70058.SEQ | G C T G C T G T G G T C T G T T G A G C G C A C C A T C G C T G G T C T G T C C | 6660 |
| X87822 orf.SEQ | G C T G C T G T G G T C T G T T G A G C G C A C C A T C G C T G G T C T G T C C | 6660 |
| FASA pMON70058.SEQ | A A C C T G G C G C A G C A A G G C G T G G A T A C C C G C T G C C A C A T T G | 6700 |
| X87822 orf.SEQ | A A C C T G G C G C A G C A A G G C G T G G A T A C C C G C T G C C A C A T T G | 6700 |

Boxed Residues Differ from pMON70058

FIG. 2G

```
FASA pMON70058.SEQ   T G C T G C C T G G T T C T C C G A A C C G C G G C A T G T T C G G T G G C G A   6740
X87822 orf.SEQ       T G C T G C C T G G T T C T C C G A A C C G C G G C A T G T T C G G T G G C G A   6740

FASA pMON70058.SEQ   C G G C G C T T A C G G C G A A G T C A A G G C A G C C T T G G A C G C T A T T   6780
X87822 orf.SEQ       C G G C G C T T A C G G C G A A G T C A A G G C A G C C T T G G A C G C T A T T   6780

FASA pMON70058.SEQ   T T G G C C A A G T G G T C T G C A G A A G C A G G C T G G C C A G A A G G T G   6820
X87822 orf.SEQ       T T G G C C A A G T G G T C T G C A G A A G C A G G C T G G C C A G A A G G T G   6820

FASA pMON70058.SEQ   T T A C C T T G G C A C A A G C C A A G A T T G G C T G G G T C T C T G G T A C   6860
X87822 orf.SEQ       T T A C C T T G G C A C A A G C C A A G A T T G G C T G G G T C T C T G G T A C   6860

FASA pMON70058.SEQ   C T C C C T G A T G G G C G G C A A C G A C G T T C T G A T T C C G G C A G C G   6900
X87822 orf.SEQ       C T C C C T G A T G G G C G G C A A C G A C G T T C T G A T T C C G G C A G C G   6900

FASA pMON70058.SEQ   G A A G C C G C T G G C A T C C A C G T G T G G G A C C C A G A A G A G A T T T   6940
X87822 orf.SEQ       G A A G C C G C T G G C A T C C A C G T G T G G G A C C C A G A A G A G A T T T   6940

FASA pMON70058.SEQ   C T T C C C A G C T C A T C T C C C T A G C T T C C G A A G A A T C C C G C G C   6980
X87822 orf.SEQ       C T T C C C A G C T C A T C T C C C T A G C T T C C G A A G A A T C C C G C G C   6980

FASA pMON70058.SEQ   G A A G G C A G C C G A G G C T C C A C T A G A G C T G G A T C T G A C C G G T   7020
X87822 orf.SEQ       G A A G G C A G C C G A G G C T C C A C T A G A G C T G G A T C T G A C C G G T   7020

FASA pMON70058.SEQ   G G T C T G G G C T C G T C C A A G A T C T C C A T C T C C G A G C T G G C T G   7060
X87822 orf.SEQ       G G T C T G G G C T C G T C C A A [C] A T C T C C A T C T C C G A G C T G G C T G   7060

FASA pMON70058.SEQ   C C C A G G C C C G C G A G G A C G C C G A G G C A C A A G C T G C T T C C G G   7100
X87822 orf.SEQ       C C C A G G C C C G C G A G G A C G C C G A G G C A C A A G C T G C T T C C G G   7100

FASA pMON70058.SEQ   T G A T A A T G C A G A C G C A G C T G C G G A A G C T C C T G C A G C C A C G   7140
X87822 orf.SEQ       T G A T A A T G C A G A C G C A G C T G C G G A A G C T C C T G C A G C C A C G   7140

FASA pMON70058.SEQ   A T T C C A G C A C T G C C T A A T A C C C G T T C A G T A G A G C T G C C T G   7180
X87822 orf.SEQ       A T T C C A G C A C T G C C T A A T A C C C G T T C A G T A G A G C T G C C T G   7180

FASA pMON70058.SEQ   C A G C G C T A C C G G A A G G T G A A G T G G G C G A C G T A A C C A C G G A   7220
X87822 orf.SEQ       C A G C G C T A C C G G A A G G T G A A G T G G G C G A C G T A A C C A C G G A   7220

FASA pMON70058.SEQ   T C T G G A T G A C A T G G T C G T C A T C G C A G G T G T C G G C G A A G T C   7260
X87822 orf.SEQ       T C T G G A T G A C A T G G T C G T C A T C G C A G G T G T C G G C G A A G T C   7260

FASA pMON70058.SEQ   T C C T C G T G G G G T T C G G G C C G T A C C C G C T T T G A G G C A G A A T   7300
X87822 orf.SEQ       T C C T C G T G G G G T T C G G G C C G T A C C C G C T T T G A G G C A G A A T   7300

FASA pMON70058.SEQ   A T G G C T T G C A G C G C G A T G G C G C T G T G G A C C T G A C C G C C G C   7340
X87822 orf.SEQ       A T G G C T T G C A G C G C G A T G G C G C T G T G G A C C T G A C C G C C G C   7340

FASA pMON70058.SEQ   T G G T G T C T T G G A A T T G G C A T G G A T G A C C G G A C T G A T T T C C   7380
X87822 orf.SEQ       T G G T G T C T T G G A A T T G G C A T G G A T G A C C G G A C T G A T T T C C   7380

FASA pMON70058.SEQ   T G G T C C A A T G A C C C A C G T C C A G C C T G G T A C G A C G A A G A G G   7420
X87822 orf.SEQ       T G G T C C A A T G A C C C A C G T C C A G C C T G G T A C G A C G A A G A G G   7420

FASA pMON70058.SEQ   G C A C C G A A G T C G A T G A A G C A G A T A T C T A C G C T C G C T T C C G   7460
X87822 orf.SEQ       G C A C C G A A G T C G A T G A A G C A G A T A T C T A C G C T C G C T T C C G   7460

FASA pMON70058.SEQ   C G A C G A G G T T G T A G C T C G C T C C G G T A T C C G T A C C T T G A C C   7500
X87822 orf.SEQ       C G A C G A G G T T G T A G C T C G C T C C G G T A T C C G T A C C T T G A C C   7500

FASA pMON70058.SEQ   G A T A A G T A C A A C A T G G T T G A C C A G G G C T C C A T T G A C C T G A   7540
X87822 orf.SEQ       G A T A A G T A C A A C A T G G T T G A C C A G G G C T C C A T T G A C C T G A   7540

FASA pMON70058.SEQ   C T T C T G T G T T C T T G G A C C G C G A T A T C G T C T T C A C C G T T C C   7580
X87822 orf.SEQ       C T T C T G T G T T C T T G G A C C G C G A T A T C G T C T T C A C C G T T C C   7580

FASA pMON70058.SEQ   T A C C G A A C A A G A A G C A C T C G A T A T T G A A G A A G C C G A C C C A   7620
X87822 orf.SEQ       T A C C G A A C A A G A A G C A C T C G A T A T T G A A G A A G C C G A C C C A   7620

FASA pMON70058.SEQ   T C G T T T A C C A A G C T G C G C G A A G T C G A C G G C G A G T G G G A A G   7660
X87822 orf.SEQ       T C G T T T A C C A A G C T G C G C G A A G T C G A C G G C G A G T G G G A A G   7660
```

Boxed Residues Differ from pMON70058

FIG. 2H

| | | |
|---|---|---|
| FASA pMON70058.SEQ | T C A C C C G T T T G A A G G G T G C C A C C G C C C G C G T G C C A C G C A A | 7700 |
| X87822 orf.SEQ | T C A C C C G T T T G A A G G G T G C C A C C G C C C G C G T G C C A C G C A A | 7700 |
| FASA pMON70058.SEQ | G G C A A C G T T G A C T C G T A C C G T T G C T G G T C A A A T G C C G G A T | 7740 |
| X87822 orf.SEQ | G G C A A C G T T G A C T C G T A C C G T T G C T G G T C A A A T G C C G G A T | 7740 |
| FASA pMON70058.SEQ | C A C T T C G A T G C T G C C A A G T G G G G C A T T C C A G A C C A C A T G C | 7780 |
| X87822 orf.SEQ | C A C T T C G A T G C T G C C A A G T G G G G C A T T C C A G A C C A C A T G C | 7780 |
| FASA pMON70058.SEQ | T G G A T G C A C T C G A C C G C A T G G C C G T G T G G A A C C T G G T G A C | 7820 |
| X87822 orf.SEQ | T G G A T G C A C T C G A C C G C A T G G C C G T G T G G A A C C T G G T G A C | 7820 |
| FASA pMON70058.SEQ | C G C A G T C G A T G C C T T T A C C C A G G C G G G C T T T A G C C C G G C T | 7860 |
| X87822 orf.SEQ | C G C A G T C G A T G C C T T T A C C C A G G C G G G C T T T A G C C C G G C T | 7860 |
| FASA pMON70058.SEQ | G A G T T G C T G C A G G T T A T T C A C C C A G C G C A G G T T G C T A C C A | 7900 |
| X87822 orf.SEQ | G A G T T G C T G C A G G T T A T T C A C C C A G C G C A G G T T G C T A C C A | 7900 |
| FASA pMON70058.SEQ | C C C A G G G C A C C G G T A T C G G C G G C A T G G A A T C C C T G C A C A A | 7940 |
| X87822 orf.SEQ | C C C A G G G C A C C G G T A T C G G C G G C A T G G A A T C C C T G C A C A A | 7940 |
| FASA pMON70058.SEQ | G G T C T T C G T G A C C C G T C T G C T C G G T G A A G A C C G T C C T T C C | 7980 |
| X87822 orf.SEQ | G G T C T T C G T G A C C C G T C T G C T C G G T G A A G A C C G T C C T T C C | 7980 |
| FASA pMON70058.SEQ | G A C A T C C T G C A G G A A G C A C T G C C T A A C G T T A T T G C A G C G C | 8020 |
| X87822 orf.SEQ | G A C A T C C T G C A G G A A G C A C T G C C T A A C G T T A T T G C A G C G C | 8020 |
| FASA pMON70058.SEQ | A C A C C A T G C A G T C T T T G G T G G G C G G C T A C G G T T C G A T G A T | 8060 |
| X87822 orf.SEQ | A C A C C A T G C A G T C T T T G G T G G G C G G C T A C G G T T C G A T G A T | 8060 |
| FASA pMON70058.SEQ | T C A C C C T A T C G G T G C T T G T G C C A C C G C T G C G G T G T C C A T C | 8100 |
| X87822 orf.SEQ | T C A C C C T A T C G G T G C T T G T G C C A C C G C T G C G G T G T C C A T C | 8100 |
| FASA pMON70058.SEQ | G A A G A A G G C G T G G A C A A G A T T G C C C T G G G C A A G G C C G A C C | 8140 |
| X87822 orf.SEQ | G A A G A A G G C G T G G A C A A G A T T G C C C T G G G C A A G G C C G A C C | 8140 |
| FASA pMON70058.SEQ | T G G T C G T T G C C G G T G G T A T C G A T G A C G T C C A A G T T G A G T C | 8180 |
| X87822 orf.SEQ | T G G T C G T T G C C G G T G G T A T C G A T G A C G T C C A A G T T G A G T C | 8180 |
| FASA pMON70058.SEQ | T T T G A C C G G C T T C G G C G A C A T G A A C G C C A C C G C T G A G A C C | 8220 |
| X87822 orf.SEQ | T T T G A C C G G C T T C G G C G A C A T G A A C G C C A C C G C T G A G A C C | 8220 |
| FASA pMON70058.SEQ | A A G A A G A T G A C C G A T C A G G G C A T T G A T G A C C G C T T C A T C T | 8260 |
| X87822 orf.SEQ | A A G A A G A T G A C C G A T C A G G G C A T T G A T G A C C G C T T C A T C T | 8260 |
| FASA pMON70058.SEQ | C C C G T G C G A A T G A C C G C C G T C G T G G C G G C T T C C T C G A G G C | 8300 |
| X87822 orf.SEQ | C C C G T G C G A A T G A C C G C C G T C G T G G C G G C T T C C T C G A G G C | 8300 |
| FASA pMON70058.SEQ | A G A A G G C G G C G G T A C C G T G C T T C T G G T T C G C G G T T C C C T G | 8340 |
| X87822 orf.SEQ | A G A A G G C G G C G G T A C C G T G C T T C T G G T T C G C G G T T C C C T G | 8340 |
| FASA pMON70058.SEQ | G C T C G T G A G A T G G G T C T G C C G G T C T A C G C G G T C G T T G C G C | 8380 |
| X87822 orf.SEQ | G C T C G T G A G A T G G G T C T G C C G G T C T A C G C G G T C G T T G C G C | 8380 |
| FASA pMON70058.SEQ | A C G C G G C G T C C T A C G G C G A C G G T G C C C A C A C C T C C A T T C C | 8420 |
| X87822 orf.SEQ | A C G [A] G G C G T C C T A C G G [- - - - - -] T G C C C A C A C C T C C A T T C C | 8420 |
| FASA pMON70058.SEQ | T G C T C C A G G T T T G G G T G C T T T G G G C G C T G G C C G T G G C C G G | 8460 |
| X87822 orf.SEQ | T G C T C C A G G T T T G G G T G C T T T G G G C G C T G G C C G T G G C C G G | 8460 |
| FASA pMON70058.SEQ | A A G A A C T C C C G C C T G G C C A A G G G C T T G G C T G G T T T G G G T C | 8500 |
| X87822 orf.SEQ | A A G A A C T C C C G C C T G G C C A A G G G C T T G G C T G G T T T G G G T C | 8500 |
| FASA pMON70058.SEQ | T G A C T C C A A A T G A C G T C T C G G T A C T G T C C A A G C A C G A C A C | 8540 |
| X87822 orf.SEQ | T G A C T C C A A A T G A C G T C T C G G T A C T G T C C A A G C A C G A C A C | 8540 |
| FASA pMON70058.SEQ | C T C G A C C A A C G C C A A T G A C C C G A A T G A G T C G G A A C T G C A C | 8580 |
| X87822 orf.SEQ | C T C G A C C A A C G C C A A T G A C C C G A A T G A G T C G G A A C T G C A C | 8580 |
| FASA pMON70058.SEQ | T C C A T C T T G T G G C C T G C T A T T G G C C G C G A T G T G G A C C A G C | 8620 |
| X87822 orf.SEQ | T C C A T C T T G T G G C C T G C T A T T G G C C G C G A T G T G G A C C A G C | 8614 |

Boxed Residues Differ from pMON70058

FIG. 2I

```
FASA pMON70058.SEQ  C A C T G T T T G T G A T T T C G C A G A A G T C A C T G A C T G G T C A C T C  8660
X87822 orf.SEQ      C A C T G T T T G T G A T T T C G C A G A A G T C A C T G A C T G G T C A C T C  8654

FASA pMON70058.SEQ  C A A G G C T G G T G C C G C G C T G T T C C A G A C C G G C G G T T T G A T T  8700
X87822 orf.SEQ      C A A G G C T G G T G C C G C G C T G T T C C A G A C C G G C G G T T T G A T T  8694

FASA pMON70058.SEQ  G A C G T C T T C C G C A C G G G A C G C A T T C C A G C T A A C C T G T C G C  8740
X87822 orf.SEQ      G A C G T C T T C C G C A C G G G A C G C A T T C C A G C T A A C C T G T C G C  8734

FASA pMON70058.SEQ  T G G A T T G T G T G G A T C C A T T G A T T G A G C C A A A G G C C A C G A A  8780
X87822 orf.SEQ      T G G A T T G T G T G G A T C C A T T G A T T G A G C C A A A G G C C A C G A A  8774

FASA pMON70058.SEQ  C T T G G T C T G G C T A C G C T C C C C A C T A G A T G T G G A A G C A G C C  8820
X87822 orf.SEQ      C T T G G T C T G G C T A C G C T C C C C A C T A G A T G T G G A A G C A G C C  8814

FASA pMON70058.SEQ  A A C C G C C C G G T C A A G G C C G C G G C G C T C A C C T C G C T C G G C T  8860
X87822 orf.SEQ      A A C C G C C C G G T C A A G G C C G C G G C G C T C A C C T C G C T C G G C T  8854

FASA pMON70058.SEQ  T C G G T C A C G T C G G T G C A T T G A T T G T C T A C G C G C A C C C A G G  8900
X87822 orf.SEQ      T C G G T C A C G T C G G T G C A T T G A T T G T C T A C G C G C A C C C A G G  8894

FASA pMON70058.SEQ  T G T C T T C G A G G C T G C C G T T G C C C A G C A G G T T T C G G C C G A G  8940
X87822 orf.SEQ      T G T C T T C G A G G C T G C C G T T G C C C A G C A G G T T T C G G C C G A G  8934

FASA pMON70058.SEQ  G C T G C T G C C G A A T G G C G C G A G A A G G C A A A T G C C C G C C T C G  8980
X87822 orf.SEQ      G C T G C T G C C G A A T G G C G C G A G A A G G C A A A T G C C C G C C T C G  8974

FASA pMON70058.SEQ  C C G C C G G T G C A G C A C G C T T C G A A G C C G G C A T G A T T G G C A A  9020
X87822 orf.SEQ      C C G C C G G T G C A G C A C G C T T C G A A G C C G G C A T G A T T G G C A A  9014

FASA pMON70058.SEQ  G G A A A C C T T G T T C G A G G T C A T C G A C G G C C G C C G C C T G C C T  9060
X87822 orf.SEQ      G G A A A C C T T G T T C G A G G T C A T C G A C G G C C G C C G C C T G C C T  9054

FASA pMON70058.SEQ  G A C G C A G C G G G C A C C G T T G A G A T T G A G A A C T A C G G C C C A G  9100
X87822 orf.SEQ      G A C G C A G C G G G C A C C G T T G A G A T T G A G A A C T A C G G C C C A G  9094

FASA pMON70058.SEQ  T C G C C G C C G A C A A G G C C G C A G A A A T T G C G C T C T T G C T T G A  9140
X87822 orf.SEQ      T C G C C G C C G A C A A G G C C G C A G A A - T T G C G C T C T T G C T T G A  9133

FASA pMON70058.SEQ  C G A C G A C A T C C G T C T T A C C G C C G A A G G C A C T T T C C C T C C G  9180
X87822 orf.SEQ      C G A C G A C A T C C G T C T T A C C G C C G A A G G C A C T T T C C C T C C G  9173

FASA pMON70058.SEQ  G C G A A G T A G                                                                9189
X87822 orf.SEQ      G C G A A G T A G G A C A A A G T A G                                            9192
```

Boxed Residues Differ from pMON70058

FIG. 2J

| | | |
|---|---|---|
| FASA pmon70058.PRO | M S L T P L H T L S N D S T A P A V L F A G Q G S A W Q K A I A D A A A S P H Q | 40 |
| FASA X87822.PRO | M S L T P L H T L S N D S T A P A V L F A G Q G S A W Q K A I A D A A A S P H Q | 40 |
| FASA pmon70058.PRO | G A Q L R D I L K E V R T T T G P V A R I I A S S C P G V Y E R L E E L A Q T P | 80 |
| FASA X87822.PRO | G A Q L R D I L K E V R T T T G P V A R I I A S S C P G V Y E R L E E L A Q T P | 80 |
| FASA pmon70058.PRO | A D Q A P V A K E Y D A Y P A Y S I P G I V L G Q I G A I E H L R E L G I D V D | 120 |
| FASA X87822.PRO | A D Q A P V A K E Y D A Y P A Y S I P G I V L G Q I G A I E H L A Q L G I D V D | 120 |
| FASA pmon70058.PRO | S A Q L A G H S Q G S L G V A A V K D A R Q A L A I A V L M G T A A A V T Q G A | 160 |
| FASA X87822.PRO | S A Q L A G H S Q G S L G V A A V K D A R Q A L A I A V L M G T A A A V T Q G A | 160 |
| FASA pmon70058.PRO | N D S R S H M L S V R G V P R E M V E E Y L A G D A A I A V V N G R V H F A L S | 200 |
| FASA X87822.PRO | N D S R T H M L S V R G V P R E M V E E Y L A G D A A I A V V N G R V H F A L S | 200 |
| FASA pmon70058.PRO | G T P E D L A K T E S N L T Q A A E S Y N D A L E E R R I G G S E I N P V F D V | 240 |
| FASA X87822.PRO | G T P E D L A K T E S N L T Q A A E S Y N D A L E E R R I G G S E I N P V F D V | 240 |
| FASA pmon70058.PRO | L A V A L P F H H A S L Q D A A D L T V D Y A T Q C G L D A E L A R E L A D S I | 280 |
| FASA X87822.PRO | L A V A L P F H H A S L Q D A A D L T V D Y A T Q C G L D A E L A R E L A D S I | 280 |
| FASA pmon70058.PRO | L V Q P H S W V E T V A G L N S T Y L L S L D R G L S S L T T F L I A G T G K V | 320 |
| FASA X87822.PRO | L V Q P H S W V E T V A G L N S T Y L L S L D R G L S S L T T F L I A G T G K V | 320 |
| FASA pmon70058.PRO | V V P A A T P A E R D N L A T P G T E L P T A V N Y E K F S P K L I S L P N G K | 360 |
| FASA X87822.PRO | V V P A A T P A E R D N L A T P G T E L P T A V N Y E K F S P K L I S L P N G K | 360 |
| FASA pmon70058.PRO | S Y T Q T R F S E W T G M S P I I L G G M T P T T M D P G I V A A A A N G G Y W | 400 |
| FASA X87822.PRO | S Y T Q T R F S E W T G M S P I I L G G M T P T T M D P G I V A A A A N G G Y W | 400 |
| FASA pmon70058.PRO | S E M A G G G Q Y S D E A F T I N K D G M M E L L E P G R T A A F N T M F F D R | 440 |
| FASA X87822.PRO | S E M A G G G Q Y S D E A F T I N K D G M M E L L E P G R T A A F N T M F F D R | 440 |
| FASA pmon70058.PRO | Y L W N L Q F G V T R I V P K A R A N G A A F T G V T I S A G I P E L D E A K E | 480 |
| FASA X87822.PRO | Y L W N L Q F G V T R I C S K A R A N G A A F T G V T I C A G I P E L D E A K E | 480 |
| FASA pmon70058.PRO | L L D Q L T S D G F P Y I S F K P G T T K Q I Q D C I A I A A D N P T H R V I I | 520 |
| FASA X87822.PRO | L L D Q L T S D G F P Y I S F K P G T T K Q I Q D C V A I A A D N P T H R V I I | 520 |
| FASA pmon70058.PRO | Q I E D G H A G G H H S W V D L D E M L L A T Y A S A R E H D N L A I T V G G G | 560 |
| FASA X87822.PRO | Q I E D A H A G G H H S W V D L D E M L L A T Y A C A R E H D N L A I T V G G G | 560 |
| FASA pmon70058.PRO | I H S P D R A S E Y L T G T W S T K Y G L P I M P V D G V F L G T V A M A T K E | 600 |
| FASA X87822.PRO | I H S P D R A S E Y L T G T W S T K Y G L P I M P V D G V F L G T V A M A T K E | 600 |
| FASA pmon70058.PRO | A T A N D D V K Q L L V D T P G I S P E T N G G W V G R L D A D G G V S S S Q S | 640 |
| FASA X87822.PRO | A T A N D D V K Q L L V D T P G I S P E T N G G W V G R L D A D G G V S S S Q S | 640 |
| FASA pmon70058.PRO | H L L A D L H E I D N S F A K A S R M I T S I P I E E Y D E R R D E I I A A L D | 680 |
| FASA X87822.PRO | H L L A D L H E I D N S F A K A S R M I T S I P I E E Y D E R R D E I I A A L D | 680 |
| FASA pmon70058.PRO | K T S K P Y F G D L S E M T Y E D W V A R F A E R A Y P W V D P T W H D R F H D | 720 |
| FASA X87822.PRO | K T S K P Y F G D L S E M T Y E D W V A R F A E R A Y P W V D P T W H D R F H D | 720 |
| FASA pmon70058.PRO | L L Q R V E A R L N D A D H G D I E T L F P T L D D S E N A P E A V A K L L A A | 760 |
| FASA X87822.PRO | L L Q R V E A R L N D A D H G D I E T L F P T L D D S E N A P E A V A K L L A A | 760 |
| FASA pmon70058.PRO | Y P N A K T T K V N T R D E A W F P T L I R K H V K P M P W T T A I D G D L K E | 800 |
| FASA X87822.PRO | Y P N A K T T K V N T R D E A W F P T L I R K H V K P M P W T T A I D G D L K E | 800 |
| FASA pmon70058.PRO | W F A K D T L W Q A Q D P R Y D A D G V R I I P G P V S V A G I T K K N E P V A | 840 |
| FASA X87822.PRO | W F A K D T L W Q A Q D P R Y D A D G V R I I P G P V S V A G I T K K N E P V A | 840 |
| FASA pmon70058.PRO | N L L G R F E D A T T A A L N D A G V A P V E L Y S R L A S A K N A E E F L R N | 880 |
| FASA X87822.PRO | N L L G R F E D A T T A A L N D A G V A P V E L Y S R L A S A K N A E E F L R N | 880 |
| FASA pmon70058.PRO | A P T I M W H G H L I A N P A Y E L P E E A F D I V D D G E G F A I R I N S D S | 920 |
| FASA X87822.PRO | A P T I M W H G H L I A N P A Y E L P E E A F D I V D D G E G F A I R I N S D S | 920 |
| FASA pmon70058.PRO | Y W D N L P E E Q R P F Y V K H V D I P V A L S E A V A T G A S P V V D D A R L | 960 |
| FASA X87822.PRO | Y R D N L P E E Q R P F Y V K H V D I P V A L S E A V A T G A S P V V D D A R L | 960 |

Boxed Residues Differ from pMON70058

FIG. 3A

```
FASA pmon70058.PRO  P K A V F D L L A G V A G V G S I S E T G D K I T E L P K V I E G S V S E E N P  1000
FASA X87822.PRO     P K A V F D L L A G V A G V G S I S E T G D K I T E L P K V I E G S V S E E N P  1000

FASA pmon70058.PRO  Y G L V E Y S F T L P S T L L T A H T A V T G A A L G T A N A G T P D A L V G P  1040
FASA X87822.PRO     Y G L V E Y S F T L P S T L L T A H T A V T G A A L G T A N A G T P D A L V G P  1040

FASA pmon70058.PRO  C W P A I Y T A L G T G R L T E E H G E P A G T D F P V I E G L L N A V H L D H  1080
FASA X87822.PRO     C W P A I Y T A L G T G R L T E E H G E P A G T D F P V I E G L L N A V H L D H  1080

FASA pmon70058.PRO  V V D V R V P L H E L A K G E K G E G R R I D V T S R C A S I A E S N S G R I V  1120
FASA X87822.PRO     V V D V R V P L H E L A K G E K G E G [G] R I D V T S R C A S I A E S N S G R I V  1120

FASA pmon70058.PRO  T V E L E L W D A A T Q E V V A T Q M Q R F A I R G R A T G T S V P V S A P S W  1160
FASA X87822.PRO     T V E L E L W D A A T Q E V V A T Q M Q R F A I R G R A T G T S V P V S A P S W  1160

FASA pmon70058.PRO  G G G K S Q D K I E T T P R S F V D R A I V T A P S D M T P F A L V S G D Y N P  1200
FASA X87822.PRO     G G G K S Q D K I E T T P R S F V D R A I V T A P S D M T P F A L V S G D Y N P  1200

FASA pmon70058.PRO  I H T S T N A A R L V N L D A P L V H G M W L S A T A Q H L A G N H G T V V G W  1240
FASA X87822.PRO     I H T S T N A A R L V N L D A P L V H G M W L S A T A Q H L A G N H G T V V G W  1240

FASA pmon70058.PRO  T Y S M Y G M V Q L N D E V E I T V E R V G R K G I H A A F E V T C R I D G E V  1280
FASA X87822.PRO     T Y S M Y G M V Q L N D E V E I T V E R V G R K G I H A A F E V T C R I D G E V  1280

FASA pmon70058.PRO  V S R G Q A L M A Q P R T A Y V Y P G Q G I Q A E G M G R G D R D A S A A A R E  1320
FASA X87822.PRO     V S R G Q A L M A Q P R T A Y V Y P G Q G I Q A E G M G R G D R D A S A A A R E  1320

FASA pmon70058.PRO  V W R R A D R H T R T A M G F S I R Q I I D D N P T E L V V R G T K F V H P N G  1360
FASA X87822.PRO     V W R R A D R H T R T A [L] G F S I R Q I I D D N P T E L V V R G T K F V H P N G  1360

FASA pmon70058.PRO  V L H L T Q F T Q V A L A V V A Y A Q T E R L R E A D A L G T N S M Y A G H S L  1400
FASA X87822.PRO     V L H L T Q F T Q V A L A V V A Y A Q T E R L R E A D A L G T N S M Y A G H S L  1400

FASA pmon70058.PRO  G E Y T A L A S L A N I F D L E A V I D I V Y S R G S A M G T L V E R D E N G N  1440
FASA X87822.PRO     G E Y T A L A S L A N I F D L E A V I D I V Y S R G S A M G T L V E R D E N G N  1440

FASA pmon70058.PRO  S N Y G M G A L R P N M I G V P A D Q V E A Y I A Q T A E E T G E F L E I V N Y  1480
FASA X87822.PRO     S N Y G M G A L R P N M I G V P A D Q V E A Y I A Q T A E E T G E F L E I V N Y  1480

FASA pmon70058.PRO  N I A G Q Q Y S I A G T K A G L A A L K K K A N S V K D R A Y V T V P G I D V P  1520
FASA X87822.PRO     N I A G Q Q Y S I A G T K A G L A A L K K K A N S V K D R A Y V T V P G I D V P  1520

FASA pmon70058.PRO  F H S Q V L R D G V P A F A E K L D E L L P E T L D L D A L V G R Y V P N L V A  1560
FASA X87822.PRO     F H S Q V L R D G V P A F A E K L D E L L P E T L D L D A L V G R Y V P N L V A  1560

FASA pmon70058.PRO  L P F E L T Q E F V D K V K P L A P S G K L D N L K V E D T D E Q A L A R L L M  1600
FASA X87822.PRO     L P F E L T Q E F V D K V K P L A P S G K L D N L K V E D T D E Q A [P S] R L L M  1600

FASA pmon70058.PRO  I E L L S W Q F A S P V R W I E T Q Q L L F E E V D Q I I E V G L A A S P T L T  1640
FASA X87822.PRO     I E L L S W Q F A S P V R W I E T Q Q L L F E E V D Q I I E V G L A [S] S P T L T  1640

FASA pmon70058.PRO  N L A K R S M D I A G V D L P V F N V E R D Q D Q V M L Q D V Q E A P A A S F D  1680
FASA X87822.PRO     N L A K R S M D I A G V D L P V F N V E R D Q D Q V M L Q D V Q E A P A A S F D  1680

FASA pmon70058.PRO  V E E G E A T S S T A A S E T P G E S A A A A S D N T Q A I P S A E P Q T V A E  1720
FASA X87822.PRO     V E E G E A T S S T A A S E T P G E S A A A A S D N T Q A I P S A E P C T V A E  1720

FASA pmon70058.PRO  A P A P S A A P A G G T A A A D A P D L P F T A A E A I M V L F A F Q N K I R Q  1760
FASA X87822.PRO     A P A P S A A P A G G T [R] A A D A P D L P F T A A E A I M V L F A F Q N K I R Q  1760

FASA pmon70058.PRO  D Q I N D S D T V E E L T N G V S S R R N Q L L M D M S A E I G V P A I D G A A  1800
FASA X87822.PRO     D Q I N D S D T V E E L T N G V S S R R N Q L L M D M S A E [N R] V P A I D G A A  1800

FASA pmon70058.PRO  D A D V A T L R E R V K T A A P G Y S P F G T V L S E A I T A R L R Q L T G A A  1840
FASA X87822.PRO     D A D V A T L R E R V K T A A P G Y S P F G T V L S E A I T A R L R Q L T G A A  1840

FASA pmon70058.PRO  G V K P A Y I S E R V T G T W G L P M S W A A H V E A E I L L G S R E E D S V R  1880
FASA X87822.PRO     G V K P A Y I S E R V T G T W G L P M S W A A H V E A E I L L G S R E E D S V R  1880

FASA pmon70058.PRO  G G S L S T V P S A A S S K A D V D A L V D A A V Q A V A A A H G T S V S N G A  1920
FASA X87822.PRO     G G S L S T V P S A A S S K A D V D A L V D A A V Q A V A A A H G T S V S [H] G A  1920
```

Boxed Residues Differ from pMON70058

FIG. 3B

```
FASA pmon70058.PRO  A S G A G G G G V V D S A A L D A Y A D I V T G E N G V L A T A A R Q V L A Q L  1960
FASA X87822.PRO     A S G A G G G G V V D S A A L D A Y A D I V T G E N G V L A T A A R Q V L A Q L  1960

FASA pmon70058.PRO  G L V E E A P E T P E T D N T L F E T V E A E L G S G W E K T V T P S F D A K R  2000
FASA X87822.PRO     G L V E E A P E T P E T D N T L F [A] T V E A E L G S G W E K T V T P S F D A K R  2000

FASA pmon70058.PRO  A V L F D D R W A S A R E D L A R V A L G E I D L P V K R F Q G T G E T I A K Q  2040
FASA X87822.PRO     A V L F D D R W A S A R E D L A R V A L G E I D L P V K R F Q G T G E T I A K Q  2040

FASA pmon70058.PRO  A E W W A E N T A A S T G A H A K A T S A E T L H A I A A A A R E E L D G E F A  2080
FASA X87822.PRO     A E W W A E N T A A S T G A H A K A T [A] A E T L H A I A A A A R E E L D G E F A  2080

FASA pmon70058.PRO  G D V A L V T G A A P G S I A T A L V E R L L E G G A T V I M T A S R V S Q S R  2120
FASA X87822.PRO     G D V A L V T G A A P G S I A T A L V E R L L E G G A T V I M T A S R V S Q S R  2120

FASA pmon70058.PRO  K E F A R K L Y A A H A I P G A A L W V V P A N L S S Y R D V D A L I D W I G N  2160
FASA X87822.PRO     K E F A R K L Y A A H A I P G A A L W V V P A N L [R] S Y R D V D A L I D W I G N  2160

FASA pmon70058.PRO  E Q R E S V G N E V K I T K P A L T P T L A F P F A A P S V S G S V A D A G P Q  2200
FASA X87822.PRO     E Q R [A] S V G N E V K I T K P A L T P T L A F P F A A P S V S G S V A D A G P Q  2200

FASA pmon70058.PRO  A E N Q T R L L L W S V E R T I A G L S N L A Q Q G V D T R C H I V L P G S P N  2240
FASA X87822.PRO     A E N Q T R L L L W S V E R T I A G L S N L A Q Q G V D T R C H I V L P G S P N  2240

FASA pmon70058.PRO  R G M F G G D G A Y G E V K A A L D A I L A K W S A E A G W P E G V T L A Q A K  2280
FASA X87822.PRO     R G M F G G D G A Y G E V K A A L D A I L A K W S A E A G W P E G V T L A Q A K  2280

FASA pmon70058.PRO  I G W V S G T S L M G G N D V L I P A A E A A G I H V W D P E E I S S Q L I S L  2320
FASA X87822.PRO     I G W V S G T S L M G G N D V L I P A A E A A G I H V W D P E E I S S Q L I S L  2320

FASA pmon70058.PRO  A S E E S R A K A A E A P L E L D L T G G L G S S K I S I S E L A A Q A R E D A  2360
FASA X87822.PRO     A S E E S R A K A A E A P L E L D L T G G L G S S [N] I S I S E L A A Q A R E D A  2360

FASA pmon70058.PRO  E A Q A A S G D N A D A A A E A P A A T I P A L P N T R S V E L P A A L P E G E  2400
FASA X87822.PRO     E A Q A A S G D N A D A A A E A P A A T I P A L P N T R S V E L P A A L P E G E  2400

FASA pmon70058.PRO  V G D V T T D L D D M V V I A G V G E V S S W G S G R T R F E A E Y G L Q R D G  2440
FASA X87822.PRO     V G D V T T D L D D M V V I A G V G E V S S W G S G R T R F E A E Y G L Q R D G  2440

FASA pmon70058.PRO  A V D L T A A G V L E L A W M T G L I S W S N D P R P A W Y D E E G T E V D E A  2480
FASA X87822.PRO     A V D L T A A G V L E L A W M T G L I S W S N D P R P A W Y D E E G T E V D E A  248

FASA pmon70058.PRO  D I Y A R F R D E V V A R S G I R T L T D K Y N M V D Q G S I D L T S V F L D R  2520
FASA X87822.PRO     D I Y A R F R D E V V A R S G I R T L T D K Y N M V D Q G S I D L T S V F L D R  2520

FASA pmon70058.PRO  D I V F T V P T E Q E A L D I E E A D P S F T K L R E V D G E W E V T R L K G A  2560
FASA X87822.PRO     D I V F T V P T E Q E A L D I E E A D P S F T K L R E V D G E W E V T R L K G A  2560

FASA pmon70058.PRO  T A R V P R K A T L T R T V A G Q M P D H F D A A K W G I P D H M L D A L D R M  2600
FASA X87822.PRO     T A R V P R K A T L T R T V A G Q M P D H F D A A K W G I P D H M L D A L D R M  2600

FASA pmon70058.PRO  A V W N L V T A V D A F T Q A G F S P A E L L Q V I H P A Q V A T T Q G T G I G  2640
FASA X87822.PRO     A V W N L V T A V D A F T Q A G F S P A E L L Q V I H P A Q V A T T Q G T G I G  2640

FASA pmon70058.PRO  G M E S L H K V F V T R L L G E D R P S D I L Q E A L P N V I A A H T M Q S L V  2680
FASA X87822.PRO     G M E S L H K V F V T R L L G E D R P S D I L Q E A L P N V I A A H T M Q S L V  2680

FASA pmon70058.PRO  G G Y G S M I H P I G A C A T A A V S I E E G V D K I A L G K A D L V V A G G I  2720
FASA X87822.PRO     G G Y G S M I H P I G A C A T A A V S I E E G V D K I A L G K A D L V V A G G I  2720

FASA pmon70058.PRO  D D V Q V E S L T G F G D M N A T A E T K K M T D Q G I D D R F I S R A N D R R  2760
FASA X87822.PRO     D D V Q V E S L T G F G D M N A T A E T K K M T D Q G I D D R F I S R A N D R R  2760

FASA pmon70058.PRO  R G G F L E A E G G G T V L L V R G S L A R E M G L P V Y A V V A H A A S Y G D  2800
FASA X87822.PRO     R G G F L E A E G G G T V L L V R G S L A R E M G L P V Y A V V A H [E] A S Y G [-]  2799

FASA pmon70058.PRO  G A H T S I P A P G L G A L G A G R G R K N S R L A K G L A G L G L T P N D V S  2840
FASA X87822.PRO     [-] A H T S I P A P G L G A L G A G R G R K N S R L A K G L A G L G L T P N D V S  2838

FASA pmon70058.PRO  V L S K H D T S T N A N D P N E S E L H S I L W P A I G R D V D Q P L F V I S Q  2880
FASA X87822.PRO     V L S K H D T S T N A N D P N E S E L H S I L W P A I G R D V D Q P L F V I S Q  2878
```

Boxed Residues Differ from pMON70058

FIG. 3C

```
FASA pmon70058.PRO   K S L T G H S K A G A A L F Q T G G L I D V F R T G R I P A N L S L D C V D P L   2920
FASA X87822.PRO      K S L T G H S K A G A A L F Q T G G L I D V F R T G R I P A N L S L D C V D P L   2918

FASA pmon70058.PRO   I E P K A T N L V W L R S P L D V E A A N R P V K A A A L T S L G F G H V G A L   2960
FASA X87822.PRO      I E P K A T N L V W L R S P L D V E A A N R P V K A A A L T S L G F G H V G A L   2958

FASA pmon70058.PRO   I V Y A H P G V F E A A V A Q Q V S A E A A A E W R E K A N A R L A A G A A R F   3000
FASA X87822.PRO      I V Y A H P G V F E A A V A Q Q V S A E A A A E W R E K A N A R L A A G A A R F   2998

FASA pmon70058.PRO   E A G M I G K E T L F E V I D G R R L P D A A G T V E I E N Y G P V A A D K A A   3040
FASA X87822.PRO      E A G M I G K E T L F E V I D G R R L P D A A G T V E I E N Y G P V A A D K A A   3038

FASA pmon70058.PRO   E I A L L L D D D I R L T A E G T F E P A K[.]                                   3063
FASA X87822.PRO      E[L R S C]L[T T T S V]L[P P K A L S L R R S R]T K                               3064
```

Boxed Residues Differ from pMON70058

FIG. 3D

**Enzyme Activity of the Cloned *B.a.* FasA Gene**

Specific Activity (nmol/min/mg protein) vs Sample (E.c, E.c. + P, E.c. + FA, E.c. + FA + P, B.a.)

SEQUENCE LISTING

```
<160> NUMBER OF SEQ ID NOS: 43

<210> SEQ ID NO 1
<211> LENGTH: 9122
<212> TYPE: DNA
<213> ORGANISM: Brevibacterium ammoniagenes

<400> SEQUENCE: 1

atgtcgttga ccccccttgca taccttgtct aatgacagca ctgctcccgc ggtgctgttt      60

gcgggtcagg gttctgcatg gcaaaaggcc atcgctgatg ccgcagccag ccctcaccag     120

ggcgcacatt gcgcgacatc ctaaaagaag ttcgcacgac caccggccca gtagcacgca     180

tcattgcgtc gtcgtgccct ggcgtttatg aacgcttgga agaacttgct cagacccccg     240

ctgaccaagc accgtggcca aggaatatga cgcgtacccg gcttactcca tccccggcat     300

cgtcctggga caaattggtg ccattgagca cctcgcgcag ctgggcatcg atgtcgattc     360

cgcgcagtta gcaggccact ccagggttca ttaggtgttg cagccgttaa ggatgcacgc     420

caggccctgg ctattgctgt tttgatgggt actgcagcag cggtgaccca gggcgcgaat     480

gattcccgca cccacatgct gtccgtgctg gcgtaccacg tgagatggtc gaagaatacc     540

tcgctggtga cgctgcgatt gccgtggtca acggccgcgt gcactttgca ctgtcgggta     600

ccccagagga tctggctaag accgagtcca acctccccag gctgccgagt cctacaacga     660

cgcgctggaa gaacgccgca tcggcggctc cgaaattaac ccagtcttcg acgtattggc     720

cgtggcactt cctttccacc acgcatcact gcaggatgca gcgatctgac cgtggactac     780

gccacccagt gtggcctgga cgctgagctt gcacgcgagc tggcagattc catcctggtt     840

cagccacata gctgggttga gaccgtggcc ggtctcaact ccacctaccg ctctccttag     900

accgtggtct gtcttcgttg actacacctt tgattgccgg caccggcaag gttgtggttc     960

cagctgctac gccagcggag cgcgataacc tggctacccc aggcactgag ctgcctccgc    1020

ggtgaactac gagaagttct caccaaagct catctccttg cccaacggca agtcctacac    1080

tcagactcgt ttctccgagt ggaccggcat gtcccccatc attttgggcg gcatgacgcc    1140

gacacgatgg atccgggcat cgttgccgca gcggccaacg gtggctactg gtcagagatg    1200

gccggtggcg gtcagtactc cgatgaagct tttaccatca acaaagacgg catgatggag    1260

ctgctggagc aggtcgcacc gcagcattta acaccatgtt ctttgaccgc tacctgtgga    1320

acctacagtt cggtgtcacc cgcatttgtt ccaaggcacg cgctaatggt gctgcgttta    1380

ccggcgtgac catctgcctg gtatcccaga gctggatgaa gccaaggaat tgctggacca    1440

gctcacctcc gatggctttc catacatctc tttcaagccg ggcaccacca agcagattca    1500

agactgcgtc gctatcgcag cggaaacccc acccaccgcg tcatcatcca aattgaagac    1560

gcccacgctg gtggccacca ctcctgggtg gatctggatg aaatgctgct ggctacctac    1620

gcatgtgccc gtgagcacga caacctggcc acactgttgg tggcggcatc cactccccag    1680
```

-continued

```
accgcgcatc ggaatacctg accggtacct ggtccaccaa gtacggtttg cccatcatgc   1740
cggttgatgg tgtcttcttg ggcaccgtag ccatggcgcc aaggaagcaa cggctaatga   1800
tgacgttaag cagttgctag ttgatacccc aggtatttcc ccagagacca atggcggttg   1860
ggtaggccga ctagatgccg acggcggcgt gtcctcctcc cagtccacct gttggctgac   1920
ttgcacgaga ttgataactc gtttgccaag gcctcgcgca tgatcacctc gatcccgatc   1980
gaggagtatg acgagcgtcg cgacgagatc attgctgctc tggacaagac ctcaagccat   2040
acttcggtga cctgtcggag atgacctacg aggattgggt cgctcgtttc gcagagcgcg   2100
cctacccttg ggtggatcca acctggcacg atcgtttcca cgatctgctc cagcgcgtaa   2160
agcgcgtctc aatgacgctg accacggcga catcgagacc ctattcccca cactcgacga   2220
ctccgagaac gcaccagagg cagtagccaa gctgctggct gcctacccga atgcaaagac   2280
caccaagtca acacccgcga tgaggcatgg ttccctaccc ttatccgcaa gcacgtcaag   2340
ccaatgccgt ggaccaccgc tattgacggt gacctgaagg aatggtttgc caaggacacc   2400
ctgtggcagg cccggaccca cgctacgacg cagacggcgt acgcatcatt ccaggaccgg   2460
tttcggttgc tggtatcacc aagaagaatg agcccgtcgc aaacctgctc ggtcgcttcg   2520
aagacgccac caccgcagcg ttaacgatgc cggcgtggca ccagttgagc tctactcccg   2580
cttggcttct gccaagaatg cagaagagtt cctgcgcaat gcaccaacca tcatgtggca   2640
cggtcacctc attgccaacc cggcgtatga gctgccagaa gaagcttttg acatcgtcga   2700
tgacggcgaa ggctttgcta ttcgcatcaa ctcgactcct acagggataa cctcccagaa   2760
gagcagcgtc cgttctacgt caagcacgtt gatatccccg ttgcgctgtc ggaagccgta   2820
gcaaccggtg cctcccctgt tgttgatgac gcgcgtttgc aaaggcagtc ttcgacctgc   2880
tcgcaggcgt tgctggtgtc gggtctatct ctgagaccgg cgataagatc accgaactgc   2940
cgaaggtcat cgaaggctct gtctccgaag aaaaccctta cggcctgtgg aatactcctt   3000
taccttgcct tctaccctgc tgaccgcaca caccgcggta accggcgctg ccttgggcac   3060
cgccaacgca ggcaccccag atgcgctggt tggcccctgc tggccagcaa tttaaccgcg   3120
ctgggcaccg gtcgattgac cgaagaacac ggtgagccag ccggcaccga cttcccggtc   3180
attgaaggcc tgctcaacgc agtccacctc gaccacgtcg tcgatgtgcg tgttcctctt   3240
ccgaactcgc aaagggtgaa aagggcgaag gcggtcgcat tgacgtcacc tcccgctgtg   3300
catccatcgc ggaatccaac tccggtcgca ttgtcaccgt ggaacttgag ttgtgggatg   3360
ccgcaactaa gaagttgtgg cgacgcagat gcagcgcttt gccatccgtg gccgcgctac   3420
cggcacctcc gttccggttt ctgcaccatc ctggggcggc ggcaagtctc aggacaagat   3480
tgagaccacc ccacgtcctt cgtggatcgc gccattgtca ccgcgccatc ggatatgacc   3540
ccattcgcgc tggtctccgg tgactacaac ccaattcaca cctccaccaa cgccgcgcgc   3600
ttggtcaacc tcgacgcccc acggtgcacg gcatgtggct atctgccacc gcgcagcacc   3660
tagctggcaa ccacggcacc gtggtgggtt ggacctattc catgtacggc atggtccagc   3720
tcaacgatga agtagaaatc accgtcgaag cgtaggccgc aagggcattc acgcagcatt   3780
cgaggtcacc tgccgcatcg acggcgaagt agtctcccgc ggccaggcgc tcatggcaca   3840
gccacgcacc gcttatgtct acccaggcca gggcatcagg ccgagggcat gggccgtggt   3900
gaccgcgatg cttcggcagc agcgcgtgag gtatggcgtc gtgcagaccg ccacacccgc   3960
accgcactgg gcttttctat tcgccagatc atcgatgaca acccaccgag ctcgtcgttc   4020
```

-continued

```
gcggcaccaa gttcgtccac cccaatggcg tgctgcactt aacgcagttc actcaggttg   4080
ccctcgcagt cgttgcttat gcacaaaccg agcgcctgcg cgaagcagat ctctgggcac   4140
caactccatg tacgccggtc actcactggg tgagtacacc gcgctggcat cgttggcgaa   4200
tatctttgac ctcgaagcgg ttatcgacat cgtctactcc cgtggctctg ccatgggacc   4260
ttggtcgaac gtgatgaaaa cggtaactcc aactacggca tgggcgcgct gcgtccaaac   4320
atgattggtg ttcccgcaga ccaggttgag gcctacatcg cgcagaccgc ggaagaaact   4380
ggcgattcct cgaaatcgtc aactacaaca tcgctggtca gcagtactcc atcgcgggta   4440
ccaaggctgg tttggccgcc ctgaagaaaa aggccaactc cgtcaaggac cgtgcttatg   4500
tcacggttcc agcatcgatg tacctttcca ctcccaggta ctgcgcgacg gcgttcctgc   4560
tttcgcagaa aagctcgatg aactgttgcc agaaaccttg gacctggacg ccctggtcgg   4620
ccgctacgtg ccgaacctgt ggcgctgcca ttcgagctga cccaggaatt tgtcgataag   4680
gtcaagcctt tggctccttc cggcaagctg gataacctca aggtcgaaga caccgatgag   4740
caagcccctt ctcgcctgct catgatgagc tattgtcctg gcagttcgca tcacctgtgc   4800
gctggattga aacccagcag ctgctctttg aagaagtaga ccagatcatc gaagtcggtc   4860
tcgcttcatc cccaacgctg accaacttgg ccagcgctcc atggatatcg ccggcgtgga   4920
cctcccggtc ttcaacgtcg aacgcgacca agaccaggtc atgctccaag acgttcagga   4980
agcaccagct gcctccttcg acgtcgagga aggagaggca cctcttcgac cgcagcgtct   5040
gaaaccccag gtgaatccgc tgcggcggcc tcggataata cccaggccat cccatcggct   5100
gagccacaaa cggtggcaga ggcaccagca ccatccgccg caccagtggc ggcacccgtg   5160
ccgcagatgc tcctgacctg ccatttaccg cagcagaagc catcatggtt ctgttcgctt   5220
tccagaacaa gatccgccag gaccagatca atgactcgga tacggtcgaa gagtcaccaa   5280
cggtgtctcc tcccgccgta accaactgtt gatggatatg tccgcagaaa atcgcgtgcc   5340
cgccattgac ggtgcagccg atgctgacgt ggcaaccttg cgtgagcgcg tcaagactgc   5400
cgctccgggc tactcgccat tcggcaccgt cttgtctgag gctataccgc tcgtctgcgc   5460
cagctcactg gtgcagcagg cgtcaagccg gcctacattt cagagcgcgt gaccggaact   5520
tgggggctgc ctatgtcctg ggcagcccac gttgaggctg aaatcttgct cgctcccgtg   5580
aagaagactc agtgcgcggt ggctccttgt ccaccgttcc ttccgcggcg tcgtcgaagg   5640
ccgatgtcga tgcgcttgtc gatgccgcgg tccaggccgt agccgcagca cacggcaccc   5700
ggtatcccat ggtgctgcga gtggcgccgg cggcggtgga gtcgtcgact ccgcagcctt   5760
ggatgcttac gcagatatcg tcaccggtga aaacggtgtc ctcgctactg ctgctcgcca   5820
ggttctgctc agctgggctt ggtcgaggaa gcccctgaga cccctgagac cgataacacc   5880
ttgttcgcga ccgtcgaggc cgagctgggt tccggttggg aaaagaccgt taccccatcc   5940
tttgacgcca agccgcagtg cttttcgatg accgctgggc gtctgctcgc gaagatctcg   6000
cccgcgtggc actcggcgag atcgacttgc cagtcaagcg tttccaggga accggagaga   6060
ccatcgccaa gcaagcggaa ggtgggcgga gaacaccgct gcttccactg gtgcgcacgc   6120
gaaggcaacc gctgccgaga ccctgcatgc tattgctgcc gcagcgcgcg aagaactcga   6180
cggcgaattc gctggcgatg tcgcgttgtc accggtgcag ccccaggctc cattgctacc   6240
gctctcgtag aacgcctgct ggaaggcggc gcgaccgtca tcatgactgc gtcacgtgtc   6300
agccagtccc gtaaggaatt tgcacgcaag ctctcgctgc acacgcgatt cctggcgctg   6360
ccctgtgggt tgttcctgcg aacttgcgct cctaccgcga tgttgatgct ctcattgact   6420
```

-continued

```
ggattggtaa tgagcagcgt gcctctgtcg gcaacgaagt cagatcacca agccagcgtt   6480
gaccccaacc ttggccttcc cattcgcggc accttccgtg tccggttctg tggccgatgc   6540
cggcccacag gctgaaaacc agactcgcct gctgctgtgg tctgttgacg caccatcgct   6600
ggtctgtcca acctggcgca gcaaggcgtg gatacccgct gccacattgt gctgcctggt   6660
tctccgaacc gcggcatgtt cggtggcgac ggcgcttacg gcgaagtcaa ggcagcttgg   6720
acgctatttt ggccaagtgg tctgcagaag caggctggcc agaaggtgtt accttggcac   6780
aagccaagat tggctgggtc tctggtacct ccctgatggg cggcaacgac gttctgattc   6840
cgcagcggaa gccgctggca tccacgtgtg ggacccagaa gagatttctt cccagctcat   6900
ctccctagct tccgaagaat cccgcgcgaa ggcagccgag gctccactag agctggatct   6960
gaccggtggc tgggctcgtc caacatctcc atctccgagc tggctgccca ggcccgcgag   7020
gacgccgagg cacaagctgc ttccggtgat aatgcagacg cagctgcgga agctcctgca   7080
gccacgattc cagcacgcct aatacccgtt cagtagagct gcctgcagcg ctaccggaag   7140
gtgaagtggg cgacgtaacc acggatctgg atgacatggt cgtcatcgca ggtgtcggcg   7200
aagtctcctc gtggggttcg ggcgtacccg ctttgaggca gaatatggct tgcagcgcga   7260
tggcgctgtg gacctgaccg ccgctggtgt cttggaattg gcatggatga ccggactgat   7320
ttcctggtcc aatgacccac gtccagcctg tacgacgaag agggcaccga agtcgatgaa   7380
gcagatatct acgctcgctt ccgcgacgag gttgtagctc gctccggtat ccgtaccttg   7440
accgataagt acaacatggt tgaccagggc tccattgcct gacttctgtg ttcttggacc   7500
gcgatatcgt cttcaccgtt cctaccgaac aagaagcact cgatattgaa gaagccgacc   7560
catcgtttac caagctgcgc gaagtcgacg gcgagtggga agtccccgtt tgaagggtgc   7620
caccgcccgc gtgccacgca aggcaacgtt gactcgtacc gttgctggtc aaatgccgga   7680
tcacttcgat gctgccaagt ggggcattcc agaccacatg ctggatgcac tgaccgcatg   7740
gccgtgtgga acctggtgac cgcagtcgat gcctttaccc aggcgggctt tagcccggct   7800
gagttgctgc aggttattca cccagcgcag gttgctacca cccagggcac cggtatcgcg   7860
gcatggaatc cctgcacaag gtcttcgtga cccgtctgct cggtgaagac cgtccttccg   7920
acatcctgca ggaagcactg cctaacgtta ttgcagcgca caccatgcag tctttggtgg   7980
gcggcacggt tcgatgattc accctatcgg tgcttgtgcc accgctgcgg tgtccatcga   8040
agaaggcgtg gacaagattg ccctgggcaa ggccgacctg gtcgttgccg gtggtatcga   8100
tgacgtccaa gttgagtctt tgaccggctt cggcgacatg aacgccaccg ctgagaccaa   8160
aagatgaccg atcagggcat tgatgaccgc ttcatctccc gtgcgaatga ccgccgtcgt   8220
ggcggcttcc tcgaggcaga aggcggcggt accgtgcttc tggttcgcgg ttccctggct   8280
cgtgagaggg tctgccggtc tacgcggtcg ttgcgcacga ggcgtcctac ggtgcccaca   8340
cctccattcc tgctccaggt ttgggtgctt tgggcgctgg ccgtggccgg aagaactccc   8400
gcctggccaa gggctggctg gtttgggtct gactccaaat gacgtctcgg tactgtccaa   8460
gcacgacacc tcgaccaacg ccaatgaccc gaatgagtcg gaactgcact ccatcttgtg   8520
gcctgctatt ggccgcgatg tgaccagcca ctgtttgtga tttcgcagaa gtcactgact   8580
ggtcactcca aggctggtgc cgcgctgttc cagaccggcg gtttgattga cgtcttccgc   8640
acgggacgca ttccagctaa cctgtcgcgg attgtgtgga tccattgatt gagccaaagg   8700
ccacgaactt ggtctggcta cgctccccac tagatgtgga agcagccaac cgcccggtca   8760
```

-continued

```
aggccgcggc gctcacctcg ctcggcttcg gtcactcggt gcattgattg tctacgcgca   8820

cccaggtgtc ttcgaggctg ccgttgccca gcaggtttcg gccgaggctg ctgccgaatg   8880

gcgcgagaag gcaaatgccc gcctcgccgc cggtgcagca cgttcgaagc cggcatgatt   8940

ggcaaggaaa ccttgttcga ggtcatcgac ggccgccgcc tgcctgacgc agcgggcacc   9000

gttgagattg agaactacgg cccagtcgcc gccgacaagg ccgcagaatg cgctcttgct   9060

tgacgacgac atccgtctta ccgccgaagg cactttccct ccggcgaagt aggacaaagt   9120

ag                                                                   9122
```

<210> SEQ ID NO 2
<211> LENGTH: 3040
<212> TYPE: PRT
<213> ORGANISM: Brevibacterium ammoniagenes

<400> SEQUENCE: 2

```
Met Ser Leu Thr Pro Leu His Thr Leu Ser Asn Asp Ser Thr Ala Pro
1               5                   10                  15

Ala Val Leu Phe Ala Gly Gln Gly Ser Ala Trp Gln Lys Ala Ile Ala
            20                  25                  30

Asp Ala Ala Ala Ser Pro His Gln Gly Ala Gln Leu Arg Asp Ile Leu
        35                  40                  45

Lys Glu Val Arg Thr Thr Thr Gly Pro Val Ala Arg Ile Ile Ala Ser
    50                  55                  60

Ser Cys Pro Gly Val Tyr Glu Arg Leu Glu Glu Leu Ala Gln Thr Pro
65                  70                  75                  80

Ala Asp Gln Ala Pro Val Ala Lys Glu Tyr Asp Ala Tyr Pro Ala Tyr
                85                  90                  95

Ser Ile Pro Gly Ile Val Leu Gly Gln Ile Gly Ala Ile Glu His Leu
            100                 105                 110

Ala Gln Leu Gly Ile Asp Val Asp Ser Ala Gln Leu Ala Gly His Gln
        115                 120                 125

Gly Ser Leu Gly Val Ala Ala Val Lys Asp Ala Arg Gln Ala Leu Ala
    130                 135                 140

Ile Ala Val Leu Met Gly Thr Ala Ala Ala Val Thr Gln Gly Ala Asn
145                 150                 155                 160

Asp Ser Arg Thr His Met Leu Ser Val Arg Gly Val Pro Arg Glu Met
                165                 170                 175

Val Glu Glu Tyr Leu Ala Gly Asp Ala Ala Ile Ala Val Val Asn Gly
            180                 185                 190

Arg Val His Phe Ala Leu Ser Gly Thr Pro Glu Asp Leu Ala Lys Thr
        195                 200                 205

Glu Ser Asn Leu Thr Gln Ala Ala Glu Ser Tyr Asn Asp Ala Leu Glu
    210                 215                 220

Glu Arg Arg Ile Gly Gly Ser Glu Ile Asn Pro Val Phe Asp Val Leu
225                 230                 235                 240

Ala Val Ala Leu Pro Phe His His Ala Ser Leu Gln Asp Ala Asp Leu
                245                 250                 255

Thr Val Asp Tyr Ala Thr Gln Cys Gly Leu Asp Ala Glu Leu Ala Arg
            260                 265                 270

Glu Leu Ala Asp Ser Ile Leu Val Gln Pro His Ser Trp Val Glu Thr
        275                 280                 285

Val Ala Gly Leu Asn Ser Thr Tyr Leu Leu Ser Leu Asp Arg Gly Leu
    290                 295                 300
```

-continued

```
Ser Ser Leu Thr Thr Pro Leu Ile Ala Gly Thr Gly Lys Val Val Val
305                 310                 315                 320

Pro Ala Ala Thr Pro Ala Glu Arg Asp Asn Leu Ala Thr Pro Gly Thr
                325                 330                 335

Glu Leu Pro Thr Ala Val Asn Tyr Glu Lys Phe Ser Pro Lys Leu Ile
            340                 345                 350

Ser Leu Pro Asn Gly Lys Ser Tyr Thr Gln Thr Arg Phe Ser Glu Trp
        355                 360                 365

Thr Gly Met Ser Pro Ile Ile Leu Gly Gly Met Thr Pro Thr Met Asp
    370                 375                 380

Pro Gly Ile Val Ala Ala Ala Ala Asn Gly Gly Tyr Trp Ser Glu Met
385                 390                 395                 400

Ala Gly Gly Gly Gln Tyr Ser Asp Glu Ala Phe Thr Ile Asn Lys Asp
                405                 410                 415

Gly Met Met Glu Leu Leu Glu Pro Gly Arg Thr Ala Ala Phe Asn Thr
            420                 425                 430

Met Phe Phe Asp Arg Tyr Leu Trp Asn Leu Gln Phe Gly Val Thr Arg
        435                 440                 445

Ile Cys Ser Lys Ala Arg Ala Asn Gly Ala Ala Phe Thr Gly Val Thr
    450                 455                 460

Ile Cys Ala Gly Ile Pro Glu Leu Asp Glu Ala Lys Glu Leu Leu Asp
465                 470                 475                 480

Gln Leu Thr Ser Asp Gly Phe Pro Tyr Ile Ser Phe Lys Pro Gly Thr
                485                 490                 495

Thr Lys Gln Ile Gln Asp Cys Val Ala Ile Ala Ala Asn Pro Thr His
            500                 505                 510

Arg Val Ile Ile Gln Ile Glu Asp Ala His Ala Gly Gly His His Ser
        515                 520                 525

Trp Val Asp Leu Asp Glu Met Leu Leu Ala Thr Tyr Ala Cys Ala Arg
    530                 535                 540

Glu His Asp Asn Leu Ala Ile Thr Val Gly Gly Gly Ile His Ser Pro
545                 550                 555                 560

Asp Arg Ala Ser Glu Tyr Leu Thr Gly Thr Trp Ser Thr Lys Tyr Gly
                565                 570                 575

Leu Pro Ile Met Pro Val Asp Gly Val Phe Leu Gly Thr Val Ala Met
            580                 585                 590

Ala Thr Lys Glu Ala Thr Ala Asn Asp Asp Val Lys Gln Leu Leu Val
        595                 600                 605

Asp Thr Pro Gly Ile Ser Pro Glu Thr Asn Gly Gly Trp Val Gly Arg
    610                 615                 620

Leu Asp Ala Asp Gly Gly Val Ser Ser Ser Gln His Leu Leu Ala Asp
625                 630                 635                 640

Leu His Glu Ile Asp Asn Ser Phe Ala Lys Ala Ser Arg Met Ile Thr
                645                 650                 655

Ser Ile Pro Ile Glu Glu Tyr Asp Glu Arg Arg Asp Glu Ile Ile Ala
            660                 665                 670

Ala Leu Asp Lys Thr Ser Lys Pro Tyr Phe Gly Asp Leu Ser Glu Met
        675                 680                 685

Thr Tyr Glu Asp Trp Val Ala Arg Phe Ala Glu Arg Ala Tyr Pro Trp
    690                 695                 700

Val Asp Pro Thr Trp His Asp Arg Phe His Asp Leu Leu Gln Arg Val
705                 710                 715                 720

Glu Ala Arg Leu Asn Asp Ala Asp His Gly Asp Ile Glu Thr Leu Phe
```

-continued

```
                725                 730                 735

Pro Thr Leu Asp Asp Ser Glu Asn Ala Pro Glu Ala Val Ala Lys Leu
            740                 745                 750

Leu Ala Ala Tyr Pro Asn Ala Lys Thr Thr Val Asn Thr Arg Asp Glu
        755                 760                 765

Ala Trp Phe Pro Thr Leu Ile Arg Lys His Val Lys Pro Met Pro Trp
    770                 775                 780

Thr Thr Ala Ile Asp Gly Asp Leu Lys Glu Trp Phe Ala Lys Asp Thr
785                 790                 795                 800

Leu Trp Gln Ala Gln Asp Pro Arg Tyr Asp Ala Asp Gly Val Arg Ile
                805                 810                 815

Ile Pro Gly Pro Val Ser Val Ala Gly Ile Thr Lys Lys Asn Glu Pro
            820                 825                 830

Val Ala Asn Leu Leu Gly Arg Phe Glu Asp Ala Thr Thr Ala Ala Leu
        835                 840                 845

Asn Asp Ala Gly Val Ala Pro Val Glu Leu Tyr Ser Arg Leu Ala Ser
    850                 855                 860

Ala Lys Asn Ala Glu Glu Phe Leu Arg Asn Ala Pro Thr Ile Met Trp
865                 870                 875                 880

His Gly His Leu Ile Ala Asn Pro Ala Glu Leu Pro Glu Glu Ala Phe
                885                 890                 895

Asp Ile Val Asp Asp Gly Glu Gly Phe Ala Ile Arg Ile Asn Ser Asp
            900                 905                 910

Ser Tyr Arg Asp Asn Leu Pro Glu Glu Gln Arg Pro Phe Tyr Val Lys
        915                 920                 925

His Val Asp Ile Pro Val Ala Leu Ser Glu Ala Val Ala Thr Gly Ala
    930                 935                 940

Ser Pro Val Val Asp Asp Ala Arg Leu Pro Lys Ala Val Phe Asp Leu
945                 950                 955                 960

Leu Ala Gly Val Ala Gly Val Gly Ser Ile Ser Glu Thr Gly Asp Lys
                965                 970                 975

Ile Thr Glu Leu Pro Lys Val Ile Glu Gly Ser Val Ser Glu Glu Asn
            980                 985                 990

Pro Tyr Gly Leu Val Glu Tyr Ser  Phe Thr Leu Pro Ser  Thr Leu Leu
        995                 1000                1005

Thr Ala  His Thr Ala Val Thr  Gly Ala Leu Gly Thr  Ala Asn Ala
    1010                1015                1020

Gly Thr  Pro Asp Ala Leu Val  Gly Pro Cys Trp Pro  Ala Ile Tyr
    1025                1030                1035

Thr Ala  Leu Gly Thr Gly Arg  Leu Thr Glu Glu His  Gly Glu Pro
    1040                1045                1050

Ala Gly  Thr Asp Phe Pro Val  Ile Glu Gly Leu Leu  Asn Ala Val
    1055                1060                1065

His Leu  Asp His Val Val Asp  Val Arg Val Pro Leu  His Glu Leu
    1070                1075                1080

Ala Lys  Gly Glu Lys Gly Glu  Gly Gly Arg Ile Asp  Val Thr Ser
    1085                1090                1095

Arg Cys  Ala Ser Ile Ala Glu  Ser Asn Ser Gly Arg  Ile Val Thr
    1100                1105                1110

Val Glu  Leu Glu Leu Trp Asp  Ala Ala Thr Gln Glu  Val Val Ala
    1115                1120                1125

Thr Gln  Met Gln Arg Phe Ala  Ile Arg Gly Arg Ala  Thr Gly Thr
    1130                1135                1140
```

-continued

Val Pro Val Ser Ala Pro Ser Trp Gly Gly Gly Lys Ser Gln Asp
1145 1150 1155

Lys Ile Glu Thr Thr Pro Arg Ser Phe Val Asp Arg Ala Ile Val
1160 1165 1170

Thr Ala Pro Ser Asp Met Thr Pro Phe Ala Leu Val Ser Gly Asp
1175 1180 1185

Tyr Asn Pro Ile His Thr Ser Thr Asn Ala Ala Arg Leu Val Asn
1190 1195 1200

Leu Asp Ala Pro Leu Val His Gly Met Trp Leu Ser Ala Thr Ala
1205 1210 1215

Gln His Leu Ala Gly Asn His Gly Thr Val Val Gly Trp Thr Tyr
1220 1225 1230

Ser Met Tyr Gly Met Val Gln Leu Asn Asp Glu Val Glu Ile Thr
1235 1240 1245

Val Glu Arg Val Gly Arg Lys Gly Ile His Ala Ala Phe Glu Val
1250 1255 1260

Thr Cys Arg Ile Asp Gly Glu Val Ser Arg Gly Gln Ala Leu Met
1265 1270 1275

Ala Gln Pro Arg Thr Ala Tyr Val Tyr Pro Gly Gln Gly Ile Gln
1280 1285 1290

Ala Glu Gly Met Gly Arg Gly Asp Arg Asp Ala Ser Ala Ala Ala
1295 1300 1305

Arg Glu Val Trp Arg Arg Ala Asp Arg His Thr Arg Thr Ala Leu
1310 1315 1320

Gly Phe Ser Ile Arg Gln Ile Ile Asp Asp Asn Pro Thr Glu Leu
1325 1330 1335

Val Val Arg Gly Thr Lys Phe Val His Pro Asn Gly Val Leu His
1340 1345 1350

Leu Thr Gln Phe Thr Gln Val Ala Leu Ala Val Val Ala Tyr Ala
1355 1360 1365

Gln Thr Glu Arg Leu Arg Glu Ala Asp Ala Leu Gly Thr Asn Ser
1370 1375 1380

Met Tyr Ala Gly His Ser Leu Gly Glu Tyr Thr Ala Leu Ala Leu
1385 1390 1395

Ala Asn Ile Phe Asp Leu Glu Ala Val Ile Asp Ile Val Tyr Ser
1400 1405 1410

Arg Gly Ser Ala Met Gly Thr Leu Val Glu Arg Asp Glu Asn Gly
1415 1420 1425

Asn Ser Asn Tyr Gly Met Gly Ala Leu Arg Pro Asn Met Ile Gly
1430 1435 1440

Val Pro Ala Asp Gln Val Glu Ala Tyr Ile Ala Gln Thr Ala Glu
1445 1450 1455

Glu Thr Gly Glu Phe Leu Glu Ile Val Asn Tyr Asn Ile Ala Gly
1460 1465 1470

Gln Gln Tyr Ser Ile Ala Gly Thr Lys Ala Gly Leu Ala Ala Leu
1475 1480 1485

Lys Lys Lys Ala Asn Ser Val Lys Asp Arg Ala Tyr Val Thr Val
1490 1495 1500

Pro Gly Ile Asp Val Pro Phe His Ser Gln Val Leu Arg Asp Gly
1505 1510 1515

Val Pro Ala Phe Ala Glu Leu Asp Glu Leu Leu Pro Glu Thr Leu
1520 1525 1530

-continued

```
Asp Leu Asp Ala Leu Val Gly Arg Tyr Val Pro Asn Leu Val Ala
    1535                1540                1545

Leu Pro Phe Glu Leu Thr Gln Glu Phe Val Asp Lys Val Lys Pro
    1550                1555                1560

Leu Ala Pro Ser Gly Lys Leu Asp Asn Leu Lys Val Glu Asp Thr
    1565                1570                1575

Asp Glu Gln Ala Pro Ser Arg Leu Leu Met Ile Glu Leu Leu Ser
    1580                1585                1590

Trp Gln Phe Ala Ser Pro Val Arg Trp Ile Glu Thr Gln Gln Leu
    1595                1600                1605

Leu Phe Glu Glu Val Asp Gln Ile Ile Glu Val Gly Leu Ala Ser
    1610                1615                1620

Ser Pro Thr Leu Thr Asn Leu Ala Lys Arg Ser Met Asp Ile Ala
    1625                1630                1635

Gly Val Asp Leu Pro Val Phe Asn Val Glu Arg Asp Gln Gln Val
    1640                1645                1650

Met Leu Gln Asp Val Gln Glu Ala Pro Ala Ala Ser Phe Asp Val
    1655                1660                1665

Glu Glu Gly Glu Ala Thr Ser Ser Thr Ala Ala Ser Glu Thr Pro
    1670                1675                1680

Gly Glu Ser Ala Ala Ala Ala Ser Asp Asn Thr Gln Ala Ile Pro
    1685                1690                1695

Ser Ala Glu Pro Gln Thr Val Ala Glu Ala Pro Ala Pro Ser Ala
    1700                1705                1710

Ala Pro Ala Gly Gly Thr Arg Ala Ala Asp Ala Pro Asp Leu Pro
    1715                1720                1725

Phe Thr Ala Ala Glu Ala Ile Met Val Leu Phe Ala Phe Gln Asn
    1730                1735                1740

Lys Ile Arg Gln Asp Gln Ile Asn Asp Ser Asp Thr Val Glu Glu
    1745                1750                1755

Leu Thr Asn Gly Val Ser Ser Arg Arg Asn Gln Leu Leu Met Asp
    1760                1765                1770

Met Ser Ala Glu Asn Val Pro Ala Ile Asp Gly Ala Ala Asp Ala
    1775                1780                1785

Asp Val Ala Thr Leu Arg Glu Arg Val Lys Thr Ala Ala Pro Gly
    1790                1795                1800

Tyr Ser Pro Phe Gly Thr Val Leu Ser Glu Ala Ile Thr Ala Arg
    1805                1810                1815

Leu Arg Gln Leu Thr Gly Ala Ala Gly Val Lys Pro Ala Tyr Ile
    1820                1825                1830

Ser Glu Arg Val Thr Gly Thr Trp Gly Leu Pro Met Ser Trp Ala
    1835                1840                1845

Ala His Val Glu Ala Glu Ile Leu Leu Gly Ser Arg Glu Glu Asp
    1850                1855                1860

Ser Val Arg Gly Gly Ser Leu Ser Thr Val Pro Ser Ala Ala Ser
    1865                1870                1875

Ser Lys Ala Asp Val Asp Ala Leu Val Asp Ala Ala Val Gln Ala
    1880                1885                1890

Val Ala Ala Ala His Gly Thr Ser Val Ser His Gly Ala Ser Gly
    1895                1900                1905

Ala Gly Gly Gly Gly Val Val Asp Ser Ala Ala Leu Asp Ala Tyr
    1910                1915                1920

Ala Asp Ile Val Thr Gly Glu Asn Gly Val Leu Ala Thr Ala Ala
```

-continued

```
    1925                1930                1935

Arg Gln  Val Leu Ala Gln Leu  Gly Leu Val Glu Glu  Ala Pro Glu
    1940                1945                1950

Thr Pro  Glu Thr Asp Asn Thr  Leu Phe Ala Thr Val  Glu Ala Glu
    1955                1960                1965

Leu Gly  Ser Gly Trp Glu Lys  Thr Val Thr Pro Ser  Phe Asp Ala
    1970                1975                1980

Lys Arg  Ala Val Leu Phe Asp  Asp Arg Trp Ala Ser  Ala Arg Glu
    1985                1990                1995

Asp Leu  Ala Arg Val Ala Leu  Gly Glu Ile Asp Leu  Pro Val Lys
    2000                2005                2010

Arg Phe  Gln Gly Thr Gly Glu  Thr Ile Ala Lys Gln  Ala Glu Trp
    2015                2020                2025

Trp Ala  Glu Asn Ala Ala Ser  Thr Gly Ala His Ala  Lys Ala Thr
    2030                2035                2040

Ala Ala  Glu Thr Leu His Ala  Ile Ala Ala Ala Ala  Arg Glu Glu
    2045                2050                2055

Leu Asp  Gly Glu Phe Ala Gly  Asp Val Ala Leu Val  Thr Gly Ala
    2060                2065                2070

Ala Pro  Gly Ser Ile Ala Thr  Ala Leu Val Glu Arg  Leu Leu Glu
    2075                2080                2085

Gly Gly  Ala Thr Val Ile Met  Thr Ala Ser Arg Val  Ser Gln Ser
    2090                2095                2100

Arg Lys  Glu Phe Ala Arg Lys  Leu Tyr Ala Ala His  Ala Ile Pro
    2105                2110                2115

Gly Ala  Ala Leu Trp Val Val  Pro Ala Asn Leu Arg  Ser Tyr Arg
    2120                2125                2130

Asp Val  Asp Ala Leu Ile Asp  Trp Ile Gly Asn Glu  Gln Arg Ala
    2135                2140                2145

Ser Val  Gly Asn Glu Val Lys  Ile Thr Lys Pro Leu  Thr Pro Thr
    2150                2155                2160

Leu Ala  Phe Pro Phe Ala Ala  Pro Ser Val Ser Gly  Ser Val Ala
    2165                2170                2175

Asp Ala  Gly Pro Gln Ala Glu  Asn Gln Thr Arg Leu  Leu Leu Trp
    2180                2185                2190

Ser Val  Glu Arg Thr Ile Ala  Gly Leu Ser Asn Leu  Ala Gln Gln
    2195                2200                2205

Gly Val  Asp Thr Arg Cys His  Ile Val Leu Pro Gly  Ser Pro Asn
    2210                2215                2220

Arg Gly  Met Phe Gly Gly Asp  Gly Ala Tyr Gly Glu  Val Lys Ala
    2225                2230                2235

Ala Leu  Asp Ala Ile Leu Ala  Lys Trp Ser Ala Glu  Ala Gly Trp
    2240                2245                2250

Pro Glu  Gly Val Thr Leu Ala  Gln Ala Lys Ile Gly  Trp Val Ser
    2255                2260                2265

Gly Thr  Ser Leu Met Gly Gly  Asn Asp Val Leu Ile  Pro Ala Ala
    2270                2275                2280

Glu Ala  Ala Ile His Val Trp  Asp Pro Glu Glu Ile  Ser Ser Gln
    2285                2290                2295

Leu Ile  Ser Leu Ala Ser Glu  Glu Ser Arg Ala Lys  Ala Ala Glu
    2300                2305                2310

Ala Pro  Leu Glu Leu Asp Leu  Thr Gly Gly Leu Gly  Ser Ser Asn
    2315                2320                2325
```

-continued

```
Ile Ser  Ile Ser Glu Leu Ala  Ala Gln Ala Arg Glu  Asp Ala Glu
    2330                 2335                 2340

Ala Gln  Ala Ala Ser Gly Asp  Asn Ala Asp Ala Ala  Ala Glu Ala
    2345                 2350                 2355

Pro Ala  Ala Thr Ile Pro Ala  Leu Pro Asn Thr Arg  Ser Val Glu
    2360                 2365                 2370

Leu Pro  Ala Ala Leu Pro Glu  Gly Glu Val Gly Asp  Val Thr Thr
    2375                 2380                 2385

Asp Leu  Asp Asp Met Val Val  Ile Ala Gly Val Gly  Glu Val Ser
    2390                 2395                 2400

Ser Trp  Gly Ser Gly Arg Thr  Arg Phe Glu Glu Tyr  Gly Leu Gln
    2405                 2410                 2415

Arg Asp  Gly Ala Val Asp Leu  Thr Ala Ala Gly Val  Leu Glu Leu
    2420                 2425                 2430

Ala Trp  Met Thr Gly Leu Ile  Ser Trp Ser Asn Asp  Pro Arg Pro
    2435                 2440                 2445

Ala Trp  Tyr Asp Glu Glu Gly  Thr Glu Val Asp Glu  Ala Asp Ile
    2450                 2455                 2460

Tyr Ala  Arg Phe Arg Asp Glu  Val Val Ala Arg Ser  Gly Ile Arg
    2465                 2470                 2475

Thr Leu  Thr Asp Lys Tyr Asn  Met Val Asp Gln Gly  Ser Ile Asp
    2480                 2485                 2490

Leu Thr  Ser Val Phe Leu Asp  Arg Asp Ile Val Phe  Thr Val Pro
    2495                 2500                 2505

Thr Glu  Gln Glu Ala Leu Asp  Ile Glu Glu Ala Asp  Pro Ser Phe
    2510                 2515                 2520

Thr Lys  Leu Arg Glu Val Asp  Gly Glu Trp Glu Val  Thr Arg Leu
    2525                 2530                 2535

Lys Gly  Thr Ala Arg Val Pro  Arg Lys Ala Thr Leu  Thr Arg Thr
    2540                 2545                 2550

Val Ala  Gly Gln Met Pro Asp  His Phe Asp Ala Ala  Lys Trp Gly
    2555                 2560                 2565

Ile Pro  Asp His Met Leu Asp  Ala Leu Asp Arg Met  Ala Val Trp
    2570                 2575                 2580

Asn Leu  Val Thr Ala Val Asp  Ala Phe Thr Gln Ala  Gly Phe Ser
    2585                 2590                 2595

Pro Ala  Glu Leu Leu Gln Val  Ile His Pro Ala Gln  Val Ala Thr
    2600                 2605                 2610

Thr Gln  Gly Thr Gly Ile Gly  Gly Met Glu Ser Leu  His Lys Val
    2615                 2620                 2625

Phe Val  Thr Arg Leu Leu Gly  Glu Asp Arg Pro Ser  Asp Ile Leu
    2630                 2635                 2640

Gln Glu  Ala Leu Pro Asn Val  Ile Ala Ala His Thr  Met Gln Ser
    2645                 2650                 2655

Leu Val  Gly Gly Tyr Gly Ser  Met Ile Pro Ile Gly  Ala Cys Ala
    2660                 2665                 2670

Thr Ala  Ala Val Ser Ile Glu  Glu Gly Val Asp Lys  Ile Ala Leu
    2675                 2680                 2685

Gly Lys  Ala Asp Leu Val Val  Ala Gly Gly Ile Asp  Asp Val Gln
    2690                 2695                 2700

Val Glu  Ser Leu Thr Gly Phe  Gly Asp Met Asn Ala  Thr Ala Glu
    2705                 2710                 2715
```

-continued

```
Thr Lys  Lys Met Thr Asp Gln  Gly Ile Asp Asp Arg  Phe Ile Ser
    2720                 2725                 2730

Arg Ala  Asn Asp Arg Arg Arg  Gly Gly Phe Leu Glu  Ala Glu Gly
    2735                 2740                 2745

Gly Gly  Thr Val Leu Leu Val  Arg Gly Ser Leu Ala  Arg Glu Met
    2750                 2755                 2760

Gly Leu  Pro Val Tyr Ala Val  Val Ala His Glu Ala  Ser Tyr Gly
    2765                 2770                 2775

Ala His  Thr Ser Ile Pro Ala  Pro Gly Leu Gly Ala  Leu Gly Ala
    2780                 2785                 2790

Gly Arg  Gly Arg Lys Asn Ser  Arg Leu Ala Lys Gly  Leu Ala Gly
    2795                 2800                 2805

Leu Gly  Leu Thr Pro Asn Asp  Val Ser Val Leu Ser  Lys His Asp
    2810                 2815                 2820

Thr Ser  Thr Asn Asn Asp Pro  Asn Glu Ser Glu Leu  His Ser Ile
    2825                 2830                 2835

Leu Trp  Pro Ala Ile Gly Arg  Asp Val Asp Gln Pro  Leu Phe Val
    2840                 2845                 2850

Ile Ser  Gln Lys Ser Leu Thr  Gly His Ser Lys Ala  Gly Ala Ala
    2855                 2860                 2865

Leu Phe  Gln Thr Gly Gly Leu  Ile Asp Val Phe Arg  Thr Gly Arg
    2870                 2875                 2880

Ile Pro  Ala Asn Leu Ser Leu  Asp Cys Val Asp Pro  Leu Ile Glu
    2885                 2890                 2895

Pro Lys  Ala Thr Asn Leu Val  Trp Leu Arg Ser Pro  Leu Asp Val
    2900                 2905                 2910

Glu Ala  Ala Asn Arg Pro Val  Lys Ala Ala Ala Leu  Thr Ser Leu
    2915                 2920                 2925

Gly Phe  Gly His Val Gly Ala  Leu Ile Val Tyr Ala  His Pro Gly
    2930                 2935                 2940

Val Phe  Glu Ala Ala Val Ala  Gln Gln Val Ser Glu  Ala Ala Ala
    2945                 2950                 2955

Glu Trp  Arg Glu Lys Ala Asn  Ala Arg Leu Ala Ala  Gly Ala Ala
    2960                 2965                 2970

Arg Phe  Glu Ala Gly Met Ile  Gly Lys Glu Thr Leu  Phe Glu Val
    2975                 2980                 2985

Ile Asp  Gly Arg Arg Leu Pro  Asp Ala Ala Gly Thr  Val Glu Ile
    2990                 2995                 3000

Glu Asn  Tyr Gly Pro Val Ala  Ala Asp Lys Ala Ala  Glu Leu Arg
    3005                 3010                 3015

Ser Cys  Leu Thr Thr Thr Ser  Val Leu Pro Pro Lys  Ala Leu Ser
    3020                 3025                 3030

Leu Arg  Arg Ser Arg Thr Lys
    3035                 3040
```

<210> SEQ ID NO 3
<211> LENGTH: 459
<212> TYPE: DNA
<213> ORGANISM: Brevibacterium ammoniagenes

<400> SEQUENCE: 3

```
gtgctcgaca accgtgaagc gatgaccgtg ggtgtggact tggtccacat ccccggcttt     60

gccgagcaat tgtcgcgccc tggttcgact tttgagcaag tgttttcgcc gttggaacgt    120

cgtcatgtca aacgcgccgt gacgctgcag cggatgctac gaattcgagc cttgcgggtt    180
```

-continued

```
cacggactga gcacctggct gggcggtggg cggcaaaaga agcgttcatc aaggcgtggt    240

cgcaagcgat ctacgcaagc caccagtgat tgaaccagac ctggtgaact tcgcagagat    300

cgaagtcttg cccgaccgct ggggcagggt agcgctgcag cttaaaggtg aagttgctgc    360

aaaacttcag gaatcaatag ggacgtggag ctggcgctga gcatcagcca tgatggcgat    420

tacgccaccg cgcagtgcct gctgcggtac cagcggtaa                           459


<210> SEQ ID NO 4
<211> LENGTH: 152
<212> TYPE: PRT
<213> ORGANISM: Brevibacterium ammoniagenes

<400> SEQUENCE: 4

Met Leu Asp Asn Arg Glu Ala Met Thr Val Gly Val Asp Leu Val His
1               5                   10                  15

Ile Pro Gly Phe Ala Glu Gln Leu Ser Arg Pro Gly Ser Thr Phe Glu
            20                  25                  30

Gln Val Phe Ser Pro Leu Glu Arg Arg His Ala Gln Thr Arg Arg Asp
        35                  40                  45

Ala Ala Ala Asp Ala Thr Asn Ser Ser Leu Ala Gly Ser Arg Thr Glu
    50                  55                  60

His Leu Ala Gly Arg Trp Ala Ala Lys Glu Ala Phe Ile Lys Ala Trp
65                  70                  75                  80

Ser Gln Ala Ile Tyr Gly Lys Pro Pro Val Ile Glu Pro Asp Leu Val
                85                  90                  95

Asn Phe Ala Glu Ile Glu Val Leu Pro Asp Arg Trp Gly Arg Val Ala
            100                 105                 110

Leu Gln Leu Lys Gly Glu Val Ala Ala Lys Leu Gln Glu Ser Ile Asp
        115                 120                 125

Val Glu Leu Ala Leu Ser Ile Ser His Asp Gly Asp Tyr Ala Thr Ala
    130                 135                 140

Gln Cys Leu Leu Arg Tyr Gln Arg
145                 150


<210> SEQ ID NO 5
<211> LENGTH: 20
<212> TYPE: DNA
<213> ORGANISM: Artificial
<220> FEATURE:
<223> OTHER INFORMATION: PCR primer sequence

<400> SEQUENCE: 5

ccagctcaac gatgaagtag                                                 20


<210> SEQ ID NO 6
<211> LENGTH: 20
<212> TYPE: DNA
<213> ORGANISM: Artificial
<220> FEATURE:
<223> OTHER INFORMATION: PCR primer sequence

<400> SEQUENCE: 6

tcgatgatct ggtctacttc                                                 20


<210> SEQ ID NO 7
<211> LENGTH: 27
<212> TYPE: DNA
<213> ORGANISM: Artificial
<220> FEATURE:
```

-continued

<223> OTHER INFORMATION: Primer Sequence

<400> SEQUENCE: 7
gtcgacatgc tcgacaaccg tgaagcg 27

<210> SEQ ID NO 8
<211> LENGTH: 31
<212> TYPE: DNA
<213> ORGANISM: Artificial
<220> FEATURE:
<223> OTHER INFORMATION: Primer Sequence

<400> SEQUENCE: 8
agatcttcac tggtggcttg ccgtagatcg c 31

<210> SEQ ID NO 9
<211> LENGTH: 37
<212> TYPE: DNA
<213> ORGANISM: Artificial
<220> FEATURE:
<223> OTHER INFORMATION: Primer Sequence

<400> SEQUENCE: 9
tctagatgca tagttaacat gtcgttgacc cccttgc 37

<210> SEQ ID NO 10
<211> LENGTH: 20
<212> TYPE: DNA
<213> ORGANISM: Artificial
<220> FEATURE:
<223> OTHER INFORMATION: Primer Sequence

<400> SEQUENCE: 10
ggtacgcgtc atattccttg 20

<210> SEQ ID NO 11
<211> LENGTH: 40
<212> TYPE: DNA
<213> ORGANISM: Artificial
<220> FEATURE:
<223> OTHER INFORMATION: Primer Sequence

<400> SEQUENCE: 11
caaggaatat gacgcgtacc ctcgaggcag aaggcggcgg 40

<210> SEQ ID NO 12
<211> LENGTH: 37
<212> TYPE: DNA
<213> ORGANISM: Artificial
<220> FEATURE:
<223> OTHER INFORMATION: Primer Sequence

<400> SEQUENCE: 12
atgcatgtta acatgtctac tttgtcctac ttcgccg 37

<210> SEQ ID NO 13
<211> LENGTH: 33
<212> TYPE: DNA
<213> ORGANISM: Artificial
<220> FEATURE:
<223> OTHER INFORMATION: Primer Sequence

<400> SEQUENCE: 13
gtcgacatgc atatgctcga caaccgtgaa gcg 33

-continued

<210> SEQ ID NO 14
<211> LENGTH: 30
<212> TYPE: DNA
<213> ORGANISM: Artificial
<220> FEATURE:
<223> OTHER INFORMATION: Primer Sequence

<400> SEQUENCE: 14
agatctatgc attaccgctg gtaccgcagc 30

<210> SEQ ID NO 15
<211> LENGTH: 2073
<212> TYPE: PRT
<213> ORGANISM: Schizosaccharomyces pombe

<400> SEQUENCE: 15

Met Val Glu Ala Glu Gln Val His Gln Ser Leu Arg Ser Leu Val Leu
1 5 10 15

Ser Tyr Ala His Phe Ser Pro Ser Ile Leu Ile Pro Ala Ser Gln Tyr
20 25 30

Leu Leu Ala Ala Gln Leu Arg Asp Glu Phe Leu Ser Leu His Pro Ala
35 40 45

Pro Ser Ala Glu Ser Val Glu Lys Glu Gly Ala Glu Leu Glu Phe Glu
50 55 60

His Glu Leu His Leu Leu Ala Gly Phe Leu Gly Leu Ile Ala Ala Lys
65 70 75 80

Glu Glu Glu Thr Pro Gly Gln Tyr Thr Gln Leu Leu Arg Ile Ile Thr
85 90 95

Leu Glu Phe Glu Arg Thr Phe Leu Ala Gly Asn Glu Val His Ala Val
100 105 110

Val His Ser Leu Gly Leu Asn Ile Pro Ala Gln Lys Asp Val Val Arg
115 120 125

Phe Tyr Tyr His Ser Cys Ala Leu Ile Gly Gln Thr Thr Lys Phe His
130 135 140

Gly Ser Ala Leu Leu Asp Glu Ser Ser Val Lys Leu Ala Ala Ile Phe
145 150 155 160

Gly Gly Gln Gly Tyr Glu Asp Tyr Phe Asp Glu Leu Ile Glu Leu Tyr
165 170 175

Glu Val Tyr Ala Pro Phe Ala Ala Glu Leu Ile Gln Val Leu Ser Lys
180 185 190

His Leu Phe Thr Leu Ser Gln Asn Glu Gln Ala Ser Lys Val Tyr Ser
195 200 205

Lys Gly Leu Asn Val Leu Asp Trp Leu Ala Gly Glu Arg Pro Glu Arg
210 215 220

Asp Tyr Leu Val Ser Ala Pro Val Ser Leu Pro Leu Val Gly Leu Thr
225 230 235 240

Gln Leu Val His Phe Ser Val Thr Ala Gln Ile Leu Gly Leu Asn Pro
245 250 255

Gly Glu Leu Ala Ser Arg Phe Ser Ala Ala Ser Gly His Ser Gln Gly
260 265 270

Ile Val Val Ala Ala Ala Val Ser Ala Ser Thr Asp Ser Ala Ser Phe
275 280 285

Met Glu Asn Ala Lys Val Ala Leu Thr Thr Leu Phe Trp Ile Gly Val
290 295 300

Arg Ser Gln Gln Thr Phe Pro Thr Thr Thr Leu Pro Pro Ser Val Val
305 310 315 320

-continued

```
Ala Asp Ser Leu Ala Ser Ser Glu Gly Asn Pro Thr Pro Met Leu Ala
                325                 330                 335

Val Arg Asp Leu Pro Ile Glu Thr Leu Asn Lys His Ile Glu Thr Thr
            340                 345                 350

Asn Thr His Leu Pro Glu Asp Arg Lys Val Ser Leu Ser Leu Val Asn
        355                 360                 365

Gly Pro Arg Ser Phe Val Val Ser Gly Pro Ala Arg Ser Leu Tyr Gly
    370                 375                 380

Leu Asn Leu Ser Leu Arg Lys Glu Lys Ala Asp Gly Gln Asn Gln Ser
385                 390                 395                 400

Arg Ile Pro His Ser Lys Arg Lys Leu Arg Phe Ile Asn Arg Phe Leu
                405                 410                 415

Ser Ile Ser Val Pro Phe His Ser Pro Tyr Leu Ala Pro Val Arg Ser
            420                 425                 430

Leu Leu Glu Lys Asp Leu Gln Gly Leu Gln Phe Ser Ala Leu Lys Val
        435                 440                 445

Pro Val Tyr Ser Thr Asp Asp Ala Gly Asp Leu Arg Phe Glu Gln Pro
    450                 455                 460

Ser Lys Leu Leu Leu Ala Leu Ala Val Met Ile Thr Glu Lys Val Val
465                 470                 475                 480

His Trp Glu Glu Ala Cys Gly Phe Pro Asp Val Thr His Ile Ile Asp
                485                 490                 495

Phe Gly Pro Gly Gly Ile Ser Gly Val Gly Ser Leu Thr Arg Ala Asn
            500                 505                 510

Lys Asp Gly Gln Gly Val Arg Val Ile Val Ala Asp Ser Phe Glu Ser
        515                 520                 525

Leu Asp Met Gly Ala Lys Phe Glu Ile Phe Asp Arg Asp Ala Lys Ser
    530                 535                 540

Ile Glu Phe Ala Pro Asn Trp Val Lys Leu Tyr Ser Pro Lys Leu Val
545                 550                 555                 560

Lys Asn Lys Leu Gly Arg Val Tyr Val Asp Thr Arg Leu Ser Arg Met
                565                 570                 575

Leu Gly Leu Pro Pro Leu Trp Val Ala Gly Met Thr Pro Thr Ser Val
            580                 585                 590

Pro Trp Gln Phe Cys Ser Ala Ile Ala Lys Ala Gly Phe Thr Tyr Glu
        595                 600                 605

Leu Ala Gly Gly Gly Tyr Phe Asp Pro Lys Met Met Arg Glu Ala Ile
    610                 615                 620

His Lys Leu Ser Leu Asn Ile Pro Pro Gly Ala Gly Ile Cys Val Asn
625                 630                 635                 640

Val Ile Tyr Ile Asn Pro Arg Thr Tyr Ala Trp Gln Ile Pro Leu Ile
                645                 650                 655

Arg Asp Met Val Ala Glu Gly Tyr Pro Ile Arg Gly Val Thr Ile Ala
            660                 665                 670

Ala Gly Ile Pro Ser Leu Glu Val Ala Asn Glu Leu Ile Ser Thr Leu
        675                 680                 685

Gly Val Gln Tyr Leu Cys Leu Lys Pro Gly Ser Val Glu Ala Val Asn
    690                 695                 700

Ala Val Ile Ser Ile Ala Lys Ala Asn Pro Thr Phe Pro Ile Val Leu
705                 710                 715                 720

Gln Trp Thr Gly Gly Arg Ala Gly Gly His His Ser Phe Glu Asp Phe
                725                 730                 735

His Ser Pro Ile Leu Leu Thr Tyr Ser Ala Ile Arg Arg Cys Asp Asn
```

-continued

```
            740                 745                 750

Ile Val Leu Ile Ala Gly Ser Gly Phe Gly Gly Ala Asp Asp Thr Glu
        755                 760                 765

Pro Tyr Leu Thr Gly Glu Trp Ser Ala Ala Phe Lys Leu Pro Pro Met
    770                 775                 780

Pro Phe Asp Gly Ile Leu Phe Gly Ser Arg Leu Met Val Ala Lys Glu
785                 790                 795                 800

Ala His Thr Ser Leu Ala Ala Lys Glu Ala Ile Val Ala Ala Lys Gly
                805                 810                 815

Val Asp Asp Ser Glu Trp Glu Lys Thr Tyr Asp Gly Pro Thr Gly Gly
            820                 825                 830

Ile Val Thr Val Leu Ser Glu Leu Gly Glu Pro Ile His Lys Leu Ala
        835                 840                 845

Thr Arg Gly Ile Met Phe Trp Lys Glu Leu Asp Asp Thr Ile Phe Ser
    850                 855                 860

Leu Pro Arg Pro Lys Arg Leu Pro Ala Leu Leu Ala Lys Lys Gln Tyr
865                 870                 875                 880

Ile Ile Lys Arg Leu Asn Asp Asp Phe Gln Lys Val Tyr Phe Pro Ala
                885                 890                 895

His Ile Val Glu Gln Val Ser Pro Glu Lys Phe Lys Phe Glu Ala Val
            900                 905                 910

Asp Ser Val Glu Asp Met Thr Tyr Ala Glu Leu Leu Tyr Arg Ala Ile
        915                 920                 925

Asp Leu Met Tyr Val Thr Lys Glu Lys Arg Trp Ile Asp Val Thr Leu
    930                 935                 940

Arg Thr Phe Thr Gly Lys Leu Met Arg Arg Ile Glu Glu Arg Phe Thr
945                 950                 955                 960

Gln Asp Val Gly Lys Thr Thr Leu Ile Glu Asn Phe Glu Asp Leu Asn
                965                 970                 975

Asp Pro Tyr Pro Val Ala Ala Arg Phe Leu Asp Ala Tyr Pro Glu Ala
            980                 985                 990

Ser Thr Gln Asp Leu Asn Thr Gln  Asp Ala Gln Phe Phe  Tyr Ser Leu
        995                 1000                1005

Cys Ser  Asn Pro Phe Gln Lys  Pro Val Pro Phe Ile  Pro Ala Ile
    1010                1015                1020

Asp Asp  Thr Phe Glu Phe Tyr  Phe Lys Lys Asp Ser  Leu Trp Gln
    1025                1030                1035

Ser Glu  Asp Leu Ala Ala Val  Val Gly Glu Asp Val  Gly Arg Val
    1040                1045                1050

Ala Ile  Leu Gln Gly Pro Met  Ala Ala Lys His Ser  Thr Lys Val
    1055                1060                1065

Asn Glu  Pro Ala Lys Glu Leu  Leu Asp Gly Ile Asn  Glu Thr His
    1070                1075                1080

Ile Gln  His Phe Ile Lys Lys  Phe Tyr Ala Gly Asp  Glu Lys Lys
    1085                1090                1095

Ile Pro  Ile Val Glu Tyr Phe  Gly Gly Val Pro Pro  Val Asn Val
    1100                1105                1110

Ser His  Lys Ser Leu Glu Ser  Val Ser Val Thr Glu  Glu Ala Gly
    1115                1120                1125

Ser Lys  Val Tyr Lys Leu Pro  Glu Ile Gly Ser Asn  Ser Ala Leu
    1130                1135                1140

Pro Ser  Lys Lys Leu Trp Phe  Glu Leu Leu Ala Gly  Pro Glu Tyr
    1145                1150                1155
```

-continued

```
Thr Trp  Phe Arg Ala Ile Phe  Thr Thr Gln Arg Val  Ala Lys Gly
    1160                 1165                 1170

Trp Lys  Leu Glu His Asn Pro  Val Arg Arg Ile Phe  Ala Pro Arg
    1175                 1180                 1185

Tyr Gly  Gln Arg Ala Val Val  Lys Gly Lys Asp Asn  Asp Thr Val
    1190                 1195                 1200

Val Glu  Leu Tyr Glu Thr Gln  Ser Gly Asn Tyr Val  Leu Ala Ala
    1205                 1210                 1215

Arg Leu  Ser Tyr Asp Gly Glu  Thr Ile Val Val Ser  Met Phe Glu
    1220                 1225                 1230

Asn Arg  Asn Ala Leu Lys Lys  Glu Val His Leu Asp  Phe Leu Phe
    1235                 1240                 1245

Lys Tyr  Glu Pro Ser Ala Gly  Tyr Ser Pro Val Ser  Glu Ile Leu
    1250                 1255                 1260

Asp Gly  Arg Asn Asp Arg Ile  Lys His Phe Tyr Trp  Ala Leu Trp
    1265                 1270                 1275

Phe Gly  Glu Glu Pro Tyr Pro  Glu Asn Ala Ser Ile  Thr Asp Thr
    1280                 1285                 1290

Phe Thr  Gly Pro Glu Val Thr  Val Thr Gly Asn Met  Ile Glu Asp
    1295                 1300                 1305

Phe Cys  Arg Thr Val Gly Asn  His Asn Glu Ala Tyr  Thr Lys Arg
    1310                 1315                 1320

Ala Ile  Arg Lys Arg Met Ala  Pro Met Asp Phe Ala  Ile Val Val
    1325                 1330                 1335

Gly Trp  Gln Ala Ile Thr Lys  Ala Ile Phe Pro Lys  Ala Ile Asp
    1340                 1345                 1350

Gly Asp  Leu Leu Arg Leu Val  His Leu Ser Asn Ser  Phe Arg Met
    1355                 1360                 1365

Val Gly  Ser His Ser Leu Met  Glu Gly Asp Lys Val  Thr Thr Ser
    1370                 1375                 1380

Ala Ser  Ile Ile Ala Ile Leu  Asn Asn Asp Ser Gly  Lys Thr Val
    1385                 1390                 1395

Thr Val  Lys Gly Thr Val Tyr  Arg Asp Gly Lys Glu  Val Ile Glu
    1400                 1405                 1410

Val Ile  Ser Arg Phe Leu Tyr  Arg Gly Thr Phe Thr  Asp Phe Glu
    1415                 1420                 1425

Asn Thr  Phe Glu His Thr Gln  Glu Thr Pro Met Gln  Leu Thr Leu
    1430                 1435                 1440

Ala Thr  Pro Lys Asp Val Ala  Val Leu Gln Ser Lys  Ser Trp Phe
    1445                 1450                 1455

Gln Leu  Leu Asp Pro Ser Gln  Asp Leu Ser Gly Ser  Ile Leu Thr
    1460                 1465                 1470

Phe Arg  Leu Asn Ser Tyr Val  Arg Phe Lys Asp Gln  Lys Val Lys
    1475                 1480                 1485

Ser Ser  Val Glu Thr Lys Gly  Ile Val Leu Ser Glu  Leu Pro Ser
    1490                 1495                 1500

Lys Ala  Ile Ile Gln Val Ala  Ser Val Asp Phe Gln  Ser Val Asp
    1505                 1510                 1515

Cys His  Gly Asn Pro Val Ile  Glu Phe Leu Lys Arg  Asn Gly Lys
    1520                 1525                 1530

Pro Ile  Glu Gln Pro Val Glu  Phe Glu Asn Gly Gly  Tyr Ser Val
    1535                 1540                 1545
```

-continued

```
Ile Gln  Val Met Asp Glu Gly  Tyr Ser Pro Val Phe  Val Thr Pro
    1550                 1555                 1560

Pro Thr  Asn Ser Pro Tyr Ala  Glu Val Ser Gly Asp  Tyr Asn Pro
    1565                 1570                 1575

Ile His  Val Ser Pro Thr Phe  Ala Ala Phe Val Glu  Leu Pro Gly
    1580                 1585                 1590

Thr His  Gly Ile Thr His Gly  Met Tyr Thr Ser Ala  Ala Ala Arg
    1595                 1600                 1605

Arg Phe  Val Glu Thr Tyr Ala  Ala Gln Asn Val Pro  Glu Arg Val
    1610                 1615                 1620

Lys His  Tyr Glu Val Thr Phe  Val Asn Met Val Leu  Pro Asn Thr
    1625                 1630                 1635

Glu Leu  Ile Thr Lys Leu Ser  His Thr Gly Met Ile  Asn Gly Arg
    1640                 1645                 1650

Lys Ile  Ile Lys Val Glu Val  Leu Asn Gln Glu Thr  Ser Glu Pro
    1655                 1660                 1665

Val Leu  Val Gly Thr Ala Glu  Val Glu Gln Pro Val  Ser Ala Tyr
    1670                 1675                 1680

Val Phe  Thr Gly Gln Gly Ser  Gln Glu Gln Gly Met  Gly Met Asp
    1685                 1690                 1695

Leu Tyr  Ala Ser Ser Pro Val  Ala Arg Lys Ile Trp  Asp Ser Ala
    1700                 1705                 1710

Asp Lys  His Phe Leu Thr Asn  Tyr Gly Phe Ser Ile  Ile Asp Ile
    1715                 1720                 1725

Val Lys  His Asn Pro His Ser  Ile Thr Ile His Phe  Gly Gly Ser
    1730                 1735                 1740

Lys Gly  Lys Lys Ile Arg Asp  Asn Tyr Met Ala Met  Ala Tyr Glu
    1745                 1750                 1755

Lys Leu  Met Glu Asp Gly Thr  Ser Lys Val Val Pro  Val Phe Glu
    1760                 1765                 1770

Thr Ile  Thr Lys Asp Ser Thr  Ser Phe Ser Phe Thr  His Pro Ser
    1775                 1780                 1785

Gly Leu  Leu Ser Ala Thr Gln  Phe Thr Gln Pro Ala  Leu Thr Leu
    1790                 1795                 1800

Met Glu  Lys Ser Ala Phe Glu  Asp Met Arg Ser Lys  Gly Leu Val
    1805                 1810                 1815

Gln Asn  Asp Cys Ala Phe Ala  Gly His Ser Leu Gly  Glu Tyr Ser
    1820                 1825                 1830

Ala Leu  Ser Ala Met Gly Asp  Val Leu Ser Ile Glu  Ala Leu Val
    1835                 1840                 1845

Asp Leu  Val Phe Leu Arg Gly  Leu Thr Met Gln Asn  Ala Val His
    1850                 1855                 1860

Arg Asp  Glu Leu Gly Arg Ser  Asp Tyr Gly Met Val  Ala Ala Asn
    1865                 1870                 1875

Pro Ser  Arg Val Ser Ala Ser  Phe Thr Asp Ala Ala  Leu Arg Phe
    1880                 1885                 1890

Ile Val  Asp His Ile Gly Gln  Gln Thr Asn Leu Leu  Leu Glu Ile
    1895                 1900                 1905

Val Asn  Tyr Asn Val Glu Asn  Gln Gln Tyr Val Val  Ser Gly Asn
    1910                 1915                 1920

Leu Leu  Ser Leu Ser Thr Leu  Gly His Val Leu Asn  Phe Leu Lys
    1925                 1930                 1935

Val Gln  Lys Ile Asp Phe Glu  Lys Leu Lys Glu Thr  Leu Thr Ile
```

-continued

```
    1940                1945                1950

Glu Gln  Leu Lys Glu Gln Leu  Thr Asp Ile Val Glu  Ala Cys His
    1955                1960                1965

Ala Lys  Thr Leu Glu Gln Gln  Lys Lys Thr Gly Arg  Ile Glu Leu
    1970                1975                1980

Glu Arg  Gly Tyr Ala Thr Ile  Pro Leu Lys Ile Asp  Val Pro Phe
    1985                1990                1995

His Ser  Ser Phe Leu Arg Gly  Gly Val Arg Met Phe  Arg Glu Tyr
    2000                2005                2010

Leu Val  Lys Lys Ile Phe Pro  His Gln Ile Asn Val  Ala Lys Leu
    2015                2020                2025

Arg Gly  Lys Tyr Ile Pro Asn  Leu Thr Ala Lys Pro  Phe Glu Ile
    2030                2035                2040

Ser Lys  Glu Tyr Phe Gln Asn  Val Tyr Asp Leu Thr  Gly Ser Gln
    2045                2050                2055

Arg Ile  Lys Lys Ile Leu Gln  Asn Trp Asp Glu Tyr  Glu Ser Ser
    2060                2065                2070
```

<210> SEQ ID NO 16
<211> LENGTH: 6232
<212> TYPE: DNA
<213> ORGANISM: Schizosaccharomyces pombe

<400> SEQUENCE: 16

```
aagcttacta tactgtgtag tagagagtga taaaatgtta attatgccac aagcagttgc     60

taattcgcta tatttgataa cgatgcgtta aatattcgtt acatgcttca aagctgatag    120

gtttaacctg agtgttccca cgcgatagta aaggatcaag ttaactagaa ccaacaacta    180

aagcaggtgt tggagttttg ttaaaccatt tgaataatga gaccagaagt tgagcaggag    240

cttgctcata ctttattatt ggagttgctt gcataccagt ttgcatctcc tgtccgttgg    300

attgagacgc aagatgtaat tctttctcct ccagtatcgg ctgaacgtat cgtcgaaatt    360

ggacctagtc ctaccttagc tggtatggct aagcgtacct tgaaattgaa atatgagaac    420

atggatgccg ctttaagtat taatcgtgaa gttctttgct actctaaaga tgctcgtgaa    480

atctattaca actttgagga cgaggttgct gatgaacctg ccgaagcccc agcttcaacc    540

agctccactc caaaggttga aactgctgct gctgccgctc ccgctgccac gccagcccct    600

gccccagcac aaacatcagc cccagctgct gctttacctg acgagcctcc caaagctctt    660

gaggtacttc atactcttgt tgcccaaaag ttgaagaaaa gcatcgagga agtctcccct    720

caaaaatcta tcaaagattt ggttggcggt aagtccactt tgcaaaacga aattcttggt    780

gatttacaga aggagttcgg tgccactccc gagaagccag aggaggttcc attggatgag    840

cttggagcta tcatgcagtc aagctttaac ggatctcttg gtaaacaatc gtcttctctt    900

atctcacgaa tgatttcctc aaaaatgcct ggtggtttca ataattctgc tgttcgtggt    960

tatttaggaa accgttatgg tttgggtcct ggtcgtttgg agtctgtgct tttgttagcg   1020

cttaccatgg aacctgcatc acgtttgggc tcggaagctg atgctaaagc ttggcttgat   1080

agtgtagctc aaaaatatgc tgctcgtaat ggtgttacat tatcttctcc tactgctgaa   1140

ggcggttctt cgtccggttc tgcagctgtt atcgatgaag aaacctttaa gaaactcacc   1200

aagaataata ccatgcttgt tactcagcaa ttagaactat ttgctcgata cctcaataaa   1260

gaccttcgtg ctggccaaaa ggctcaagtt gctgaaaagg ttatttccga taccttacgc   1320

gctcaattag atttatggaa cgaagaacat ggtgaatttt atgcatcagg aattgctcct   1380
```

-continued

```
atttttttcgc ctttaaaagc tcgcgtttac gactccgact ggaattgggc tcgtcaagat   1440
gctcttaaga tgttttttga cattatcttt ggtcgtctta ggcatgttga tactgaaata   1500
gtcgctcgtt gtatttctgt tatgaataga tccaacccta ctttacttga atttatgcaa   1560
tatcatattg atcattgtcc cgccgaaaag ggtgaaacat atcaacttgc taaaaccttg   1620
ggccaacagc taattgataa ttgcaaatcc gtgatagatg ctcctccagt tttcaaaaat   1680
gtgaatcatc caactgctcc ttctacgacg attgacgaac gtggtaattt gaattatgaa   1740
gaaatcccta gaccaggtgt tcgcaaatta actcattacg ttactgagat ggccaaaggt   1800
ggtaaattac caacggagtc caaaaacaaa gctaaggtac aaaacgattt ggctcgaatt   1860
tatcgcatta ttaagtctca aaacaaaatg tctcgttcgt ctaagttgca gattaaacag   1920
ttgtacggtc aggttttaca tgccctttcc cttccattgc cttcttccaa cgatgaacaa   1980
acgcctgtta aagaaaccat tcctttcctt catattagga agaagtccgt tgatggtaat   2040
tgggaattca acaagtcatt gactggcact tatttagatg ttttagaatc gggtgctaag   2100
aatggtataa cataccaaga caaatatgct ctagtgactg gtgcaggtgc aggctccatt   2160
ggtgctcaga ttgttgaagg tctccttgct ggtggtgcta aagttgtagt tactacatcc   2220
cggttttcgc gcaaggttac tgaattttat caatcccttt acacccgcca tggaagccgt   2280
ggttcatgtc tgatcgtggt tccatttaac caaggatcta agacagacgt agaagctctt   2340
attgattata tttatgacga aaagaagggt cttggatgga acttggacta cattgttcct   2400
ttcgctgcca ttccagaaaa tggtcgtgaa attgatggca ttgattctcg ttccgagttt   2460
gctcaccgta ttatgttgac aaacattttg agactgcttg gcgccgtcaa aagtcaaaag   2520
gcctctcgtg gtatggatac ccgacccgct caagttattt tgcctctttc tcccaatcac   2580
ggtacctttg gaaacgatgg tttatactcg gaatctaagt taggtttaga aactttgttt   2640
aaccgttggt actccgagtc atgggctaat tacctaacca tttgtggggc tgtcattggt   2700
tggactcgtg gtacaggctt aatggcacct aataatattg tttctcaggg aatcgaaaaa   2760
tatggtgttc gtactttttc gcagagtgag atggctttta acattttggg tttgatgtcc   2820
cagaaagtcg tcgacttgtg tcaatctgaa ccaatttatg ccaaccttaa cggtggtctt   2880
gagcttttac ctgatctcaa ggacctttcc actcgtttgc gtaccgaatt gttagaaact   2940
gccgaaatcc gccgcgctgt tgccgcagag actgcctttg atcatagcat taccaacgga   3000
cctgactctg aagcagtttt ccagaaaact gccattcagc ctagggccaa tcttaaattt   3060
aatttcccca aattgaaacc ttatgaagcc ctttctcatt tatctgatct tcgtggaatg   3120
gttgatttag aaaaagttcc tgttgttact ggtttttccg aagtaggtcc atggggtaac   3180
tctcgtacta gatgggatat ggagtgttat ggtgagtttt cactagaagg atgtgtcgaa   3240
attgcttgga ttatgggatt aattaaaaac ttcaatggca agggcaaaga cggcaagccc   3300
tattcaggtt gggttgatac aaagaccggt gaacctgtgg acgacaaaga cgttaaagct   3360
aagtatgaga agtatatact ggagcattgc ggtatccgta ttattgaagc tgaactcttc   3420
catggatata atcctgaaaa gaaagagctt ttgcaagaag ttgttattga tcatgactta   3480
gagccttttg aagcatccaa agaggctgct catgagttca agcttcgtca tggtgatcaa   3540
gttgaaattt ttgaaattcc tgattctacc gaatggtccg tacgcttcaa gcgcggtaca   3600
agtatgctaa ttcctaaggc tttgcgcttt gatcgatttg ttgctggcca gattccactt   3660
ggttgggatc ccaaacgtta tggcattcct gacgatatta tttctcaagt tgaccctaca   3720
```

-continued

```
actttgtacg ttttagtgtc tactgtagaa gctctggttg catcaggtat tacagatcct   3780
tatgaatgct ataagtatat tcacgtatct gaacttggta atacagttgg ttctggtatt   3840
ggtggtatgt ctgctcttcg tggaatgtac aaggaccgct ggactgataa acctgttcaa   3900
aaagatattt tacaagaatc attcattaac actgccaatg cttggattaa catgcttttg   3960
ctctctgcct ctggtcctat taagactcct gttggtgctt gcgctaccgc tgtcgaatct   4020
gttgatgcag ctgtcgactt gatcacttct ggtaaggcca ggatatgtat tagcggtggt   4080
tatgacgact tttcagaaga aggttcatac gagtttgcga acatgggtgc tacatcaaat   4140
gctgctaagg aaacagaaag gggacgtact cctcaagaaa tgtctcgtcc tgctacttct   4200
actcgtgatg gatttatgga gtctcaaggt gctggtgtac agattatcat gcaagcaaag   4260
cttgctattg agatgggtgt ccctatacat ggtattgttg gttatgtttc cacagctatg   4320
gataaacaag gtcgttcggt tcctgcccct gggcaaggta ttttgactgg tgctcgtgaa   4380
atcgcgacta agacacccct tcccatagtt gaccttaaat tccgttctcg tcaactccaa   4440
cgccgccgtt ctcaaattgg tgaatgggcc gaacgcgagt atctttattt agaagaagaa   4500
cttgatgcga tgaaggttca aaatcctgac ttggatttag aggcttaccg tatagagcgt   4560
atcaacgtta ttaaggagga ggttgttcga caagaaaagg aggcgctcaa tacttttgga   4620
aatgaatttt ggaaacgtga tcctactatt gctcctatcc gtggtgcatt agctgtttgg   4680
ggtcttacta ttgacgattt gggcgttgca tcattccatg gtacctctac caaagccaat   4740
gagaagaatg aatgcgatgt cattgacagt cagttaacac atctcggacg ctctaagggt   4800
aacgctgtgt acggtgtttt ccagaaatat ctcactggac atagcaaggg tggtgctgga   4860
gcttggatgc tcaacggagc tctccaaatt cttcgctctg ggtttgttcc gggtaatcgt   4920
aacgccgata acattgatga gtatctagca cgattcgacc gggttatgtt ccctagtgaa   4980
ggtatacaaa ctgatggcat aaaggcagca tctgttactg catttggttt tggacaagtt   5040
ggtggacaag ttatagttat ccatcctgat tacatttacg gtgtgattga tgaggctact   5100
tataatgctt acaaagctaa aactgctgct cgttataagg catcttatcg ttacacccac   5160
gatgcgctgg tttacaacaa tttggtccgc gccaaggatt ctcctcctta caccaaagaa   5220
caagagaaag ccgtttatct caatcctttg gcacgcgctt cgaagagcaa agctggcact   5280
tggactttcc ctgccacact gcctgctgaa tccgacattt ctaaaaccaa cgaaactaca   5340
cgtactctac aaagcctaac aacctcattg accaactcca atgaaaatgt tggcgtggat   5400
gttgaacttg tatcagcgat tagcattgat aatgagacct ttatagaaag gaattttact   5460
gataccgagc gaaagtactg ttttgcagct cctaatcccc aagctagctt tgccggacgt   5520
tggtcagcca aagaggctgt ctttaagtct ttgggtattt ccggtaaagg cgctgcagct   5580
ccattgaagg atatcgaaat tatttcttca gagtctggtg ctcctgaagt agttttgcac   5640
ggagaggctg cgaaggctgc aacgaccgcc ggtgtgaaga gtgtttccgt cagtatttcc   5700
cacgatgata atcaaagtgt cagtgttgct ttggctcaca agtaatttac gttatattgt   5760
ctttcaacat tggtatgcgg attttcgcat tcccttcaat cgtttgattt aatacactat   5820
ctttaatctt tttgtttacc tcaaatgctt tgaaatggtt atcgattttt gtagtcgtta   5880
tatacgcagt tagaaataaa ttacttttaa ccttataaat tattatgctc taaaaaaatg   5940
cagtatcatt aaatttaaac gaatgtcctt acacgtatga gtatttaaac tgatattgag   6000
ttatcttcat aaatttctga agccaggcag cggttgttgt ttcatcgaaa gaaatggggt   6060
tcatatatgc tgttgaagtg ttttgctcga acaaaatttc agttagatgc ttaatcactg   6120
```

-continued tccaaccgta agcattcgga aaccgcctac gacaatcatg gtattgtgtg catcaccatc 6180
gagtctaaca gcaacctttc tccacgcaag cctatgccag tttttggcaa tg 6232

<210> SEQ ID NO 17
<211> LENGTH: 1842
<212> TYPE: PRT
<213> ORGANISM: Schizosaccharomyces pombe

<400> SEQUENCE: 17

Met Arg Pro Glu Val Glu Gln Glu Leu Ala His Thr Leu Leu Leu Glu
1 5 10 15

Leu Leu Ala Tyr Gln Phe Ala Ser Pro Val Arg Trp Ile Glu Thr Gln
20 25 30

Asp Val Ile Leu Ser Pro Pro Val Ser Ala Glu Arg Ile Val Glu Ile
35 40 45

Gly Pro Ser Pro Thr Leu Ala Gly Met Ala Lys Arg Thr Leu Lys Leu
50 55 60

Lys Tyr Glu Asn Met Asp Ala Ala Leu Ser Ile Asn Arg Glu Val Leu
65 70 75 80

Cys Tyr Ser Lys Asp Ala Arg Glu Ile Tyr Tyr Asn Phe Glu Asp Glu
85 90 95

Val Ala Asp Glu Pro Ala Glu Ala Pro Ala Ser Thr Ser Ser Thr Pro
100 105 110

Lys Val Glu Thr Ala Ala Ala Ala Ala Pro Ala Ala Thr Pro Ala Pro
115 120 125

Ala Pro Ala Gln Thr Ser Ala Pro Ala Ala Ala Leu Pro Asp Glu Pro
130 135 140

Pro Lys Ala Leu Glu Val Leu His Thr Leu Val Ala Gln Lys Leu Lys
145 150 155 160

Lys Ser Ile Glu Glu Val Ser Pro Gln Lys Ser Ile Lys Asp Leu Val
165 170 175

Gly Gly Lys Ser Thr Leu Gln Asn Glu Ile Leu Gly Asp Leu Gln Lys
180 185 190

Glu Phe Gly Ala Thr Pro Glu Lys Pro Glu Glu Val Pro Leu Asp Glu
195 200 205

Leu Gly Ala Ile Met Gln Ser Ser Phe Asn Gly Ser Leu Gly Lys Gln
210 215 220

Ser Ser Ser Leu Ile Ser Arg Met Ile Ser Ser Lys Met Pro Gly Gly
225 230 235 240

Phe Asn Asn Ser Ala Val Arg Gly Tyr Leu Gly Asn Arg Tyr Gly Leu
245 250 255

Gly Pro Gly Arg Leu Glu Ser Val Leu Leu Leu Ala Leu Thr Met Glu
260 265 270

Pro Ala Ser Arg Leu Gly Ser Glu Ala Asp Ala Lys Ala Trp Leu Asp
275 280 285

Ser Val Ala Gln Lys Tyr Ala Ala Arg Asn Gly Val Thr Leu Ser Ser
290 295 300

Pro Thr Ala Glu Gly Gly Ser Ser Ser Gly Ser Ala Ala Val Ile Asp
305 310 315 320

Glu Glu Thr Phe Lys Lys Leu Thr Lys Asn Asn Thr Met Leu Val Thr
325 330 335

Gln Gln Leu Glu Leu Phe Ala Arg Tyr Leu Asn Lys Asp Leu Arg Ala
340 345 350

-continued

Gly Gln Lys Ala Gln Val Ala Glu Lys Val Ile Ser Asp Thr Leu Arg
355 360 365

Ala Gln Leu Asp Leu Trp Asn Glu Glu His Gly Glu Phe Tyr Ala Ser
370 375 380

Gly Ile Ala Pro Ile Phe Ser Pro Leu Lys Ala Arg Val Tyr Asp Ser
385 390 395 400

Asp Trp Asn Trp Ala Arg Gln Asp Ala Leu Lys Met Phe Phe Asp Ile
405 410 415

Ile Phe Gly Arg Leu Arg His Val Asp Thr Glu Ile Val Ala Arg Cys
420 425 430

Ile Ser Val Met Asn Arg Ser Asn Pro Thr Leu Leu Glu Phe Met Gln
435 440 445

Tyr His Ile Asp His Cys Pro Ala Glu Lys Gly Glu Thr Tyr Gln Leu
450 455 460

Ala Lys Thr Leu Gly Gln Gln Leu Ile Asp Asn Cys Lys Ser Val Ile
465 470 475 480

Asp Ala Pro Pro Val Phe Lys Asn Val Asn His Pro Thr Ala Pro Ser
485 490 495

Thr Thr Ile Asp Glu Arg Gly Asn Leu Asn Tyr Glu Glu Ile Pro Arg
500 505 510

Pro Gly Val Arg Lys Leu Thr His Tyr Val Thr Glu Met Ala Lys Gly
515 520 525

Gly Lys Leu Pro Thr Glu Ser Lys Asn Lys Ala Lys Val Gln Asn Asp
530 535 540

Leu Ala Arg Ile Tyr Arg Ile Ile Lys Ser Gln Asn Lys Met Ser Arg
545 550 555 560

Ser Ser Lys Leu Gln Ile Lys Gln Leu Tyr Gly Gln Val Leu His Ala
565 570 575

Leu Ser Leu Pro Leu Pro Ser Ser Asn Asp Glu Gln Thr Pro Val Lys
580 585 590

Glu Thr Ile Pro Phe Leu His Ile Arg Lys Lys Ser Val Asp Gly Asn
595 600 605

Trp Glu Phe Asn Lys Ser Leu Thr Gly Thr Tyr Leu Asp Val Leu Glu
610 615 620

Ser Gly Ala Lys Asn Gly Ile Thr Tyr Gln Asp Lys Tyr Ala Leu Val
625 630 635 640

Thr Gly Ala Gly Ala Gly Ser Ile Gly Ala Gln Ile Val Glu Gly Leu
645 650 655

Leu Ala Gly Gly Ala Lys Val Val Val Thr Thr Ser Arg Phe Ser Arg
660 665 670

Lys Val Thr Glu Phe Tyr Gln Ser Leu Tyr Thr Arg His Gly Ser Arg
675 680 685

Gly Ser Cys Leu Ile Val Val Pro Phe Asn Gln Gly Ser Lys Thr Asp
690 695 700

Val Glu Ala Leu Ile Asp Tyr Ile Tyr Asp Glu Lys Lys Gly Leu Gly
705 710 715 720

Trp Asn Leu Asp Tyr Ile Val Pro Phe Ala Ala Ile Pro Glu Asn Gly
725 730 735

Arg Glu Ile Asp Gly Ile Asp Ser Arg Ser Glu Phe Ala His Arg Ile
740 745 750

Met Leu Thr Asn Ile Leu Arg Leu Leu Gly Ala Val Lys Ser Gln Lys
755 760 765

Ala Ser Arg Gly Met Asp Thr Arg Pro Ala Gln Val Ile Leu Pro Leu

-continued

```
    770                 775                 780

Ser Pro Asn His Gly Thr Phe Gly Asn Asp Gly Leu Tyr Ser Glu Ser
785                 790                 795                 800

Lys Leu Gly Leu Glu Thr Leu Phe Asn Arg Trp Tyr Ser Glu Ser Trp
                805                 810                 815

Ala Asn Tyr Leu Thr Ile Cys Gly Ala Val Ile Gly Trp Thr Arg Gly
            820                 825                 830

Thr Gly Leu Met Ala Pro Asn Asn Ile Val Ser Gln Gly Ile Glu Lys
        835                 840                 845

Tyr Gly Val Arg Thr Phe Ser Gln Ser Glu Met Ala Phe Asn Ile Leu
    850                 855                 860

Gly Leu Met Ser Gln Lys Val Val Asp Leu Cys Gln Ser Glu Pro Ile
865                 870                 875                 880

Tyr Ala Asn Leu Asn Gly Gly Leu Glu Leu Leu Pro Asp Leu Lys Asp
                885                 890                 895

Leu Ser Thr Arg Leu Arg Thr Glu Leu Leu Glu Thr Ala Glu Ile Arg
            900                 905                 910

Arg Ala Val Ala Ala Glu Thr Ala Phe Asp His Ser Ile Thr Asn Gly
        915                 920                 925

Pro Asp Ser Glu Ala Val Phe Gln Lys Thr Ala Ile Gln Pro Arg Ala
    930                 935                 940

Asn Leu Lys Phe Asn Phe Pro Lys Leu Lys Pro Tyr Glu Ala Leu Ser
945                 950                 955                 960

His Leu Ser Asp Leu Arg Gly Met Val Asp Leu Glu Lys Val Pro Val
                965                 970                 975

Val Thr Gly Phe Ser Glu Val Gly Pro Trp Gly Asn Ser Arg Thr Arg
            980                 985                 990

Trp Asp Met Glu Cys Tyr Gly Glu  Phe Ser Leu Glu Gly  Cys Val Glu
        995                 1000                1005

Ile Ala  Trp Ile Met Gly Leu  Ile Lys Asn Phe Asn  Gly Lys Gly
    1010                1015                1020

Lys Asp  Gly Lys Pro Tyr Ser  Gly Trp Val Asp Thr  Lys Thr Gly
    1025                1030                1035

Glu Pro  Val Asp Asp Lys Asp  Val Lys Ala Lys Tyr  Glu Lys Tyr
    1040                1045                1050

Ile Leu  Glu His Cys Gly Ile  Arg Ile Ile Glu Ala  Glu Leu Phe
    1055                1060                1065

His Gly  Tyr Asn Pro Glu Lys  Lys Glu Leu Leu Gln  Glu Val Val
    1070                1075                1080

Ile Asp  His Asp Leu Glu Pro  Phe Glu Ala Ser Lys  Glu Ala Ala
    1085                1090                1095

His Glu  Phe Lys Leu Arg His  Gly Asp Gln Val Glu  Ile Phe Glu
    1100                1105                1110

Ile Pro  Asp Ser Thr Glu Trp  Ser Val Arg Phe Lys  Arg Gly Thr
    1115                1120                1125

Ser Met  Leu Ile Pro Lys Ala  Leu Arg Phe Asp Arg  Phe Val Ala
    1130                1135                1140

Gly Gln  Ile Pro Leu Gly Trp  Asp Pro Lys Arg Tyr  Gly Ile Pro
    1145                1150                1155

Asp Asp  Ile Ile Ser Gln Val  Asp Pro Thr Thr Leu  Tyr Val Leu
    1160                1165                1170

Val Ser  Thr Val Glu Ala Leu  Val Ala Ser Gly Ile  Thr Asp Pro
    1175                1180                1185
```

-continued

```
Tyr Glu  Cys Tyr Lys Tyr Ile  His Val Ser Glu Leu  Gly Asn Thr
    1190                 1195                 1200

Val Gly  Ser Gly Ile Gly Gly  Met Ser Ala Leu Arg  Gly Met Tyr
    1205                 1210                 1215

Lys Asp  Arg Trp Thr Asp Lys  Pro Val Gln Lys Asp  Ile Leu Gln
    1220                 1225                 1230

Glu Ser  Phe Ile Asn Thr Ala  Asn Ala Trp Ile Asn  Met Leu Leu
    1235                 1240                 1245

Leu Ser  Ala Ser Gly Pro Ile  Lys Thr Pro Val Gly  Ala Cys Ala
    1250                 1255                 1260

Thr Ala  Val Glu Ser Val Asp  Ala Ala Val Asp Leu  Ile Thr Ser
    1265                 1270                 1275

Gly Lys  Ala Arg Ile Cys Ile  Ser Gly Gly Tyr Asp  Asp Phe Ser
    1280                 1285                 1290

Glu Glu  Gly Ser Tyr Glu Phe  Ala Asn Met Gly Ala  Thr Ser Asn
    1295                 1300                 1305

Ala Ala  Lys Glu Thr Glu Arg  Gly Arg Thr Pro Gln  Glu Met Ser
    1310                 1315                 1320

Arg Pro  Ala Thr Ser Thr Arg  Asp Gly Phe Met Glu  Ser Gln Gly
    1325                 1330                 1335

Ala Gly  Val Gln Ile Ile Met  Gln Ala Lys Leu Ala  Ile Glu Met
    1340                 1345                 1350

Gly Val  Pro Ile His Gly Ile  Val Gly Tyr Val Ser  Thr Ala Met
    1355                 1360                 1365

Asp Lys  Gln Gly Arg Ser Val  Pro Ala Pro Gly Gln  Gly Ile Leu
    1370                 1375                 1380

Thr Gly  Ala Arg Glu Ile Ala  Thr Lys Thr Pro Leu  Pro Ile Val
    1385                 1390                 1395

Asp Leu  Lys Phe Arg Ser Arg  Gln Leu Gln Arg Arg  Arg Ser Gln
    1400                 1405                 1410

Ile Gly  Glu Trp Ala Glu Arg  Glu Tyr Leu Tyr Leu  Glu Glu Glu
    1415                 1420                 1425

Leu Asp  Ala Met Lys Val Gln  Asn Pro Asp Leu Asp  Leu Glu Ala
    1430                 1435                 1440

Tyr Arg  Ile Glu Arg Ile Asn  Val Ile Lys Glu Glu  Val Val Arg
    1445                 1450                 1455

Gln Glu  Lys Glu Ala Leu Asn  Thr Phe Gly Asn Glu  Phe Trp Lys
    1460                 1465                 1470

Arg Asp  Pro Thr Ile Ala Pro  Ile Arg Gly Ala Leu  Ala Val Trp
    1475                 1480                 1485

Gly Leu  Thr Ile Asp Asp Leu  Gly Val Ala Ser Phe  His Gly Thr
    1490                 1495                 1500

Ser Thr  Lys Ala Asn Glu Lys  Asn Glu Cys Asp Val  Ile Asp Ser
    1505                 1510                 1515

Gln Leu  Thr His Leu Gly Arg  Ser Lys Gly Asn Ala  Val Tyr Gly
    1520                 1525                 1530

Val Phe  Gln Lys Tyr Leu Thr  Gly His Ser Lys Gly  Gly Ala Gly
    1535                 1540                 1545

Ala Trp  Met Leu Asn Gly Ala  Leu Gln Ile Leu Arg  Ser Gly Phe
    1550                 1555                 1560

Val Pro  Gly Asn Arg Asn Ala  Asp Asn Ile Asp Glu  Tyr Leu Ala
    1565                 1570                 1575
```

-continued

```
Arg Phe  Asp Arg Val Met Phe  Pro Ser Glu Gly Ile  Gln Thr Asp
    1580                 1585                 1590

Gly Ile  Lys Ala Ala Ser Val  Thr Ala Phe Gly Phe  Gly Gln Val
    1595                 1600                 1605

Gly Gly  Gln Val Ile Val Ile  His Pro Asp Tyr Ile  Tyr Gly Val
    1610                 1615                 1620

Ile Asp  Glu Ala Thr Tyr Asn  Ala Tyr Lys Ala Lys  Thr Ala Ala
    1625                 1630                 1635

Arg Tyr  Lys Ala Ser Tyr Arg  Tyr Thr His Asp Ala  Leu Val Tyr
    1640                 1645                 1650

Asn Asn  Leu Val Arg Ala Lys  Asp Ser Pro Pro Tyr  Thr Lys Glu
    1655                 1660                 1665

Gln Glu  Lys Ala Val Tyr Leu  Asn Pro Leu Ala Arg  Ala Ser Lys
    1670                 1675                 1680

Ser Lys  Ala Gly Thr Trp Thr  Phe Pro Ala Thr Leu  Pro Ala Glu
    1685                 1690                 1695

Ser Asp  Ile Ser Lys Thr Asn  Glu Thr Thr Arg Thr  Leu Gln Ser
    1700                 1705                 1710

Leu Thr  Thr Ser Leu Thr Asn  Ser Asn Glu Asn Val  Gly Val Asp
    1715                 1720                 1725

Val Glu  Leu Val Ser Ala Ile  Ser Ile Asp Asn Glu  Thr Phe Ile
    1730                 1735                 1740

Glu Arg  Asn Phe Thr Asp Thr  Glu Arg Lys Tyr Cys  Phe Ala Ala
    1745                 1750                 1755

Pro Asn  Pro Gln Ala Ser Phe  Ala Gly Arg Trp Ser  Ala Lys Glu
    1760                 1765                 1770

Ala Val  Phe Lys Ser Leu Gly  Ile Ser Gly Lys Gly  Ala Ala Ala
    1775                 1780                 1785

Pro Leu  Lys Asp Ile Glu Ile  Ile Ser Ser Glu Ser  Gly Ala Pro
    1790                 1795                 1800

Glu Val  Val Leu His Gly Glu  Ala Ala Lys Ala Ala  Thr Thr Ala
    1805                 1810                 1815

Gly Val  Lys Ser Val Ser Val  Ser Ile Ser His Asp  Asp Asn Gln
    1820                 1825                 1830

Ser Val  Ser Val Ala Leu Ala  His Lys
    1835                 1840


<210> SEQ ID NO 18
<211> LENGTH: 2051
<212> TYPE: PRT
<213> ORGANISM: Saccharomyces cerevisiae

<400> SEQUENCE: 18

Met Asp Ala Tyr Ser Thr Arg Pro Leu Thr Leu Ser His Gly Ser Leu
1               5                   10                  15

Glu His Val Leu Leu Val Pro Thr Ala Ser Phe Phe Ile Ala Ser Gln
            20                  25                  30

Leu Gln Glu Gln Phe Asn Lys Ile Leu Pro Glu Pro Thr Glu Gly Phe
        35                  40                  45

Ala Ala Asp Asp Glu Pro Thr Thr Pro Ala Glu Leu Val Gly Lys Phe
    50                  55                  60

Leu Gly Tyr Val Ser Ser Leu Val Glu Pro Ser Lys Val Gly Gln Phe
65                  70                  75                  80

Asp Gln Val Leu Asn Leu Cys Leu Thr Glu Phe Glu Asn Cys Tyr Leu
                85                  90                  95
```

-continued

```
Glu Gly Asn Asp Ile His Ala Leu Ala Ala Lys Leu Leu Gln Glu Asn
            100                 105                 110

Asp Thr Thr Leu Val Lys Thr Lys Glu Leu Ile Lys Asn Tyr Ile Thr
        115                 120                 125

Ala Arg Ile Met Ala Lys Arg Pro Phe Asp Lys Lys Ser Asn Ser Ala
    130                 135                 140

Leu Phe Arg Ala Val Gly Glu Gly Asn Ala Gln Leu Val Ala Ile Phe
145                 150                 155                 160

Gly Gly Gln Gly Asn Thr Asp Asp Tyr Phe Glu Glu Leu Arg Asp Leu
                165                 170                 175

Tyr Gln Thr Tyr His Val Leu Val Gly Asp Leu Ile Lys Phe Ser Ala
            180                 185                 190

Glu Thr Leu Ser Glu Leu Ile Arg Thr Thr Leu Asp Ala Glu Lys Val
        195                 200                 205

Phe Thr Gln Gly Leu Asn Ile Leu Glu Trp Leu Glu Asn Pro Ser Asn
    210                 215                 220

Thr Pro Asp Lys Asp Tyr Leu Leu Ser Ile Pro Ile Ser Cys Pro Leu
225                 230                 235                 240

Ile Gly Val Ile Gln Leu Ala His Tyr Val Val Thr Ala Lys Leu Leu
                245                 250                 255

Gly Phe Thr Pro Gly Glu Leu Arg Ser Tyr Leu Lys Gly Ala Thr Gly
            260                 265                 270

His Ser Gln Gly Leu Val Thr Ala Val Ala Ile Ala Glu Thr Asp Ser
        275                 280                 285

Trp Glu Ser Phe Phe Val Ser Val Arg Lys Ala Ile Thr Val Leu Phe
    290                 295                 300

Phe Ile Gly Val Arg Cys Tyr Glu Ala Tyr Pro Asn Thr Ser Leu Pro
305                 310                 315                 320

Pro Ser Ile Leu Glu Asp Ser Leu Glu Asn Asn Glu Gly Val Pro Ser
                325                 330                 335

Pro Met Leu Ser Ile Ser Asn Leu Thr Gln Glu Gln Val Gln Asp Tyr
            340                 345                 350

Val Asn Lys Thr Asn Ser His Leu Pro Ala Gly Lys Gln Val Glu Ile
        355                 360                 365

Ser Leu Val Asn Gly Ala Lys Asn Leu Val Val Ser Gly Pro Pro Gln
    370                 375                 380

Ser Leu Tyr Gly Leu Asn Leu Thr Leu Arg Lys Ala Lys Ala Pro Ser
385                 390                 395                 400

Gly Leu Asp Gln Ser Arg Ile Pro Phe Ser Glu Arg Lys Leu Lys Phe
                405                 410                 415

Ser Asn Arg Phe Leu Pro Val Ala Ser Pro Phe His Ser His Leu Leu
            420                 425                 430

Val Pro Ala Ser Asp Leu Ile Asn Lys Asp Leu Val Lys Asn Asn Val
        435                 440                 445

Ser Phe Asn Ala Lys Asp Ile Gln Ile Pro Val Tyr Asp Thr Phe Asp
    450                 455                 460

Gly Ser Asp Leu Arg Val Leu Ser Gly Ser Ile Ser Glu Arg Ile Val
465                 470                 475                 480

Asp Cys Ile Ile Arg Leu Pro Val Lys Trp Glu Thr Thr Thr Gln Phe
                485                 490                 495

Lys Ala Thr His Ile Leu Asp Phe Gly Pro Gly Gly Ala Ser Gly Leu
            500                 505                 510
```

-continued

```
Gly Val Leu Thr His Arg Asn Lys Asp Gly Thr Gly Val Arg Val Ile
        515                 520                 525

Val Ala Gly Thr Leu Asp Ile Asn Pro Asp Asp Asp Tyr Gly Phe Lys
    530                 535                 540

Gln Glu Ile Phe Asp Val Thr Ser Asn Gly Leu Lys Lys Asn Pro Asn
545                 550                 555                 560

Trp Leu Glu Glu Tyr His Pro Lys Leu Ile Lys Asn Lys Ser Gly Lys
                565                 570                 575

Ile Phe Val Glu Thr Lys Phe Ser Lys Leu Ile Gly Arg Pro Pro Leu
            580                 585                 590

Leu Val Pro Gly Met Thr Pro Cys Thr Val Ser Pro Asp Phe Val Ala
        595                 600                 605

Ala Thr Thr Asn Ala Gly Tyr Thr Ile Glu Leu Ala Gly Gly Gly Tyr
    610                 615                 620

Phe Ser Ala Ala Gly Met Thr Ala Ala Ile Asp Ser Val Val Ser Gln
625                 630                 635                 640

Ile Glu Lys Gly Ser Thr Phe Gly Ile Asn Leu Ile Tyr Val Asn Pro
                645                 650                 655

Phe Met Leu Gln Trp Gly Ile Pro Leu Ile Lys Glu Leu Arg Ser Lys
            660                 665                 670

Gly Tyr Pro Ile Gln Phe Leu Thr Ile Gly Ala Gly Val Pro Ser Leu
        675                 680                 685

Glu Val Ala Ser Glu Tyr Ile Glu Thr Leu Gly Leu Lys Tyr Leu Gly
    690                 695                 700

Leu Lys Pro Gly Ser Ile Asp Ala Ile Ser Gln Val Ile Asn Ile Ala
705                 710                 715                 720

Lys Ala His Pro Asn Phe Pro Ile Ala Leu Gln Trp Thr Gly Gly Arg
                725                 730                 735

Gly Gly Gly His His Ser Phe Glu Asp Ala His Thr Pro Met Leu Gln
            740                 745                 750

Met Tyr Ser Lys Ile Arg Arg His Pro Asn Ile Met Leu Ile Phe Gly
        755                 760                 765

Ser Gly Phe Gly Ser Ala Asp Asp Thr Tyr Pro Tyr Leu Thr Gly Glu
    770                 775                 780

Trp Ser Thr Lys Phe Asp Tyr Pro Pro Met Pro Phe Asp Gly Phe Leu
785                 790                 795                 800

Phe Gly Ser Arg Val Met Ile Ala Lys Glu Val Lys Thr Ser Pro Asp
                805                 810                 815

Ala Lys Lys Cys Ile Ala Ala Cys Thr Gly Val Pro Asp Asp Lys Trp
            820                 825                 830

Glu Gln Thr Tyr Lys Lys Pro Thr Gly Gly Ile Val Thr Val Arg Ser
        835                 840                 845

Glu Met Gly Glu Pro Ile His Lys Ile Ala Thr Arg Gly Val Met Leu
    850                 855                 860

Trp Lys Glu Phe Asp Glu Thr Ile Phe Asn Leu Pro Lys Asn Lys Leu
865                 870                 875                 880

Val Pro Thr Leu Glu Ala Lys Arg Asp Tyr Ile Ile Ser Arg Leu Asn
                885                 890                 895

Ala Asp Phe Gln Lys Pro Trp Phe Ala Thr Val Asn Gly Gln Ala Arg
            900                 905                 910

Asp Leu Ala Thr Met Thr Tyr Glu Glu Val Ala Lys Arg Leu Val Glu
        915                 920                 925

Leu Met Phe Ile Arg Ser Thr Asn Ser Trp Phe Asp Val Thr Trp Arg
```

-continued

```
    930                 935                 940

Thr Phe Thr Gly Asp Phe Leu Arg Arg Val Glu Glu Arg Phe Thr Lys
945                 950                 955                 960

Ser Lys Thr Leu Ser Leu Ile Gln Ser Tyr Ser Leu Leu Asp Lys Pro
                965                 970                 975

Asp Glu Ala Ile Glu Lys Val Phe Asn Ala Tyr Pro Ala Ala Arg Glu
            980                 985                 990

Gln Phe Leu Asn Ala Gln Asp Ile  Asp His Phe Leu Ser  Met Cys Gln
        995                 1000                1005

Asn Pro  Met Gln Lys Pro Val  Pro Phe Val Pro Val  Leu Asp Arg
    1010                 1015                 1020

Arg Phe  Glu Ile Phe Phe Lys  Lys Asp Ser Leu Trp  Gln Ser Glu
    1025                 1030                 1035

His Leu  Glu Ala Val Val Asp  Gln Asp Val Gln Arg  Thr Cys Ile
    1040                 1045                 1050

Leu His  Gly Pro Val Ala Ala  Gln Phe Thr Lys Val  Ile Asp Glu
    1055                 1060                 1065

Pro Ile  Lys Ser Ile Met Asp  Gly Ile His Asp Gly  His Ile Lys
    1070                 1075                 1080

Lys Leu  Leu His Gln Tyr Tyr  Gly Asp Asp Glu Ser  Lys Ile Pro
    1085                 1090                 1095

Ala Val  Glu Tyr Phe Gly Gly  Glu Ser Pro Val Asp  Val Gln Ser
    1100                 1105                 1110

Gln Val  Asp Ser Ser Ser Val  Ser Glu Asp Ser Ala  Val Phe Lys
    1115                 1120                 1125

Ala Thr  Ser Ser Thr Asp Glu  Glu Ser Trp Phe Lys  Ala Leu Ala
    1130                 1135                 1140

Gly Ser  Glu Ile Asn Trp Arg  His Ala Ser Phe Leu  Cys Ser Phe
    1145                 1150                 1155

Ile Thr  Gln Asp Lys Met Phe  Val Ser Asn Pro Ile  Arg Lys Val
    1160                 1165                 1170

Phe Lys  Pro Ser Gln Gly Met  Val Val Glu Ile Ser  Asn Gly Asn
    1175                 1180                 1185

Thr Ser  Ser Lys Thr Val Val  Thr Leu Ser Glu Pro  Val Gln Gly
    1190                 1195                 1200

Glu Leu  Lys Pro Thr Val Ile  Leu Lys Leu Leu Lys  Glu Asn Ile
    1205                 1210                 1215

Ile Gln  Met Glu Met Ile Glu  Asn Arg Thr Met Asp  Gly Lys Pro
    1220                 1225                 1230

Val Ser  Leu Pro Leu Leu Tyr  Asn Phe Asn Pro Asp  Asn Gly Phe
    1235                 1240                 1245

Ala Pro  Ile Ser Glu Val Met  Glu Asp Arg Asn Gln  Arg Ile Lys
    1250                 1255                 1260

Glu Met  Tyr Trp Lys Leu Trp  Ile Asp Glu Pro Phe  Asn Leu Asp
    1265                 1270                 1275

Phe Asp  Pro Arg Asp Val Ile  Lys Gly Lys Asp Phe  Glu Ile Thr
    1280                 1285                 1290

Ala Lys  Glu Val Tyr Asp Phe  Thr His Ala Val Gly  Asn Asn Cys
    1295                 1300                 1305

Glu Asp  Phe Val Ser Arg Pro  Asp Arg Thr Met Leu  Ala Pro Met
    1310                 1315                 1320

Asp Phe  Ala Ile Val Val Gly  Trp Arg Ala Ile Ile  Lys Ala Ile
    1325                 1330                 1335
```

-continued

```
Phe Pro Asn Thr Val Asp Gly Asp Leu Leu Lys Leu Val His Leu
    1340                1345                1350

Ser Asn Gly Tyr Lys Met Ile Pro Gly Ala Lys Pro Leu Gln Val
    1355                1360                1365

Gly Asp Val Val Ser Thr Thr Ala Val Ile Glu Ser Val Val Asn
    1370                1375                1380

Gln Pro Thr Gly Lys Ile Val Asp Val Val Gly Thr Leu Ser Arg
    1385                1390                1395

Asn Gly Lys Pro Val Met Glu Val Thr Ser Ser Phe Phe Tyr Arg
    1400                1405                1410

Gly Asn Tyr Thr Asp Phe Glu Asn Thr Phe Gln Lys Thr Val Glu
    1415                1420                1425

Pro Val Tyr Gln Met His Ile Lys Thr Ser Lys Asp Ile Ala Val
    1430                1435                1440

Leu Arg Ser Lys Glu Trp Phe Gln Leu Asp Asp Glu Asp Phe Asp
    1445                1450                1455

Leu Leu Asn Lys Thr Leu Thr Phe Glu Thr Glu Thr Glu Val Thr
    1460                1465                1470

Phe Lys Asn Ala Asn Ile Phe Ser Ser Val Lys Cys Phe Gly Pro
    1475                1480                1485

Ile Lys Val Glu Leu Pro Thr Lys Glu Thr Val Glu Ile Gly Ile
    1490                1495                1500

Val Asp Tyr Glu Ala Gly Ala Ser His Gly Asn Pro Val Val Asp
    1505                1510                1515

Phe Leu Lys Arg Asn Gly Ser Thr Leu Glu Gln Lys Val Asn Leu
    1520                1525                1530

Glu Asn Pro Ile Pro Ile Ala Val Leu Asp Ser Tyr Thr Pro Ser
    1535                1540                1545

Thr Asn Glu Pro Tyr Ala Arg Val Ser Gly Asp Leu Asn Pro Ile
    1550                1555                1560

His Val Ser Arg His Phe Ala Ser Tyr Ala Asn Leu Pro Gly Thr
    1565                1570                1575

Ile Thr His Gly Met Phe Ser Ser Ala Ser Val Arg Ala Leu Ile
    1580                1585                1590

Glu Asn Trp Ala Ala Asp Ser Val Ser Ser Arg Val Arg Gly Tyr
    1595                1600                1605

Thr Cys Gln Phe Val Asp Met Val Leu Pro Asn Thr Ala Leu Lys
    1610                1615                1620

Thr Ser Ile Gln His Val Gly Met Ile Asn Gly Arg Lys Leu Ile
    1625                1630                1635

Lys Phe Glu Thr Arg Asn Glu Asp Asp Val Val Val Leu Thr Gly
    1640                1645                1650

Glu Ala Glu Ile Glu Gln Pro Val Thr Thr Phe Val Phe Thr Gly
    1655                1660                1665

Gln Gly Ser Gln Glu Gln Gly Met Gly Met Asp Leu Tyr Lys Thr
    1670                1675                1680

Ser Lys Ala Ala Gln Asp Val Trp Asn Arg Ala Asp Asn His Phe
    1685                1690                1695

Lys Asp Thr Tyr Gly Phe Ser Ile Leu Asp Ile Val Ile Asn Asn
    1700                1705                1710

Pro Val Asn Leu Thr Ile His Phe Gly Gly Glu Lys Gly Lys Arg
    1715                1720                1725
```

-continued

Ile Arg Glu Asn Tyr Ser Ala Met Ile Phe Glu Thr Ile Val Asp
1730 1735 1740

Gly Lys Leu Lys Thr Glu Lys Ile Phe Lys Glu Ile Asn Glu His
1745 1750 1755

Ser Thr Ser Tyr Thr Phe Arg Ser Glu Lys Gly Leu Leu Ser Ala
1760 1765 1770

Thr Gln Phe Thr Gln Pro Ala Leu Thr Leu Met Glu Lys Ala Ala
1775 1780 1785

Phe Glu Asp Leu Lys Ser Lys Gly Leu Ile Pro Ala Asp Ala Thr
1790 1795 1800

Phe Ala Gly His Ser Leu Gly Glu Tyr Ala Ala Leu Ala Ser Leu
1805 1810 1815

Ala Asp Val Met Ser Ile Glu Ser Leu Val Glu Val Val Phe Tyr
1820 1825 1830

Arg Gly Met Thr Met Gln Val Ala Val Pro Arg Asp Glu Leu Gly
1835 1840 1845

Arg Ser Asn Tyr Gly Met Ile Ala Ile Asn Pro Gly Arg Val Ala
1850 1855 1860

Ala Ser Phe Ser Gln Glu Ala Leu Gln Tyr Val Val Glu Arg Val
1865 1870 1875

Gly Lys Arg Thr Gly Trp Leu Val Glu Ile Val Asn Tyr Asn Val
1880 1885 1890

Glu Asn Gln Gln Tyr Val Ala Ala Gly Asp Leu Arg Ala Leu Asp
1895 1900 1905

Thr Val Thr Asn Val Leu Asn Phe Ile Lys Leu Gln Lys Ile Asp
1910 1915 1920

Ile Ile Glu Leu Gln Lys Ser Leu Ser Leu Glu Glu Val Glu Gly
1925 1930 1935

His Leu Phe Glu Ile Ile Asp Glu Ala Ser Lys Lys Ser Ala Val
1940 1945 1950

Lys Pro Arg Pro Leu Lys Leu Glu Arg Gly Phe Ala Cys Ile Pro
1955 1960 1965

Leu Val Gly Ile Ser Val Pro Phe His Ser Thr Tyr Leu Met Asn
1970 1975 1980

Gly Val Lys Pro Phe Lys Ser Phe Leu Lys Lys Asn Ile Ile Lys
1985 1990 1995

Glu Asn Val Lys Val Ala Arg Leu Ala Gly Lys Tyr Ile Pro Asn
2000 2005 2010

Leu Thr Ala Lys Pro Phe Gln Val Thr Lys Glu Tyr Phe Gln Asp
2015 2020 2025

Val Tyr Asp Leu Thr Gly Ser Glu Pro Ile Lys Glu Ile Ile Asp
2030 2035 2040

Asn Trp Glu Lys Tyr Glu Gln Ser
2045 2050

<210> SEQ ID NO 19
<211> LENGTH: 1887
<212> TYPE: PRT
<213> ORGANISM: Saccharomyces cerevisiae

<400> SEQUENCE: 19

Met Lys Pro Glu Val Glu Gln Glu Leu Ala His Ile Leu Leu Thr Glu
1 5 10 15

Leu Leu Ala Tyr Gln Phe Ala Ser Pro Val Arg Trp Ile Glu Thr Gln
20 25 30

-continued

```
Asp Val Phe Leu Lys Asp Phe Asn Thr Glu Arg Val Val Glu Ile Gly
        35                  40                  45

Pro Ser Pro Thr Leu Ala Gly Met Ala Gln Arg Thr Leu Lys Asn Lys
    50                  55                  60

Tyr Glu Ser Tyr Asp Ala Ala Leu Ser Leu His Arg Glu Ile Leu Cys
65                  70                  75                  80

Tyr Ser Lys Asp Ala Lys Glu Ile Tyr Tyr Thr Pro Asp Pro Ser Glu
                85                  90                  95

Leu Ala Ala Lys Glu Glu Pro Ala Lys Glu Glu Ala Pro Ala Pro Thr
            100                 105                 110

Pro Ala Ala Ser Ala Pro Ala Pro Ala Ala Ala Ala Pro Ala Pro Val
        115                 120                 125

Ala Ala Ala Ala Pro Ala Ala Ala Ala Ala Glu Ile Ala Asp Glu Pro
    130                 135                 140

Val Lys Ala Ser Leu Leu Leu His Val Leu Val Ala His Lys Leu Lys
145                 150                 155                 160

Lys Ser Leu Asp Ser Ile Pro Met Ser Lys Thr Ile Lys Asp Leu Val
                165                 170                 175

Gly Gly Lys Ser Thr Val Gln Asn Glu Ile Leu Gly Asp Leu Gly Lys
            180                 185                 190

Glu Phe Gly Thr Thr Pro Glu Lys Pro Glu Glu Thr Pro Leu Glu Glu
        195                 200                 205

Leu Ala Glu Thr Phe Gln Asp Thr Phe Ser Gly Ala Leu Gly Lys Gln
    210                 215                 220

Ser Ser Ser Leu Leu Ser Arg Leu Ile Ser Ser Lys Met Pro Gly Gly
225                 230                 235                 240

Phe Thr Ile Thr Val Ala Arg Lys Tyr Leu Gln Thr Arg Trp Gly Leu
                245                 250                 255

Pro Ser Gly Arg Gln Asp Gly Val Leu Leu Val Ala Leu Ser Asn Glu
            260                 265                 270

Pro Ala Ala Arg Leu Gly Ser Glu Ala Asp Ala Lys Ala Phe Leu Asp
        275                 280                 285

Ser Met Ala Gln Lys Tyr Ala Ser Ile Val Gly Val Asp Leu Ser Ser
    290                 295                 300

Ala Ala Ser Ala Ser Gly Ala Ala Gly Ala Gly Ala Ala Ala Gly Ala
305                 310                 315                 320

Ala Met Ile Asp Ala Gly Ala Leu Glu Glu Ile Thr Lys Asp His Lys
                325                 330                 335

Val Leu Ala Arg Gln Gln Leu Gln Val Leu Ala Arg Tyr Leu Lys Met
            340                 345                 350

Asp Leu Asp Asn Gly Glu Arg Lys Phe Leu Lys Glu Lys Asp Thr Val
        355                 360                 365

Ala Glu Leu Gln Ala Gln Leu Asp Tyr Leu Asn Ala Glu Leu Gly Glu
    370                 375                 380

Phe Phe Val Asn Gly Val Ala Thr Ser Phe Ser Arg Lys Lys Ala Arg
385                 390                 395                 400

Thr Phe Asp Ser Ser Trp Asn Trp Ala Lys Gln Ser Leu Leu Ser Leu
                405                 410                 415

Tyr Phe Glu Ile Ile His Gly Val Leu Lys Asn Val Asp Arg Glu Val
            420                 425                 430

Val Ser Glu Ala Ile Asn Ile Met Asn Arg Ser Asn Asp Ala Leu Ile
        435                 440                 445
```

-continued

```
Lys Phe Met Glu Tyr His Ile Ser Asn Thr Asp Glu Thr Lys Gly Glu
    450                 455                 460

Asn Tyr Gln Leu Val Lys Thr Leu Gly Glu Gln Leu Ile Glu Asn Cys
465                 470                 475                 480

Lys Gln Val Leu Asp Val Asp Pro Val Tyr Lys Asp Val Ala Lys Pro
                485                 490                 495

Thr Gly Pro Lys Thr Ala Ile Asp Lys Asn Gly Asn Ile Thr Tyr Ser
            500                 505                 510

Glu Glu Pro Arg Glu Lys Val Arg Lys Leu Ser Gln Tyr Val Gln Glu
        515                 520                 525

Met Ala Leu Gly Gly Pro Ile Thr Lys Glu Ser Gln Pro Thr Ile Glu
    530                 535                 540

Glu Asp Leu Thr Arg Val Tyr Lys Ala Ile Ser Ala Gln Ala Asp Lys
545                 550                 555                 560

Gln Asp Ile Ser Ser Ser Thr Arg Val Glu Phe Glu Lys Leu Tyr Ser
                565                 570                 575

Asp Leu Met Lys Phe Leu Glu Ser Ser Lys Glu Ile Asp Pro Ser Gln
            580                 585                 590

Thr Thr Gln Leu Ala Gly Met Asp Val Glu Asp Ala Leu Asp Lys Asp
        595                 600                 605

Ser Thr Lys Glu Val Ala Ser Leu Pro Asn Lys Ser Thr Ile Ser Lys
    610                 615                 620

Thr Val Ser Ser Thr Ile Pro Arg Glu Thr Ile Pro Phe Leu His Leu
625                 630                 635                 640

Arg Lys Lys Thr Pro Ala Gly Asp Trp Lys Tyr Asp Arg Gln Leu Ser
                645                 650                 655

Ser Leu Phe Leu Asp Gly Leu Glu Lys Ala Ala Phe Asn Gly Val Thr
            660                 665                 670

Phe Lys Asp Lys Tyr Val Leu Ile Thr Gly Ala Gly Lys Gly Ser Ile
        675                 680                 685

Gly Ala Glu Val Leu Gln Gly Leu Leu Gln Gly Gly Ala Lys Val Val
    690                 695                 700

Val Thr Thr Ser Arg Phe Ser Lys Gln Val Thr Asp Tyr Tyr Gln Ser
705                 710                 715                 720

Ile Tyr Ala Lys Tyr Gly Ala Lys Gly Ser Thr Leu Ile Val Val Pro
                725                 730                 735

Phe Asn Gln Gly Ser Lys Gln Asp Val Glu Ala Leu Ile Glu Phe Ile
            740                 745                 750

Tyr Asp Thr Glu Lys Asn Gly Gly Leu Gly Trp Asp Leu Asp Ala Ile
        755                 760                 765

Ile Pro Phe Ala Ala Ile Pro Glu Gln Gly Ile Glu Leu Glu His Ile
    770                 775                 780

Asp Ser Lys Ser Glu Phe Ala His Arg Ile Met Leu Thr Asn Ile Leu
785                 790                 795                 800

Arg Met Met Gly Cys Val Lys Lys Gln Lys Ser Ala Arg Gly Ile Glu
                805                 810                 815

Thr Arg Pro Ala Gln Val Ile Leu Pro Met Ser Pro Asn His Gly Thr
            820                 825                 830

Phe Gly Gly Asp Gly Met Tyr Ser Glu Ser Lys Leu Ser Leu Glu Thr
        835                 840                 845

Leu Phe Asn Arg Trp His Ser Glu Ser Trp Ala Asn Gln Leu Thr Val
    850                 855                 860

Cys Gly Ala Ile Ile Gly Trp Thr Arg Gly Thr Gly Leu Met Ser Ala
```

-continued

```
865                 870                 875                 880

Asn Asn Ile Ile Ala Glu Gly Ile Glu Lys Met Gly Val Arg Thr Phe
                885                 890                 895

Ser Gln Lys Glu Met Ala Phe Asn Leu Leu Gly Leu Leu Thr Pro Glu
            900                 905                 910

Val Val Glu Leu Cys Gln Lys Ser Pro Val Met Ala Asp Leu Asn Gly
        915                 920                 925

Gly Leu Gln Phe Val Pro Glu Leu Lys Glu Phe Thr Ala Lys Leu Arg
    930                 935                 940

Lys Glu Leu Val Glu Thr Ser Glu Val Arg Lys Ala Val Ser Ile Glu
945                 950                 955                 960

Thr Ala Leu Glu His Lys Val Val Asn Gly Asn Ser Ala Asp Ala Ala
                965                 970                 975

Tyr Ala Gln Val Glu Ile Gln Pro Arg Ala Asn Ile Gln Leu Asp Phe
            980                 985                 990

Pro Glu Leu Lys Pro Tyr Lys Gln  Val Lys Gln Ile Ala  Pro Ala Glu
        995                 1000                1005

Leu Glu  Gly Leu Leu Asp Leu  Glu Arg Val Ile Val  Val Thr Gly
    1010                1015                1020

Phe Ala  Glu Val Gly Pro Trp  Gly Ser Ala Arg Thr  Arg Trp Glu
    1025                1030                1035

Met Glu  Ala Phe Gly Glu Phe  Ser Leu Glu Gly Cys  Val Glu Met
    1040                1045                1050

Ala Trp  Ile Met Gly Phe Ile  Ser Tyr His Asn Gly  Asn Leu Lys
    1055                1060                1065

Gly Arg  Pro Tyr Thr Gly Trp  Val Asp Ser Lys Thr  Lys Glu Pro
    1070                1075                1080

Val Asp  Asp Lys Asp Val Lys  Ala Lys Tyr Glu Thr  Ser Ile Leu
    1085                1090                1095

Glu His  Ser Gly Ile Arg Leu  Ile Glu Pro Glu Leu  Phe Asn Gly
    1100                1105                1110

Tyr Asn  Pro Glu Lys Lys Glu  Met Ile Gln Glu Val  Ile Val Glu
    1115                1120                1125

Glu Asp  Leu Glu Pro Phe Glu  Ala Ser Lys Glu Thr  Ala Glu Gln
    1130                1135                1140

Phe Lys  His Gln His Gly Asp  Lys Val Asp Ile Phe  Glu Ile Pro
    1145                1150                1155

Glu Thr  Gly Glu Tyr Ser Val  Lys Leu Leu Lys Gly  Ala Thr Leu
    1160                1165                1170

Tyr Ile  Pro Lys Ala Leu Arg  Phe Asp Arg Leu Val  Ala Gly Gln
    1175                1180                1185

Ile Pro  Thr Gly Trp Asn Ala  Lys Thr Tyr Gly Ile  Ser Asp Asp
    1190                1195                1200

Ile Ile  Ser Gln Val Asp Pro  Ile Thr Leu Phe Val  Leu Val Ser
    1205                1210                1215

Val Val  Glu Ala Phe Ile Ala  Ser Gly Ile Thr Asp  Pro Tyr Glu
    1220                1225                1230

Met Tyr  Lys Tyr Val His Val  Ser Glu Val Gly Asn  Cys Ser Gly
    1235                1240                1245

Ser Gly  Met Gly Gly Val Ser  Ala Leu Arg Gly Met  Phe Lys Asp
    1250                1255                1260

Arg Phe  Lys Asp Glu Pro Val  Gln Asn Asp Ile Leu  Gln Glu Ser
    1265                1270                1275
```

-continued

```
Phe Ile  Asn Thr Met Ser Ala  Trp Val Asn Met Leu  Leu Ile Ser
    1280                 1285                 1290

Ser Ser  Gly Pro Ile Lys Thr  Pro Val Gly Ala Cys  Ala Thr Ser
    1295                 1300                 1305

Val Glu  Ser Val Asp Ile Gly  Val Glu Thr Ile Leu  Ser Gly Lys
    1310                 1315                 1320

Ala Arg  Ile Cys Ile Val Gly  Gly Tyr Asp Asp Phe  Gln Glu Glu
    1325                 1330                 1335

Gly Ser  Phe Glu Phe Gly Asn  Met Lys Ala Thr Ser  Asn Thr Leu
    1340                 1345                 1350

Glu Glu  Phe Glu His Gly Arg  Thr Pro Ala Glu Met  Ser Arg Pro
    1355                 1360                 1365

Ala Thr  Thr Thr Arg Asn Gly  Phe Met Glu Ala Gln  Gly Ala Gly
    1370                 1375                 1380

Ile Gln  Ile Ile Met Gln Ala  Asp Leu Ala Leu Lys  Met Gly Val
    1385                 1390                 1395

Pro Ile  Tyr Gly Ile Val Ala  Met Ala Ala Thr Ala  Thr Asp Lys
    1400                 1405                 1410

Ile Gly  Arg Ser Val Pro Ala  Pro Gly Lys Gly Ile  Leu Thr Thr
    1415                 1420                 1425

Ala Arg  Glu His His Ser Ser  Val Lys Tyr Ala Ser  Pro Asn Leu
    1430                 1435                 1440

Asn Met  Lys Tyr Arg Lys Arg  Gln Leu Val Thr Arg  Glu Ala Gln
    1445                 1450                 1455

Ile Lys  Asp Trp Val Glu Asn  Glu Leu Glu Ala Leu  Lys Leu Glu
    1460                 1465                 1470

Ala Glu  Glu Ile Pro Ser Glu  Asp Gln Asn Glu Phe  Leu Leu Glu
    1475                 1480                 1485

Arg Thr  Arg Glu Ile His Asn  Glu Ala Glu Ser Gln  Leu Arg Ala
    1490                 1495                 1500

Ala Gln  Gln Gln Trp Gly Asn  Asp Phe Tyr Lys Arg  Asp Pro Arg
    1505                 1510                 1515

Ile Ala  Pro Leu Arg Gly Ala  Leu Ala Thr Tyr Gly  Leu Thr Ile
    1520                 1525                 1530

Asp Asp  Leu Gly Val Ala Ser  Phe His Gly Thr Ser  Thr Lys Ala
    1535                 1540                 1545

Asn Asp  Lys Asn Glu Ser Ala  Thr Ile Asn Glu Met  Met Lys His
    1550                 1555                 1560

Leu Gly  Arg Ser Glu Gly Asn  Pro Val Ile Gly Val  Phe Gln Lys
    1565                 1570                 1575

Phe Leu  Thr Gly His Pro Lys  Gly Ala Ala Gly Ala  Trp Met Met
    1580                 1585                 1590

Asn Gly  Ala Leu Gln Ile Leu  Asn Ser Gly Ile Ile  Pro Gly Asn
    1595                 1600                 1605

Arg Asn  Ala Asp Asn Val Asp  Lys Ile Leu Glu Gln  Phe Glu Tyr
    1610                 1615                 1620

Val Leu  Tyr Pro Ser Lys Thr  Leu Lys Thr Asp Gly  Val Arg Ala
    1625                 1630                 1635

Val Ser  Ile Thr Ser Phe Gly  Phe Gly Gln Lys Gly  Gly Gln Ala
    1640                 1645                 1650

Ile Val  Val His Pro Asp Tyr  Leu Tyr Gly Ala Ile  Thr Glu Asp
    1655                 1660                 1665
```

-continued

```
Arg Tyr  Asn Glu Tyr Val Ala  Lys Val Ser Ala Arg  Glu Lys Ser
    1670                 1675                 1680

Ala Tyr  Lys Phe Phe His Asn  Gly Met Ile Tyr Asn  Lys Leu Phe
    1685                 1690                 1695

Val Ser  Lys Glu His Ala Pro  Tyr Thr Asp Glu Leu  Glu Glu Asp
    1700                 1705                 1710

Val Tyr  Leu Asp Pro Leu Ala  Arg Val Ser Lys Asp  Lys Lys Ser
    1715                 1720                 1725

Gly Ser  Leu Thr Phe Asn Ser  Lys Asn Ile Gln Ser  Lys Asp Ser
    1730                 1735                 1740

Tyr Ile  Asn Ala Asn Thr Ile  Glu Thr Ala Lys Met  Ile Glu Asn
    1745                 1750                 1755

Met Thr  Lys Glu Lys Val Ser  Asn Gly Gly Val Gly  Val Asp Val
    1760                 1765                 1770

Glu Leu  Ile Thr Ser Ile Asn  Val Glu Asn Asp Thr  Phe Ile Glu
    1775                 1780                 1785

Arg Asn  Phe Thr Pro Gln Glu  Ile Glu Tyr Cys Ser  Ala Gln Pro
    1790                 1795                 1800

Ser Val  Gln Ser Ser Phe Ala  Gly Thr Trp Ser Ala  Lys Glu Ala
    1805                 1810                 1815

Val Phe  Lys Ser Leu Gly Val  Lys Ser Leu Gly Gly  Gly Ala Ala
    1820                 1825                 1830

Leu Lys  Asp Ile Glu Ile Val  Arg Val Asn Lys Asn  Ala Pro Ala
    1835                 1840                 1845

Val Glu  Leu His Gly Asn Ala  Lys Lys Ala Ala Glu  Glu Ala Gly
    1850                 1855                 1860

Val Thr  Asp Val Lys Val Ser  Ile Ser His Asp Asp  Leu Gln Ala
    1865                 1870                 1875

Val Ala  Val Ala Val Ser Thr  Lys Lys
    1880                 1885
```

<210> SEQ ID NO 20
<211> LENGTH: 2037
<212> TYPE: PRT
<213> ORGANISM: Candida albicans

<400> SEQUENCE: 20

```
Met Ser Thr His Arg Pro Phe Gln Leu Thr His Gly Ser Ile Glu His
1               5                   10                  15

Thr Leu Leu Val Pro Asn Asp Leu Phe Phe Asn Tyr Ser Gln Leu Lys
            20                  25                  30

Asp Glu Phe Ile Lys Thr Leu Pro Glu Pro Thr Glu Gly Phe Ala Gly
        35                  40                  45

Asp Asp Glu Pro Ser Ser Pro Ala Glu Leu Tyr Gly Lys Phe Ile Gly
    50                  55                  60

Phe Ile Ser Asn Ala Gln Phe Pro Gln Ile Val Glu Leu Ser Leu Lys
65                  70                  75                  80

Asp Phe Glu Ser Arg Phe Leu Asp Asn Asn Asn Asp Asn Ile His Ser
                85                  90                  95

Phe Ala Val Lys Leu Leu Asp Asp Glu Thr Tyr Pro Thr Thr Ile Ala
            100                 105                 110

Lys Val Lys Glu Asn Ile Val Lys Asn Tyr Tyr Lys Ala Val Lys Ser
        115                 120                 125

Ile Asn Lys Val Glu Ser Asn Leu Leu Tyr His Cys Lys His Asp Ala
    130                 135                 140
```

-continued

```
Lys Leu Val Ala Ile Phe Gly Gly Gln Gly Asn Thr Asp Asp Tyr Phe
145                 150                 155                 160

Glu Glu Leu Arg Glu Leu Tyr Thr Leu Tyr Gln Gly Leu Ile Glu Asp
                165                 170                 175

Leu Leu Val Ser Ile Ala Glu Lys Leu Asn Gln Leu His Pro Ser Phe
            180                 185                 190

Asp Lys Ile Tyr Thr Gln Gly Leu Asn Ile Leu Ser Trp Leu Lys His
        195                 200                 205

Pro Glu Thr Thr Pro Asp Gln Asp Tyr Leu Leu Ser Val Pro Val Ser
    210                 215                 220

Cys Pro Val Ile Cys Val Ile Gln Leu Cys His Tyr Thr Ile Thr Cys
225                 230                 235                 240

Lys Val Leu Gly Leu Thr Pro Gly Glu Phe Arg Asn Ser Leu Lys Trp
                245                 250                 255

Ser Thr Gly His Ser Gln Gly Leu Val Thr Ala Val Thr Ile Ala Ala
            260                 265                 270

Ser Asp Ser Trp Asp Ser Phe Leu Lys Asn Ser Leu Thr Ala Val Ser
        275                 280                 285

Leu Leu Leu Phe Ile Gly Ser Arg Cys Leu Ser Thr Tyr Pro Arg Thr
    290                 295                 300

Ser Leu Pro Pro Thr Met Leu Gln Asp Ser Leu Asp Asn Gly Glu Gly
305                 310                 315                 320

Arg Pro Ser Pro Met Leu Ser Val Arg Asp Leu Ser Ile Lys Gln Val
                325                 330                 335

Glu Lys Phe Ile Glu Gln Thr Asn Ser His Leu Pro Arg Glu Lys His
            340                 345                 350

Ile Ala Ile Ser Leu Ile Asn Gly Ala Arg Asn Leu Val Leu Ser Gly
        355                 360                 365

Pro Pro Glu Ser Leu Tyr Gly Phe Asn Leu Asn Leu Arg Asn Gln Lys
    370                 375                 380

Ala Pro Met Gly Leu Asp Gln Ser Arg Val Pro Phe Ser Glu Arg Lys
385                 390                 395                 400

Leu Lys Cys Ser Asn Arg Phe Leu Pro Ile Phe Ala Pro Phe His Ser
                405                 410                 415

His Leu Leu Ala Asp Ala Thr Glu Leu Ile Leu Asp Asp Val Lys Glu
            420                 425                 430

His Gly Leu Ser Phe Glu Gly Leu Lys Ile Pro Val Tyr Asp Thr Phe
        435                 440                 445

Asp Gly Ser Asp Phe Gln Ala Leu Lys Glu Pro Ile Ile Asp Arg Val
    450                 455                 460

Val Lys Leu Ile Thr Glu Leu Pro Val His Trp Glu Glu Ala Thr Asn
465                 470                 475                 480

His Lys Ala Thr His Ile Leu Asp Phe Gly Pro Gly Gly Val Ser Gly
                485                 490                 495

Leu Gly Val Leu Thr His Arg Asn Lys Glu Gly Thr Gly Ala Arg Ile
            500                 505                 510

Ile Leu Ala Gly Thr Leu Asp Ser Asn Pro Ile Asp Asp Glu Tyr Gly
        515                 520                 525

Phe Lys His Glu Ile Phe Gln Thr Ser Ala Asp Lys Ala Ile Lys Trp
    530                 535                 540

Ala Pro Asp Trp Leu Lys Glu Leu Arg Pro Thr Leu Val Lys Asn Ser
545                 550                 555                 560
```

-continued

```
Glu Gly Lys Ile Tyr Val Lys Thr Lys Phe Ser Gln Leu Leu Gly Arg
                565                 570                 575

Ala Pro Leu Met Val Ala Gly Met Thr Pro Thr Thr Val Asn Thr Asp
            580                 585                 590

Ile Val Ser Ala Ser Leu Asn Ala Gly Tyr His Ile Glu Leu Ala Gly
        595                 600                 605

Gly Gly Tyr Phe Ser Pro Val Met Met Thr Arg Ala Ile Asp Asp Ile
    610                 615                 620

Val Ser Arg Ile Lys Pro Gly Tyr Gly Leu Gly Ile Asn Leu Ile Tyr
625                 630                 635                 640

Val Asn Pro Phe Met Leu Gln Trp Gly Ile Pro Leu Ile Lys Asp Leu
                645                 650                 655

Arg Glu Lys Gly Tyr Pro Ile Gln Ser Leu Thr Ile Gly Ala Gly Val
            660                 665                 670

Pro Ser Ile Glu Val Ala Thr Glu Tyr Ile Glu Asp Leu Gly Leu Thr
        675                 680                 685

His Leu Gly Leu Lys Pro Gly Ser Val Asp Ala Ile Ser Gln Val Ile
    690                 695                 700

Ala Ile Ala Lys Ala His Pro Thr Phe Pro Ile Val Leu Gln Trp Thr
705                 710                 715                 720

Gly Gly Arg Gly Gly Gly His His Ser Phe Glu Asp Phe His Gln Pro
                725                 730                 735

Ile Ile Gln Met Tyr Ser Lys Ile Arg Arg Cys Ser Asn Ile Val Leu
            740                 745                 750

Val Ala Gly Ser Gly Phe Gly Ser Asp Glu Asp Thr Tyr Pro Tyr Leu
        755                 760                 765

Ser Gly Tyr Trp Ser Glu Lys Phe Asn Tyr Pro Pro Met Pro Phe Asp
    770                 775                 780

Gly Val Leu Phe Gly Ser Arg Val Met Thr Ser Lys Glu Ser His Thr
785                 790                 795                 800

Ser Leu Ala Ala Lys Lys Leu Ile Val Glu Cys Lys Gly Val Pro Asp
                805                 810                 815

Gln Gln Trp Glu Gln Thr Tyr Lys Lys Pro Thr Gly Gly Ile Ile Thr
            820                 825                 830

Val Arg Ser Glu Met Gly Glu Pro Ile His Lys Ile Ala Thr Arg Gly
        835                 840                 845

Val Met Phe Trp Lys Glu Leu Asp Asp Thr Ile Phe Asn Leu Pro Lys
    850                 855                 860

Asn Lys Leu Leu Asp Ala Leu Asn Lys Lys Arg Asp His Ile Ile Lys
865                 870                 875                 880

Lys Leu Asn Asn Asp Phe Gln Lys Pro Trp Phe Gly Lys Asn Ala Asn
                885                 890                 895

Gly Val Cys Asp Leu Gln Glu Met Thr Tyr Lys Glu Val Ala Asn Arg
            900                 905                 910

Leu Val Glu Leu Met Tyr Val Lys Lys Ser His Arg Trp Ile Asp Val
        915                 920                 925

Ser Leu Arg Asn Met Tyr Gly Asp Phe Leu Arg Arg Val Glu Glu Arg
    930                 935                 940

Phe Thr Ser Ser Ala Gly Thr Val Ser Leu Leu Gln Asn Phe Asn Gln
945                 950                 955                 960

Leu Asn Glu Pro Glu Gln Phe Thr Ala Asp Phe Phe Glu Lys Phe Pro
                965                 970                 975

Gln Ala Gly Lys Gln Leu Ile Ser Glu Glu Asp Cys Asp Tyr Phe Leu
```

-continued

```
            980                 985                 990

Met Leu Ala Ala Arg Pro Gly Gln  Lys Pro Val Pro Phe  Val Pro Val
        995                 1000                1005

Leu Asp  Glu Arg Phe Glu Phe  Phe Phe Lys Lys Asp  Ser Leu Trp
    1010                 1015                 1020

Gln Ser  Glu Asp Leu Glu Ser  Val Val Asp Glu Asp  Val Gln Arg
    1025                 1030                 1035

Thr Cys  Ile Leu His Gly Pro  Val Ala Ser Gln Tyr  Thr Ser Lys
    1040                 1045                 1050

Val Asp  Glu Pro Ile Gly Asp  Ile Leu Asn Ser Ile  His Glu Gly
    1055                 1060                 1065

His Ile  Ala Arg Leu Ile Lys  Glu Glu Tyr Ala Gly  Asp Glu Ser
    1070                 1075                 1080

Lys Ile  Pro Val Val Glu Tyr  Phe Gly Gly Lys Lys  Pro Ala Ser
    1085                 1090                 1095

Val Ser  Ala Thr Ser Val Asn  Ile Ile Asp Gly Asn  Gln Val Val
    1100                 1105                 1110

Tyr Glu  Ile Asp Ser Glu Leu  Pro Asn Lys Gln Glu  Trp Leu Asp
    1115                 1120                 1125

Leu Leu  Ala Gly Thr Glu Leu  Asn Trp Leu Gln Ala  Phe Ile Ser
    1130                 1135                 1140

Thr Asp  Arg Ile Val Gln Gly  Ser Lys His Val Ser  Asn Pro Leu
    1145                 1150                 1155

His Asp  Ile Leu Thr Pro Ala  Lys His Ser Lys Val  Thr Ile Asp
    1160                 1165                 1170

Lys Lys  Thr Lys Lys Leu Thr  Ala Phe Glu Asn Ile  Lys Gly Asp
    1175                 1180                 1185

Leu Leu  Pro Val Val Glu Ile  Glu Leu Val Lys Pro  Asn Thr Ile
    1190                 1195                 1200

Gln Leu  Ser Leu Ile Glu His  Arg Thr Ala Asp Thr  Asn Pro Val
    1205                 1210                 1215

Ala Leu  Pro Phe Leu Tyr Lys  Tyr Asn Pro Ala Asp  Gly Phe Ala
    1220                 1225                 1230

Pro Ile  Leu Glu Ile Met Glu  Asp Arg Asn Glu Arg  Ile Lys Glu
    1235                 1240                 1245

Phe Tyr  Trp Lys Leu Trp Phe  Gly Ser Ser Val Pro  Tyr Ser Asn
    1250                 1255                 1260

Asp Ile  Asn Val Glu Lys Ala  Ile Leu Gly Asp Glu  Ile Thr Ile
    1265                 1270                 1275

Ser Ser  Gln Thr Ile Ser Glu  Phe Thr His Ala Ile  Gly Asn Lys
    1280                 1285                 1290

Cys Asp  Ala Phe Val Asp Arg  Pro Gly Lys Ala Thr  Leu Ala Pro
    1295                 1300                 1305

Met Asp  Phe Ala Ile Val Ile  Gly Trp Lys Ala Ile  Ile Lys Ala
    1310                 1315                 1320

Ile Phe  Pro Lys Ser Val Asp  Gly Asp Leu Leu Lys  Leu Val His
    1325                 1330                 1335

Leu Ser  Asn Gly Tyr Lys Met  Ile Thr Gly Ala Ala  Pro Leu Lys
    1340                 1345                 1350

Lys Gly  Asp Val Val Ser Thr  Lys Ala Glu Ile Lys  Ala Val Leu
    1355                 1360                 1365

Asn Gln  Pro Ser Gly Lys Leu  Val Glu Val Val Gly  Thr Ile Tyr
    1370                 1375                 1380
```

-continued

```
Arg Glu  Gly Lys Pro Val Met  Glu Val Thr Ser Gln  Phe Leu Tyr
    1385                 1390                 1395

Arg Gly  Glu Tyr Asn Asp Tyr  Cys Asn Thr Phe Gln  Lys Val Thr
    1400                 1405                 1410

Glu Thr  Pro Val Gln Val Ala  Phe Lys Ser Ala Lys  Asp Leu Ala
    1415                 1420                 1425

Val Leu  Arg Ser Lys Glu Trp  Phe His Leu Glu Lys  Asp Val Gln
    1430                 1435                 1440

Phe Asp  Val Leu Thr Phe Arg  Cys Glu Ser Thr Tyr  Lys Phe Lys
    1445                 1450                 1455

Ser Ala  Asn Val Tyr Ser Ser  Ile Lys Thr Thr Gly  Gln Val Leu
    1460                 1465                 1470

Leu Glu  Leu Pro Thr Lys Glu  Val Ile Gln Val Gly  Ser Val Asp
    1475                 1480                 1485

Tyr Glu  Ala Gly Thr Ser Tyr  Gly Asn Pro Val Thr  Asp Tyr Leu
    1490                 1495                 1500

Ser Arg  Asn Gly Lys Thr Ile  Glu Glu Ser Val Ile  Phe Glu Asn
    1505                 1510                 1515

Ala Ile  Pro Leu Ser Ser Gly  Glu Glu Leu Thr Ser  Lys Ala Pro
    1520                 1525                 1530

Gly Thr  Asn Glu Pro Tyr Ala  Ile Val Ser Gly Asp  Tyr Asn Pro
    1535                 1540                 1545

Ile His  Val Ser Arg Val Phe  Ala Ala Tyr Ala Lys  Leu Pro Gly
    1550                 1555                 1560

Thr Ile  Thr His Gly Met Tyr  Ser Ser Ala Ser Ile  Arg Ala Leu
    1565                 1570                 1575

Val Glu  Glu Trp Ala Ala Asn  Asn Val Ala Ala Arg  Val Arg Ala
    1580                 1585                 1590

Phe Lys  Cys Asp Phe Val Gly  Met Val Leu Pro Asn  Asp Thr Leu
    1595                 1600                 1605

Gln Thr  Thr Met Glu His Val  Gly Met Ile Asn Gly  Arg Lys Ile
    1610                 1615                 1620

Ile Lys  Val Glu Thr Arg Asn  Val Glu Thr Glu Leu  Pro Val Leu
    1625                 1630                 1635

Ile Gly  Glu Ala Glu Ile Glu  Gln Pro Thr Thr Thr  Tyr Val Phe
    1640                 1645                 1650

Thr Gly  Gln Gly Ser Gln Glu  Gln Gly Met Gly Met  Glu Leu Tyr
    1655                 1660                 1665

Asn Ser  Ser Glu Val Ala Arg  Glu Val Trp Asp Lys  Ala Asp Arg
    1670                 1675                 1680

His Phe  Val Asn Asn Tyr Gly  Phe Ser Ile Leu Asp  Ile Val Gln
    1685                 1690                 1695

Asn Asn  Pro Asn Glu Leu Thr  Ile His Phe Gly Gly  Ala Lys Gly
    1700                 1705                 1710

Arg Ala  Ile Arg Asp Asn Tyr  Ile Gly Met Met Phe  Glu Thr Ile
    1715                 1720                 1725

Gly Glu  Asp Gly Ala Leu Lys  Ser Glu Lys Ile Phe  Lys Asp Ile
    1730                 1735                 1740

Asp Glu  Thr Thr Thr Ser Tyr  Thr Phe Val Ser Pro  Thr Gly Leu
    1745                 1750                 1755

Leu Ser  Ala Thr Gln Phe Thr  Gln Pro Ala Leu Thr  Leu Met Glu
    1760                 1765                 1770
```

-continued

```
Lys Ala  Ala Tyr Glu Asp Ile  Lys Ser Lys Gly Leu  Ile Pro Ser
    1775                 1780                 1785

Asp Ile  Met Phe Ala Gly His  Ser Leu Gly Glu Tyr  Ser Ala Leu
    1790                 1795                 1800

Ser Ser  Leu Ala Asn Val Met  Pro Ile Glu Ser Leu  Val Asp Val
    1805                 1810                 1815

Val Phe  Tyr Arg Gly Met Thr  Met Gln Val Ala Val  Pro Arg Asp
    1820                 1825                 1830

Glu Leu  Gly Arg Ser Asn Tyr  Gly Met Val Ala Val  Asn Pro Ser
    1835                 1840                 1845

Arg Val  Ser Ala Thr Phe Asp  Asp Ser Ala Leu Arg  Phe Val Val
    1850                 1855                 1860

Asp Glu  Val Ala Asn Lys Thr  Lys Trp Leu Leu Glu  Ile Val Asn
    1865                 1870                 1875

Tyr Asn  Val Glu Asn Gln Gln  Tyr Val Ala Ala Gly  Asp Leu Arg
    1880                 1885                 1890

Ala Leu  Asp Thr Leu Thr Asn  Val Leu Asn Val Leu  Lys Ile Asn
    1895                 1900                 1905

Lys Ile  Asp Ile Val Lys Leu  Gln Glu Gln Met Ser  Ile Glu Lys
    1910                 1915                 1920

Val Lys  Glu His Leu Tyr Glu  Ile Val Asp Glu Val  Ala Ala Lys
    1925                 1930                 1935

Ser Leu  Ala Lys Pro Gln Pro  Ile Asp Leu Glu Arg  Gly Phe Ala
    1940                 1945                 1950

Val Ile  Pro Leu Lys Gly Ile  Ser Val Pro Phe His  Ser Ser Tyr
    1955                 1960                 1965

Leu Met  Ser Gly Val Lys Pro  Phe Gln Arg Phe Leu  Cys Lys Lys
    1970                 1975                 1980

Ile Pro  Lys Ser Ser Val Lys  Pro Gln Asp Leu Ile  Gly Lys Tyr
    1985                 1990                 1995

Ile Pro  Asn Leu Thr Ala Lys  Pro Phe Glu Leu Thr  Lys Glu Tyr
    2000                 2005                 2010

Phe Gln  Ser Val Tyr Asp Leu  Thr Lys Ser Glu Lys  Ile Lys Ser
    2015                 2020                 2025

Ile Leu  Asp Asn Trp Glu Gln  Tyr Glu
    2030                 2035
```

<210> SEQ ID NO 21
<211> LENGTH: 6072
<212> TYPE: DNA
<213> ORGANISM: Candida albicans

<400> SEQUENCE: 21

```
ggatcctttt ttttttgggt aatattaaca atccagctta ggccatattg ttgggtgtcc     60

ttaaaaatta tgtgccaatt atttacttat atattgatat agctctcctt ttctcttttt    120

tatatttttc aaagtttttt ttattctttt actgtttatt caactaactt gtttttattt    180

ctcccccaat taacaatgaa accagaaatt gaacaagaat tatcccacac tttgttaact    240

gaattgttgg catatcaatt tgcttctcca gttagatgga ttgaaactca agatgtcttt    300

ttaaaacagc ataatactga aagaatcatc gaaattggtc cttcaccaac tttagctggt    360

atggccaata gaactatcaa agccaaatat gaatcctatg atgctgcttt atctttgcaa    420

cgacaagtct tgtgttactc caaagatgct aaggagattt actacaagcc agatccagca    480

gatcttgctc ctaaggaaac accaaagcaa gaagagagta ccccatcagc tcctgccgct    540
```

-continued

```
gccactccaa cacctgctgc tgccgctgct cctactccag caccagctcc tgcaagtgct    600
ggcccagttg aatctattcc agatgaacca gtcaaggcta acttgttaat ccatgttttg    660
gttgcacaaa aattaaagaa acctttagat gctgttccaa tgaccaaggc aattaaggat    720
ttggttaatg gtaaatccac tgttcaaaat gaaattcttg gtgacttggg taaggaattt    780
ggctctactc ctgaaaaacc ggaagacact ccattggaag aattagctga acaattccaa    840
gattcattca gcggtcaatt aggaaagact tctacttcat tgattggtag attaatgtcc    900
tcaaagatgc cgggtggatt ttccatcact actgctagaa agtatttgga atcaagattt    960
ggtttgggtg ctggtagaca agattctgtc ttgttgatgg ctttaacaaa tgaaccagct   1020
aatagattag gttctgaagc cgatgcaaaa actttctttg atggaattgc tcaaaaatac   1080
gcatcaagtg ctgggatctc cttgtcatca ggagcaggct ccggtgcagg cgccgcaaat   1140
agtggtggtg ctgttgttga tagtgctgcc ttagatgctt taacagctga aaacaagaaa   1200
ttagccaaac agcaattaga agttttagca agatacttgc aaagtcgact taaacaaggg   1260
agccttaaat cttttatcaa ggaaaaggaa gcttctgctg ttttacaaaa agagttagat   1320
ttgtgggaag cagaacacgg agaattctat gctaagggta tccaaccaac tttctccgca   1380
ttaaagtcta gaacttatga ctcctattgg aattgggccc gtcaagacgt tttatcaatg   1440
tatttcgaca ttatttttgg caagttaact tctgttgata gagaaaccat caaccaatgt   1500
attcaaatca tgaacagagc caatccaact ttaatcaagt ttatgcaata tcatatcgac   1560
cattgtccag aatataaagg tgaaacttat aaattggcca agagattggg tcaacaattg   1620
attgacaact gtaaacaagt tttgactgaa gatccagttt acaaagatgt ttccagaatt   1680
actggtccaa agactaaagt cagtgctaag ggtaacattg aatatgagga aactcaaaag   1740
gattcagtta gaaaatttga acaatatgtg tatgaaatgg cccaaggtgg tgctatgacc   1800
aaagttagtc aaccaactat tcaagaagat ttagctagag tttacaaggc tatttccaaa   1860
caagcttcca aagatagcaa attggaattg caaagagttt acgaagattt attgaaggtg   1920
gttgaaagtt ccaaggaaat cgaaaccgaa caattgacta aagatatttt acaagctgct   1980
acagttccaa caaccccaac agaggaagta gacgatcctt gtactccttc ttcggatgat   2040
gaaattgctt ctttaccaga taagacttct atcattcaac ctgtctcgtc tactattcca   2100
tctcaaacta ttccattttt gcacattcag aaaaagacca aagacggttg ggaatacaat   2160
aagaaattat cttctcttta cttggatgga ttggaatcag ctgccattaa tggtttaact   2220
ttcaaagaca agtatgtctt agttactggt gctggtgctg gctctattgg tgccgaaatt   2280
ttgcaaggtt taatcagtgg tggtgccaaa gttattgtca caacctctag attttccaag   2340
aaagttaccg agtattatca aaacatgtat gccagatatg gtgctgctgg gtctacttta   2400
attgttgttc cgttcaacca aggttctaaa caagatgttg atgcattggt tcaatacatt   2460
tatgatgagc caaagaaagg tggtttgggt tgggatttgg atgcaatcat tccatttgct   2520
gctattccag aaaatggtaa tggtctcgac aacattgatt ctaaatctga atttgcccac   2580
agaatcatgt tgaccaacct tttaagattg ttaggtgctg ttaaatccaa aaagcccact   2640
gacactagac ctgctcaatg tattttgcca ttatctccaa atcacggaac ttttggtttt   2700
gacgggttgt actctgaatc taaaatctca ttggaaacct tattcaacag atggtattct   2760
gaagattggg gatccaagtt gactgtttgt ggtgccgtaa ttgggtggac tagaggtaca   2820
ggtttgatga gtgccaataa cattattgct gaaggtattg aaaaattggg tgtcagaact   2880
```

-continued

```
ttctcccaaa aggaaatggc tttcaatatt ttaggtttat tgacaccaga aattgtacaa   2940
ttatgtcaag aagaaccagt tatggctgac ttgaatggtg gtttgcaatt cattgacaac   3000
ttgaaggatt tcacatctaa attaagaacc gacttgttgg aaactgcaga cattagaaga   3060
gctgtttcta ttgaatcagc tatcgagcaa aaagttgtca atggtgacaa tgtcgatgca   3120
aactactcaa aggttatggt tgaacctaga gccaacatga aatttgattt cccaactttg   3180
aaatcttatg atgaaatcaa acaaattgct ccagaattgg aaggtatgtt ggatttggaa   3240
aatgttgtcg ttgtgacagg ttttgctgaa gttggtccat ggggtaactc tagaaccaga   3300
tgggaaatgg aagcttatgg tgagttctca ttggaaggtg ccattgaaat ggcttggatt   3360
atgggtttca tcaagtatca taatggtaat ttgcaaggga aaccatactc tggatgggtt   3420
gatgccaaga ctcaaactcc aattgacgaa aaggatatca aatccaaata tgaagaagaa   3480
attttagaac attccggtat tagattgatt gagccagaat tgttcaatgg ctatgatcca   3540
aagaaaaaac aaatgattca agaaattgtt gttcaacacg atttagaacc atttgaatgt   3600
tctaaagaaa cagctgagca atacaaacac gaacacggag aaaaatgtga aatttttgaa   3660
attgaagaaa gtggtgaata cacagttaga atcttgaaag gtgcaacatt gtacgttccg   3720
aaagctttga gatttgatag attagttgct ggtcaaattc caactggttg ggacgctcgt   3780
acctatggta tcccagaaga cactattagt caagttgatc caatcacttt gtacgtgttg   3840
gttgccactg ttgaagcctt gttgtctgct ggtattactg atccatatga attctacaaa   3900
tacgttcatg tgtctgaagt tggtaactgt tctggttccg gtatgggagg tgtctctgct   3960
ttgagaggaa tgttcaaaga tagatatgct gacaaaccag ttcaaaatga cattttgcaa   4020
gaatcattta tcaacactat gtctgcttgg gtcaatatgt tgttgttgtc ttcctctggt   4080
ccaatcaaga caccagtcgg tgcttgtgcc actgctgttg aatcggttga cattggtatt   4140
gaaacaattt tgtctggtaa agctaaagta gttttggtag gtggttacga tgacttccaa   4200
gaagaagggt cttatgaatt cgccaatatg aatgctactt ctaattctat tgaagagttc   4260
aaacacggaa gaacaccaaa ggaaatgtca agaccaacta ctactaccag aaatggtttc   4320
atggaagctc aaggttctgg tattcaagtt atcatgactg ctgatttggc tctcaagatg   4380
ggtgttccaa tccacgctgt attggccatg actgctactg ccactgataa gattggtaga   4440
tctgttccag caccaggtaa aggtattttg accactgcca gagaacatca tggcaacttg   4500
aagtacccat ctccactttt gaacatcaag tacaggaaga gacaattgaa caaaagattg   4560
gaacaaatca aatcttggga agaaacagaa ctttcttact tgcaagaaga agccgagttg   4620
gccaaagaag aatttggtga cgaattttct atgcatgagt tcttgaaaga gagaactgaa   4680
gaagtgtacc gtgaatcaaa gagacaagtt tctgatgcta agaaacaatg ggtaattca    4740
ttctacaagt ctgatccaag aattgctcca ttgagaggag cattggctgc cttcaactta   4800
accatcgatg atattggtgt tgcatccttc catggtactt ccaccgttgc taacgataag   4860
aatgaatctg ccacaatcaa caatatgatg aaacacttgg gtagatccga aggtaaccca   4920
gtatttggtg ttttccaaaa atacttgaca ggtcatccaa aaggtgcagc tggtgcttgg   4980
atgttgaatg gtgccattca aattcttgag tctggtcttg ttccaggtaa cagaaatgcg   5040
gataatgttg ataagctttt agaacaatac gaatatgtat tgtacccatc aagatcaatt   5100
caaaccgatg gtattaaagc cgtttctgtt acatcatttg gtttcggtca aaaaggtgca   5160
caagccgttg ttgttcatcc agattactta tttgctgttt tggatagatc cacttatgaa   5220
gaatatgcta ctaaggtctc tgctagaaat aaaaagacct accgttacat gcacaatgca   5280
```

-continued

```
atcaccagaa acactatgtt tgttgccaaa gacaaagctc catatagtga cgaattggaa   5340
caaccagttt acttggatcc attggctcgt gttgaagaaa acaagaaaaa gttggtattc   5400
agtgacaaaa caattcaatc gaaccaatct tatgttggag aagttgctca aaaaactgct   5460
aaggcattgt ctactttaaa caaatcatca aagggagttg gtgtagatgt tgaattgttg   5520
tcagcaatca atatcgacaa tgaaaccttt attgaaagaa actttactgg taatgaagtt   5580
gaatactgtt tgaatactgc tcacccacaa gcttcattca ctggaacttg gtcagcaaag   5640
gaagctgttt tcaaagcctt gggtgttgaa tcaaaaggtg ctggagcaag cttgattgat   5700
attgaaatca ctcgtgacgt taatggtgct cctaaagtaa ttttgcatgg tgaggccaaa   5760
aaagctgctg ctaaagctgg tgttaaaaat gtcaatattt caatttctca tgatgatttc   5820
caagctactg ctgttgcttt aagtgaattt taaaattagt agtgtttaga aatattcgtg   5880
tatatctgat caaaaacttt tttgattttt aatatatgtc cggttgtaca attttttttt   5940
ctgttgattt aaactgatct cattattttg ttctctcaca gctcacagcc tacaaccata   6000
aaaaaagccc aacactcact tttgctcact ggttcaccac cactacggaa aaaataagaa   6060
caacaaataa aa                                                       6072
```

<210> SEQ ID NO 22
<211> LENGTH: 1885
<212> TYPE: PRT
<213> ORGANISM: Candida albicans

<400> SEQUENCE: 22

```
Met Lys Pro Glu Ile Glu Gln Glu Leu Ser His Thr Leu Leu Thr Glu
1               5                   10                  15

Leu Leu Ala Tyr Gln Phe Ala Ser Pro Val Arg Trp Ile Glu Thr Gln
            20                  25                  30

Asp Val Phe Leu Lys Gln His Asn Thr Glu Arg Ile Ile Glu Ile Gly
        35                  40                  45

Pro Ser Pro Thr Leu Ala Gly Met Ala Asn Arg Thr Ile Lys Ala Lys
    50                  55                  60

Tyr Glu Ser Tyr Asp Ala Ala Leu Ser Leu Gln Arg Gln Val Leu Cys
65                  70                  75                  80

Tyr Ser Lys Asp Ala Lys Glu Ile Tyr Tyr Lys Pro Asp Pro Ala Asp
                85                  90                  95

Leu Ala Pro Lys Glu Thr Pro Lys Gln Glu Glu Ser Thr Pro Ser Ala
            100                 105                 110

Pro Ala Ala Ala Thr Pro Thr Pro Ala Ala Ala Ala Ala Pro Thr Pro
        115                 120                 125

Ala Pro Ala Pro Ala Ser Ala Gly Pro Val Glu Ser Ile Pro Asp Glu
    130                 135                 140

Pro Val Lys Ala Asn Leu Leu Ile His Val Leu Val Ala Gln Lys Leu
145                 150                 155                 160

Lys Lys Pro Leu Asp Ala Val Pro Met Thr Lys Ala Ile Lys Asp Leu
                165                 170                 175

Val Asn Gly Lys Ser Thr Val Gln Asn Glu Ile Leu Gly Asp Leu Gly
            180                 185                 190

Lys Glu Phe Gly Ser Thr Pro Glu Lys Pro Glu Asp Thr Pro Leu Glu
        195                 200                 205

Glu Leu Ala Glu Gln Phe Gln Asp Ser Phe Ser Gly Gln Leu Gly Lys
    210                 215                 220
```

-continued

```
Thr Ser Thr Ser Leu Ile Gly Arg Leu Met Ser Ser Lys Met Pro Gly
225                 230                 235                 240

Gly Phe Ser Ile Thr Thr Ala Arg Lys Tyr Leu Glu Ser Arg Phe Gly
                245                 250                 255

Leu Gly Ala Gly Arg Gln Asp Ser Val Leu Leu Met Ala Leu Thr Asn
            260                 265                 270

Glu Pro Ala Asn Arg Leu Gly Ser Glu Ala Asp Ala Lys Thr Phe Phe
        275                 280                 285

Asp Gly Ile Ala Gln Lys Tyr Ala Ser Ser Ala Gly Ile Ser Leu Ser
    290                 295                 300

Ser Gly Ala Gly Ser Gly Ala Gly Ala Ala Asn Ser Gly Gly Ala Val
305                 310                 315                 320

Val Asp Ser Ala Ala Leu Asp Ala Leu Thr Ala Glu Asn Lys Lys Leu
                325                 330                 335

Ala Lys Gln Gln Leu Glu Val Leu Ala Arg Tyr Leu Gln Ser Arg Leu
            340                 345                 350

Lys Gln Gly Ser Leu Lys Ser Phe Ile Lys Glu Lys Glu Ala Ser Ala
        355                 360                 365

Val Leu Gln Lys Glu Leu Asp Leu Trp Glu Ala Glu His Gly Glu Phe
    370                 375                 380

Tyr Ala Lys Gly Ile Gln Pro Thr Phe Ser Ala Leu Lys Ser Arg Thr
385                 390                 395                 400

Tyr Asp Ser Tyr Trp Asn Trp Ala Arg Gln Asp Val Leu Ser Met Tyr
                405                 410                 415

Phe Asp Ile Ile Phe Gly Lys Leu Thr Ser Val Asp Arg Glu Thr Ile
            420                 425                 430

Asn Gln Cys Ile Gln Ile Met Asn Arg Ala Asn Pro Thr Leu Ile Lys
        435                 440                 445

Phe Met Gln Tyr His Ile Asp His Cys Pro Glu Tyr Lys Gly Glu Thr
    450                 455                 460

Tyr Lys Leu Ala Lys Arg Leu Gly Gln Gln Leu Ile Asp Asn Cys Lys
465                 470                 475                 480

Gln Val Leu Thr Glu Asp Pro Val Tyr Lys Asp Val Ser Arg Ile Thr
                485                 490                 495

Gly Pro Lys Thr Lys Val Ser Ala Lys Gly Asn Ile Glu Tyr Glu Glu
            500                 505                 510

Thr Gln Lys Asp Ser Val Arg Lys Phe Glu Gln Tyr Val Tyr Glu Met
        515                 520                 525

Ala Gln Gly Gly Ala Met Thr Lys Val Ser Gln Pro Thr Ile Gln Glu
    530                 535                 540

Asp Leu Ala Arg Val Tyr Lys Ala Ile Ser Lys Gln Ala Ser Lys Asp
545                 550                 555                 560

Ser Lys Leu Glu Leu Gln Arg Val Tyr Glu Asp Leu Leu Lys Val Val
                565                 570                 575

Glu Ser Ser Lys Glu Ile Glu Thr Glu Gln Leu Thr Lys Asp Ile Leu
            580                 585                 590

Gln Ala Ala Thr Val Pro Thr Thr Pro Thr Glu Glu Val Asp Asp Pro
        595                 600                 605

Cys Thr Pro Ser Ser Asp Asp Glu Ile Ala Ser Leu Pro Asp Lys Thr
    610                 615                 620

Ser Ile Ile Gln Pro Val Ser Ser Thr Ile Pro Ser Gln Thr Ile Pro
625                 630                 635                 640

Phe Leu His Ile Gln Lys Lys Thr Lys Asp Gly Trp Glu Tyr Asn Lys
```

-continued

```
                645                 650                 655

Lys Leu Ser Ser Leu Tyr Leu Asp Gly Leu Glu Ser Ala Ala Ile Asn
            660                 665                 670

Gly Leu Thr Phe Lys Asp Lys Tyr Val Leu Val Thr Gly Ala Gly Ala
        675                 680                 685

Gly Ser Ile Gly Ala Glu Ile Leu Gln Gly Leu Ile Ser Gly Gly Ala
    690                 695                 700

Lys Val Ile Val Thr Thr Ser Arg Phe Ser Lys Lys Val Thr Glu Tyr
705                 710                 715                 720

Tyr Gln Asn Met Tyr Ala Arg Tyr Gly Ala Ala Gly Ser Thr Leu Ile
                725                 730                 735

Val Val Pro Phe Asn Gln Gly Ser Lys Gln Asp Val Asp Ala Leu Val
            740                 745                 750

Gln Tyr Ile Tyr Asp Glu Pro Lys Lys Gly Gly Leu Gly Trp Asp Leu
        755                 760                 765

Asp Ala Ile Ile Pro Phe Ala Ala Ile Pro Glu Asn Gly Asn Gly Leu
    770                 775                 780

Asp Asn Ile Asp Ser Lys Ser Glu Phe Ala His Arg Ile Met Leu Thr
785                 790                 795                 800

Asn Leu Leu Arg Leu Leu Gly Ala Val Lys Ser Lys Lys Pro Thr Asp
                805                 810                 815

Thr Arg Pro Ala Gln Cys Ile Leu Pro Leu Ser Pro Asn His Gly Thr
            820                 825                 830

Phe Gly Phe Asp Gly Leu Tyr Ser Glu Ser Lys Ile Ser Leu Glu Thr
        835                 840                 845

Leu Phe Asn Arg Trp Tyr Ser Glu Asp Trp Gly Ser Lys Leu Thr Val
    850                 855                 860

Cys Gly Ala Val Ile Gly Trp Thr Arg Gly Thr Gly Leu Met Ser Ala
865                 870                 875                 880

Asn Asn Ile Ile Ala Glu Gly Ile Glu Lys Leu Gly Val Arg Thr Phe
                885                 890                 895

Ser Gln Lys Glu Met Ala Phe Asn Ile Leu Gly Leu Leu Thr Pro Glu
            900                 905                 910

Ile Val Gln Leu Cys Gln Glu Glu Pro Val Met Ala Asp Leu Asn Gly
        915                 920                 925

Gly Leu Gln Phe Ile Asp Asn Leu Lys Asp Phe Thr Ser Lys Leu Arg
    930                 935                 940

Thr Asp Leu Leu Glu Thr Ala Asp Ile Arg Arg Ala Val Ser Ile Glu
945                 950                 955                 960

Ser Ala Ile Glu Gln Lys Val Val Asn Gly Asp Asn Val Asp Ala Asn
                965                 970                 975

Tyr Ser Lys Val Met Val Glu Pro Arg Ala Asn Met Lys Phe Asp Phe
            980                 985                 990

Pro Thr Leu Lys Ser Tyr Asp Glu  Ile Lys Gln Ile Ala  Pro Glu Leu
        995                 1000                1005

Glu Gly  Met Leu Asp Leu Glu  Asn Val Val Val Val  Thr Gly Phe
    1010                1015                1020

Ala Glu  Val Gly Pro Trp Gly  Asn Ser Arg Thr Arg  Trp Glu Met
    1025                1030                1035

Glu Ala  Tyr Gly Glu Phe Ser  Leu Glu Gly Ala Ile  Glu Met Ala
    1040                1045                1050

Trp Ile  Met Gly Phe Ile Lys  Tyr His Asn Gly Asn  Leu Gln Gly
    1055                1060                1065
```

-continued

```
Lys Pro  Tyr Ser Gly Trp Val  Asp Ala Lys Thr Gln  Thr Pro Ile
    1070                 1075                 1080

Asp Glu  Lys Asp Ile Lys Ser  Lys Tyr Glu Glu Glu  Ile Leu Glu
    1085                 1090                 1095

His Ser  Gly Ile Arg Leu Ile  Glu Pro Glu Leu Phe  Asn Gly Tyr
    1100                 1105                 1110

Asp Pro  Lys Lys Lys Gln Met  Ile Gln Glu Ile Val  Val Gln His
    1115                 1120                 1125

Asp Leu  Glu Pro Phe Glu Cys  Ser Lys Glu Thr Ala  Glu Gln Tyr
    1130                 1135                 1140

Lys His  Glu His Gly Glu Lys  Cys Glu Ile Phe Glu  Ile Glu Glu
    1145                 1150                 1155

Ser Gly  Glu Tyr Thr Val Arg  Ile Leu Lys Gly Ala  Thr Leu Tyr
    1160                 1165                 1170

Val Pro  Lys Ala Leu Arg Phe  Asp Arg Leu Val Ala  Gly Gln Ile
    1175                 1180                 1185

Pro Thr  Gly Trp Asp Ala Arg  Thr Tyr Gly Ile Pro  Glu Asp Thr
    1190                 1195                 1200

Ile Ser  Gln Val Asp Pro Ile  Thr Leu Tyr Val Leu  Val Ala Thr
    1205                 1210                 1215

Val Glu  Ala Leu Leu Ser Ala  Gly Ile Thr Asp Pro  Tyr Glu Phe
    1220                 1225                 1230

Tyr Lys  Tyr Val His Val Ser  Glu Val Gly Asn Cys  Ser Gly Ser
    1235                 1240                 1245

Gly Met  Gly Gly Val Ser Ala  Leu Arg Gly Met Phe  Lys Asp Arg
    1250                 1255                 1260

Tyr Ala  Asp Lys Pro Val Gln  Asn Asp Ile Leu Gln  Glu Ser Phe
    1265                 1270                 1275

Ile Asn  Thr Met Ser Ala Trp  Val Asn Met Leu Leu  Leu Ser Ser
    1280                 1285                 1290

Ser Gly  Pro Ile Lys Thr Pro  Val Gly Ala Cys Ala  Thr Ala Val
    1295                 1300                 1305

Glu Ser  Val Asp Ile Gly Ile  Glu Thr Ile Leu Ser  Gly Lys Ala
    1310                 1315                 1320

Lys Val  Val Leu Val Gly Gly  Tyr Asp Asp Phe Gln  Glu Glu Gly
    1325                 1330                 1335

Ser Tyr  Glu Phe Ala Asn Met  Asn Ala Thr Ser Asn  Ser Ile Glu
    1340                 1345                 1350

Glu Phe  Lys His Gly Arg Thr  Pro Lys Glu Met Ser  Arg Pro Thr
    1355                 1360                 1365

Thr Thr  Thr Arg Asn Gly Phe  Met Glu Ala Gln Gly  Ser Gly Ile
    1370                 1375                 1380

Gln Val  Ile Met Thr Ala Asp  Leu Ala Leu Lys Met  Gly Val Pro
    1385                 1390                 1395

Ile His  Ala Val Leu Ala Met  Thr Ala Thr Ala Thr  Asp Lys Ile
    1400                 1405                 1410

Gly Arg  Ser Val Pro Ala Pro  Gly Lys Gly Ile Leu  Thr Thr Ala
    1415                 1420                 1425

Arg Glu  His His Gly Asn Leu  Lys Tyr Pro Ser Pro  Leu Leu Asn
    1430                 1435                 1440

Ile Lys  Tyr Arg Lys Arg Gln  Leu Asn Lys Arg Leu  Glu Gln Ile
    1445                 1450                 1455
```

-continued

```
Lys Ser  Trp Glu Glu Thr Glu  Leu Ser Tyr Leu Gln  Glu Glu Ala
    1460                 1465                 1470

Glu Leu  Ala Lys Glu Glu Phe  Gly Asp Glu Phe Ser  Met His Glu
    1475                 1480                 1485

Phe Leu  Lys Glu Arg Thr Glu  Glu Val Tyr Arg Glu  Ser Lys Arg
    1490                 1495                 1500

Gln Val  Ser Asp Ala Lys Lys  Gln Trp Gly Asn Ser  Phe Tyr Lys
    1505                 1510                 1515

Ser Asp  Pro Arg Ile Ala Pro  Leu Arg Gly Ala Leu  Ala Ala Phe
    1520                 1525                 1530

Asn Leu  Thr Ile Asp Asp Ile  Gly Val Ala Ser Phe  His Gly Thr
    1535                 1540                 1545

Ser Thr  Val Ala Asn Asp Lys  Asn Glu Ser Ala Thr  Ile Asn Asn
    1550                 1555                 1560

Met Met  Lys His Leu Gly Arg  Ser Glu Gly Asn Pro  Val Phe Gly
    1565                 1570                 1575

Val Phe  Gln Lys Tyr Leu Thr  Gly His Pro Lys Gly  Ala Ala Gly
    1580                 1585                 1590

Ala Trp  Met Leu Asn Gly Ala  Ile Gln Ile Leu Glu  Ser Gly Leu
    1595                 1600                 1605

Val Pro  Gly Asn Arg Asn Ala  Asp Asn Val Asp Lys  Leu Leu Glu
    1610                 1615                 1620

Gln Tyr  Glu Tyr Val Leu Tyr  Pro Ser Arg Ser Ile  Gln Thr Asp
    1625                 1630                 1635

Gly Ile  Lys Ala Val Ser Val  Thr Ser Phe Gly Phe  Gly Gln Lys
    1640                 1645                 1650

Gly Ala  Gln Ala Val Val Val  His Pro Asp Tyr Leu  Phe Ala Val
    1655                 1660                 1665

Leu Asp  Arg Ser Thr Tyr Glu  Glu Tyr Ala Thr Lys  Val Ser Ala
    1670                 1675                 1680

Arg Asn  Lys Lys Thr Tyr Arg  Tyr Met His Asn Ala  Ile Thr Arg
    1685                 1690                 1695

Asn Thr  Met Phe Val Ala Lys  Asp Lys Ala Pro Tyr  Ser Asp Glu
    1700                 1705                 1710

Leu Glu  Gln Pro Val Tyr Leu  Asp Pro Leu Ala Arg  Val Glu Glu
    1715                 1720                 1725

Asn Lys  Lys Lys Leu Val Phe  Ser Asp Lys Thr Ile  Gln Ser Asn
    1730                 1735                 1740

Gln Ser  Tyr Val Gly Glu Val  Ala Gln Lys Thr Ala  Lys Ala Leu
    1745                 1750                 1755

Ser Thr  Leu Asn Lys Ser Ser  Lys Gly Val Gly Val  Asp Val Glu
    1760                 1765                 1770

Leu Leu  Ser Ala Ile Asn Ile  Asp Asn Glu Thr Phe  Ile Glu Arg
    1775                 1780                 1785

Asn Phe  Thr Gly Asn Glu Val  Glu Tyr Cys Leu Asn  Thr Ala His
    1790                 1795                 1800

Pro Gln  Ala Ser Phe Thr Gly  Thr Trp Ser Ala Lys  Glu Ala Val
    1805                 1810                 1815

Phe Lys  Ala Leu Gly Val Glu  Ser Lys Gly Ala Gly  Ala Ser Leu
    1820                 1825                 1830

Ile Asp  Ile Glu Ile Thr Arg  Asp Val Asn Gly Ala  Pro Lys Val
    1835                 1840                 1845

Ile Leu  His Gly Glu Ala Lys  Lys Ala Ala Ala Lys  Ala Gly Val
```

-continued 1850 1855 1860

Lys Asn Val Asn Ile Ser Ile Ser His Asp Asp Phe Gln Ala Thr
1865 1870 1875

Ala Val Ala Leu Ser Glu Phe
1880 1885

<210> SEQ ID NO 23
<211> LENGTH: 3069
<212> TYPE: PRT
<213> ORGANISM: Mycobacterium tuberculosis

<400> SEQUENCE: 23

Met Thr Ile His Glu His Asp Arg Val Ser Ala Asp Arg Gly Gly Asp
1 5 10 15

Ser Pro His Thr Thr His Ala Leu Val Asp Arg Leu Met Ala Gly Glu
20 25 30

Pro Tyr Ala Val Ala Phe Gly Gly Gln Gly Ser Ala Trp Leu Glu Thr
35 40 45

Leu Glu Glu Leu Val Ser Ala Thr Gly Ile Glu Thr Glu Leu Ala Thr
50 55 60

Leu Val Gly Glu Ala Glu Leu Leu Leu Asp Pro Val Thr Asp Glu Leu
65 70 75 80

Ile Val Val Arg Pro Ile Gly Phe Glu Pro Leu Gln Trp Val Arg Ala
85 90 95

Leu Ala Ala Glu Asp Pro Val Pro Ser Asp Lys His Leu Thr Ser Ala
100 105 110

Ala Val Ser Val Pro Gly Val Leu Leu Thr Gln Ile Ala Ala Thr Arg
115 120 125

Ala Leu Ala Arg Gln Gly Met Asp Leu Val Ala Thr Pro Pro Val Ala
130 135 140

Met Ala Gly His Ser Gln Gly Val Leu Ala Val Glu Ala Leu Lys Ala
145 150 155 160

Gly Gly Ala Arg Asp Val Glu Leu Phe Ala Leu Ala Gln Leu Ile Gly
165 170 175

Ala Ala Gly Thr Leu Val Ala Arg Arg Arg Gly Ile Ser Val Leu Gly
180 185 190

Asp Arg Pro Pro Met Val Ser Val Thr Asn Ala Asp Pro Glu Arg Ile
195 200 205

Gly Arg Leu Leu Asp Glu Phe Ala Gln Asp Val Arg Thr Val Leu Pro
210 215 220

Pro Val Leu Ser Ile Arg Asn Gly Arg Arg Ala Val Val Ile Thr Gly
225 230 235 240

Thr Pro Glu Gln Leu Ser Arg Phe Glu Leu Tyr Cys Arg Gln Ile Ser
245 250 255

Glu Lys Glu Glu Ala Asp Arg Lys Asn Lys Val Arg Gly Gly Asp Val
260 265 270

Phe Ser Pro Val Phe Glu Pro Val Gln Val Glu Val Gly Phe His Thr
275 280 285

Pro Arg Leu Ser Asp Gly Ile Asp Ile Val Ala Gly Trp Ala Glu Lys
290 295 300

Ala Gly Leu Asp Val Ala Leu Ala Arg Glu Leu Ala Asp Ala Ile Leu
305 310 315 320

Ile Arg Lys Val Asp Trp Val Asp Glu Ile Thr Arg Val His Ala Ala
325 330 335

-continued

```
Gly Ala Arg Trp Ile Leu Asp Leu Gly Pro Gly Asp Ile Leu Thr Arg
            340                 345                 350

Leu Thr Ala Pro Val Ile Arg Gly Leu Gly Ile Gly Ile Val Pro Ala
        355                 360                 365

Ala Thr Arg Gly Gly Gln Arg Asn Leu Phe Thr Val Gly Ala Thr Pro
    370                 375                 380

Glu Val Ala Arg Ala Trp Ser Ser Tyr Ala Pro Thr Val Val Arg Leu
385                 390                 395                 400

Pro Asp Gly Arg Val Lys Leu Ser Thr Lys Phe Thr Arg Leu Thr Gly
                405                 410                 415

Arg Ser Pro Ile Leu Leu Ala Gly Met Thr Pro Thr Thr Val Asp Ala
            420                 425                 430

Lys Ile Val Ala Ala Ala Ala Asn Ala Gly His Trp Ala Glu Leu Ala
        435                 440                 445

Gly Gly Gly Gln Val Thr Glu Glu Ile Phe Gly Asn Arg Ile Glu Gln
    450                 455                 460

Met Ala Gly Leu Leu Glu Pro Gly Arg Thr Tyr Gln Phe Asn Ala Leu
465                 470                 475                 480

Phe Leu Asp Pro Tyr Leu Trp Lys Leu Gln Val Gly Gly Lys Arg Leu
                485                 490                 495

Val Gln Lys Ala Arg Gln Ser Gly Ala Ala Ile Asp Gly Val Val Ile
            500                 505                 510

Ser Ala Gly Ile Pro Asp Leu Asp Glu Ala Val Glu Leu Ile Asp Glu
        515                 520                 525

Leu Gly Asp Ile Gly Ile Ser His Val Val Phe Lys Pro Gly Thr Ile
    530                 535                 540

Glu Gln Ile Arg Ser Val Ile Arg Ile Ala Thr Glu Val Pro Thr Lys
545                 550                 555                 560

Pro Val Ile Met His Val Glu Gly Gly Arg Ala Gly Gly His His Ser
                565                 570                 575

Trp Glu Asp Leu Asp Asp Leu Leu Leu Ala Thr Tyr Ser Glu Leu Arg
            580                 585                 590

Ser Arg Ala Asn Ile Thr Val Cys Val Gly Gly Gly Ile Gly Thr Pro
        595                 600                 605

Arg Arg Ala Ala Glu Tyr Leu Ser Gly Arg Trp Ala Gln Ala Tyr Gly
    610                 615                 620

Phe Pro Leu Met Pro Ile Asp Gly Ile Leu Val Gly Thr Ala Ala Met
625                 630                 635                 640

Ala Thr Lys Glu Ser Thr Thr Ser Pro Ser Val Lys Arg Met Leu Val
                645                 650                 655

Asp Thr Gln Gly Thr Asp Gln Trp Ile Ser Ala Gly Lys Ala Gln Gly
            660                 665                 670

Gly Met Ala Ser Ser Arg Ser Gln Leu Gly Ala Asp Ile His Glu Ile
        675                 680                 685

Asp Asn Ser Ala Ser Arg Cys Gly Arg Leu Leu Asp Glu Val Ala Gly
    690                 695                 700

Asp Ala Glu Ala Val Ala Glu Arg Arg Asp Glu Ile Ile Ala Ala Met
705                 710                 715                 720

Ala Lys Thr Ala Lys Pro Tyr Phe Gly Asp Val Ala Asp Met Thr Tyr
                725                 730                 735

Leu Gln Trp Leu Arg Arg Tyr Val Glu Leu Ala Ile Gly Glu Gly Asn
            740                 745                 750

Ser Thr Ala Asp Thr Ala Ser Val Gly Ser Pro Trp Leu Ala Asp Thr
```

-continued

```
        755                 760                 765

Trp Arg Asp Arg Phe Glu Gln Met Leu Gln Arg Ala Glu Ala Arg Leu
    770                 775                 780

His Pro Gln Asp Phe Gly Pro Ile Gln Thr Leu Phe Thr Asp Ala Gly
785                 790                 795                 800

Leu Leu Asp Asn Pro Gln Gln Ala Ile Ala Ala Leu Leu Ala Arg Tyr
                805                 810                 815

Pro Asp Ala Glu Thr Val Gln Leu His Pro Ala Asp Val Pro Phe Phe
            820                 825                 830

Val Thr Leu Cys Lys Thr Leu Gly Lys Pro Val Asn Phe Val Pro Val
        835                 840                 845

Ile Asp Gln Asp Val Arg Arg Trp Trp Arg Ser Asp Ser Leu Trp Gln
    850                 855                 860

Ala His Asp Ala Arg Tyr Asp Ala Asp Ala Val Cys Ile Ile Pro Gly
865                 870                 875                 880

Thr Ala Ser Val Ala Gly Ile Thr Arg Met Asp Glu Pro Val Gly Glu
                885                 890                 895

Leu Leu Asp Arg Phe Glu Gln Ala Ala Ile Asp Glu Val Leu Gly Ala
            900                 905                 910

Gly Val Glu Pro Lys Asp Val Ala Ser Arg Arg Leu Gly Arg Ala Asp
        915                 920                 925

Val Ala Gly Pro Leu Ala Val Val Leu Asp Ala Pro Asp Val Arg Trp
    930                 935                 940

Ala Gly Arg Thr Val Thr Asn Pro Val His Arg Ile Ala Asp Pro Ala
945                 950                 955                 960

Glu Trp Gln Val His Asp Gly Pro Glu Asn Pro Arg Ala Thr His Ser
                965                 970                 975

Ser Thr Gly Ala Arg Leu Gln Thr His Gly Asp Asp Val Ala Leu Ser
            980                 985                 990

Val Pro Val Ser Gly Thr Trp Val  Asp Ile Arg Phe Thr  Leu Pro Ala
        995                 1000                1005

Asn Thr  Val Asp Gly Gly Thr  Pro Val Ile Ala Thr  Glu Asp Ala
    1010                1015                1020

Thr Ser  Ala Met Arg Thr Val  Leu Ala Ile Ala Ala  Gly Val Asp
    1025                1030                1035

Ser Pro  Glu Phe Leu Pro Ala  Val Ala Asn Gly Thr  Ala Thr Leu
    1040                1045                1050

Thr Val  Asp Trp His Pro Glu  Arg Val Ala Asp His  Thr Gly Val
    1055                1060                1065

Thr Ala  Thr Phe Gly Glu Pro  Leu Ala Pro Ser Leu  Thr Asn Val
    1070                1075                1080

Pro Asp  Ala Leu Val Gly Pro  Cys Trp Pro Ala Val  Phe Ala Ala
    1085                1090                1095

Ile Gly  Ser Ala Val Thr Asp  Thr Gly Glu Pro Val  Val Glu Gly
    1100                1105                1110

Leu Leu  Ser Leu Val His Leu  Asp His Ala Ala Arg  Val Val Gly
    1115                1120                1125

Gln Leu  Pro Thr Val Pro Ala  Gln Leu Thr Val Thr  Ala Thr Ala
    1130                1135                1140

Ala Asn  Ala Thr Asp Thr Asp  Met Gly Arg Val Val  Pro Val Ser
    1145                1150                1155

Val Val  Val Thr Gly Ala Asp  Gly Ala Val Ile Ala  Thr Leu Glu
    1160                1165                1170
```

-continued

Glu Arg Phe Ala Ile Leu Gly Arg Thr Gly Ser Ala Glu Leu Ala
1175 1180 1185

Asp Pro Ala Arg Ala Gly Gly Ala Val Ser Ala Asn Ala Thr Asp
1190 1195 1200

Thr Pro Arg Arg Arg Arg Arg Asp Val Thr Ile Thr Ala Pro Val
1205 1210 1215

Asp Met Arg Pro Phe Ala Val Val Ser Gly Asp His Asn Pro Ile
1220 1225 1230

His Thr Asp Arg Ala Ala Ala Leu Leu Ala Gly Leu Glu Ser Pro
1235 1240 1245

Ile Val His Gly Met Trp Leu Ser Ala Ala Ala Gln His Ala Val
1250 1255 1260

Thr Ala Thr Asp Gly Gln Ala Arg Pro Pro Ala Arg Leu Val Gly
1265 1270 1275

Trp Thr Ala Arg Phe Leu Gly Met Val Arg Pro Gly Asp Glu Val
1280 1285 1290

Asp Phe Arg Val Glu Arg Val Gly Ile Asp Gln Gly Ala Glu Ile
1295 1300 1305

Val Asp Val Ala Ala Arg Val Gly Ser Asp Leu Val Met Ser Ala
1310 1315 1320

Ser Ala Arg Leu Ala Ala Pro Lys Thr Val Tyr Ala Phe Pro Gly
1325 1330 1335

Gln Gly Ile Gln His Lys Gly Met Gly Met Glu Val Arg Ala Arg
1340 1345 1350

Ser Lys Ala Ala Arg Lys Val Trp Asp Thr Ala Asp Lys Phe Thr
1355 1360 1365

Arg Asp Thr Leu Gly Phe Ser Val Leu His Val Val Arg Asp Asn
1370 1375 1380

Pro Thr Ser Ile Ile Ala Ser Gly Val His Tyr His His Pro Asp
1385 1390 1395

Gly Val Leu Tyr Leu Thr Gln Phe Thr Gln Val Ala Met Ala Thr
1400 1405 1410

Val Ala Ala Ala Gln Val Ala Glu Met Arg Glu Gln Gly Ala Phe
1415 1420 1425

Val Glu Gly Ala Ile Ala Cys Gly His Ser Val Gly Glu Tyr Thr
1430 1435 1440

Ala Leu Ala Cys Val Thr Gly Ile Tyr Gln Leu Glu Ala Leu Leu
1445 1450 1455

Glu Met Val Phe His Arg Gly Ser Lys Met His Asp Ile Val Pro
1460 1465 1470

Arg Asp Glu Leu Gly Arg Ser Asn Tyr Arg Leu Ala Ala Ile Arg
1475 1480 1485

Pro Ser Gln Ile Asp Leu Asp Asp Ala Asp Val Pro Ala Phe Val
1490 1495 1500

Ala Gly Ile Ala Glu Ser Thr Gly Glu Phe Leu Glu Ile Val Asn
1505 1510 1515

Phe Asn Leu Arg Gly Ser Gln Tyr Ala Ile Ala Gly Thr Val Arg
1520 1525 1530

Gly Leu Glu Ala Leu Glu Ala Glu Val Glu Arg Arg Arg Glu Leu
1535 1540 1545

Thr Gly Gly Arg Arg Ser Phe Ile Leu Val Pro Gly Ile Asp Val
1550 1555 1560

-continued

```
Pro Phe His Ser Arg Val Leu Arg Val Gly Val Ala Glu Phe Arg
    1565                1570                1575

Arg Ser Leu Asp Arg Val Met Pro Arg Asp Ala Asp Pro Asp Leu
    1580                1585                1590

Ile Ile Gly Arg Tyr Ile Pro Asn Leu Val Pro Arg Leu Phe Thr
    1595                1600                1605

Leu Asp Arg Asp Phe Ile Gln Glu Ile Arg Asp Leu Val Pro Ala
    1610                1615                1620

Glu Pro Leu Asp Glu Ile Leu Ala Asp Tyr Asp Thr Trp Leu Arg
    1625                1630                1635

Glu Arg Pro Arg Glu Met Ala Arg Thr Val Phe Ile Glu Leu Leu
    1640                1645                1650

Ala Trp Gln Phe Ala Ser Pro Val Arg Trp Ile Glu Thr Gln Asp
    1655                1660                1665

Leu Leu Phe Ile Glu Glu Ala Ala Gly Gly Leu Gly Val Glu Arg
    1670                1675                1680

Phe Val Glu Ile Gly Val Lys Ser Ser Pro Thr Val Ala Gly Leu
    1685                1690                1695

Ala Thr Asn Thr Leu Lys Leu Pro Glu Tyr Ala His Ser Thr Val
    1700                1705                1710

Glu Val Leu Asn Ala Glu Arg Asp Ala Ala Val Leu Phe Ala Thr
    1715                1720                1725

Asp Thr Asp Pro Glu Pro Glu Pro Glu Glu Asp Glu Pro Val Ala
    1730                1735                1740

Glu Ser Pro Ala Pro Asp Val Val Ser Glu Ala Ala Pro Val Ala
    1745                1750                1755

Pro Ala Ala Ser Ser Ala Gly Pro Arg Pro Asp Asp Leu Val Phe
    1760                1765                1770

Asp Ala Ala Asp Ala Thr Leu Ala Leu Ile Ala Leu Ser Ala Lys
    1775                1780                1785

Met Arg Ile Asp Gln Ile Glu Glu Leu Asp Ser Ile Glu Ser Ile
    1790                1795                1800

Thr Asp Gly Ala Ser Ser Arg Arg Asn Gln Leu Leu Val Asp Leu
    1805                1810                1815

Gly Ser Glu Leu Asn Leu Gly Ala Ile Asp Gly Ala Ala Glu Ser
    1820                1825                1830

Asp Leu Ala Gly Leu Arg Ser Gln Val Thr Lys Leu Ala Arg Thr
    1835                1840                1845

Tyr Lys Pro Tyr Gly Pro Val Leu Ser Asp Ala Ile Asn Asp Gln
    1850                1855                1860

Leu Arg Thr Val Leu Gly Pro Ser Gly Lys Arg Pro Gly Ala Ile
    1865                1870                1875

Ala Glu Arg Val Lys Lys Thr Trp Glu Leu Gly Glu Gly Trp Ala
    1880                1885                1890

Lys His Val Thr Val Glu Val Ala Leu Gly Thr Arg Glu Gly Ser
    1895                1900                1905

Ser Val Arg Gly Gly Ala Met Gly His Leu His Glu Gly Ala Leu
    1910                1915                1920

Ala Asp Ala Ala Ser Val Asp Lys Val Ile Asp Ala Ala Val Ala
    1925                1930                1935

Ser Val Ala Ala Arg Gln Gly Val Ser Val Ala Leu Pro Ser Ala
    1940                1945                1950

Gly Ser Gly Gly Gly Ala Thr Ile Asp Ala Ala Ala Leu Ser Glu
```

-continued

```
    1955                1960                1965

Phe Thr  Asp Gln Ile Thr Gly  Arg Glu Gly Val Leu  Ala Ser Ala
    1970                1975                1980

Ala Arg  Leu Val Leu Gly Gln  Leu Gly Leu Asp Asp  Pro Val Asn
    1985                1990                1995

Ala Leu  Pro Ala Ala Pro Asp  Ser Glu Leu Ile Asp  Leu Val Thr
    2000                2005                2010

Ala Glu  Leu Gly Ala Asp Trp  Pro Arg Leu Val Ala  Pro Val Phe
    2015                2020                2025

Asp Pro  Lys Lys Ala Val Val  Phe Asp Asp Arg Trp  Ala Ser Ala
    2030                2035                2040

Arg Glu  Asp Leu Val Lys Leu  Trp Leu Thr Asp Glu  Gly Asp Ile
    2045                2050                2055

Asp Ala  Asp Trp Pro Arg Leu  Ala Glu Arg Phe Glu  Gly Ala Gly
    2060                2065                2070

His Val  Val Ala Thr Gln Ala  Thr Trp Trp Gln Gly  Lys Ser Leu
    2075                2080                2085

Ala Ala  Gly Arg Gln Ile His  Ala Ser Leu Tyr Gly  Arg Ile Ala
    2090                2095                2100

Ala Gly  Ala Glu Asn Pro Glu  Pro Gly Arg Tyr Gly  Gly Glu Val
    2105                2110                2115

Ala Val  Val Thr Gly Ala Ser  Lys Gly Ser Ile Ala  Ala Ser Val
    2120                2125                2130

Val Ala  Arg Leu Leu Asp Gly  Gly Ala Thr Val Ile  Ala Thr Thr
    2135                2140                2145

Ser Lys  Leu Asp Glu Glu Arg  Leu Ala Phe Tyr Arg  Thr Leu Tyr
    2150                2155                2160

Arg Asp  His Ala Arg Tyr Gly  Ala Ala Leu Trp Leu  Val Ala Ala
    2165                2170                2175

Asn Met  Ala Ser Tyr Ser Asp  Val Asp Ala Leu Val  Glu Trp Ile
    2180                2185                2190

Gly Thr  Glu Gln Thr Glu Ser  Leu Gly Pro Gln Ser  Ile His Ile
    2195                2200                2205

Lys Asp  Ala Gln Thr Pro Thr  Leu Leu Phe Pro Phe  Ala Ala Pro
    2210                2215                2220

Arg Val  Val Gly Asp Leu Ser  Glu Ala Gly Ser Arg  Ala Glu Met
    2225                2230                2235

Glu Met  Lys Val Leu Leu Trp  Ala Val Gln Arg Leu  Ile Gly Gly
    2240                2245                2250

Leu Ser  Thr Ile Gly Ala Glu  Arg Asp Ile Ala Ser  Arg Leu His
    2255                2260                2265

Val Val  Leu Pro Gly Ser Pro  Asn Arg Gly Met Phe  Gly Gly Asp
    2270                2275                2280

Gly Ala  Tyr Gly Glu Ala Lys  Ser Ala Leu Asp Ala  Val Val Ser
    2285                2290                2295

Arg Trp  His Ala Glu Ser Ser  Trp Ala Ala Arg Val  Ser Leu Ala
    2300                2305                2310

His Ala  Leu Ile Gly Trp Thr  Arg Gly Thr Gly Leu  Met Gly His
    2315                2320                2325

Asn Asp  Ala Ile Val Ala Ala  Val Glu Glu Ala Gly  Val Thr Thr
    2330                2335                2340

Tyr Ser  Thr Asp Glu Met Ala  Ala Leu Leu Leu Asp  Leu Cys Asp
    2345                2350                2355
```

-continued

Ala Glu Ser Lys Val Ala Ala Ala Arg Ser Pro Ile Lys Ala Asp
2360 2365 2370

Leu Thr Gly Gly Leu Ala Glu Ala Asn Leu Asp Met Ala Glu Leu
2375 2380 2385

Ala Ala Lys Ala Arg Glu Gln Met Ser Ala Ala Ala Ala Val Asp
2390 2395 2400

Glu Asp Ala Glu Ala Pro Gly Ala Ile Ala Ala Leu Pro Ser Pro
2405 2410 2415

Pro Arg Gly Phe Thr Pro Ala Pro Pro Pro Gln Trp Asp Asp Leu
2420 2425 2430

Asp Val Asp Pro Ala Asp Leu Val Val Ile Val Gly Gly Ala Glu
2435 2440 2445

Ile Gly Pro Tyr Gly Ser Ser Arg Thr Arg Phe Glu Met Glu Val
2450 2455 2460

Glu Asn Glu Leu Ser Ala Ala Gly Val Leu Glu Leu Ala Trp Thr
2465 2470 2475

Thr Gly Leu Ile Arg Trp Glu Asp Asp Pro Gln Pro Gly Trp Tyr
2480 2485 2490

Asp Thr Glu Ser Gly Glu Met Val Asp Glu Ser Glu Leu Val Gln
2495 2500 2505

Arg Tyr His Asp Ala Val Val Gln Arg Val Gly Ile Arg Glu Phe
2510 2515 2520

Val Asp Asp Gly Ala Ile Asp Pro Asp His Ala Ser Pro Leu Leu
2525 2530 2535

Val Ser Val Phe Leu Glu Lys Asp Phe Ala Phe Val Val Ser Ser
2540 2545 2550

Glu Ala Asp Ala Arg Ala Phe Val Glu Phe Asp Pro Glu His Thr
2555 2560 2565

Val Ile Arg Pro Val Pro Asp Ser Thr Asp Trp Gln Val Ile Arg
2570 2575 2580

Lys Ala Gly Thr Glu Ile Arg Val Pro Arg Lys Thr Lys Leu Ser
2585 2590 2595

Arg Val Val Gly Gly Gln Ile Pro Thr Gly Phe Asp Pro Thr Val
2600 2605 2610

Trp Gly Ile Ser Ala Asp Met Ala Gly Ser Ile Asp Arg Leu Ala
2615 2620 2625

Val Trp Asn Met Val Ala Thr Val Asp Ala Phe Leu Ser Ser Gly
2630 2635 2640

Phe Ser Pro Ala Glu Val Met Arg Tyr Val His Pro Ser Leu Val
2645 2650 2655

Ala Asn Thr Gln Gly Thr Gly Met Gly Gly Gly Thr Ser Met Gln
2660 2665 2670

Thr Met Tyr His Gly Asn Leu Leu Gly Arg Asn Lys Pro Asn Asp
2675 2680 2685

Ile Phe Gln Glu Val Leu Pro Asn Ile Ile Ala Ala His Val Val
2690 2695 2700

Gln Ser Tyr Val Gly Ser Tyr Gly Ala Met Ile His Pro Val Ala
2705 2710 2715

Ala Cys Ala Thr Ala Ala Val Ser Val Glu Glu Gly Val Asp Lys
2720 2725 2730

Ile Arg Leu Gly Lys Ala Gln Leu Val Val Ala Gly Gly Leu Asp
2735 2740 2745

-continued

```
Asp Leu  Thr Leu Glu Gly Ile  Ile Gly Phe Gly Asp  Met Ala Ala
    2750                 2755                 2760

Thr Ala  Asp Thr Ser Met Met  Cys Gly Arg Gly Ile  His Asp Ser
    2765                 2770                 2775

Lys Phe  Ser Arg Pro Asn Asp  Arg Arg Arg Leu Gly  Phe Val Glu
    2780                 2785                 2790

Ala Gln  Gly Gly Gly Thr Ile  Leu Leu Ala Arg Gly  Asp Leu Ala
    2795                 2800                 2805

Leu Arg  Met Gly Leu Pro Val  Leu Ala Val Val Ala  Phe Ala Gln
    2810                 2815                 2820

Ser Phe  Gly Asp Gly Val His  Thr Ser Ile Pro Ala  Pro Gly Leu
    2825                 2830                 2835

Gly Ala  Leu Gly Ala Gly Arg  Gly Gly Lys Asp Ser  Pro Leu Ala
    2840                 2845                 2850

Arg Ala  Leu Ala Lys Leu Gly  Val Ala Ala Asp Asp  Val Ala Val
    2855                 2860                 2865

Ile Ser  Lys His Asp Thr Ser  Thr Leu Ala Asn Asp  Pro Asn Glu
    2870                 2875                 2880

Thr Glu  Leu His Glu Arg Leu  Ala Asp Ala Leu Gly  Arg Ser Glu
    2885                 2890                 2895

Gly Ala  Pro Leu Phe Val Val  Ser Gln Lys Ser Leu  Thr Gly His
    2900                 2905                 2910

Ala Lys  Gly Gly Ala Ala Val  Phe Gln Met Met Gly  Leu Cys Gln
    2915                 2920                 2925

Ile Leu  Arg Asp Gly Val Ile  Pro Pro Asn Arg Ser  Leu Asp Cys
    2930                 2935                 2940

Val Asp  Asp Glu Leu Ala Gly  Ser Ala His Phe Val  Trp Val Arg
    2945                 2950                 2955

Asp Thr  Leu Arg Leu Gly Gly  Lys Phe Pro Leu Lys  Ala Gly Met
    2960                 2965                 2970

Leu Thr  Ser Leu Gly Phe Gly  His Val Ser Gly Leu  Val Ala Leu
    2975                 2980                 2985

Val His  Pro Gln Ala Phe Ile  Ala Ser Leu Asp Pro  Ala Gln Arg
    2990                 2995                 3000

Ala Asp  Tyr Gln Arg Arg Ala  Asp Ala Arg Leu Leu  Ala Gly Gln
    3005                 3010                 3015

Arg Arg  Leu Ala Ser Ala Ile  Ala Gly Gly Ala Pro  Met Tyr Gln
    3020                 3025                 3030

Arg Pro  Gly Asp Arg Arg Phe  Asp His His Ala Pro  Glu Arg Pro
    3035                 3040                 3045

Gln Glu  Ala Ser Met Leu Leu  Asn Pro Ala Ala Arg  Leu Gly Asp
    3050                 3055                 3060

Gly Glu  Ala Tyr Ile Gly
    3065
```

<210> SEQ ID NO 24
<211> LENGTH: 3076
<212> TYPE: PRT
<213> ORGANISM: Mycobacterium tuberculosis

<400> SEQUENCE: 24

```
Met Thr Ile His Glu His Asp Gln Val Ser Ala Asp Arg Asn Gly Asn
1               5                   10                  15

Ser Leu His Gly Ser Arg Ala Leu Ala Asp Arg Leu Lys Ala Gly Glu
            20                  25                  30
```

-continued

```
Pro Tyr Val Val Ala Phe Gly Gly Gln Gly Ser Ala Trp Leu Glu Thr
        35                  40                  45

Leu Glu Glu Leu Val Ser Ser Ala Gly Leu Glu Ala Asp Leu Ala Thr
    50                  55                  60

Leu Val Cys Glu Val Glu Leu Leu Leu Glu Pro Val Ala Lys Glu Leu
65                  70                  75                  80

Val Val Val Arg Pro Ile Gly Phe Glu Pro Leu Gln Trp Val Arg Ala
                85                  90                  95

Leu Leu Ala Glu Asp Leu Val Pro Ser Asp Lys His Leu Thr Ser Ala
            100                 105                 110

Ala Val Ser Val Pro Gly Val Leu Leu Thr Gln Ile Ala Val Gly Arg
        115                 120                 125

Ala Leu Ala Arg Gln Gly Met Asp Leu Ile Ala Thr Pro Pro Val Gly
    130                 135                 140

Ile Val Gly His Ser Gln Gly Val Leu Ala Val Glu Ala Leu Lys Ala
145                 150                 155                 160

Gly Gly Ala Arg Asp Ala Glu Leu Leu Ala Met Ala Gln Leu Ile Gly
                165                 170                 175

Ala Ala Gly Thr Leu Val Ala Arg Arg Arg Gly Ile Ser Val Leu Gly
            180                 185                 190

Asp Arg Pro Pro Met Val Ser Val Thr Asn Ala Asp Pro Glu Arg Ile
        195                 200                 205

Arg Arg Leu Leu Asp Glu Phe Ala Gln Asp Val Arg Thr Val Leu Pro
    210                 215                 220

Pro Val Leu Ser Ile Arg Asn Gly Trp Arg Ser Val Val Ile Thr Gly
225                 230                 235                 240

Thr Pro Glu Gln Leu Ser Arg Phe Glu Arg Tyr Cys Arg Gln Ile Ser
                245                 250                 255

Asp Lys Glu Glu Glu Asp Arg Arg Lys Lys Ile Arg Gly Gly Asp Ile
            260                 265                 270

Phe Ala Pro Val Phe Asp Pro Val Gln Val Glu Ile Gly Phe His Thr
        275                 280                 285

Pro His Leu Ala Asp Gly Ile Gly Ile Val Gly Gly Trp Ala Glu Lys
    290                 295                 300

Val Gly Leu Asp Val Thr Leu Ala Arg Glu Leu Thr Glu Ala Ile Leu
305                 310                 315                 320

Val Arg Gly Val Asp Trp Val Arg Glu Ile Thr Arg Val His Gly Ala
                325                 330                 335

Gly Val Arg Trp Ile Ile Asp Leu Gly Pro Gly Asp Ile Leu Thr Arg
            340                 345                 350

Leu Thr Ala Pro Val Ile Arg Gly Leu Gly Val Gly Ile Val Pro Val
        355                 360                 365

Ala Asn Arg Gly Gly Gln Arg Thr Leu Phe Thr Val Gly Ala Val Pro
    370                 375                 380

Glu Val Val Arg Ala Trp Leu Ser Tyr Ala Pro Thr Val Val Gln Leu
385                 390                 395                 400

Pro Asp Gly Arg Ile Lys Leu Ser Thr Lys Phe Thr Arg Leu Thr Gly
                405                 410                 415

Arg Ser Pro Ile Leu Leu Ala Gly Met Thr Pro Thr Thr Val Asp Ala
            420                 425                 430

Asn Ile Val Ala Ala Ala Ala Asn Ala Gly His Trp Ala Glu Leu Ala
        435                 440                 445
```

-continued

```
Gly Gly Gly Gln Val Thr Glu Glu Ile Phe Ala Asn Arg Val Glu Gln
    450                 455                 460

Leu Ser Gly Leu Leu Glu Pro Gly Arg Thr Tyr Gln Phe Asn Ala Leu
465                 470                 475                 480

Phe Leu Asp Pro Tyr Leu Trp Lys Leu Gln Val Gly Gly Lys Arg Leu
                485                 490                 495

Val Gln Lys Ala Arg Gln Ser Gly Ala Ala Ile Asp Gly Val Val Ile
            500                 505                 510

Ser Gly Gly Ile Leu Asp Leu Glu Asp Ala Val Glu Leu Ile Glu Glu
        515                 520                 525

Leu Gly Gly Ile Gly Ile Ser Tyr Val Val Phe Lys Pro Gly Thr Ile
    530                 535                 540

Glu Gln Ile Arg Ser Val Ile Arg Ile Ala Thr Glu Met Ser Thr Lys
545                 550                 555                 560

Pro Val Ile Met His Val Glu Gly Gly Arg Ala Gly Gly His His Ser
                565                 570                 575

Trp Glu Asp Leu Asp Asp Leu Leu Leu Ala Thr Tyr Ser Glu Leu Arg
            580                 585                 590

Ser His Ala Asn Ile Thr Val Cys Val Gly Gly Gly Ile Gly Thr Pro
        595                 600                 605

Glu Lys Ala Ala Glu Tyr Leu Ser Gly Arg Trp Ala Gln Ala Tyr Gly
    610                 615                 620

Phe Pro Leu Met Pro Ile Asp Gly Ile Leu Val Gly Thr Ala Ala Met
625                 630                 635                 640

Ala Thr Lys Glu Ala Thr Thr Ser Pro Ser Val Lys Arg Met Leu Val
                645                 650                 655

Glu Thr Gln Gly Thr Asp Gln Trp Ile Gly Ser Gly Lys Ala Gln Gly
            660                 665                 670

Gly Met Ala Ser Ser Arg Ser Gln Leu Gly Ala Asp Ile His Glu Ile
        675                 680                 685

Asp Asn Ala Ala Ser Arg Cys Gly Arg Leu Leu Asp Glu Val Ala Gly
    690                 695                 700

Asp Ala Glu Ala Val Ala Glu Arg Arg Asp Glu Ile Ile Ala Ala Met
705                 710                 715                 720

Ala Asn Thr Ala Lys Pro Tyr Phe Gly Asp Val Ser Glu Met Thr Tyr
                725                 730                 735

Leu Gln Trp Leu Gln Arg Tyr Val Glu Leu Thr Ile Gly Glu Gly Asn
            740                 745                 750

Ser Thr Ala Asp Thr Ala Ser Pro Gly Ser Pro Trp Leu Ala Asp Thr
        755                 760                 765

Trp Arg Asp Arg Phe Gln Lys Met Leu Gln Arg Ala Glu Ser Arg Leu
    770                 775                 780

His Pro Ser Asp Phe Gly Leu Ile Lys Thr Ile Phe Thr Asp Pro Val
785                 790                 795                 800

Leu Leu Glu Lys Pro Asn Gln Ala Ile Ala Ala Leu Leu Lys Tyr Tyr
                805                 810                 815

Pro Asp Ala Glu Thr Val Gln Leu His Pro Ala Asp Ala Pro Phe Phe
            820                 825                 830

Val Met Leu Cys Gln Met Leu Gly Lys Pro Val Asn Phe Val Pro Val
        835                 840                 845

Ile Asp Lys Asp Val Arg Arg Trp Trp Arg Ser Asp Ser Leu Trp Gln
    850                 855                 860

Ala His Asp Ala Arg Tyr Asp Ala Asp Gln Val Cys Ile Ile Pro Gly
```

-continued

```
865                 870                 875                 880

Ile Ala Ala Val Ala Gly Ile Thr Gln Met Asp Glu Pro Val Gly Glu
                885                 890                 895

Leu Leu Asp Arg Phe Glu Gln Ala Ala Ile Asp Glu Val Leu Ala Gly
            900                 905                 910

Gly Ala Glu Pro Val Val Val Met Ser Arg Arg Leu Gly Arg Ala Asp
        915                 920                 925

Val Ala Gly Pro Leu Ala Val Val Leu Asp Ala Pro Asp Val Leu Trp
    930                 935                 940

Ala Gly Arg Ile Ala Thr Asn Pro Val His Arg Ile Ala Asp Pro Asn
945                 950                 955                 960

Glu Trp Gln Val Asn Gly Asn Leu Ser Ala Thr His Ser Ser Thr Gly
                965                 970                 975

Ala Gln Leu Gln Val Lys Ser Glu Asp Gln Gln Val Val Leu Ser Val
            980                 985                 990

Pro Val Ser Asn Gly Trp Ile Asp  Ile Pro Phe Thr Leu  Pro Thr Asn
        995                 1000                1005

Thr Val  Asp Gly Gly Ala Leu  Leu Val Ser Thr Glu  Asp Ala Thr
    1010                1015                1020

Ser Ala  Met Arg Ala Val Leu  Ala Ile Val Ala Gly  Val Asp Gly
    1025                1030                1035

Pro Glu  Leu Leu Ser Pro Val  Lys Asp Gly Thr Ala  Ile Val Thr
    1040                1045                1050

Val Asp  Trp Asn Pro Glu Arg  Val Ala Asp His Thr  Gly Val Thr
    1055                1060                1065

Ala Thr  Phe Arg Glu Pro Leu  Ala Pro Ser Leu Ala  Thr Val Pro
    1070                1075                1080

Asp Ala  Leu Val Gly Ala Cys  Trp Pro Ala Val Phe  Ser Ala Ile
    1085                1090                1095

Gly Ser  Ala Val Thr Glu Ala  Gly Val Leu Val Val  Glu Gly Leu
    1100                1105                1110

Leu Asn  Leu Leu His Leu Asp  His Ala Val Cys Val  Val Gly Lys
    1115                1120                1125

Leu Pro  Thr Val Pro Ala Gln  Leu Thr Val Thr Ala  Thr Val Ser
    1130                1135                1140

Leu Ala  Ile Asp Thr Asp Met  Gly Arg Val Val Pro  Val Ser Val
    1145                1150                1155

Thr Ile  Arg Asp Thr Thr Gly  Ala Asp Gly Ala Val  Leu Ala Thr
    1160                1165                1170

Leu Glu  Glu Arg Phe Val Ile  Leu Gly Arg Thr Gly  Thr Ala Glu
    1175                1180                1185

Leu Thr  Gly Pro Val Arg Ala  Gly Gly Ala Ile Ser  Glu Asn Ala
    1190                1195                1200

Thr Asp  Thr Pro Arg Arg Arg  Arg Arg Asp Val Thr  Leu Thr Ala
    1205                1210                1215

Pro Ile  Asp Met Arg Pro Phe  Ala Val Val Ser Gly  Asp His Asn
    1220                1225                1230

Pro Ile  His Thr Asp Arg Thr  Ala Ala Leu Leu Ala  Gly Leu Glu
    1235                1240                1245

Ser Pro  Ile Val His Gly Met  Trp Leu Ser Ala Ala  Ala Gln His
    1250                1255                1260

Val Val  Met Ala Thr Asp Gly  Gln Ala Arg Pro Ala  Ala Arg Leu
    1265                1270                1275
```

-continued

```
Ile Gly Trp Thr Ala Arg Phe Leu Gly Met Ala His Pro Gly Asp
    1280                1285                1290

Lys Val Asp Phe Arg Val Asp Arg Ile Gly Ile Asp Gln Gly Ala
    1295                1300                1305

Glu Ile Leu Glu Val Ser Ala Arg Ile Ser Ser Gly Leu Val Met
    1310                1315                1320

Ser Ala Thr Ala Arg Leu Ala Ala Pro Lys Thr Val Tyr Ala Phe
    1325                1330                1335

Pro Gly Gln Gly Ile Gln His Lys Gly Met Gly Met Asp Val Arg
    1340                1345                1350

Ala Arg Ser Lys Ala Ala Arg Arg Val Trp Asp Asp Ala Asp Lys
    1355                1360                1365

Phe Thr Arg Ser Gly Leu Gly Phe Ser Val Leu His Val Val Arg
    1370                1375                1380

Asp Asn Pro Thr Asn Ile Thr Ala Asn Gly Val His Tyr His His
    1385                1390                1395

Pro Asp Gly Val Leu Tyr Leu Thr Gln Phe Thr Gln Val Ala Met
    1400                1405                1410

Ala Thr Val Ala Val Ala Gln Val Ala Glu Met Arg Glu Gln Gly
    1415                1420                1425

Ala Phe Val Glu Gly Ala Ile Ala Cys Gly His Ser Val Gly Glu
    1430                1435                1440

Tyr Thr Ala Leu Ala Cys Val Met Gly Val Tyr Glu Leu Glu Ala
    1445                1450                1455

Leu Leu Glu Thr Val Phe His Arg Gly Ser Lys Met His Asp Ile
    1460                1465                1470

Val Leu Arg Asp Glu Leu Gly Arg Ser Asn Tyr Arg Leu Ala Ala
    1475                1480                1485

Ile Arg Pro Ser Gln Ile Gly Leu Pro Asp Asp Glu Val Pro Ala
    1490                1495                1500

Phe Val Arg Gly Ile Ala Glu Ser Thr Gly Glu Phe Leu Glu Ile
    1505                1510                1515

Val Asn Phe Asn Leu Arg Gly Ser Gln Tyr Ala Ile Ala Gly Thr
    1520                1525                1530

Val His Gly Leu Glu Ala Leu Glu Ala Glu Val Glu Arg Arg Arg
    1535                1540                1545

Glu Leu Thr Gly Gly Arg Arg Ser Phe Ile Leu Val Pro Gly Ile
    1550                1555                1560

Asp Val Pro Phe His Ser Arg Val Leu Arg Val Gly Val Ala Glu
    1565                1570                1575

Phe Arg Arg Ser Leu Asp Arg Val Leu Pro Gln Asp Gln Asp Pro
    1580                1585                1590

Asp Trp Ile Ile Gly Arg Tyr Ile Pro Asn Leu Val Pro Arg Pro
    1595                1600                1605

Phe Thr Leu Ala Arg Asp Phe Ile Gln Glu Ile Arg Asp Leu Val
    1610                1615                1620

Pro Ala Glu Pro Leu Asp Asp Ile Leu Ala Asp Tyr Asp Thr Trp
    1625                1630                1635

Arg Arg Glu Arg Pro Ser Glu Met Ala Arg Arg Val Leu Ile Glu
    1640                1645                1650

Leu Leu Ala Trp Gln Phe Ala Ser Pro Val Arg Trp Ile Glu Thr
    1655                1660                1665
```

-continued

```
Gln Asp  Leu Leu Phe Thr Glu  Glu Ala Ala Gly Gly  Leu Gly Val
    1670                 1675                 1680

Glu Arg  Phe Val Glu Ile Gly  Val Lys Ser Ala Pro  Thr Val Ala
    1685                 1690                 1695

Gly Leu  Ala Thr Asp Thr Leu  Lys Leu Pro Glu Tyr  Ser His Asn
    1700                 1705                 1710

Thr Val  Glu Val Leu Asn Val  Glu Arg Asp Ala Ala  Val Leu Phe
    1715                 1720                 1725

Ala Thr  Asp Thr Asp Pro Glu  Leu Glu Pro Glu Pro  Glu Asn Val
    1730                 1735                 1740

Ser Asp  Ala Ser Ala Ala Leu  Pro Ala Glu Ser Ala  Leu Ala Leu
    1745                 1750                 1755

Gly Thr  Val Ala Pro Ala Pro  Val Val Pro Ser Gly  Pro Arg Pro
    1760                 1765                 1770

Glu Asp  Ile Ser Phe Gly Ala  Ala Asp Ala Thr Leu  Ala Leu Ile
    1775                 1780                 1785

Ala Leu  Ser Ala Lys Met Arg  Leu Asp Gln Ile Glu  Glu Met Asp
    1790                 1795                 1800

Ser Ile  Glu Ser Ile Thr Asp  Gly Ala Ser Ser Arg  Arg Asn Gln
    1805                 1810                 1815

Leu Leu  Val Asp Leu Gly Ser  Glu Leu Ser Leu Gly  Ala Ile Asp
    1820                 1825                 1830

Gly Val  Ala Glu Ala Asp Leu  Ala Gly Leu Arg Ser  Gln Val Thr
    1835                 1840                 1845

Lys Leu  Ala Arg Thr Tyr Lys  Pro Tyr Gly Pro Val  Leu Ser Glu
    1850                 1855                 1860

Leu Ile  Asn Asp Gln Leu Arg  Ser Ala Leu Gly Pro  Ser Gly Lys
    1865                 1870                 1875

Arg Pro  Gly Val Ile Ala Glu  Arg Val Lys Lys Ile  Trp Glu Leu
    1880                 1885                 1890

Gly Asp  Gly Trp Val Lys His  Val Thr Val Glu Ile  Ala Leu Gly
    1895                 1900                 1905

Thr Arg  Glu Gly Thr Ser Val  Arg Gly Gly Pro Leu  Gly Asn Leu
    1910                 1915                 1920

Asn Glu  Gly Ala Leu Ala Asp  Val Asp Ser Val Asp  Lys Ala Val
    1925                 1930                 1935

Asp Ala  Ala Val Ala Ser Val  Ala Ala Arg His Gly  Val Val Val
    1940                 1945                 1950

Ala Leu  Pro Ser Ala Gly Ser  Gly Gly Ser Ala Thr  Val Asp Val
    1955                 1960                 1965

Ala Ala  Leu Ser Glu Phe Thr  Asp Gln Ile Thr Gly  His Asp Gly
    1970                 1975                 1980

Val Leu  Ala Ser Ala Ala Arg  Leu Val Leu Gly Gln  Leu Gly Leu
    1985                 1990                 1995

Asp Gly  Pro Val Thr Ala Ala  Pro Ala Thr Thr Asp  Thr Gly Leu
    2000                 2005                 2010

Ile Asp  Leu Val Thr Ala Glu  Leu Ser Thr Asp Trp  Pro Arg Leu
    2015                 2020                 2025

Val Ala  Pro Val Phe Asp Val  Lys Lys Ala Val Val  Phe Asp Asp
    2030                 2035                 2040

Arg Trp  Ala Ser Ala Arg Glu  Asp Leu Val Arg Leu  Trp Leu Asn
    2045                 2050                 2055

Asp Glu  Gly Glu Ile Glu Ala  Gln Trp Ser His Leu  Ser Glu Arg
```

-continued

```
    2060                2065                2070

Phe Glu  Gly Ala Gly His Val  Val Ala Thr Gln Ala  Thr Trp Trp
    2075                2080                2085

Gln Gly  Lys Ser Leu Ala Ala  Gly Arg Gln Ile His  Ala Ser Leu
    2090                2095                2100

Tyr Gly  Arg Ile Ala Ala Gly  Ala Gln Asn Pro Asp  Arg Gly Leu
    2105                2110                2115

Tyr Ser  Ser Glu Ile Ala Val  Val Thr Gly Ala Ser  Lys Gly Ser
    2120                2125                2130

Ile Ala  Ala Ser Val Ala Ala  Arg Leu Leu Asp Gly  Gly Ala Thr
    2135                2140                2145

Val Ile  Ala Thr Thr Ser Lys  Leu Asp Glu Glu Arg  Ile Thr Phe
    2150                2155                2160

Tyr Arg  Ala Leu Tyr Arg Asp  His Ala Arg Tyr Gly  Ala Ala Leu
    2165                2170                2175

Trp Val  Val Ala Ala Asn Met  Ala Ser Tyr Ser Asp  Ile Asp Ala
    2180                2185                2190

Leu Val  Glu Trp Ile Gly Asn  Glu Gln Thr Glu Ser  Leu Gly Pro
    2195                2200                2205

Gln Ser  Ile His Ile Lys Asp  Ala Gln Thr Pro Thr  Leu Leu Phe
    2210                2215                2220

Pro Phe  Ala Ala Pro Arg Val  Ile Gly Asp Leu Ser  Glu Ala Gly
    2225                2230                2235

Ala Arg  Ser Glu Ile Glu Met  Lys Val Leu Leu Trp  Ala Val Gln
    2240                2245                2250

Arg Leu  Ile Val Gly Leu Ser  Lys Ile Gly Thr Glu  Arg Asp Val
    2255                2260                2265

Ala Ser  Arg Leu His Val Val  Leu Pro Gly Ser Pro  Asn Arg Gly
    2270                2275                2280

Met Phe  Gly Gly Asp Gly Ala  Tyr Gly Glu Ala Lys  Ser Ala Leu
    2285                2290                2295

Asp Ala  Val Val Ser Arg Trp  His Ala Glu Ser Ser  Trp Ala Ala
    2300                2305                2310

Arg Val  Ser Leu Ala His Ala  Leu Ile Gly Trp Thr  Arg Gly Thr
    2315                2320                2325

Gly Leu  Met Gly His Asn Asp  Val Ile Val Ser Ala  Val Glu Glu
    2330                2335                2340

Ala Gly  Val Thr Thr Tyr Ser  Thr Asp Glu Met Ala  Ala Met Leu
    2345                2350                2355

Leu Asp  Leu Cys Asn Ala Glu  Ser Lys Val Ala Ala  Ala Gly Thr
    2360                2365                2370

Pro Ile  Thr Val Asp Leu Thr  Gly Gly Leu Gly Glu  Val Asp Leu
    2375                2380                2385

Asp Met  Ala Glu Leu Ala Ala  Lys Ala Arg Glu Asp  His Ala Ala
    2390                2395                2400

Gln Ala  Ala Glu Asp Glu Ala  Thr Glu Ala Ser Glu  Val Ala Gly
    2405                2410                2415

Thr Ile  Ala Ala Leu Pro Ser  Pro Pro Arg Gly Tyr  Thr Pro Ala
    2420                2425                2430

Ser Pro  His Trp Asp Asp Leu  Asp Val Asp Pro Ala  Asp Leu Val
    2435                2440                2445

Val Ile  Val Gly Gly Ala Glu  Ile Gly Pro Tyr Gly  Ser Ser Arg
    2450                2455                2460
```

-continued

Thr Arg Phe Glu Met Glu Val Ala Gly Glu Leu Ser Ala Ala Gly
2465 2470 2475

Val Leu Glu Leu Val Trp Thr Thr Gly Leu Ile Arg Trp Glu Asp
2480 2485 2490

Asp Pro Gln Pro Gly Trp Tyr Asp Thr Glu Ser Gly Glu Leu Val
2495 2500 2505

Asp Glu Ser Glu Leu Val Glu Arg Tyr His Asp Thr Val Val Gln
2510 2515 2520

Arg Cys Gly Ile Arg Glu Phe Val Asp Asp Gly Thr Ile Asp Pro
2525 2530 2535

Asp His Ala Tyr Pro Leu Leu Val Ser Val Phe Leu Asp Lys Asp
2540 2545 2550

Phe Ala Phe Val Val Ser Ser Glu Ala Asp Ala Arg Ala Phe Val
2555 2560 2565

Glu Phe Asp Pro Glu His Thr Val Ile Arg Pro Val Pro Asp Ser
2570 2575 2580

Ser Asp Trp Gln Val Ile Arg Lys Ala Gly Thr Glu Ile Arg Val
2585 2590 2595

Pro Arg Lys Met Lys Leu Ser Arg Val Val Gly Gly Gln Ile Pro
2600 2605 2610

Thr Gly Phe Asp Pro Thr Val Trp Gly Ile Ser Pro Asp Met Val
2615 2620 2625

Ser Ser Ile Asp Arg Val Ala Val Trp Ser Ile Val Ala Thr Val
2630 2635 2640

Asp Ala Phe Leu Ser Ala Gly Phe Thr Pro Ala Glu Val Met Arg
2645 2650 2655

Tyr Val His Pro Ser Leu Val Ala Asn Thr Met Gly Thr Gly Met
2660 2665 2670

Gly Gly Gly Thr Ser Ile Gln Arg Leu Tyr His Ser Ser Leu Leu
2675 2680 2685

Gly Arg Asn Lys Pro Asn Asp Ile Phe Gln Glu Ile Leu Pro Asn
2690 2695 2700

Ile Val Ala Ala His Val Val Gln Ser Tyr Ile Gly Ser Tyr Gly
2705 2710 2715

Ser Met Ile His Pro Val Ala Ala Cys Ala Thr Ala Ala Val Ser
2720 2725 2730

Val Glu Glu Gly Val Asp Lys Ile Arg Leu Gly Lys Ala Glu Leu
2735 2740 2745

Val Val Ala Gly Gly Ile Asp Asp Leu Thr Leu Glu Gly Ile Ile
2750 2755 2760

Gly Phe Gly Asp Met Ala Ala Thr Ala Asp Thr Ala Met Met Arg
2765 2770 2775

Gly Arg Gly Ile His Asp Ser Lys Phe Ser Arg Pro Asn Asp Arg
2780 2785 2790

Arg Arg Leu Gly Phe Val Glu Ala Gln Gly Gly Gly Thr Ile Leu
2795 2800 2805

Leu Ala Arg Gly Asp Leu Ala Leu Lys Met Gly Leu Pro Val Phe
2810 2815 2820

Ala Val Val Ala Phe Ala Gln Ser Phe Gly Asp Gly Val His Thr
2825 2830 2835

Ser Ile Pro Ala Pro Gly Leu Gly Ala Leu Gly Ala Gly Arg Gly
2840 2845 2850

-continued

```
Gly Lys  Asp Ser Pro Leu Val  Gln Ser Leu Ala Lys  Leu Gly Val
    2855                 2860                 2865

Ser Ala  Asp Asp Ile Ala Val  Ile Ser Lys His Asp  Thr Ser Thr
    2870                 2875                 2880

Leu Ala  Asn Asp Pro Asn Glu  Thr Glu Leu His Glu  Arg Leu Ala
    2885                 2890                 2895

Asp Ala  Met Gly Arg Ser Ala  Gly Ala Pro Leu Phe  Val Val Ser
    2900                 2905                 2910

Gln Lys  Ser Leu Thr Gly His  Ala Lys Gly Gly Ala  Ala Val Phe
    2915                 2920                 2925

Gln Met  Met Gly Leu Cys Gln  Met Leu Arg Asp Gly  Val Ile Pro
    2930                 2935                 2940

Pro Asn  Arg Ser Leu Asp Cys  Val Asp Glu Glu Leu  Ala Gly Ala
    2945                 2950                 2955

Ala His  Phe Val Trp Leu Arg  Asp Thr Leu Arg Leu  Gly Glu Lys
    2960                 2965                 2970

Phe Pro  Leu Lys Ala Gly Met  Leu Thr Ser Leu Gly  Phe Gly His
    2975                 2980                 2985

Val Ser  Gly Leu Val Ala Leu  Val His Pro Gln Ala  Phe Ile Ala
    2990                 2995                 3000

Ala Leu  Asp Pro Gly Gln Arg  Asp Asp Tyr Gln Arg  Arg Ala Asn
    3005                 3010                 3015

Val Arg  Leu Leu Ala Gly Gln  Arg Arg Leu Ala Ser  Ala Ile Ala
    3020                 3025                 3030

Gly Gly  Ala Pro Met Tyr Glu  Arg Pro Pro Asp Arg  Arg Phe Asp
    3035                 3040                 3045

His His  Val Pro Glu Lys Leu  Gln Glu Ala Ala Met  Leu Leu Asn
    3050                 3055                 3060

Pro Ala  Ala Arg Leu Gly Asp  Gly Asp Ala Tyr Ile  Gly
    3065                 3070                 3075


<210> SEQ ID NO 25
<211> LENGTH: 2586
<212> TYPE: PRT
<213> ORGANISM: Caenorhabditis elegans

<400> SEQUENCE: 25

Met Asp Pro Thr Gln Trp Trp Gln Lys Gln Asp Asp Ile Val Ile Ser
1               5                   10                  15

Gly Val Ser Gly Arg Phe Pro Arg Cys Asp Asn Val Lys Met Phe Gly
            20                  25                  30

Asp Met Leu Leu Ala Gly Glu Asp Leu Val Thr Glu Asp Ser Leu Arg
        35                  40                  45

Trp Thr Pro Gly Phe Cys Asp Leu Pro Lys Arg His Gly Lys Leu Lys
    50                  55                  60

Val Leu Asn Lys Phe Asp Ala Gly Phe Phe Gln Val Thr Pro Lys Gln
65                  70                  75                  80

Ala Asn Phe Met Asp Pro Gln Val Arg Leu Leu Leu Glu Ala Ser Trp
                85                  90                  95

Glu Ala Met Val Asp Ala Gly Ile Asn Pro Thr Asp Leu Arg Gly Ser
            100                 105                 110

Lys Thr Gly Val Phe Val Gly Cys Ser Ala Ser Glu Thr Ser Gly Met
        115                 120                 125

Leu Thr Gln Asp Pro Asp Thr Val Thr Gly Tyr Thr Leu Thr Gly Cys
    130                 135                 140
```

-continued

```
Val Arg Ser Met Phe Ser Asn Arg Ile Ser Tyr Thr Phe Asp Leu Gln
145                 150                 155                 160

Gly Pro Ser Phe Ser Val Asp Thr Ala Cys Ser Ser Ser Leu Leu Ala
                165                 170                 175

Leu Gln Leu Ala Val Asp Ser Ile Arg Gln Gly Gln Cys Asp Ala Ala
            180                 185                 190

Ile Val Ala Gly Ala His Leu Thr Leu Thr Pro Thr Ala Ala Leu Gln
        195                 200                 205

Phe Leu Arg Leu Gly Met Leu Thr Asp Lys Gly Ser Cys Arg Ser Phe
    210                 215                 220

Asp Glu Ser Gly Asp Gly Tyr Cys Arg Thr Glu Gly Val Ala Ala Ile
225                 230                 235                 240

Phe Ile Gln Arg Lys Lys Lys Ala Gln Arg Leu Tyr Ala Thr Val Val
                245                 250                 255

His Ala Lys Ser Asn Thr Asp Gly His Lys Glu His Gly Ile Thr Phe
            260                 265                 270

Pro Ser Gly Glu Arg Gln Ala Gln Leu Leu Gln Glu Val Tyr Ser Glu
        275                 280                 285

Ala Gly Ile Asp Pro Asn Ser Val Tyr Tyr Val Glu Ala His Gly Thr
    290                 295                 300

Gly Thr Lys Val Gly Asp Pro Gln Glu Ala Asn Ala Ile Cys Glu Val
305                 310                 315                 320

Phe Cys Ser Lys Arg Thr Asp Ser Leu Leu Ile Gly Ser Val Lys Ser
                325                 330                 335

Asn Met Gly His Ala Glu Pro Ala Ser Gly Val Cys Ser Leu Thr Lys
            340                 345                 350

Ile Leu Leu Ser Ile Glu Arg Gln Leu Ile Pro Pro Asn Leu His Tyr
        355                 360                 365

Asn Thr Pro Asn Gln Tyr Ile Pro Gly Leu Thr Asp Gly Arg Leu Lys
    370                 375                 380

Val Val Thr Glu Pro Thr Ala Leu Pro Gly Gly Leu Ile Gly Ile Asn
385                 390                 395                 400

Ser Phe Gly Phe Gly Gly Ser Asn Thr His Val Ile Leu Lys Ala Ala
                405                 410                 415

Asp His Ile Ala Pro Pro Ile Thr Pro His Pro Phe Thr Lys Leu Val
            420                 425                 430

Thr Tyr Cys Gly Arg Thr Gln Glu Ala Val Glu Asn Ile Phe Thr Glu
        435                 440                 445

Ile Glu Ser Asn Lys Asp Asp Leu Tyr Leu Gln Ala Leu Leu Ala Asn
    450                 455                 460

Gln Ala Asn Met Pro Ala Asn Leu Leu Pro Phe Arg Gly Tyr Met Leu
465                 470                 475                 480

Leu Asp Arg Glu Asn Asn Val Glu Thr Leu Lys Ser Ile Thr Lys Val
                485                 490                 495

Pro Ile Thr Glu Ala Arg Pro Ile Tyr Phe Ile Tyr Ser Gly Met Gly
            500                 505                 510

Ser Gln Trp Pro Gly Met Ala Ile Lys Leu Met Lys Ile Pro Met Phe
        515                 520                 525

Asp Asp Ser Leu Arg Ala Ser Ser Lys Thr Leu Glu Glu Phe Gly Leu
    530                 535                 540

Asp Val Tyr Gly Met Leu Cys Asn Pro Asp Pro Glu Gln Tyr Ser Asn
545                 550                 555                 560
```

-continued

```
Asn Thr Met Asn Cys Met Leu Ala Ile Thr Ala Ile Gln Ile Ala Leu
                565                 570                 575

Thr Asp Val Leu Thr Ala Leu Gly Val Ser Pro Asp Gly Ile Ile Gly
            580                 585                 590

His Ser Thr Gly Glu Met Gly Cys Gly Tyr Ala Asp Gly Gly Ile Thr
        595                 600                 605

Arg Glu Gln Thr Met Arg Leu Ala Tyr His Arg Gly Thr Thr Ile Met
    610                 615                 620

Lys His Thr Glu Ile Lys Gly Ala Met Ala Ala Val Gly Leu Thr Trp
625                 630                 635                 640

Glu Gln Val Lys Glu Gln Ala Pro Pro Gly Val Val Ala Ala Cys His
                645                 650                 655

Asn Gly Ala Asp Ser Val Thr Ile Ser Gly Asp Ala Glu Gly Val Ala
            660                 665                 670

Thr Phe Cys Ala Gln Leu Lys Glu Lys Asp Ile Phe Ala Lys Val Val
        675                 680                 685

Asp Thr Ser Gly Ile Pro Phe His Ser Pro Ala Met Leu Ala Val Gln
    690                 695                 700

Asp Glu Met Ile Glu Cys Met Arg Thr Ala Val Pro Glu Pro Lys Pro
705                 710                 715                 720

Arg Ser Ser Lys Trp Ile Ser Thr Ser Ile Pro Glu Asp Asp Trp Glu
                725                 730                 735

Ser Asp Leu Ala Ala Thr Cys Ser Ala Glu Tyr His Val His Asn Ala
            740                 745                 750

Cys Ser Pro Val Leu Phe Tyr Glu Ala Ile Gln Lys Ile Pro Ala Asn
        755                 760                 765

Ala Val Thr Ile Glu Met Ala Pro His Ser Leu Met Gln Ala Ile Leu
    770                 775                 780

Arg Arg Ser Leu Gln Lys Thr Val Thr Asn Val Gly Leu Met Asn Arg
785                 790                 795                 800

Pro Lys Ser Glu Asn Asp Asp Glu Leu Glu Ser Phe Leu Gly Ser Leu
                805                 810                 815

Gly Lys Ile Tyr Gln Ala Gly Val Asn Ile Gln Ile Thr Glu Leu Tyr
            820                 825                 830

Pro Gly Gly Gln Tyr Lys Gly Val Val Pro Lys Gly Thr Pro Met Ile
        835                 840                 845

Gly Pro Met Trp Lys Trp Asp His Thr Gln Asp Trp Leu Thr Ile Asp
    850                 855                 860

Gly Arg Gln Val Leu Ala Gly Gly Ser Gly Ser Val Ala Ser Ser Ala
865                 870                 875                 880

Thr Tyr Asn Ile Asp Pro Phe Ala Thr Asp Ser Lys Glu Thr Tyr Leu
                885                 890                 895

Leu Asp His Val Ile Asp Gly Arg Val Leu Tyr Pro Phe Thr Gly His
            900                 905                 910

Met Val Leu Ala Trp Arg Thr Leu Cys Lys Leu Lys Gly Leu Asp Tyr
        915                 920                 925

Thr Lys Thr Pro Val Val Phe Glu Asn Ile Asn Val Phe Ser Ala Thr
    930                 935                 940

Ile Leu Thr Lys Pro Ile Lys Leu Asp Val Val Leu Ser Pro Gly Asn
945                 950                 955                 960

Gly Tyr Phe Glu Ile Ile Ser Asp Asp Gln Val Ala Ala Ser Gly Arg
                965                 970                 975

Ile Tyr Ile Pro Glu Asp Asn Gln Pro Phe Tyr Tyr Gly Lys Leu Glu
```

-continued

```
                980                 985                 990

Asp Ile Arg Thr Ser Glu Ile Ala  Asp Arg Ile Glu Leu  Asp Thr Glu
            995                 1000                1005

Asp Ala  Tyr Lys Glu Phe Leu  Leu Arg Gly Tyr Glu  Tyr Gly Gln
    1010                 1015                 1020

Ala Phe  Arg Gly Ile Tyr Lys  Thr Cys Asn Ser Gly  Glu Arg Gly
    1025                 1030                 1035

Phe Leu  Tyr Trp Thr Gly Asn  Trp Val Thr Phe Leu  Asp Ser Leu
    1040                 1045                 1050

Leu Gln  Thr Ala Leu Leu Ala  Glu Arg Ser Asp Thr  Leu Arg Leu
    1055                 1060                 1065

Pro Thr  Arg Val Arg His Leu  Arg Ile Asp Pro Asn  Lys His Leu
    1070                 1075                 1080

Glu His  Val Val Glu Lys Asp  Gly Ile Gln Val Ile  Glu Leu Arg
    1085                 1090                 1095

Asn Asp  His Ser Thr Asn Gly  Cys Ile Ala Gly Gly  Val Glu Cys
    1100                 1105                 1110

Cys Asp  Leu Asn Ala His Ser  Val Ala Arg Arg Ile  Gln Val Ser
    1115                 1120                 1125

Gly Gln  Leu Tyr His Glu Lys  Ile Phe Phe Val Pro  His Phe Asp
    1130                 1135                 1140

His Asn  Cys Leu Ser Gly His  Lys Lys Thr Ser Thr  Ile Leu Lys
    1145                 1150                 1155

Asp Tyr  Ser Ala Val Ile Lys  Gln Gln Leu Tyr Thr  Gly Phe Ser
    1160                 1165                 1170

Lys Trp  Gln Ser Ala Gly Leu  Leu Lys Lys Leu Lys  Asn Gly Ala
    1175                 1180                 1185

Gln Ile  Val Lys Ala Leu Ala  Val Leu Lys Ala Ser  Gln Ser Asp
    1190                 1195                 1200

Val Val  Leu Asp Asp Thr Val  Thr Arg Phe Thr His  Asp Gly Lys
    1205                 1210                 1215

Cys Thr  Val Leu His His Ile  Ala Asp Met Phe Lys  Ile Glu Asp
    1220                 1225                 1230

Cys Glu  Asp Phe Glu Asp Arg  Val Ala Ala Lys Leu  Lys Ser Val
    1235                 1240                 1245

Arg Gly  Ile Phe Glu Leu Asp  Arg Leu Trp Ala Gly  Ala Val Leu
    1250                 1255                 1260

Asn Asp  Arg Ile Val Lys Ser  Leu Gln Asp Ile Cys  Ile Glu Asn
    1265                 1270                 1275

Ser Ala  Gly His His Ala Thr  Met Ala Ala Val Asp  Leu Val Ser
    1280                 1285                 1290

Thr Asp  Gln Ile Arg His Cys  Ile Glu Ala Asn Ser  Ser His Pro
    1295                 1300                 1305

Leu Leu  Glu Thr Asp Tyr Thr  Cys Ile Gly Ala Asn  Val Asp His
    1310                 1315                 1320

Leu Asp  Glu Ser Thr Leu Glu  Ile Ile Gly Gly Lys  Lys Gln Lys
    1325                 1330                 1335

Ile Asp  Leu Glu Asn Asn Phe  Thr Gly His Gly Glu  Val Lys Asn
    1340                 1345                 1350

Leu Asp  Tyr Val Leu Leu Asp  Lys Val Ile Ser Lys  Lys Ala Asp
    1355                 1360                 1365

Pro Ile  Ala Phe Ile Glu Ala  Cys Lys His Leu Ile  Arg Glu Thr
    1370                 1375                 1380
```

-continued

Gly Phe Leu Leu Val Val Glu Val Thr Ser Gln Tyr Glu Ile Ala
1385 1390 1395

Leu Ala Ile Glu Gly Leu Leu Gly Asn Glu Met Val Gly Asp Ala
1400 1405 1410

Ser Arg Lys Tyr Asn Gln Phe Phe Thr His Glu Gln Leu Leu Asp
1415 1420 1425

Met Phe Lys Ser Thr Gly Phe Leu Ile Cys Asn Phe Gln Ser Asp
1430 1435 1440

Pro Ala Leu Met Thr Thr Thr Tyr Ala Val Arg Arg Val Ser Pro
1445 1450 1455

Ile Pro Arg Asp Pro Val Phe Ile Asp Val Asp Asp Val Lys Glu
1460 1465 1470

Phe Asn Trp Ile Glu Pro Leu Gln Lys Val Ser Glu Glu Arg Leu
1475 1480 1485

Asn Glu Pro Asp Ser Lys Thr Ile Trp Leu Val Ser Asn Lys Cys
1490 1495 1500

Arg Asn Asn Gly Ile Val Gly Leu Gly Leu Cys Phe Val Glu Glu
1505 1510 1515

Asn Leu Lys Ile Asn Arg Phe Arg Ser Ala Phe Asp Met Ser Ala
1520 1525 1530

Asn Lys Glu Ile Arg Asp Gly Pro Pro Val Trp Asn Ile Gly Asp
1535 1540 1545

Glu Glu Thr Lys Lys Ile Val Glu Leu Asp Leu His Ala Asn Asp
1550 1555 1560

Tyr Met Asp Gly Gln Trp Gly Ser Met Arg His Ile Val Val Lys
1565 1570 1575

Asp Glu Asp Val His Val Tyr Lys Asp Cys Glu His Ala Phe Ile
1580 1585 1590

Asn Thr Leu Thr Arg Gly Asp Val Ser Ser Leu Thr Trp Phe Glu
1595 1600 1605

Ser Pro Asn Gln Tyr Phe Asp Ser Met Val Lys Ser Lys Ala Thr
1610 1615 1620

Gln Glu Leu Cys Ser Val Tyr Tyr Ala Pro Ile Asn Phe Arg Asp
1625 1630 1635

Ile Met Leu Ala Tyr Gly Arg Leu Pro Pro Asp Ala Ile Pro Gly
1640 1645 1650

Asn Phe Ala Asp Arg Glu Cys Leu Leu Gly Met Glu Phe Ser Gly
1655 1660 1665

Arg Leu Lys Asp Gly Thr Arg Leu Met Gly Ile Leu Pro Ala Gln
1670 1675 1680

Ala Leu Ala Thr Thr Val Met Val Asp Arg Asp Tyr Ala Trp Glu
1685 1690 1695

Val Pro Arg Asp Trp Thr Leu Ala Glu Ala Ser Thr Val Pro Val
1700 1705 1710

Val Tyr Thr Thr Ala Tyr Tyr Ala Leu Val Arg Arg Gly Leu Met
1715 1720 1725

Lys Lys Gly Asp Lys Ile Leu Ile His Gly Gly Ala Gly Gly Val
1730 1735 1740

Gly Gln Ala Ala Ile Ala Ile Ala Leu Ala Ala Gly Cys Glu Val
1745 1750 1755

Phe Thr Thr Val Gly Ser Ala Glu Lys Arg Glu Phe Leu Lys Asn
1760 1765 1770

-continued

```
Leu Phe  Pro Gln Leu Gln Glu  His His Phe Ala Asn  Ser Arg Ser
    1775                 1780                 1785

Ala Asp  Phe Glu Leu His Ile  Arg Gln His Thr Lys  Gly Arg Gly
    1790                 1795                 1800

Val Asn  Ile Val Leu Asn Ser  Leu Ala Asn Glu Met  Leu Gln Ala
    1805                 1810                 1815

Ser Leu  Arg Cys Leu Ala Arg  His Gly Arg Phe Leu  Glu Ile Gly
    1820                 1825                 1830

Lys Val  Asp Leu Ser Gln Asn  Ser Ser Leu Gly Met  Ala Lys Leu
    1835                 1840                 1845

Leu Asp  Asn Val Ser Val His  Gly Ile Leu Leu Asp  Ser Ile Met
    1850                 1855                 1860

Asp Pro  Thr Val Gly Asp Leu  Asp Glu Trp Lys Glu  Ile Ala Arg
    1865                 1870                 1875

Leu Leu  Glu Gln Gly Ile Lys  Ser Gly Val Val Lys  Pro Leu His
    1880                 1885                 1890

Ser His  Ser Phe Pro Ala Asp  Lys Ala Glu Glu Ala  Phe Arg Phe
    1895                 1900                 1905

Met Ser  Ala Gly Lys His Ile  Gly Lys Val Ile Met  Glu Ile Arg
    1910                 1915                 1920

Pro Asp  Glu Gly Thr Lys Val  Cys Pro Pro Ser Lys  Ile Ser Val
    1925                 1930                 1935

Arg Ala  Ile Cys Arg Thr Leu  Cys His Pro Gln His  Thr Tyr Leu
    1940                 1945                 1950

Ile Thr  Gly Gly Leu Gly Gly  Phe Gly Leu Glu Leu  Ala Gln Trp
    1955                 1960                 1965

Leu Ile  Asn Arg Gly Ala Arg  Lys Leu Val Leu Thr  Ser Arg Thr
    1970                 1975                 1980

Gly Ile  Arg Thr Gly Tyr Gln  Ala Arg Cys Val His  Phe Trp Arg
    1985                 1990                 1995

Arg Thr  Gly Val Ser Val Leu  Val Ser Thr Leu Asn  Ile Ala Lys
    2000                 2005                 2010

Lys Ser  Asp Ala Val Glu Leu  Ile Asn Gln Cys Thr  Ala Met Gly
    2015                 2020                 2025

Pro Ile  Gly Gly Ile Phe His  Leu Ala Met Val Leu  Arg Asp Cys
    2030                 2035                 2040

Leu Phe  Glu Asn Gln Asn Val  Gln Asn Phe Lys Asp  Ala Ala Glu
    2045                 2050                 2055

Ala Lys  Tyr Tyr Gly Thr Ile  Asn Leu Asp Tyr Ala  Ser Arg Glu
    2060                 2065                 2070

His Cys  Asp Lys Asn Ile Leu  Lys Trp Phe Val Val  Phe Ser Ser
    2075                 2080                 2085

Ile Thr  Ser Gly Arg Gly Asn  Ala Gly Gln Thr Asn  Tyr Gly Trp
    2090                 2095                 2100

Ser Asn  Ser Cys Met Glu Arg  Met Ile Asp Gln Arg  Arg Ala Asp
    2105                 2110                 2115

Gly Phe  Pro Gly Ile Ala Ile  Gln Trp Gly Ala Ile  Gly Asp Val
    2120                 2125                 2130

Gly Val  Ile Leu Glu Asn Met  Gly Asp Asn Asn Thr  Val Val Gly
    2135                 2140                 2145

Gly Thr  Leu Pro Gln Arg Met  Pro Ser Cys Leu Ser  Ser Leu Asp
    2150                 2155                 2160

Asn Phe  Leu Ser Trp Asn His  Pro Ile Val Ser Ser  Phe Ile Lys
```

-continued

```
    2165                2170                2175

Ala Glu  Leu Gly Ser Lys Lys  Asn Val Gly Gly Gly  Asp Leu Met
    2180                2185                2190

Ala Thr  Ile Ala His Ile Leu  Gly Val Asn Asp Ile  Ser Gln Leu
    2195                2200                2205

Asn Ala  Asp Ala Asn Leu Ser  Asp Leu Gly Leu Asp  Ser Leu Met
    2210                2215                2220

Gly Val  Glu Ile Lys Gln Ala  Leu Glu Arg Asp His  Asp Ile Val
    2225                2230                2235

Leu Ser  Met Lys Glu Ile Arg  Thr Leu Thr Leu Asn  Lys Leu Gln
    2240                2245                2250

Gln Leu  Ala Asp Gln Gly Gly  Thr Gly Arg Thr Ala  Leu Gln Val
    2255                2260                2265

Asn Glu  Leu Glu Met Lys Lys  Asp Gly Glu Arg Asp  Ala Glu Leu
    2270                2275                2280

Asn Thr  Ala Glu Met Leu Glu  Gln Gln Met Asn Gln  Leu Phe Lys
    2285                2290                2295

Met Arg  Val Asp Val Asn Asp  Leu Asp Pro Gln Asp  Ile Ile Val
    2300                2305                2310

Lys Ala  Asn Lys Val Glu Glu  Gly Pro Ile Thr Phe  Phe Val His
    2315                2320                2325

Ser Ile  Glu Gly Ile Ala Thr  Pro Leu Lys Lys Val  Met Asn Lys
    2330                2335                2340

Cys Glu  Phe Pro Ala Tyr Cys  Phe Gln Ser Thr Lys  Asn Val Pro
    2345                2350                2355

Gln Thr  Ser Ile Glu Asp Val  Ala Lys Cys Tyr Ile  Arg Glu Met
    2360                2365                2370

Lys Lys  Ile Gln Pro Ser Gly  Pro Tyr Arg Leu Val  Gly Tyr Ser
    2375                2380                2385

Tyr Gly  Ala Cys Ile Gly Phe  Glu Met Ala Asn Met  Leu Gln Glu
    2390                2395                2400

Ser Asp  Gly Arg Asp Ala Val  Glu Arg Leu Ile Leu  Leu Asp Gly
    2405                2410                2415

Ser His  Leu Tyr Met Gln Thr  Tyr Arg Asn Val Tyr  Arg Met Ala
    2420                2425                2430

Phe Gly  Val Thr Gly Asp Ser  Leu Val Asn Asn Pro  Leu Phe Glu
    2435                2440                2445

Ser Glu  Ile Met Cys Ala Met  Thr Leu Arg Phe Ala  Asn Val Asp
    2450                2455                2460

Tyr Lys  Lys Phe Arg Phe Glu  Leu Leu Gln Gln Pro  Gly Phe Lys
    2465                2470                2475

Ala Arg  Val Gln Lys Val Val  Asp Gln Val Met Leu  Thr Gly Leu
    2480                2485                2490

Phe Lys  Ser Pro Glu Thr Val  Ala Phe Ala Cys Glu  Ala Met His
    2495                2500                2505

Ser Lys  Phe Leu Met Ala Asp  Lys Tyr Lys Pro Arg  Arg Asn Phe
    2510                2515                2520

Gly Gly  His Ile Thr Leu Ile  Arg Ala Glu Gln Gly  Ala Ala Arg
    2525                2530                2535

Glu Glu  Asp Val Gly Glu Asp  Tyr Gly Val Ala Ala  Val Ser Glu
    2540                2545                2550

Asp Cys  Glu Val Leu Lys Val  Lys Gly Asp His Asp  Thr Phe Val
    2555                2560                2565
```

-continued

Gln Gly Lys Ser Ser Ser Val Thr Val Glu His Ile Asn Arg Ile
2570 2575 2580

Ile Leu Gln
2585

<210> SEQ ID NO 26
<211> LENGTH: 8936
<212> TYPE: DNA
<213> ORGANISM: Rattus norvegicus

<400> SEQUENCE: 26
aggctgggct ctatgggttg cctaagcggt ctggaaagct gaaggatctg tccaagttcg 60
acgcctcctt ttttggggtc caccccaagc aggcacacac aatggacccg cagctccggc 120
tgctgctgga agtcagctat gaagctattg tggacggagg tatcaacccg gcctcactcc 180
gaggaacaaa cactggtgtc tgggtgggtg tgagtggttc cgaggcgtcg gaggccctga 240
gcagagatcc tgagactctt ctgggctaca gcatggtggg ctgccagaga gcaatgatgg 300
ccaaccggct ctctttcttc ttcgacttca aaggacccag cattgccctg gacacagcct 360
gctcctctag cctactggca ctacagaatg cctatcaggc tatccgcagt ggggagtgcc 420
ctgctgccat tgtgggcggg atcaacctgc tgctaaagcc taacacctct gtgcagttca 480
tgaagctagg catgctcagc ccgatggca cctgcagatc ctttgatgat tcagggaacg 540
ggtattgccg tgctgaggct gtcgtggcag ttctgctgac taagaagtcc ttggctcggc 600
gagtctatgc cactattctg aatgccggga cgaacacaga tggctgcaag gagcaaggcg 660
tgacattccc ctctggagaa gcccaggaac aactcatccg ttctctgtat cagccgggcg 720
gtgtggcccc cgagtctctt gaatatattg aagcccatgg cacgggcacc aaggtggggg 780
acccccagga actgaacggc attactcggt ccctgtgtgc tttccgccag agccctttgt 840
taattggctc caccaaatcc aacatgggac accctgagcc tgcctcgggg cttgcagccc 900
tgaccaaggt gctgttatcc ctagaaaatg ggggtttggc ccccaacctg catttccaca 960
accccaaccc tgaaatccca gcacttcttg atgggcggct gcaggtggtc gataggcccc 1020
tgcctgttcg tggtggcatc gtgggcatca actcgtttgg cttcggaggt gccaatgttc 1080
acgtcatcct ccagcccaac acacagcagg ccccagcacc tgccccacat gctgccctac 1140
cgcatttgct gcatgccagt ggacggacca tggaggcagt gcagggcctg ctggaacagg 1200
gccgccagca cagtcaggac ttggcctttg ttagcatgct caatgacatt gcagcaaccc 1260
ctacagcagc catgcccttc agaggttaca ctgtgttagg tgttgagggc catgtccagg 1320
aagtgcagca agtgcctgcc agccagcgcc cactctggtt catctgctca gggatgggca 1380
cacagtggcg tggaatgggg ctgagcctta tgcgcctgga cagtttccgt gagtccatcc 1440
tgcgctctga tgaggctctg aagcccttgg gagtcaaagt gtcagacctg ctgctgagca 1500
ctgatgagca cacctttgat gacatcgtgc attcctttgt gagcctcacc gccatccaga 1560
ttgccctcat cgacctgctg acgtctatgg ggctgaaacc tgatggcatc attgggcact 1620
ccttgggaga ggttgcctgt ggctatgcag atggctgtct ctcccagaga gaggctgtgc 1680
ttgcagccta ctggagaggc cagtgcatta aggatgccaa ccttccggct ggatccatgg 1740
cagctgttgg tttgtcctgg gaagaatgta aacaacgctg ccctcctggt gtggtgcctg 1800
cctgccacaa ctctgaggac actgtgacca tctctggacc tcaggctgca gtgaatgaat 1860
ttgtggagca gctaaagcaa gagggcgtgt ttgccaagga ggtgcgaaca ggtggcctgg 1920

-continued

```
ccttccactc ctacttcatg gaaggaattg cccccacgct gctgcaggct ctcaagaagg   1980
tgatccggga gccacggcca cgctcagcac gctggctcag cacctctatc cctgaggccc   2040
agtggcagag cagcctggcc cgcacatctt ctgctgagta caacgtcaac aacctggtga   2100
gccctgtgct cttccaggaa gcactgtggc acgtccccga gcacgccgtg gtgctggaga   2160
ttgcacccca tgcactgttg caggctgtcc tgaagcgagg cgtgaagcct agctgcacca   2220
tcatcccctt gatgaagagg gaccataaag ataacttgga gttcttcctc accaacctcg   2280
gcaaggtgca cctcacaggc atcgacatca accctaatgc cttgttccca cctgtggaat   2340
tcccggttcc ccgagggact cctctcatct cccctcacat caagtgggac cacagtcaga   2400
cttgggatat cccagttgct gaagacttcc ccaacggttc cagctcctcc tcagctacag   2460
tctacaacat tgacgccagt tccgagtcac ctgaccacta cctggtcgac cactgcattg   2520
acggccgtgt cctcttccct ggcactggct acctgtacct ggtgtggaag acactggctc   2580
gaagcctgag cttgtcccta gaagagaccc ctgtggtgtt tgagaacgtg acatttcatc   2640
aggccaccat cctgcccagg acaggaaccg tgcctctgga ggtgcggctg ctagaggcct   2700
cacatgcatt tgaggtgtct gacagtggca acctgatagt gagcgggaaa gtgtaccagt   2760
gggaagaccc tgactccaag ttattcgacc acccagaagt cccgatcccc gccgagtccg   2820
agtctgtctc ccgcttgacg cagggagaag tatacaagga gctgcggcta cgtggctatg   2880
actatggccc tcatttccag ggcgtctatg aggccaccct cgaaggtgag caaggcaagc   2940
tgctctggaa agacaactgg gtgaccttca tggacacaat gctgcagata tccatcctgg   3000
gcttcagcaa gcagagtctg cagctaccca cccgtgtgac tgccatctat attgaccctg   3060
caacccacct gcagaaggtg tacatgctgg agggagacac tcaagtggct gacgtgacca   3120
cgagccgctg tctgggcgtg accgtctctg gtggtgtcta catttcgaga ctacagacaa   3180
cagcaacctc acggcggcag caggaacagc tggtccccac cctggagaag tttgtcttca   3240
caccccatgt ggagcctgag tgcctgtctg agagtgctat cctgcagaaa gagctgcagc   3300
tgtgcaaggg tctggcaaag gctctgcaga ccaaggccac ccagcaaggg ctgaagatga   3360
cagtgcctgg gctagaggac cttccccagc atggactgcc tcgactcttg gctgctgcct   3420
gccagctgca gctcaacggg aacctgcaac tggagttagg tgaggtactg gctcgagaga   3480
ggctcctgct gccagaagac cctctgatca gtggcctcct taactcccag gccctcaagg   3540
cctgcataga cacagccctg gagaacttgt ctactctcaa gatgaaggtg gtggaggtgc   3600
tggctggaga aggccacttg tattcccaca tctcagcact gctcaacacc cagcctatgc   3660
tgcaactgga gtatacagcc accgaccggc acccccaggc cctgaaggat gttcagacca   3720
agctgcagca gcatgatgta gcacagggcc agtgggaccc ttctggtcct gctcctacca   3780
acctgggtgc tcttgacctt gtggtgtgca actgtgcgtt agccaccctg ggggatccag   3840
ccctggccct ggacaacatg gtagctgccc tcaaggatgg tggtttcctg ctaatgcaca   3900
cagtgctcaa aggacatgcc cttggggaga ccctggcctg cctcccttct gaggtgcagc   3960
ctgggcccag cttcttaagc caggaagagt gggagagcct gttctcaagg aaggcactgc   4020
acctggtggg ccttaaaaag tcattctacg gtactgcgct gttcctgtgc cgccgtctca   4080
gcccacagga caagcccatc ttcctgcctg tggaggatac tagtttccag tgggtggact   4140
ctctgaagag cattctggcc acatcctcct cccagcctgt gtggctaaca gccatgaact   4200
gccccacctc aggtgtggta ggcttggtga actgtctccg aaaagagccg ggtggacacc   4260
ggattcggtg tatcctgctg tccaacctca gcagcacatc tcacgtcccc aagctggacc   4320
```

-continued

```
ctggctcttc agagctacag aaggtgctag agagtgatct ggtgatgaac gtgtacaggg   4380
acggtgcctg gggtgccttc cgtcacttcc agttagagca ggacaagccc gaggagcaga   4440
cagcacatgc ctttgtaaac gtccttaccc gaggggacct tgcctccatc cgctgggtct   4500
cttctcccct gaaacacatg cagccgccct cgagctcagg agcacagctc tgcactgtct   4560
actatgcctc actgaacttc cgagatatca tgctggccac gggcaagctg tcccctgatg   4620
ccattccagg taaatgggcc agccgggact gcatgcttgg catggagttc tcaggccgtg   4680
ataagtgcgg ccggcgtgtg atggggctgg tacccgcaga aggcctggcc acctcagtcc   4740
tgttatcacc cgacttcctc tgggatgtac cctctagctg gaccctggag gaggcggctt   4800
ctgtgcctgt tgtctacacc accgcctact actccttagt agtgcgtggt cgtattcagc   4860
acggggaaac tgtgctcatt cactcgggct ccggtggtgt gggccaagcg gccatttcca   4920
ttgcccttag cctgggctgc cgagtcttca ccactgtggg ctccgctgag aagcgagctt   4980
acctccaggc cagattccct cagctggatg acaccagctt tgctaactct cgagacacat   5040
cgtttgagca gcatgtgtta ctgcacacag gtggcaaagg ggtggacctg gtcctcaact   5100
ccctggcaga agagaagctg caggccagtg tgcggtgctt ggctcagcat ggccgcttcc   5160
tagagatcgg caaatttgat ctttctaaca accaccctct gggcatggcc atcttcttga   5220
agaacgtcac tttccatggg atcctgctgg atgcactttt tgagggggcc aacgacagct   5280
ggcgggaggt ggcagagctg ctgaaggccg gcatccgtga tggggttgtg aagcctctca   5340
agtgtacagt gtttcccaag gcccaggtgg aggacgcctt ccgatacatg gctcaaggaa   5400
aacatattgg caaagtcctt gtccaggtac gggaggagga gcccgaggct atgctgccag   5460
gggctcagcc caccctgatt tccgccatct ccaagacctt ctgcccagag cataagagtt   5520
acatcatcac tggtggccta ggtggctttg gcctggaact ggcccggtgg cttgtgcttc   5580
gtggggccca aaggcttgta ctaacttccc gatctggaat ccgcacaggc taccaagcca   5640
agcacgttcg ggagtggagg cgccagggca tccatgtgct agtgtcgaca agcaatgtca   5700
gttcactgga gggggcccgt gctctcatcg ctgaagccac aaagcttggg cccgttggag   5760
gtgtcttcaa cctggccatg gttttaaggg atgccatgct ggagaaccag actccagaac   5820
tcttccagga tgtcaacaag cccaagtaca atggcaccct gaaccttgac agggcgaccc   5880
gggaagcctg tcctgagctg gactactttg tggccttctc ctctgtaagc tgcgggcgtg   5940
gtaatgctgg ccaatccaac tatggcttcg ccaactctac catggagcgt atttgcgaac   6000
agcgccggca cgatggcctc ccaggtcttg ccgtgcaatg ggtgccatt ggtgacgtgg    6060
gcattatctt ggaagcgatg ggtaccaatg acacagtcgt tggcggcaca ctgccacagc   6120
gcatctcctc ctgcatggag gtgctggacc tcttcctgaa tcagccccac gcagtcctga   6180
gcagttttgt gctggctgag aagaaagctg tggcccatgg tgatggtgaa gcccagaggg   6240
atctggtgaa agcagtggca cacatcctag gcatccgcga cctcgcaggg attaacctgg   6300
acagctcgct ggcagacctc ggcctggact cgctcatggg tgtggaagtg cgccagatcc   6360
tggaacgtga acatgatctg gtgctaccca ttcgtgaagt acggcaactc acactgcgga   6420
agcttcagga aatgtcctcc aaggctggct cagacactga gttggcagcc cccaagtcca   6480
agaatgatac atccctgaag caggcccagc tgaatctgag tatcctgctg gtgaaccctg   6540
agggccctac cttaacacga ctcaactcag tgcagagctc tgagcggcct ctgttcctgg   6600
tgcaccccat tgaaggttcc atcactgtgt tccacagcct ggctgccaag ctcagtgtgc   6660
```

-continued

```
ccacctacgg tctgcagtgc acccaagcgg ccccccctgga cagcattcca aacctggctg   6720
cctactacat tgattgcatc aagcaggtgc agcctgaggg gccctaccga gtggctgggt   6780
attcttttgg agcttgtgta gccttcgaga tgtgctccca gctgcaggcc cagcagggcc   6840
cagccccccgc ccacaacaac ctcttcttgt ttgatggctc acacacctac gtattggcgt   6900
acacccagag ctaccgggca aagctgaccc caggctgtga ggctgaggct gaagctgaag   6960
ccatatgctt cttcattaag cagtttgttg atgcagagca tagcaaggtg ctagaggccc   7020
tgctaccact gaagagcctg gaggaccggg ttgctgctgc tgtggacctc atcactagaa   7080
gccaccagag cctggaccgc cgtgacctga gctttgctgc cgtgtccttc tactacaagc   7140
ttcgagccgc cgaccagtat aaacccaagg ccaagtacca cggcaatgtg atcctgctgc   7200
gggccaagac aggtggcacc tacggcgagg acttgggtgc cgattacaac ctgtcccagg   7260
tgtgtgatgg gaaggtgtct gtgcacatca ttgagggtga ccaccgtacg ctgctggagg   7320
gcaggggcct ggagtctatc atcaacatca tccacagctc cctggctgag cctcgagtga   7380
gtgtacggga gggctagacc tgcctaccat gaagccacga cccacaccgg ccaccagaga   7440
tgctccgatc cccaccacac cctgagtgca gggactgggg agggtcctgc tggtgggacc   7500
ccctcacccc agtggcccag caccaccccc tcccctggtg gctgctacaa acaggaccat   7560
cacatgtgtc ccagccactt agtggggttc ccagagccac tgacttggag gcaccctggt   7620
ctgtgaagag tcagtggagg ccagcaagag ccaaactgag ccttttctgc caagtgacat   7680
ttgtcacact ggttgtttct ccattaaatt ctcatattta ttgcattgct gggaaagacc   7740
gcccaccccca gggttaactc attccagaac ccctaaagtg ggaaaagcca tgtggggaag   7800
gctgctggct ggagcccctt tttgtcttag ccctgtaccc gctcactgca gggcagggta   7860
tggagagggc tggttcgcgg ggaacgagga ccccagcaga cactgtagcc catggccctt   7920
ggtccccagc actcccggct gcacccatga tgcagggcct accagactct gcggaccgca   7980
ccgggcactc actgtatttg ttttccaaga ttcaaattgc tgcttgggtt ttgaatttac   8040
tgcagctgtc agtgtaaaga aacatgtctg aactgtgtcc tttttacacc aacctggtaa   8100
aaatgctctt gatgctgtcc cgttgccaca attaaactgc acgtgagctc tggcttccgt   8160
tcagtctctt tccagtccca gacctgagtc cccagagcct ccacagctct tacagtgaga   8220
atcaaattgg cccactcctt ggaaggcgtg gcattctgtc agagtaaaag gaaagtagag   8280
tgtgctgatt cacgttcagc gtgtggggct ggctagagac cttggcactg tagtgaacag   8340
aatgtgtcca cctttaagtc accctgaagg catcaccata gctacagcct cacccagggg   8400
tagagaatag tactgtctac ttgttgacta cctggcagtt ggtgccagcc cctatagagg   8460
aaaacagcag tgtgtggcca ctgtgagaag catatccctg gaaacaggtg accagagcag   8520
agggctaacg cctacctgag tcacacaaaa ctgaccaggc ttgagtgtcc agaagagtct   8580
atcagaaggc cacagcattc agtcctatcc acagagagca gcagactaag ttgtctcctt   8640
gccagcttag aaaactgcag tgctggggta caggtagggt gttcaggagg tccgggcccc   8700
agtgattagt ctaagactga agcatctggt tggctgtggt cccacctaga aaattcttaa   8760
agctcttgtc atgtacttcc tgggaaggac ctaccctgtc tcaataatgt ctctagctcg   8820
ttggagtcta ctgactcaaa catttataaa gtgtcctaga aaggcctgac tcccctacaa   8880
ggctgtgtga tccttcaaac tcacatatgt gagccaataa aaccttgaga ctctag       8936
```

<210> SEQ ID NO 27
<211> LENGTH: 2431

-continued

```
<212> TYPE: PRT
<213> ORGANISM: Rattus norvegicus

<400> SEQUENCE: 27

Met Asp Pro Gln Leu Arg Leu Leu Leu Glu Val Ser Tyr Glu Ala Ile
1               5                   10                  15

Val Asp Gly Gly Ile Asn Pro Ala Ser Leu Arg Gly Thr Asn Thr Gly
            20                  25                  30

Val Trp Val Gly Val Ser Gly Ser Glu Ala Ser Glu Ala Leu Ser Arg
        35                  40                  45

Asp Pro Glu Thr Leu Leu Gly Tyr Ser Met Val Gly Cys Gln Arg Ala
    50                  55                  60

Met Met Ala Asn Arg Leu Ser Phe Phe Phe Asp Phe Lys Gly Pro Ser
65                  70                  75                  80

Ile Ala Leu Asp Thr Ala Cys Ser Ser Ser Leu Leu Ala Leu Gln Asn
                85                  90                  95

Ala Tyr Gln Ala Ile Arg Ser Gly Glu Cys Pro Ala Ala Ile Val Gly
            100                 105                 110

Gly Ile Asn Leu Leu Leu Lys Pro Asn Thr Ser Val Gln Phe Met Lys
        115                 120                 125

Leu Gly Met Leu Ser Pro Asp Gly Thr Cys Arg Ser Phe Asp Asp Ser
    130                 135                 140

Gly Asn Gly Tyr Cys Arg Ala Glu Ala Val Val Ala Val Leu Leu Thr
145                 150                 155                 160

Lys Lys Ser Leu Ala Arg Arg Val Tyr Ala Thr Ile Leu Asn Ala Gly
                165                 170                 175

Thr Asn Thr Asp Gly Cys Lys Glu Gln Gly Val Thr Phe Pro Ser Gly
            180                 185                 190

Glu Ala Gln Glu Gln Leu Ile Arg Ser Leu Tyr Gln Pro Gly Gly Val
        195                 200                 205

Ala Pro Glu Ser Leu Glu Tyr Ile Glu Ala His Gly Thr Gly Thr Lys
    210                 215                 220

Val Gly Asp Pro Gln Glu Leu Asn Gly Ile Thr Arg Ser Leu Cys Ala
225                 230                 235                 240

Phe Arg Gln Ser Pro Leu Leu Ile Gly Ser Thr Lys Ser Asn Met Gly
                245                 250                 255

His Pro Glu Pro Ala Ser Gly Leu Ala Ala Leu Thr Lys Val Leu Leu
            260                 265                 270

Ser Leu Glu Asn Gly Val Trp Ala Pro Asn Leu His Phe His Asn Pro
        275                 280                 285

Asn Pro Glu Ile Pro Ala Leu Leu Asp Gly Arg Leu Gln Val Val Asp
    290                 295                 300

Arg Pro Leu Pro Val Arg Gly Gly Ile Val Gly Ile Asn Ser Phe Gly
305                 310                 315                 320

Phe Gly Gly Ala Asn Val His Val Ile Leu Gln Pro Asn Thr Gln Gln
                325                 330                 335

Ala Pro Ala Pro Ala Pro His Ala Ala Leu Pro His Leu Leu His Ala
            340                 345                 350

Ser Gly Arg Thr Met Glu Ala Val Gln Gly Leu Leu Glu Gln Gly Arg
        355                 360                 365

Gln His Ser Gln Asp Leu Ala Phe Val Ser Met Leu Asn Asp Ile Ala
    370                 375                 380

Ala Thr Pro Thr Ala Ala Met Pro Phe Arg Gly Tyr Thr Val Leu Gly
385                 390                 395                 400
```

-continued

```
Val Glu Gly His Val Gln Glu Val Gln Gln Val Pro Ala Ser Gln Arg
                405                 410                 415

Pro Leu Trp Phe Ile Cys Ser Gly Met Gly Thr Gln Trp Arg Gly Met
            420                 425                 430

Gly Leu Ser Leu Met Arg Leu Asp Ser Phe Arg Glu Ser Ile Leu Arg
        435                 440                 445

Ser Asp Glu Ala Leu Lys Pro Leu Gly Val Lys Val Ser Asp Leu Leu
    450                 455                 460

Leu Ser Thr Asp Glu His Thr Phe Asp Asp Ile Val His Ser Phe Val
465                 470                 475                 480

Ser Leu Thr Ala Ile Gln Ile Ala Leu Ile Asp Leu Leu Thr Ser Met
                485                 490                 495

Gly Leu Lys Pro Asp Gly Ile Ile Gly His Ser Leu Gly Glu Val Ala
            500                 505                 510

Cys Gly Tyr Ala Asp Gly Cys Leu Ser Gln Arg Glu Ala Val Leu Ala
        515                 520                 525

Ala Tyr Trp Arg Gly Gln Cys Ile Lys Asp Ala Asn Leu Pro Ala Gly
    530                 535                 540

Ser Met Ala Ala Val Gly Leu Ser Trp Glu Glu Cys Lys Gln Arg Cys
545                 550                 555                 560

Pro Pro Gly Val Val Pro Ala Cys His Asn Ser Glu Asp Thr Val Thr
                565                 570                 575

Ile Ser Gly Pro Gln Ala Ala Val Asn Glu Phe Val Glu Gln Leu Lys
            580                 585                 590

Gln Glu Gly Val Phe Ala Lys Glu Val Arg Thr Gly Gly Leu Ala Phe
        595                 600                 605

His Ser Tyr Phe Met Glu Gly Ile Ala Pro Thr Leu Leu Gln Ala Leu
    610                 615                 620

Lys Lys Val Ile Arg Glu Pro Arg Pro Arg Ser Ala Arg Trp Leu Ser
625                 630                 635                 640

Thr Ser Ile Pro Glu Ala Gln Trp Gln Ser Ser Leu Ala Arg Thr Ser
                645                 650                 655

Ser Ala Glu Tyr Asn Val Asn Asn Leu Val Ser Pro Val Leu Phe Gln
            660                 665                 670

Glu Ala Leu Trp His Val Pro Glu His Ala Val Val Leu Glu Ile Ala
        675                 680                 685

Pro His Ala Leu Leu Gln Ala Val Leu Lys Arg Gly Val Lys Pro Ser
    690                 695                 700

Cys Thr Ile Ile Pro Leu Met Lys Arg Asp His Lys Asp Asn Leu Glu
705                 710                 715                 720

Phe Phe Leu Thr Asn Leu Gly Lys Val His Leu Thr Gly Ile Asp Ile
                725                 730                 735

Asn Pro Asn Ala Leu Phe Pro Pro Val Glu Phe Pro Val Pro Arg Gly
            740                 745                 750

Thr Pro Leu Ile Ser Pro His Ile Lys Trp Asp His Ser Gln Thr Trp
        755                 760                 765

Asp Ile Pro Val Ala Glu Asp Phe Pro Asn Gly Ser Ser Ser Ser Ser
    770                 775                 780

Ala Thr Val Tyr Asn Ile Asp Ala Ser Ser Glu Ser Pro Asp His Tyr
785                 790                 795                 800

Leu Val Asp His Cys Ile Asp Gly Arg Val Leu Phe Pro Gly Thr Gly
                805                 810                 815
```

-continued

```
Tyr Leu Tyr Leu Val Trp Lys Thr Leu Ala Arg Ser Leu Ser Leu Ser
            820                 825                 830

Leu Glu Glu Thr Pro Val Val Phe Glu Asn Val Thr Phe His Gln Ala
        835                 840                 845

Thr Ile Leu Pro Arg Thr Gly Thr Val Pro Leu Glu Val Arg Leu Leu
    850                 855                 860

Glu Ala Ser His Ala Phe Glu Val Ser Asp Ser Gly Asn Leu Ile Val
865                 870                 875                 880

Ser Gly Lys Val Tyr Gln Trp Glu Asp Pro Asp Ser Lys Leu Phe Asp
                885                 890                 895

His Pro Glu Val Pro Ile Pro Ala Glu Ser Glu Ser Val Ser Arg Leu
            900                 905                 910

Thr Gln Gly Glu Val Tyr Lys Glu Leu Arg Leu Arg Gly Tyr Asp Tyr
        915                 920                 925

Gly Pro His Phe Gln Gly Val Tyr Glu Ala Thr Leu Glu Gly Glu Gln
    930                 935                 940

Gly Lys Leu Leu Trp Lys Asp Asn Trp Val Thr Phe Met Asp Thr Met
945                 950                 955                 960

Leu Gln Ile Ser Ile Leu Gly Phe Ser Lys Gln Ser Leu Gln Leu Pro
                965                 970                 975

Thr Arg Val Thr Ala Ile Tyr Ile Asp Pro Ala Thr His Leu Gln Lys
            980                 985                 990

Val Tyr Met Leu Glu Gly Asp Thr  Gln Val Ala Asp Val  Thr Thr Ser
        995                 1000                1005

Arg Cys  Leu Gly Val Thr Val  Ser Gly Gly Val Tyr  Ile Ser Arg
    1010                1015                1020

Leu Gln  Thr Thr Ala Thr Ser  Arg Arg Gln Gln Glu  Gln Leu Val
    1025                1030                1035

Pro Thr  Leu Glu Lys Phe Val  Phe Thr Pro His Val  Glu Pro Glu
    1040                1045                1050

Cys Leu  Ser Glu Ser Ala Ile  Leu Gln Lys Glu Leu  Gln Leu Cys
    1055                1060                1065

Lys Gly  Leu Ala Lys Ala Leu  Gln Thr Lys Ala Thr  Gln Gln Gly
    1070                1075                1080

Leu Lys  Met Thr Val Pro Gly  Leu Glu Asp Leu Pro  Gln His Gly
    1085                1090                1095

Leu Pro  Arg Leu Leu Ala Ala  Ala Cys Gln Leu Gln  Leu Asn Gly
    1100                1105                1110

Asn Leu  Gln Leu Glu Leu Gly  Glu Val Leu Ala Arg  Glu Arg Leu
    1115                1120                1125

Leu Leu  Pro Glu Asp Pro Leu  Ile Ser Gly Leu Leu  Asn Ser Gln
    1130                1135                1140

Ala Leu  Lys Ala Cys Ile Asp  Thr Ala Leu Glu Asn  Leu Ser Thr
    1145                1150                1155

Leu Lys  Met Lys Val Val Glu  Val Leu Ala Gly Glu  Gly His Leu
    1160                1165                1170

Tyr Ser  His Ile Ser Ala Leu  Leu Asn Thr Gln Pro  Met Leu Gln
    1175                1180                1185

Leu Glu  Tyr Thr Ala Thr Asp  Arg His Pro Gln Ala  Leu Lys Asp
    1190                1195                1200

Val Gln  Thr Lys Leu Gln Gln  His Asp Val Ala Gln  Gly Gln Trp
    1205                1210                1215

Asp Pro  Ser Gly Pro Ala Pro  Thr Asn Leu Gly Ala  Leu Asp Leu
```

-continued

```
    1220                1225                1230

Val Val  Cys Asn Cys Ala Leu  Ala Thr Leu Gly Asp  Pro Ala Leu
    1235                1240                1245

Ala Leu  Asp Asn Met Val Ala  Ala Leu Lys Asp Gly  Gly Phe Leu
    1250                1255                1260

Leu Met  His Thr Val Leu Lys  Gly His Ala Leu Gly  Glu Thr Leu
    1265                1270                1275

Ala Cys  Leu Pro Ser Glu Val  Gln Pro Gly Pro Ser  Phe Leu Ser
    1280                1285                1290

Gln Glu  Glu Trp Glu Ser Leu  Phe Ser Arg Lys Ala  Leu His Leu
    1295                1300                1305

Val Gly  Leu Lys Lys Ser Phe  Tyr Gly Thr Ala Leu  Phe Leu Cys
    1310                1315                1320

Arg Arg  Leu Ser Pro Gln Asp  Lys Pro Ile Phe Leu  Pro Val Glu
    1325                1330                1335

Asp Thr  Ser Phe Gln Trp Val  Asp Ser Leu Lys Ser  Ile Leu Ala
    1340                1345                1350

Thr Ser  Ser Ser Gln Pro Val  Trp Leu Thr Ala Met  Asn Cys Pro
    1355                1360                1365

Thr Ser  Gly Val Val Gly Leu  Val Asn Cys Leu Arg  Lys Glu Pro
    1370                1375                1380

Gly Gly  His Arg Ile Arg Cys  Ile Leu Leu Ser Asn  Leu Ser Ser
    1385                1390                1395

Thr Ser  His Val Pro Lys Leu  Asp Pro Gly Ser Ser  Glu Leu Gln
    1400                1405                1410

Lys Val  Leu Glu Ser Asp Leu  Val Met Asn Val Tyr  Arg Asp Gly
    1415                1420                1425

Ala Trp  Gly Ala Phe Arg His  Phe Gln Leu Glu Gln  Asp Lys Pro
    1430                1435                1440

Glu Glu  Gln Thr Ala His Ala  Phe Val Asn Val Leu  Thr Arg Gly
    1445                1450                1455

Asp Leu  Ala Ser Ile Arg Trp  Val Ser Ser Pro Leu  Lys His Met
    1460                1465                1470

Gln Pro  Pro Ser Ser Ser Gly  Ala Gln Leu Cys Thr  Val Tyr Tyr
    1475                1480                1485

Ala Ser  Leu Asn Phe Arg Asp  Ile Met Leu Ala Thr  Gly Lys Leu
    1490                1495                1500

Ser Pro  Asp Ala Ile Pro Gly  Lys Trp Ala Ser Arg  Asp Cys Met
    1505                1510                1515

Leu Gly  Met Glu Phe Ser Gly  Arg Asp Lys Cys Gly  Arg Arg Val
    1520                1525                1530

Met Gly  Leu Val Pro Ala Glu  Gly Leu Ala Thr Ser  Val Leu Leu
    1535                1540                1545

Ser Pro  Asp Phe Leu Trp Asp  Val Pro Ser Ser Trp  Thr Leu Glu
    1550                1555                1560

Glu Ala  Ala Ser Val Pro Val  Val Tyr Thr Thr Ala  Tyr Tyr Ser
    1565                1570                1575

Leu Val  Val Arg Gly Arg Ile  Gln His Gly Glu Thr  Val Leu Ile
    1580                1585                1590

His Ser  Gly Ser Gly Gly Val  Gly Gln Ala Ala Ile  Ser Ile Ala
    1595                1600                1605

Leu Ser  Leu Gly Cys Arg Val  Phe Thr Thr Val Gly  Ser Ala Glu
    1610                1615                1620
```

-continued

```
Lys Arg  Ala Tyr Leu Gln Ala  Arg Phe Pro Gln Leu  Asp Asp Thr
    1625                 1630                 1635

Ser Phe  Ala Asn Ser Arg Asp  Thr Ser Phe Glu Gln  His Val Leu
    1640                 1645                 1650

Leu His  Thr Gly Gly Lys Gly  Val Asp Leu Val Leu  Asn Ser Leu
    1655                 1660                 1665

Ala Glu  Glu Lys Leu Gln Ala  Ser Val Arg Cys Leu  Ala Gln His
    1670                 1675                 1680

Gly Arg  Phe Leu Glu Ile Gly  Lys Phe Asp Leu Ser  Asn Asn His
    1685                 1690                 1695

Pro Leu  Gly Met Ala Ile Phe  Leu Lys Asn Val Thr  Phe His Gly
    1700                 1705                 1710

Ile Leu  Leu Asp Ala Leu Phe  Glu Gly Ala Asn Asp  Ser Trp Arg
    1715                 1720                 1725

Glu Val  Ala Glu Leu Leu Lys  Ala Gly Ile Arg Asp  Gly Val Val
    1730                 1735                 1740

Lys Pro  Leu Lys Cys Thr Val  Phe Pro Lys Ala Gln  Val Glu Asp
    1745                 1750                 1755

Ala Phe  Arg Tyr Met Ala Gln  Gly Lys His Ile Gly  Lys Val Leu
    1760                 1765                 1770

Val Gln  Val Arg Glu Glu Glu  Pro Glu Ala Met Leu  Pro Gly Ala
    1775                 1780                 1785

Gln Pro  Thr Leu Ile Ser Ala  Ile Ser Lys Thr Phe  Cys Pro Glu
    1790                 1795                 1800

His Lys  Ser Tyr Ile Ile Thr  Gly Gly Leu Gly Gly  Phe Gly Leu
    1805                 1810                 1815

Glu Leu  Ala Arg Trp Leu Val  Leu Arg Gly Ala Gln  Arg Leu Val
    1820                 1825                 1830

Leu Thr  Ser Arg Ser Gly Ile  Arg Thr Gly Tyr Gln  Ala Lys His
    1835                 1840                 1845

Val Arg  Glu Trp Arg Arg Gln  Gly Ile His Val Leu  Val Ser Thr
    1850                 1855                 1860

Ser Asn  Val Ser Ser Leu Glu  Gly Ala Arg Ala Leu  Ile Ala Glu
    1865                 1870                 1875

Ala Thr  Lys Leu Gly Pro Val  Gly Gly Val Phe Asn  Leu Ala Met
    1880                 1885                 1890

Val Leu  Arg Asp Ala Met Leu  Glu Asn Gln Thr Pro  Glu Leu Phe
    1895                 1900                 1905

Gln Asp  Val Asn Lys Pro Lys  Tyr Asn Gly Thr Leu  Asn Leu Asp
    1910                 1915                 1920

Arg Ala  Thr Arg Glu Ala Cys  Pro Glu Leu Asp Tyr  Phe Val Ala
    1925                 1930                 1935

Phe Ser  Ser Val Ser Cys Gly  Arg Gly Asn Ala Gly  Gln Ser Asn
    1940                 1945                 1950

Tyr Gly  Phe Ala Asn Ser Thr  Met Glu Arg Ile Cys  Glu Gln Arg
    1955                 1960                 1965

Arg His  Asp Gly Leu Pro Gly  Leu Ala Val Gln Trp  Gly Ala Ile
    1970                 1975                 1980

Gly Asp  Val Gly Ile Ile Leu  Glu Ala Met Gly Thr  Asn Asp Thr
    1985                 1990                 1995

Val Val  Gly Gly Thr Leu Pro  Gln Arg Ile Ser Ser  Cys Met Glu
    2000                 2005                 2010
```

-continued

```
Val Leu  Asp Leu Phe Leu Asn  Gln Pro His Ala Val  Leu Ser Ser
    2015                 2020                 2025

Phe Val  Leu Ala Glu Lys Lys  Ala Val Ala His Gly  Asp Gly Glu
    2030                 2035                 2040

Ala Gln  Arg Asp Leu Val Lys  Ala Val Ala His Ile  Leu Gly Ile
    2045                 2050                 2055

Arg Asp  Leu Ala Gly Ile Asn  Leu Asp Ser Ser Leu  Ala Asp Leu
    2060                 2065                 2070

Gly Leu  Asp Ser Leu Met Gly  Val Glu Val Arg Gln  Ile Leu Glu
    2075                 2080                 2085

Arg Glu  His Asp Leu Val Leu  Pro Ile Arg Glu Val  Arg Gln Leu
    2090                 2095                 2100

Thr Leu  Arg Lys Leu Gln Glu  Met Ser Ser Lys Ala  Gly Ser Asp
    2105                 2110                 2115

Thr Glu  Leu Ala Ala Pro Lys  Ser Lys Asn Asp Thr  Ser Leu Lys
    2120                 2125                 2130

Gln Ala  Gln Leu Asn Leu Ser  Ile Leu Leu Val Asn  Pro Glu Gly
    2135                 2140                 2145

Pro Thr  Leu Thr Arg Leu Asn  Ser Val Gln Ser Ser  Glu Arg Pro
    2150                 2155                 2160

Leu Phe  Leu Val His Pro Ile  Glu Gly Ser Ile Thr  Val Phe His
    2165                 2170                 2175

Ser Leu  Ala Ala Lys Leu Ser  Val Pro Thr Tyr Gly  Leu Gln Cys
    2180                 2185                 2190

Thr Gln  Ala Ala Pro Leu Asp  Ser Ile Pro Asn Leu  Ala Ala Tyr
    2195                 2200                 2205

Tyr Ile  Asp Cys Ile Lys Gln  Val Gln Pro Glu Gly  Pro Tyr Arg
    2210                 2215                 2220

Val Ala  Gly Tyr Ser Phe Gly  Ala Cys Val Ala Phe  Glu Met Cys
    2225                 2230                 2235

Ser Gln  Leu Gln Ala Gln Gln  Gly Pro Ala Pro Ala  His Asn Asn
    2240                 2245                 2250

Leu Phe  Leu Phe Asp Gly Ser  His Thr Tyr Val Leu  Ala Tyr Thr
    2255                 2260                 2265

Gln Ser  Tyr Arg Ala Lys Leu  Thr Pro Gly Cys Glu  Ala Glu Ala
    2270                 2275                 2280

Glu Ala  Glu Ala Ile Cys Phe  Phe Ile Lys Gln Phe  Val Asp Ala
    2285                 2290                 2295

Glu His  Ser Lys Val Leu Glu  Ala Leu Leu Pro Leu  Lys Ser Leu
    2300                 2305                 2310

Glu Asp  Arg Val Ala Ala Ala  Val Asp Leu Ile Thr  Arg Ser His
    2315                 2320                 2325

Gln Ser  Leu Asp Arg Arg Asp  Leu Ser Phe Ala Ala  Val Ser Phe
    2330                 2335                 2340

Tyr Tyr  Lys Leu Arg Ala Ala  Asp Gln Tyr Lys Pro  Lys Ala Lys
    2345                 2350                 2355

Tyr His  Gly Asn Val Ile Leu  Leu Arg Ala Lys Thr  Gly Gly Thr
    2360                 2365                 2370

Tyr Gly  Glu Asp Leu Gly Ala  Asp Tyr Asn Leu Ser  Gln Val Cys
    2375                 2380                 2385

Asp Gly  Lys Val Ser Val His  Ile Ile Glu Gly Asp  His Arg Thr
    2390                 2395                 2400

Leu Leu  Glu Gly Arg Gly Leu  Glu Ser Ile Ile Asn  Ile Ile His
```

-continued 2405 2410 2415

Ser Ser Leu Ala Glu Pro Arg Val Ser Val Arg Glu Gly
2420 2425 2430

<210> SEQ ID NO 28
<211> LENGTH: 9345
<212> TYPE: DNA
<213> ORGANISM: Gallus gallus

<400> SEQUENCE: 28
agaacctgct caatggggtt gatatggtca cagaggacga tcggaggtgg aagccaggga 60
tttatggact gcccaaaaga aatggaaagc tcaaggacat aaaaaaattc gatgcctcct 120
tctttgggtc caccccaaac aagctcatac aatggatcct ccagttcgct tgttgttgga 180
agtttcttat gaggctattt tggatggagg cattaatcca actgccctcc gtggcacaga 240
cacgggtgta tgggttggtg caagtggctc agaagctgct gaagccctta gccaagatcc 300
agaagagctt ttgggataca gtatgactgg ctgccagcgt gctatgcttg ccaacaggat 360
ttcttacttc tatgatttta caggaccaag cttaactatc gacacagcct gctcctccag 420
tctcatggct ttagaaaatg cttataaagc aattcgtcac ggacagtgca gtgcagccct 480
ggtaggaggg gtcaacattc tgctgaagcc caacacttct gtgcagttca tgaagctggg 540
catgcttagt cctgatggtg cctgcaaggc tttcgatgtt tcaggaaatg ggtattgtcg 600
ctctgaagct gttgttgttg tgctcttgac caagaaatcc atggctaaac gcgtctatgc 660
cactatagtc aatgctggga gtaacactga tggctttaag gagcaaggtg tgacattccc 720
atctggagag atgcagcagc agctggttgg ttctctgtac agagaatgtg gtatcaagcc 780
tggagatgtg gagtatgttg aagctcatgg gacaggcacc aaggttggag atcctcaaga 840
agtaaatggc attgtaaatg tcttctgcca gtgtgagaga gagcctctgt taattggatc 900
aaccaagtca aacatgggtc atccagagcc tgcttctggg cttgctgcat tagccaaggt 960
cattctttct ctggaacatg gactgtgggc tccaaatctt catttcaatg atccaaatcc 1020
agatattcct gctttacacg atggctcctt gaaggtggtt tgcaaaccaa caccggtgaa 1080
aggtggcctt gtcagcatca attcttttgg ctttggaggc tctaatgctc atgttattct 1140
gaggccaaat gagaagaaat gtcagcctca agagacttgt aacttgccaa gactggttca 1200
agtttgtggc agaacacagg aagctgtgga aatactaatt gaagaaagca ggaaacatgg 1260
aggatgcagt ccatttttaa gcctgctcag tgatatctct gcagttcctg tatcttctat 1320
gccctacagg ggctacacac tagttggcac tgagagtgac ataacagaga ttcagcaagt 1380
tcaagcatct ggtagaccac tctggtacat ctgctcaggc atgggaacac agtggaaagg 1440
tatgggcctg agccttatga aattggatct gtttcgccag tctatattgc gctcagatga 1500
ggctttgaag agcacaggac tgaaggtctc agacctgctt ctgaatgcag atgagaacac 1560
ttttgatgac actgtccatg cttttgttgg actagctgct atacagattg cccaaattga 1620
tgtgctaaag gctgcgggtc tgcaacctga tgggattttg ggccactcag tgggagaact 1680
agcttgtggc tatgcagata attccttaag tcatgaagaa gctgttcttg ctgcttattg 1740
gaggggccga tgtgtgaaag aggccaaatt gcccccggga gggatggctg ctgttggtct 1800
gacatgggag gaatgtaagc agcgctgtcc tccaaacgtg gtaccagcat gtcacaactc 1860
tgaggatact gtcactgttt cggggcctct ggattctgtg tctgagtttg taaccaaact 1920
gaagaaagat ggggtgtttg caaaggaggt gcgcagcgcc ggagttgcat ttcattccta 1980

-continued

```
ttacatggca tccattgcac cagcactgct cagtgcactg aaaaaggtca ttccacaccc   2040
taagcctcgt tcagcacggt ggatcagtac atctatccct gaatctcagt ggcagagtga   2100
tcttgctagg aattcctctg cagagtatca tgtgaacaac ctagtgaatc ctgtgctgtt   2160
ccatgaaggc ctgaagcata ttccagagaa tgctgttgta gtggagattg ctccacatgc   2220
tctcttacag gctatcttga ggagaacttt gaagccaact tgcactattc tacctctgat   2280
gaagaaggac cacaaaaata acttggagtt cttcctaacg cagactggaa agattcattt   2340
aactgggata aatgttcttg gaaataactt gttcccacct gtggaatacc ctgtccctgt   2400
gggaacacct ctcatttctc catatatcaa atgggaccac agccaagact gggatgttcc   2460
aaaagctgaa gacttcccct caggttccaa aggctctgcg tctgcttcag tctacaacat   2520
cgatgtgagt cctgactctc ctgaccatta cttggttggc cattgcattg atggcagagt   2580
cctgtaccca gcaactgggt acttagtgct ggcgtggcga actctggcac gatctcttgg   2640
catggtcatg gaacaaacag ctgttatgtt tgaagaagtt acaatccatc aggcaactat   2700
ccttcccaaa aagggatcaa cacagctgga agtacgaatc atgcctgctt ctcacagctt   2760
tgaagtgtca gggaatggga atttggctgt gagtgggaag atctccctcc tagaaaacga   2820
tgctctgaag aactttcata accagctggc tgactttcag agtcaagcaa acgtgactgc   2880
gaagtctggc ctcttgatgg aagatgttta ccaagagctg catcttcgtg gatataacta   2940
tggaccaact tttcagggtg ttctggaatg caacagtgaa ggaagtgcag ggaaaattct   3000
gtggaatgga aactgggtaa ccttccttga caccctgcta cacttgatag tcttagcaga   3060
gactgggcgc agtctacgat tgcccaccag gattcgctca gtgtatattg accctgtgct   3120
tcatcaggag caggtgtacc agtaccagga caatgtagaa gcttttgatg ttgttgttga   3180
ccgctgtctt gatagcctca aagcaggagg tgttcagatc aatggacttc atgcctcggt   3240
ggcaccacgg cgacaacagg agcggatctc tcccactctg gaaaaattct cctttgttcc   3300
ctatattgag agtgactgtt tgtcttccag tacccagctt catgcctacc tggagcactg   3360
caaaggcctg atccagaaat tacaagctaa gatggcattg cacggagtca aactagttat   3420
ccatggccta gaaaccaacg gggctgctgc aggatcccca cccacacaga agggccttca   3480
gcatatcctt actgaaatct gccatctgga actgaatgga aacctacatt ctgagctgga   3540
acagattgtg actcaggaga agatgcacct ccaggacgat ccccttctca atggcttgct   3600
ggattcttca gagttgaaga cttgcctgga tgtggcaaag gagaacacga ccagtcacag   3660
gatgaagata gtggaggctc tggcaggaag tggacgtctg ttctctcgtg tccaaagtat   3720
tctgaatact cagcccctgt tgcagctgga ctacattgcc actgactgca cccctgaaac   3780
tctttcaaat gatgaaacag agctgcacga tgctggaatc tcctttagcc agtgggatcc   3840
ctctagcctt ccctctggaa atctgaccaa tgctgacctg gcagtatgca actgttcaac   3900
aagtgttctg gggaacacag ctgaaattat ctctaactta gcagctgcag tgaaagaagg   3960
agggtttgtt ttgctgcaca cccttcttaa agaggaaact cttggagaaa ttgtcagctt   4020
tcttacaagt ccagacctac agcaagagca cagcttcctg tctcaggcac agtgggagga   4080
gttattcagc aaggcctcat tgaatctggt tgcaatgaag agatctttct ttggctcagt   4140
tattttcctg tgtcgacggc agtcccctgc caaagcaccc attcttctgc cagtagatga   4200
cactcattat aagtgggttg actccttaaa ggagatcttg gctgactcat cagagcagcc   4260
tctgtggttg actgccacca attgtgggaa ctctggaatt ttgggtatgg tgaactgcct   4320
ccgcctggaa gcagagggcc acagaatcag gtgtgtgttt gtttccaacc tgagcccttc   4380
```

-continued

```
atcaactgtc ccagccacta gtctttcttc cctggagatg cagaagatta ttgagagaga   4440
tctggtgatg aatgtgtatc gtgatggaaa gtggggttcc ttcaggcatc tcccattgca   4500
gcaagctcag cctcaggagc tgacagaata tgcctacgta aatgtgttga ctcgtggaga   4560
tctctcttcc cttcgttgga ttgtttcccc acttcgacac ttccaaacaa ccaatccaaa   4620
tgttcagctc tgcaaagtct actatgcatc tctcaatttc cgggacatta tgctggcaac   4680
aggaaagctt tctccagatg ctatccctgg taactggacg ttgcagcagt gcatgctggg   4740
catggagttc tcaggacggg acctggctgg aaggagagtg atgggattgc tgccagcaaa   4800
agggctggcg acagtggtgg actgtgacaa gaggtttcta tgggaagtgc ctgaaaactg   4860
gactctggaa gaagcagctt cggtgcctgt ggtttatgcc actgcttatt atgctttggt   4920
ggttcgaggt ggtatgaaga agggggagag tgtcctcatt cactctggct caggaggtgt   4980
gggcgcaagc agccattgcc atcgccttga gcatgggctg gcgcgtgttt ttgctactgt   5040
aggctctgct gagaaacgtg agtatctcca agcaaggttc ccacagctgg atgctaatag   5100
ctttgccagc tcccgaaata caacctttga gcaacacata ctgcgagtta ccaatgggaa   5160
aggtgtcaac cttgtgttaa attccttggc agaagagaag ctccaagcca gtttgcgttg   5220
tcttgctcaa catgggcgct tcttggaaat aggcaaattt gatctatcaa acaacagcca   5280
gcttggaatg gctcttttcc tcaagaatgt ggcgtttcat ggaatcctgc tggattcaat   5340
ctttgaggaa ggaaaccaag agtgggaggt ggtatcagag ttgttgacaa aaggcataaa   5400
agatggtgtg gtaaagcccc tgagaaccac agtcttcggt aaagaagagg tagaagctgc   5460
cttcaggttc atggcgcaag gaaaacatat tggcaaagtt atgatcaaga tccaagaaga   5520
ggagaagcaa tatcctttaa ggtctgaacc agtaaaactc tctgccatct cccgaacttc   5580
ctgcccacct accaagtctt acatcatcac agggggccta ggaggatttg ggcttgagtt   5640
ggcacagtgg ctaattgaga gaggagcaca gaagcttgta ctgacatctc gatctggcat   5700
acgaactggc taccaggcta aatgtgttag agaatggaag gcgctgggaa tccaagtgtt   5760
ggtctctacc agtgatgttg gaactctaga aggaacgcag cttttgatag aagaggcttt   5820
gaagctcgga ccagttgggg gcatctttaa tttggctgtg gtccttaaag atgccatgat   5880
tgaaaatcag accccggaat tattctggga ggtcaacaag cccaagtatt caggcaccct   5940
tcatttggac tgggtgactc gtaagaagtg cccagacctg gactattttg ttgtattctc   6000
ctctgtaagc tgtggaagag gaaatgctgg gcaaagtaat tatggctttg ctaattctgc   6060
catggagcgt atctgtgagc agcggcatca cgatgggctc ccaggcctgg cagtccagtg   6120
gggagccatt ggtgatgtgg gcatcctgaa ggcaatggga aacagggagg ttgtgattgg   6180
gggaaccgtt ctccagcaaa tcagctcctg cctggaggtg ctcgatatgt tcctgaatca   6240
acctcatcct gttatgtcca gttttgtcct agcagagaag gtctctgtga aaagtgaagg   6300
aggaagtcaa cgggatcttg tagaagctgt tgctcatatc cttggtgttc gtgacgtgag   6360
cagtctgaat gctgagagct ccctagcaga cttgggcctg gattccttga tgggtgtgga   6420
ggtgcgccag acgctggaga gagactacga catcgtaatg accatgaggg agatccgact   6480
cctcaccatc aacaaactgc gtgaactgtc ctccaagact gggacagcag aggagctgaa   6540
gccatcacaa gtgttgaaga caggcccagg tgagcctcca aaactggatt tgaacaactt   6600
gctggtgaat ccagaagggc caacgattac ccgtctcaat gaagttcaga gcacagaacg   6660
ccctcttttc cttgttcacc ccattgaggg atccattgca gtcttctata ctcttgcctc   6720
```

-continued

```
caaacttcat atgccctgct atggactcca gtgcacaaaa gctgctccct tggacagcat   6780
acagagcctg gcatcctatt atattgactg tatgaagcag atacagcctg aaggacctta   6840
tcgcattgct ggatactctt ttggtgcctg cgtagccttt gaaatgtgct cccagctgca   6900
agcacaacaa aatgcttccc atgcactcaa cagtttattc ctctttgatg ggtctcattc   6960
ctttgtggca gcatacactc agtgtttttc cttttctctt tttcagagct acagagcaaa   7020
gctgacccaa ggaaatgagg ctgcgttgga gacagaagca ctgtgtgcct ttgttcagca   7080
gtttacaggc attgaataca ataagttgtt ggagattctt ctgcccttgg aagatctgga   7140
ggctcgtgtc aatgctgctg cagaccttat aactcagatt cataaaaaca tcaaccgtga   7200
agcactcagc tttgctgctg cttcctttta ccataagctg aaggctgctg acaagtatat   7260
accagaatcc aagtatcatg ggaacgtgac actgatgcgg gcaaagactc acaatgagta   7320
tgaagaaggt ctgggtggag actacagact ctcagaggtc tgcgatggaa aagtatcagt   7380
ccacatcatt gaaggagatc accgcacctt attggaggga gatggtgttg aatcaatcat   7440
tgggatcatc catggctcac tggcagagcc acgtgtcagt gtcagagaag gttaacttct   7500
gccacttact gtcagtggtg aagaaaatgc caacaacatt cctagttatg acagacccca   7560
aggaactctt cctgttgaac aacatctcat ctctctgctg ccagagctgg gaaggccagc   7620
tgaacttgat tggtctcttt gtttcctctc tcactcagtc atctttccta actttcacgt   7680
gttctctctc tctcctcttc ccttcctatg ctttgtctat ttccccacta tccctgcccg   7740
tgttactgcg gtgctgtgac tgtcactgtg caccgggggt tccccggcga tggtggcttc   7800
ccacagcttt ggcagtatgt ttttcaaatt taggagtaga cttctacgtg ctctatattg   7860
ttttgtctta acagtattcc aaagggtaag tgatagcact tgttgaccaa gcccagtgag   7920
cagagagggg aactgcagct gatttcggag atacctgttg tctgtgaaga atctgtctgt   7980
agtgaggtca gaaagagaat tccatttgag gcttttgtaa ctatattttt ttaatttgat   8040
atagtctaag tatttattgt gtcaaatcag agacttcttg ctttgtttta atttatcgtg   8100
ggtatcagaa aaggaaacat ccgttttgaa gggataggtt cattctacaa ggggaggttg   8160
cccatttgtt aaaccaaagt gcatctatgg aacagcccat ttcttttttt tttttaagtt   8220
gattttttgt ttgtgtttcg ttttttgttg tttgtttttt gtggcgtttt gttaattttg   8280
attagtgatt tttctgtgtg tggtttttct ttcccccccc cccccaccct gccttgttca   8340
gaagggtgga agtgaggttc cttgccatca cccacccttg tggggagaga ggcgtggagg   8400
gcaggatgga tggttcaaca gatgccactg tattgaacag ccttaacttg ggctgataca   8460
agcaggcaga gctctcccta ggtatgtact tagtttatat ctctgcaagg ttctgtgctt   8520
tgcattacca gaaacacagt aaagcattac ggctattgct tcacctttgt tccttcccac   8580
ctccagttgc tccatccaac caggcatttg gaatgtcagg gggaatagag ttctccattg   8640
gtcacggtat aaatcctcct acccttgctc tcccataacc aaagttcatg caaacataga   8700
aggcatctac ccagtacccc agtgtatttt atgtagcata ggcttgctta agccttgagt   8760
atgcattttc ctctggcagt gagactggag atcccacata agttagctaa gtaaaagttt   8820
gatggcatga ttttaagata cagtaccttt ttaaaggaaa cttgcataaa attcaattta   8880
aaaatgactg acttttgcta tgctggatct gtcttttcca aaatcagtaa atcctcttga   8940
cgcctatgat acagaggaga cctgaatagc aatgaagtac caaccaggag gcattccact   9000
gcctctcaga acttctgtaa acccctgttc tttctgtatt catcccctag tgaagcatcc   9060
tgtgagttca ggagcattcc agtgagagga acagctggtt cctcgtggca ggttctacct   9120
```

-continued

```
agcgtctctt gcttatacaa ccctctgtgg agagtggctg ggttaactgg ttttagtttt   9180

ataaagtatt tcttttgtga aatctgaaat acaaacaaca taatgtcagc ttaaagcatt   9240

tctagaatta agttttgttt tttacttttt tttttttttt tttttaatct gaagagtgtc   9300

tttttcctct ttggctttcc tagaattaaa cagaattgat cactg                   9345


<210> SEQ ID NO 29
<211> LENGTH: 2447
<212> TYPE: PRT
<213> ORGANISM: Gallus gallus

<400> SEQUENCE: 29

Met Asp Pro Pro Val Arg Leu Leu Leu Glu Val Ser Tyr Glu Ala Ile
1               5                   10                  15

Leu Asp Gly Gly Ile Asn Pro Thr Ala Leu Arg Gly Thr Asp Thr Gly
            20                  25                  30

Val Trp Val Gly Ala Ser Gly Ser Glu Ala Ala Glu Ala Leu Ser Gln
        35                  40                  45

Asp Pro Glu Glu Leu Leu Gly Tyr Ser Met Thr Gly Cys Gln Arg Ala
    50                  55                  60

Met Leu Ala Asn Arg Ile Ser Tyr Phe Tyr Asp Phe Thr Gly Pro Ser
65                  70                  75                  80

Leu Thr Ile Asp Thr Ala Cys Ser Ser Ser Leu Met Ala Leu Glu Asn
                85                  90                  95

Ala Tyr Lys Ala Ile Arg His Gly Gln Cys Ser Ala Ala Leu Val Gly
            100                 105                 110

Gly Val Asn Ile Leu Leu Lys Pro Asn Thr Ser Val Gln Phe Met Lys
        115                 120                 125

Leu Gly Met Leu Ser Pro Asp Gly Ala Cys Lys Ala Phe Asp Val Ser
    130                 135                 140

Gly Asn Gly Tyr Cys Arg Ser Glu Ala Val Val Val Val Leu Leu Thr
145                 150                 155                 160

Lys Lys Ser Met Ala Lys Arg Val Tyr Ala Thr Ile Val Asn Ala Gly
                165                 170                 175

Ser Asn Thr Asp Gly Phe Lys Glu Gln Gly Val Thr Phe Pro Ser Gly
            180                 185                 190

Glu Met Gln Gln Gln Leu Val Gly Ser Leu Tyr Arg Glu Cys Gly Ile
        195                 200                 205

Lys Pro Gly Asp Val Glu Tyr Val Glu Ala His Gly Thr Gly Thr Lys
    210                 215                 220

Val Gly Asp Pro Gln Glu Val Asn Gly Ile Val Asn Val Phe Cys Gln
225                 230                 235                 240

Cys Glu Arg Glu Pro Leu Leu Ile Gly Ser Thr Lys Ser Asn Met Gly
                245                 250                 255

His Pro Glu Pro Ala Ser Gly Leu Ala Ala Leu Ala Lys Val Ile Leu
            260                 265                 270

Ser Leu Glu His Gly Leu Trp Ala Pro Asn Leu His Phe Asn Asp Pro
        275                 280                 285

Asn Pro Asp Ile Pro Ala Leu His Asp Gly Ser Leu Lys Val Val Cys
    290                 295                 300

Lys Pro Thr Pro Val Lys Gly Gly Leu Val Ser Ile Asn Ser Phe Gly
305                 310                 315                 320

Phe Gly Gly Ser Asn Ala His Val Ile Leu Arg Pro Asn Glu Lys Lys
                325                 330                 335
```

-continued

```
Cys Gln Pro Gln Glu Thr Cys Asn Leu Pro Arg Leu Val Gln Val Cys
            340                 345                 350

Gly Arg Thr Gln Glu Ala Val Glu Ile Leu Ile Glu Glu Ser Arg Lys
        355                 360                 365

His Gly Gly Cys Ser Pro Phe Leu Ser Leu Leu Ser Asp Ile Ser Ala
    370                 375                 380

Val Pro Val Ser Ser Met Pro Tyr Arg Gly Tyr Thr Leu Val Gly Thr
385                 390                 395                 400

Glu Ser Asp Ile Thr Glu Ile Gln Gln Val Gln Ala Ser Gly Arg Pro
                405                 410                 415

Leu Trp Tyr Ile Cys Ser Gly Met Gly Thr Gln Trp Lys Gly Met Gly
            420                 425                 430

Leu Ser Leu Met Lys Leu Asp Leu Phe Arg Gln Ser Ile Leu Arg Ser
        435                 440                 445

Asp Glu Ala Leu Lys Ser Thr Gly Leu Lys Val Ser Asp Leu Leu Leu
    450                 455                 460

Asn Ala Asp Glu Asn Thr Phe Asp Asp Thr Val His Ala Phe Val Gly
465                 470                 475                 480

Leu Ala Ala Ile Gln Ile Ala Gln Ile Asp Val Leu Lys Ala Ala Gly
                485                 490                 495

Leu Gln Pro Asp Gly Ile Leu Gly His Ser Val Gly Glu Leu Ala Cys
            500                 505                 510

Gly Tyr Ala Asp Asn Ser Leu Ser His Glu Glu Ala Val Leu Ala Ala
        515                 520                 525

Tyr Trp Arg Gly Arg Cys Val Lys Glu Ala Lys Leu Pro Pro Gly Gly
    530                 535                 540

Met Ala Ala Val Gly Leu Thr Trp Glu Glu Cys Lys Gln Arg Cys Pro
545                 550                 555                 560

Pro Asn Val Val Pro Ala Cys His Asn Ser Glu Asp Thr Val Thr Val
                565                 570                 575

Ser Gly Pro Leu Asp Ser Val Ser Glu Phe Val Thr Lys Leu Lys Lys
            580                 585                 590

Asp Gly Val Phe Ala Lys Glu Val Arg Ser Ala Gly Val Ala Phe His
        595                 600                 605

Ser Tyr Tyr Met Ala Ser Ile Ala Pro Ala Leu Leu Ser Ala Leu Lys
    610                 615                 620

Lys Val Ile Pro His Pro Lys Pro Arg Ser Ala Arg Trp Ile Ser Thr
625                 630                 635                 640

Ser Ile Pro Glu Ser Gln Trp Gln Ser Asp Leu Ala Arg Asn Ser Ser
                645                 650                 655

Ala Glu Tyr His Val Asn Asn Leu Val Asn Pro Val Leu Phe His Glu
            660                 665                 670

Gly Leu Lys His Ile Pro Glu Asn Ala Val Val Val Glu Ile Ala Pro
        675                 680                 685

His Ala Leu Leu Gln Ala Ile Leu Arg Arg Thr Leu Lys Pro Thr Cys
    690                 695                 700

Thr Ile Leu Pro Leu Met Lys Lys Asp His Lys Asn Asn Leu Glu Phe
705                 710                 715                 720

Phe Leu Thr Gln Thr Gly Lys Ile His Leu Thr Gly Ile Asn Val Leu
                725                 730                 735

Gly Asn Asn Leu Phe Pro Pro Val Glu Tyr Pro Val Pro Val Gly Thr
            740                 745                 750
```

-continued

```
Pro Leu Ile Ser Pro Tyr Ile Lys Trp Asp His Ser Gln Asp Trp Asp
        755                 760                 765

Val Pro Lys Ala Glu Asp Phe Pro Ser Gly Ser Lys Gly Ser Ala Ser
    770                 775                 780

Ala Ser Val Tyr Asn Ile Asp Val Ser Pro Asp Ser Pro Asp His Tyr
785                 790                 795                 800

Leu Val Gly His Cys Ile Asp Gly Arg Val Leu Tyr Pro Ala Thr Gly
                805                 810                 815

Tyr Leu Val Leu Ala Trp Arg Thr Leu Ala Arg Ser Leu Gly Met Val
            820                 825                 830

Met Glu Gln Thr Ala Val Met Phe Glu Glu Val Thr Ile His Gln Ala
        835                 840                 845

Thr Ile Leu Pro Lys Lys Gly Ser Thr Gln Leu Glu Val Arg Ile Met
    850                 855                 860

Pro Ala Ser His Ser Phe Glu Val Ser Gly Asn Gly Asn Leu Ala Val
865                 870                 875                 880

Ser Gly Lys Ile Ser Leu Leu Glu Asn Asp Ala Leu Lys Asn Phe His
                885                 890                 895

Asn Gln Leu Ala Asp Phe Gln Ser Gln Ala Asn Val Thr Ala Lys Ser
            900                 905                 910

Gly Leu Leu Met Glu Asp Val Tyr Gln Glu Leu His Leu Arg Gly Tyr
        915                 920                 925

Asn Tyr Gly Pro Thr Phe Gln Gly Val Leu Glu Cys Asn Ser Glu Gly
    930                 935                 940

Ser Ala Gly Lys Ile Leu Trp Asn Gly Asn Trp Val Thr Phe Leu Asp
945                 950                 955                 960

Thr Leu Leu His Leu Ile Val Leu Ala Glu Thr Gly Arg Ser Leu Arg
                965                 970                 975

Leu Pro Thr Arg Ile Arg Ser Val Tyr Ile Asp Pro Val Leu His Gln
            980                 985                 990

Glu Gln Val Tyr Gln Tyr Gln Asp  Asn Val Glu Ala Phe  Asp Val Val
        995                 1000                1005

Val Asp  Arg Cys Leu Asp Ser  Leu Lys Ala Gly Gly  Val Gln Ile
    1010                1015                1020

Asn Gly  Leu His Ala Ser Val  Ala Pro Arg Arg Gln  Gln Glu Arg
    1025                1030                1035

Ile Ser  Pro Thr Leu Glu Lys  Phe Ser Phe Val Pro  Tyr Ile Glu
    1040                1045                1050

Ser Asp  Cys Leu Ser Ser Ser  Thr Gln Leu His Ala  Tyr Leu Glu
    1055                1060                1065

His Cys  Lys Gly Leu Ile Gln  Lys Leu Gln Ala Lys  Met Ala Leu
    1070                1075                1080

His Gly  Val Lys Leu Val Ile  His Gly Leu Glu Thr  Asn Gly Ala
    1085                1090                1095

Ala Ala  Gly Ser Pro Pro Thr  Gln Lys Gly Leu Gln  His Ile Leu
    1100                1105                1110

Thr Glu  Ile Cys His Leu Glu  Leu Asn Gly Asn Leu  His Ser Glu
    1115                1120                1125

Leu Glu  Gln Ile Val Thr Gln  Glu Lys Met His Leu  Gln Asp Asp
    1130                1135                1140

Pro Leu  Leu Asn Gly Leu Leu  Asp Ser Ser Glu Leu  Lys Thr Cys
    1145                1150                1155

Leu Asp  Val Ala Lys Glu Asn  Thr Thr Ser His Arg  Met Lys Ile
```

-continued

```
    1160                1165                1170

Val Glu  Ala Leu Ala Gly Ser  Gly Arg Leu Phe Ser  Arg Val Gln
    1175                1180                1185

Ser Ile  Leu Asn Thr Gln Pro  Leu Leu Gln Leu Asp  Tyr Ile Ala
    1190                1195                1200

Thr Asp  Cys Thr Pro Glu Thr  Leu Ser Asn Asp Glu  Thr Glu Leu
    1205                1210                1215

His Asp  Ala Gly Ile Ser Phe  Ser Gln Trp Asp Pro  Ser Ser Leu
    1220                1225                1230

Pro Ser  Gly Asn Leu Thr Asn  Ala Asp Leu Ala Val  Cys Asn Cys
    1235                1240                1245

Ser Thr  Ser Val Leu Gly Asn  Thr Ala Glu Ile Ile  Ser Asn Leu
    1250                1255                1260

Ala Ala  Ala Val Lys Glu Gly  Gly Phe Val Leu Leu  His Thr Leu
    1265                1270                1275

Leu Lys  Glu Glu Thr Leu Gly  Glu Ile Val Ser Phe  Leu Thr Ser
    1280                1285                1290

Pro Asp  Leu Gln Gln Glu His  Ser Phe Leu Ser Gln  Ala Gln Trp
    1295                1300                1305

Glu Glu  Leu Phe Ser Lys Ala  Ser Leu Asn Leu Val  Ala Met Lys
    1310                1315                1320

Arg Ser  Phe Phe Gly Ser Val  Ile Phe Leu Cys Arg  Arg Gln Ser
    1325                1330                1335

Pro Ala  Lys Ala Pro Ile Leu  Leu Pro Val Asp Asp  Thr His Tyr
    1340                1345                1350

Lys Trp  Val Asp Ser Leu Lys  Glu Ile Leu Ala Asp  Ser Ser Glu
    1355                1360                1365

Gln Pro  Leu Trp Leu Thr Ala  Thr Asn Cys Gly Asn  Ser Gly Ile
    1370                1375                1380

Leu Gly  Met Val Asn Cys Leu  Arg Leu Glu Ala Glu  Gly His Arg
    1385                1390                1395

Ile Arg  Cys Val Phe Val Ser  Asn Leu Ser Pro Ser  Ser Thr Val
    1400                1405                1410

Pro Ala  Thr Ser Leu Ser Ser  Leu Glu Met Gln Lys  Ile Ile Glu
    1415                1420                1425

Arg Asp  Leu Val Met Asn Val  Tyr Arg Asp Gly Lys  Trp Gly Ser
    1430                1435                1440

Phe Arg  His Leu Pro Leu Gln  Gln Ala Gln Pro Gln  Glu Leu Thr
    1445                1450                1455

Glu Tyr  Ala Tyr Val Asn Val  Leu Thr Arg Gly Asp  Leu Ser Ser
    1460                1465                1470

Leu Arg  Trp Ile Val Ser Pro  Leu Arg His Phe Gln  Thr Thr Asn
    1475                1480                1485

Pro Asn  Val Gln Leu Cys Lys  Val Tyr Tyr Ala Ser  Leu Asn Phe
    1490                1495                1500

Arg Asp  Ile Met Leu Ala Thr  Gly Lys Leu Ser Pro  Asp Ala Ile
    1505                1510                1515

Pro Gly  Asn Trp Thr Leu Gln  Gln Cys Met Leu Gly  Met Glu Phe
    1520                1525                1530

Ser Gly  Arg Asp Leu Ala Gly  Arg Arg Val Met Gly  Leu Leu Pro
    1535                1540                1545

Ala Lys  Gly Leu Ala Thr Val  Val Asp Cys Asp Lys  Arg Phe Leu
    1550                1555                1560
```

-continued

```
Trp Glu  Val Pro Glu Asn Trp  Thr Leu Glu Glu Ala  Ala Ser Val
    1565                 1570                 1575

Pro Val  Val Tyr Ala Thr Ala  Tyr Tyr Ala Leu Val  Val Arg Gly
    1580                 1585                 1590

Gly Met  Lys Lys Gly Glu Ser  Val Leu Ile His Ser  Gly Ser Gly
    1595                 1600                 1605

Gly Val  Gly Ala Ser Ser His  Cys His Arg Leu Glu  His Gly Leu
    1610                 1615                 1620

Ala Arg  Val Phe Ala Thr Val  Gly Ser Ala Glu Lys  Arg Glu Tyr
    1625                 1630                 1635

Leu Gln  Ala Arg Phe Pro Gln  Leu Asp Ala Asn Ser  Phe Ala Ser
    1640                 1645                 1650

Ser Arg  Asn Thr Thr Phe Glu  Gln His Ile Leu Arg  Val Thr Asn
    1655                 1660                 1665

Gly Lys  Gly Val Asn Leu Val  Leu Asn Ser Leu Ala  Glu Glu Lys
    1670                 1675                 1680

Leu Gln  Ala Ser Leu Arg Cys  Leu Ala Gln His Gly  Arg Phe Leu
    1685                 1690                 1695

Glu Ile  Gly Lys Phe Asp Leu  Ser Asn Asn Ser Gln  Leu Gly Met
    1700                 1705                 1710

Ala Leu  Phe Leu Lys Asn Val  Ala Phe His Gly Ile  Leu Leu Asp
    1715                 1720                 1725

Ser Ile  Phe Glu Glu Gly Asn  Gln Glu Trp Glu Val  Val Ser Glu
    1730                 1735                 1740

Leu Leu  Thr Lys Gly Ile Lys  Asp Gly Val Val Lys  Pro Leu Arg
    1745                 1750                 1755

Thr Thr  Val Phe Gly Lys Glu  Glu Val Glu Ala Ala  Phe Arg Phe
    1760                 1765                 1770

Met Ala  Gln Gly Lys His Ile  Gly Lys Val Met Ile  Lys Ile Gln
    1775                 1780                 1785

Glu Glu  Glu Lys Gln Tyr Pro  Leu Arg Ser Glu Pro  Val Lys Leu
    1790                 1795                 1800

Ser Ala  Ile Ser Arg Thr Ser  Cys Pro Pro Thr Lys  Ser Tyr Ile
    1805                 1810                 1815

Ile Thr  Gly Gly Leu Gly Gly  Phe Gly Leu Glu Leu  Ala Gln Trp
    1820                 1825                 1830

Leu Ile  Glu Arg Gly Ala Gln  Lys Leu Val Leu Thr  Ser Arg Ser
    1835                 1840                 1845

Gly Ile  Arg Thr Gly Tyr Gln  Ala Lys Cys Val Arg  Glu Trp Lys
    1850                 1855                 1860

Ala Leu  Gly Ile Gln Val Leu  Val Ser Thr Ser Asp  Val Gly Thr
    1865                 1870                 1875

Leu Glu  Gly Thr Gln Leu Leu  Ile Glu Glu Ala Leu  Lys Leu Gly
    1880                 1885                 1890

Pro Val  Gly Gly Ile Phe Asn  Leu Ala Val Val Leu  Lys Asp Ala
    1895                 1900                 1905

Met Ile  Glu Asn Gln Thr Pro  Glu Leu Phe Trp Glu  Val Asn Lys
    1910                 1915                 1920

Pro Lys  Tyr Ser Gly Thr Leu  His Leu Asp Trp Val  Thr Arg Lys
    1925                 1930                 1935

Lys Cys  Pro Asp Leu Asp Tyr  Phe Val Val Phe Ser  Ser Val Ser
    1940                 1945                 1950
```

-continued

```
Cys Gly Arg Gly Asn Ala Gly Gln Ser Asn Tyr Gly Phe Ala Asn
    1955                1960                1965

Ser Ala Met Glu Arg Ile Cys Glu Gln Arg His His Asp Gly Leu
    1970                1975                1980

Pro Gly Leu Ala Val Gln Trp Gly Ala Ile Gly Asp Val Gly Ile
    1985                1990                1995

Leu Lys Ala Met Gly Asn Arg Glu Val Val Ile Gly Gly Thr Val
    2000                2005                2010

Leu Gln Gln Ile Ser Ser Cys Leu Glu Val Leu Asp Met Phe Leu
    2015                2020                2025

Asn Gln Pro His Pro Val Met Ser Ser Phe Val Leu Ala Glu Lys
    2030                2035                2040

Val Ser Val Lys Ser Glu Gly Gly Ser Gln Arg Asp Leu Val Glu
    2045                2050                2055

Ala Val Ala His Ile Leu Gly Val Arg Asp Val Ser Ser Leu Asn
    2060                2065                2070

Ala Glu Ser Ser Leu Ala Asp Leu Gly Leu Asp Ser Leu Met Gly
    2075                2080                2085

Val Glu Val Arg Gln Thr Leu Glu Arg Asp Tyr Asp Ile Val Met
    2090                2095                2100

Thr Met Arg Glu Ile Arg Leu Leu Thr Ile Asn Lys Leu Arg Glu
    2105                2110                2115

Leu Ser Ser Lys Thr Gly Thr Ala Glu Glu Leu Lys Pro Ser Gln
    2120                2125                2130

Val Leu Lys Thr Gly Pro Gly Glu Pro Pro Lys Leu Asp Leu Asn
    2135                2140                2145

Asn Leu Leu Val Asn Pro Glu Gly Pro Thr Ile Thr Arg Leu Asn
    2150                2155                2160

Glu Val Gln Ser Thr Glu Arg Pro Leu Phe Leu Val His Pro Ile
    2165                2170                2175

Glu Gly Ser Ile Ala Val Phe Tyr Thr Leu Ala Ser Lys Leu His
    2180                2185                2190

Met Pro Cys Tyr Gly Leu Gln Cys Thr Lys Ala Ala Pro Leu Asp
    2195                2200                2205

Ser Ile Gln Ser Leu Ala Ser Tyr Tyr Ile Asp Cys Met Lys Gln
    2210                2215                2220

Ile Gln Pro Glu Gly Pro Tyr Arg Ile Ala Gly Tyr Ser Phe Gly
    2225                2230                2235

Ala Cys Val Ala Phe Glu Met Cys Ser Gln Leu Gln Ala Gln Gln
    2240                2245                2250

Asn Ala Ser His Ala Leu Asn Ser Leu Phe Leu Phe Asp Gly Ser
    2255                2260                2265

His Ser Phe Val Ala Ala Tyr Thr Gln Cys Phe Ser Phe Ser Leu
    2270                2275                2280

Phe Gln Ser Tyr Arg Ala Lys Leu Thr Gln Gly Asn Glu Ala Ala
    2285                2290                2295

Leu Glu Thr Glu Ala Leu Cys Ala Phe Val Gln Gln Phe Thr Gly
    2300                2305                2310

Ile Glu Tyr Asn Lys Leu Leu Glu Ile Leu Leu Pro Leu Glu Asp
    2315                2320                2325

Leu Glu Ala Arg Val Asn Ala Ala Ala Asp Leu Ile Thr Gln Ile
    2330                2335                2340

His Lys Asn Ile Asn Arg Glu Ala Leu Ser Phe Ala Ala Ala Ser
```

-continued

```
    2345                2350                2355

Phe Tyr  His Lys Leu Lys Ala  Ala Asp Lys Tyr Ile  Pro Glu Ser
    2360                2365                2370

Lys Tyr  His Gly Asn Val Thr  Leu Met Arg Ala Lys  Thr His Asn
    2375                2380                2385

Glu Tyr  Glu Glu Gly Leu Gly  Gly Asp Tyr Arg Leu  Ser Glu Val
    2390                2395                2400

Cys Asp  Gly Lys Val Ser Val  His Ile Ile Glu Gly  Asp His Arg
    2405                2410                2415

Thr Leu  Leu Glu Gly Asp Gly  Val Glu Ser Ile Ile  Gly Ile Ile
    2420                2425                2430

His Gly  Ser Leu Ala Glu Pro  Arg Val Ser Val Arg  Glu Gly
    2435                2440                2445
```

<210> SEQ ID NO 30
<211> LENGTH: 8391
<212> TYPE: DNA
<213> ORGANISM: Mycobacterium bovis

<400> SEQUENCE: 30

```
atgggtacgc gcactggcgg ccgaggaccc ggttccgtcc gacaagcacc tgacgtcggc     60
cgccgtgtcg gtgcccggcg tgttgcttac ccagatcgcg gcgacccggg cgctggcccg    120
tcaaggcatg gacctcgtgg ccaccccgcc ggtcgccatg gcgggcattc gcaaggtgtg    180
ctggcggtgg aagccctcaa ggctggtggg gcacgcgacg tcgagctgtt tgccttggcc    240
cagttgatcg gtgccgccgg aacgctggtg gcccgccggc gcgaatttcc gtcctgggcg    300
atcgcgccga tggtatcggt caccaacgcc gaccccgagc gcatcggccg gttgctcgac    360
gagttcgccc aggacgtgcg cacggtgctg ccaccggtgt tgtccatccg caacggccgg    420
cgtgccgtcg tcatcaccgg cacccccgag cagctgtcgc gtttcgagct ttattgccgc    480
cagatctccg agaaggaaga agccgaccgc aagaacaagg tccgcggcgg cgacgtcttc    540
tcgccggtct tcgagccggt gcaggtggag gtgggctttc acaccccgcg gctatccgac    600
gggatcgaca tcgtcgcggg ctgggccgag aaggcgggcc tcgatgtcgc cttggctcgg    660
gagctggccg atgccatctt gatcagaaag gtcgactggg tcgacgagat cacccgtgtc    720
caccgggccg gcgcccgctg gatcctcgac ctggggccgg gcgacatcct gacccgactg    780
accgcaccgg tgatccgcgg cctgggcatc ggcatcgtgc cggcgcgtac ccgcggtggc    840
cagcgcaacc tgttcaccgt cggcgccacc cccgaggttg cccgggcctg gtcgagctac    900
gcaccgaccg tggttcgcct ccccgacggc agggtcaagc tctcgacgaa gttcacccgg    960
ctgacccgcc gctcgccgat cctgctcgcg ggcatgaccc cgaccaccgt ggacgccaag   1020
atcgtcgccg cggcggccaa cggccggcac tgggccgagc tggcggcgcg gggcaggtca   1080
ccgaagagat cttcggtaac cgcatcgaac aaatggccgg cctgctcgag ccgggccgca   1140
cctatcagtt caacgcgctg ttcctcgatc cctacctgtg aagcttcagg tgggcggcaa   1200
gcggttggtg cagaaggccc gccagtccgg cgccgcgatc gacggcgtgg tgatcagcgc   1260
cggcatccca gacctcgacg aggccgtcga gctgatcgac gaactgggcg acatcggcat   1320
cagccacgtc gtgttcaaac ccgggaccat cgagcagatc cgctcggtga ttcgcatcgc   1380
caccgaggtg cccaccaagc cggtgatcat gcacgtcgag ggccgggcgc gccggcgggc   1440
accattcctg ggaggatctc acacctgctg ctggctacct actcggcaga tcgggcaccg   1500
cgccaacatc acgtgtgcgt cggcggcggc catctcggca ccccgaagaa gggctgcgga   1560
```

-continued

```
tatttgtccg ggcctgggcg cagcgtacgg cttcccattg atgccgatcg acgcatcctg   1620
gtcggcaccg cggcgatggc caccaaggaa tccaccacgt cgccatcggt caagcggatg   1680
ctcgtcgaca ctcagggcac cgaccaatgg atcagcgccg gaaaagcgca gggccgcatg   1740
cctccagccg agtcagctcg gtgccgacat ccacgagatc gacacagcgc atccgtgcgg   1800
cgctgctcga cgaggtggcc ggtgacgcgg aggcggtcgc ggagcgtcgc atggccaaga   1860
ccgccaagcc ctacttgccg acgtcgccga catgacctac ctgcagtggc tgcgggcgct   1920
acgtcgaact ggccatcggg gaaggcaact cgaccgccga caccgcctcg gtgggcagcc   1980
cgtggctggc cgacactggc gggaccgctt cgagcagatg ctgcagcgtg ccgaagcccg   2040
gttgcaccca caggatttcg gcccgatcca gacgctattc accgatgctg gcctgctgga   2100
caatccgcag cagcgatcgc cgccctcgtg gcgcgctacc ccgacgccga gaccgtgcag   2160
ttgcatcccg cggatgtgcc ctttttcgtg acgttgtgca agacgctggg caagccggtc   2220
aacttcgtgc cggcgatcga cctcgtcgtg cgcgctggtg gcgcagcgac tcgctgtggc   2280
aggcccacga cgcccgctac gacgccgatg cggtgtgcat cattccgggc acgcgtcggt   2340
agccgcatca cccggatgga tgaacccgtc ggtgagttgc tggacgcttt cgagcaagcc   2400
gcaatcgatg aagtgctcgg cgccggtgtc gagccgaagg atgtcgcgtc cggccggctg   2460
ggccgggccg acgtggccgg accgttggct gtcgtcctcg acgcacccga tgtgcgctgg   2520
gccggtcgca ccgtgaccaa cccggtgcat cggatccgcg acccggccga atggcaggtg   2580
cacgatggac ccgaaaaccc gcgcgccgca cactcatcca ccggcgcccg gctgcagacg   2640
cacggcgacg acgtcgcctt gagcgtcgcg cgtctcgggc acctgggtcg acatccgatt   2700
cacgttgccg gccaacaccg tcgatggcgg caccccggtg atcgccaccg aggacgccac   2760
cacgccatgc gcacggtgct gcgatcgccg ccggtgtcga cagcccggag ttcttgctgc   2820
ggtggccaac gggacggcca ctttgacggt ggactggcac cccgagcgtg ttgccgacca   2880
caccgtcacc gccacgttcg gtgcgcgctg gcacccagcc tcaccaacgt gccgacgcga   2940
ctcgtcggcc cttgttggcc agcggttttc gcggccatcg gatcggcggt caccgacacc   3000
ggtgagccgg tggtggaagg cctgctgagc ctggtgcatc tggacacgcg gccgcgcgtg   3060
gtcggtcagc tgcccacggt cccggcccaa ttgaccgtca cgcaacggct gccaacgcaa   3120
ccgatacgga catgggccgc gtcgtgccgg tctcggtcgt cgttcaccgc atggcgccgt   3180
gatcgccact ctcgaggagc gattcgcgat cctgggtcgc accggttcgc cgagctggac   3240
cggcgcgagc cggtggcgcg gtgtcgcgaa cgccaccgac accccgcgcg tcgccgccgc   3300
gacgtcacga tcaccgcgcc ggtcgacatg cgcccgttcg cggtggtgtc cggcgaccac   3360
aaccccattc acaccgaccg ggccgccgct gcttgccggc ctggagtcgc cgatcgtgca   3420
cggcatgtgg ctgtcggccg cggcgcaaca cgcggtgacc ggcaccgacg ggcaggcccg   3480
ccaccggccc ggctggtcgg ctggaccgcg cggtttttgg gcatggtggc cccggcgacg   3540
aggtggactt ccggtcgagc gcgtcggatc gaccagggcg cagagattgt ggacgtggcc   3600
gcgcgcgtcg ggtcggatct agtgatgtcg gcctccgcgc gactggccgc acccaagacg   3660
gtctacgcat tccccggcca gggcatccaa cacaagggca tgggcatgga ggtgcgcgcc   3720
gctccaaggc ggcccgcaag gtgtgggaca ccgcggacaa gttcacccgc gacaccctgg   3780
gcttctcggt actgcacgtg gtccgcgaca acccgaccag catcatcgcc agcggtgtgc   3840
actaccacca ccgacggggt gctctacctg acgcagttca cccaggtcgc gatggcgacg   3900
```

-continued

```
gtggcggccg ggcaggtcgc cgagatgcgt gaacagggag ccttcgtcga aggcgccatc   3960
gcgtgcggcc actcggtcgg cgagtacacc gcgctggcct gcgtgaccgg catctaccaa   4020
ctggaagcct tgctggagat ggtgtttcac cgcgggtcga agatgcacga catcgttccg   4080
cgcgacgagc tcggccgctc caactatcgg ctgtcggcca tccggccgtc ccagatcgac   4140
ctcgacgacg ccgacgtgcc cgcgttcgtc gccgggatcg cggagagcac cggtgaattc   4200
ctggagatcg agaatttcaa cctcggtggc tcgcaatacg cgatcgcggg cacggtacgc   4260
ggcctcgagg cgctcgaggc cgaggtggag cggcgccgcg agctcaccgg cggccgacgg   4320
tcgttcattt tggtgcccgg catcgatgtt ccgttccact cgcgagtgct gcgggtcggg   4380
gtggccgaat tccggcgctc gctggaccgg gtcatgcggc cgacgcggac ccgacctgat   4440
catcgggcgc tacattccca acctggtgcc gcggaagttc aaccctggac cgcgacttca   4500
tccaggaaat ccgggatttg gtgccccgcc gagccgctcg acgagatcct cgccgactac   4560
gacacctggc ttcgcgacga ccggcgagat ggcgcgcacg gtgttcatcg agctgctggc   4620
atggcaattc gccagcccgg tgcgctggat cgagacgcag gatctgctgt tcatcgagga   4680
ggcgccggcg ggctgggtgt ggagcgattc gtcgagatcg gtgtgaagag ctcaccgacg   4740
gtggcggggt cttgccacca acaccctcaa actgcccgaa tacgcccaca gcacagtgaa   4800
gtgctcaacg ccgagcgtga tgcgcggtgc tgttcgccac cgacaccgac ccggagccgg   4860
agccggagga agacgagccg gtcgcggaat cgcccgcgcc ggacgtcgtc tcggaagccg   4920
cccccgtcgc gccggccgct tcgtcggcgg gcccgcgtcc cgacgatctg gttttcgacg   4980
ccgccgatgc cacgctgcgt gatcgcgctc tcggccaaga tgcgcatcga ccagatcgaa   5040
gaactcgact ccatcgagtc catcaccgac ggtgcgtcgt cgcggcgcaa ccagctgctg   5100
gtggacctgg gctccgagct gaacctcggt gccattgaac ggcgccgccg aatcggacct   5160
ggccggtctg cgctcacagg tgaccaaact ggcgcgcacc tacaacgtta cggcccagtg   5220
ctttccgacg ccatcaacga ccacgttcgc accgtcctcg gaccgtcggg caagcggccc   5280
ggcgccatcg ccgagcgggt gaagaagacc tgggagctcg gtgaggctgg gccaagcatg   5340
tcaccgtcga ggtcgcgctg ggcacccgcg agggcagcag cgttcgcggc ggcgccatgg   5400
gccacctgca cgagggcgcg ctggccgatg ccgcctccgt cgacaaggtc atcgacgcgg   5460
cggtcgcatc ggtggccgcg gccagggcgt ttcggtagcg ctgcgtcggc cggtagtggc   5520
ggcgccacca tcgacgcggc cgcgctcagc gagttcaccg accaaatcac cggccgtgag   5580
ggcgtgctgc ctccgcggcc cgcctggtgc tggggcagct gggactggac gaccccatca   5640
accgttgccg gccgccccga ttccgagctg atcgacttgg tcaccgccga actgggacgg   5700
actggccgcg gttggtggca ccggtgttcg accccaagaa ggccgtcgta ttcgacgacc   5760
gctggccagc gcccgcgagg acctggtgaa gctgtggctg accgacggaa ggaccgaagg   5820
cgacatcgac gccgactggc cgcgctggcg gagcgcttcg agggtgccgc cacgtcgtgg   5880
cgacccaggc tacctggtgg caaggtaagt cgctcgcgcg ggccggcaga tccatgcatc   5940
gctgtacggc cgcatgccgc cggcgccgag aaccccgaac cccgcgtacg gcggcgaagt   6000
tgccgtggtg accggcgctt cgaagggttc gatcgccgcg tcggtggtgg ctcggctgct   6060
cgacgcggag ccaccgtcat cgcgaccacc tccaagctcg acgaggagcg gctgcggttc   6120
taccgcacgc tgtatcgcga ccacgcccgt tacggcgcgg cgctgtggct ggtcgcggcg   6180
aacatggcgt cctactccga cgtcgacgcc ctggtcgaat ggatcggcac cgaacagacc   6240
gaaagccttg ggccgcagtc gattcacatc aaagacgcgc agaccccgac gctgctgttc   6300
```

-continued

```
cgttcgcggc gcacgcgtgt cgggactgtc ggaggccggt tcgcgcgccg agatggagat   6360
gaaagtgctg ctgtggcggt gcaacggctg atcggcggcc tgtcgacgat cggcgccgaa   6420
cgcgacatgc cgtcgcggct cgagcgtggt gctgcccggc tcgcccaacc gtggcatgtt   6480
cggcggcgac gggccctacg gcgaagccaa gtccgcgctg gatgccgtgg tgacgcgctg   6540
gcacgccgag tcgtcctggg cggcacgggt cagcctggcg cacgcgctca tcggctggac   6600
ccgcggcacc gggctgatgg gccacaacga tgccatcgtg gccgccgtcg aagaggccgg   6660
ggtcaccacc tactcgaccg acgagatggc gcggctgctg ctcgacctgt gtcatgcgga   6720
atccaaggtg gctgcggccg ttcgccgatc aaggccgacc tgaccggggg cctgccgagg   6780
ccaacctcga catggccgag ctggcggcca aggcgcgcga gcagatgtcg gcagcggcgg   6840
ccgtcgacga ggacgccgag gcccctggcg ccatcgccgc gctgccgtcg ccgccccggt   6900
ttcacccccg caccgccgcc gcaatgggac gacctcgatg tcgacccggc cgacctggtg   6960
gtgatcgtcg gcggccgcga aatcggcccg tacggctcgt cacgcacccg gttcgagatg   7020
gaggtcgaaa acgagctgtc ggcggccggc gtgctggagc tggcctggac cactgggttg   7080
atcgctggga gacgacccgc aacccggttg gtacgacacc gaatccggcg aaatggtcga   7140
cgaatccgag ttggtgcagc gctacacgac gccgtggtgc agcgcgtcgg cattcgcgaa   7200
ttcgttgatg acggcgcgat cgaccccgac cacgcctcgc cgctgctggt gtcggtgttc   7260
ctggagaagg acttcgcgtt cgtggtgtcc tcggaggccg atgcgcgcgc cttcgtcgag   7320
ttcgatcccg agcacacggt catccggccg gtgcccgact ccaccgactg gcaggtcatc   7380
cgcaaggccg gcaccgagat ccgggtgccg cgaaagacca agctgtcccg cgtcgtcggc   7440
ggccagatcc cgaccgggtt cgacccgacg gtgtggggca tcagcgcaga catggccggt   7500
tccatcgacc ggttggcggt atggaacatg tggcggaccg tcgaccggtt cctgtcgtcc   7560
ggtttcagcc cggccgaggt gatgcgttac gtgcacccga gtttggtggc caacacccag   7620
ggcaccggca tgggcggcgg cacgtcgatg cagacgatgt accacggcaa tctgttgggc   7680
cgcaacaagc cgaacgacat cttccaggaa gtcttgccga tatcattcgc cgcgcacgtg   7740
gttcagtcct acgtcggtag ctacggtgcg atgatccacc cggtagccgc gtgcgccacc   7800
gccgcggtgt cggtcgagga aggtgtcgac aagatccggt tgggaaggct caactggtgg   7860
tcggcggccg tggatgacct gacgctggag ggcatcatcg gattcggtga catggccgcc   7920
accgccgaca cgtccatgat gcgcggccgc ggcatccacg actcgaagtt ttcccggccc   7980
aacgaccgcc gccgtctggc ttcgtcgaag cccaaggcgg cgggacgatc ctgttgggcg   8040
cggggacctg gcgctgcgga tggggctgcc ggtgctggcg gtggtgggtt cgcgcagtcg   8100
ttcggcgacg gcgtgcacac ctcgatccgc cccgggcctg ggcgcgctgg gggcggcgcg   8160
cggcggcaag gattcagctg cggcgggcgc tggccaagct gcgtggccgc cgacgacgtg   8220
gcggtcatct ccaagcacga cacctcgacg ctggccaacg atcccaacga gaccgagttg   8280
catgaacggc tcgccgacgc cctgggccgt tccgagggcg ccccgctgtt cgtggtgtcg   8340
cagaagagcc tgaccggcca gccaagggcg gcgcggcggt cttccagatg a            8391
```

<210> SEQ ID NO 31
<211> LENGTH: 2796
<212> TYPE: PRT
<213> ORGANISM: Mycobacterium bovis

<400> SEQUENCE: 31

-continued

```
Met Gly Thr Arg Thr Gly Gly Arg Gly Pro Gly Ser Val Arg Gln Ala
1               5                   10                  15

Pro Asp Val Gly Arg Arg Val Gly Ala Arg Arg Val Ala Tyr Pro Asp
            20                  25                  30

Arg Gly Asp Pro Gly Ala Gly Pro Ser Arg His Gly Pro Arg Gly His
        35                  40                  45

Pro Ala Gly Arg His Gly Gly His Ser Gln Gly Val Leu Ala Val Glu
    50                  55                  60

Ala Leu Lys Ala Gly Gly Ala Arg Asp Val Glu Leu Phe Ala Leu Ala
65                  70                  75                  80

Gln Leu Ile Gly Ala Ala Gly Thr Leu Val Ala Arg Arg Arg Glu Phe
                85                  90                  95

Pro Ser Trp Ala Ile Ala Pro Met Val Ser Val Thr Asn Ala Asp Pro
            100                 105                 110

Glu Arg Ile Gly Arg Leu Leu Asp Glu Phe Ala Gln Asp Val Arg Thr
        115                 120                 125

Val Leu Pro Pro Val Leu Ser Ile Arg Asn Gly Arg Arg Ala Val Val
    130                 135                 140

Ile Thr Gly Thr Pro Glu Gln Leu Ser Arg Phe Glu Leu Tyr Cys Arg
145                 150                 155                 160

Gln Ile Ser Glu Lys Glu Glu Ala Asp Arg Lys Asn Lys Val Arg Gly
                165                 170                 175

Gly Asp Val Phe Ser Pro Val Phe Glu Pro Val Gln Val Glu Val Gly
            180                 185                 190

Phe His Thr Pro Arg Leu Ser Asp Gly Ile Asp Ile Val Ala Gly Trp
        195                 200                 205

Ala Glu Lys Ala Gly Leu Asp Val Ala Leu Ala Arg Glu Leu Ala Asp
    210                 215                 220

Ala Ile Leu Ile Arg Lys Val Asp Trp Val Asp Glu Ile Thr Arg Val
225                 230                 235                 240

His Arg Ala Gly Ala Arg Trp Ile Leu Asp Leu Gly Pro Gly Asp Ile
                245                 250                 255

Leu Thr Arg Leu Thr Ala Pro Val Ile Arg Gly Leu Gly Ile Gly Ile
            260                 265                 270

Val Pro Ala Arg Thr Arg Gly Gly Gln Arg Asn Leu Phe Thr Val Gly
        275                 280                 285

Ala Thr Pro Glu Val Ala Arg Ala Trp Ser Ser Tyr Ala Pro Thr Val
    290                 295                 300

Val Arg Leu Pro Asp Gly Arg Val Lys Leu Ser Thr Lys Phe Thr Arg
305                 310                 315                 320

Leu Thr Arg Arg Ser Pro Ile Leu Leu Ala Gly Met Thr Pro Thr Thr
                325                 330                 335

Val Asp Ala Lys Ile Val Ala Ala Ala Ala Asn Gly Arg His Trp Ala
            340                 345                 350

Glu Leu Ala Ala Arg Gly Arg Ser Pro Lys Arg Ser Ser Val Thr Ala
        355                 360                 365

Ser Asn Lys Trp Pro Ala Cys Ser Ser Arg Ala Ala Pro Ile Ser Ser
    370                 375                 380

Thr Arg Cys Ser Ser Ile Pro Thr Cys Glu Ala Ser Gly Gly Arg Gln
385                 390                 395                 400

Ala Val Gly Ala Glu Gly Pro Pro Val Arg Arg Arg Asp Arg Arg Arg
                405                 410                 415

Gly Asp Gln Arg Arg His Pro Arg Pro Arg Arg Gly Arg Arg Ala Asp
```

-continued

```
            420                 425                 430

Arg Arg Thr Gly Arg His Arg His Gln Pro Arg Arg Val Gln Thr Arg
        435                 440                 445

Asp His Arg Ala Asp Pro Leu Gly Asp Ser His Arg His Arg Gly Ala
    450                 455                 460

His Gln Ala Gly Asp His Ala Arg Arg Gly Pro Gly Ala Pro Ala Gly
465                 470                 475                 480

Thr Ile Pro Gly Arg Ile Ser His Leu Leu Leu Ala Thr Tyr Ser Ala
                485                 490                 495

Asp Arg Ala Pro Arg Gln His His Val Cys Val Gly Gly Gly His Leu
            500                 505                 510

Gly Thr Pro Lys Lys Gly Cys Gly Tyr Leu Ser Gly Pro Gly Arg Ser
        515                 520                 525

Val Arg Leu Pro Ile Asp Ala Asp Arg Arg Ile Leu Val Gly Thr Ala
    530                 535                 540

Ala Met Ala Thr Lys Glu Ser Thr Thr Ser Pro Ser Val Lys Arg Met
545                 550                 555                 560

Leu Val Asp Thr Gln Gly Thr Asp Gln Trp Ile Ser Ala Gly Lys Ala
                565                 570                 575

Gln Gly Arg Met Pro Pro Ala Glu Ser Ala Arg Cys Arg His Pro Arg
            580                 585                 590

Asp Arg His Ser Ala Ser Val Arg Arg Cys Ser Thr Arg Trp Pro Val
        595                 600                 605

Thr Arg Arg Arg Ser Arg Ser Val Ala Trp Pro Arg Pro Pro Ser Pro
    610                 615                 620

Thr Cys Arg Arg Arg Arg His Asp Leu Pro Ala Val Ala Ala Gly Ala
625                 630                 635                 640

Thr Ser Asn Trp Pro Ser Gly Lys Ala Thr Arg Pro Pro Thr Pro Pro
                645                 650                 655

Arg Trp Ala Ala Arg Gly Trp Pro Thr Leu Ala Gly Pro Leu Arg Ala
            660                 665                 670

Asp Ala Ala Ala Cys Arg Ser Pro Val Ala Pro Thr Gly Phe Arg Pro
        675                 680                 685

Asp Pro Asp Ala Ile His Arg Cys Trp Pro Ala Gly Gln Ser Ala Ala
    690                 695                 700

Ala Ile Ala Ala Leu Val Ala Arg Tyr Pro Asp Ala Glu Thr Val Gln
705                 710                 715                 720

Leu His Pro Ala Asp Val Pro Phe Phe Val Thr Leu Cys Lys Thr Leu
                725                 730                 735

Gly Lys Pro Val Asn Phe Val Pro Ala Ile Asp Leu Val Val Arg Ala
            740                 745                 750

Gly Gly Ala Ala Thr Arg Cys Gly Arg Pro Thr Thr Pro Ala Thr Thr
        755                 760                 765

Pro Met Arg Cys Ala Ser Phe Arg Ala Arg Val Gly Ser Arg Ile Thr
    770                 775                 780

Arg Met Asp Glu Pro Val Gly Glu Leu Leu Asp Ala Phe Glu Gln Ala
785                 790                 795                 800

Ala Ile Asp Glu Val Leu Gly Ala Gly Val Glu Pro Lys Asp Val Ala
                805                 810                 815

Ser Gly Arg Leu Gly Arg Ala Asp Val Ala Gly Pro Leu Ala Val Val
            820                 825                 830

Leu Asp Ala Pro Asp Val Arg Trp Ala Gly Arg Thr Val Thr Asn Pro
        835                 840                 845
```

-continued

```
Val His Arg Ile Arg Asp Pro Ala Glu Trp Gln Val His Asp Gly Pro
    850                 855                 860

Glu Asn Pro Arg Ala Ala His Ser Ser Thr Gly Ala Arg Leu Gln Thr
865                 870                 875                 880

His Gly Asp Asp Val Ala Leu Ser Val Ala Arg Leu Gly His Leu Gly
                885                 890                 895

Arg His Pro Ile His Val Ala Gly Gln His Arg Arg Trp Arg His Pro
            900                 905                 910

Gly Asp Arg His Arg Gly Arg His His Ala Met Arg Thr Val Leu Arg
        915                 920                 925

Ser Pro Pro Val Ser Thr Ala Arg Ser Ser Cys Cys Gly Gly Gln Arg
    930                 935                 940

Asp Gly His Phe Asp Gly Gly Leu Ala Pro Arg Ala Cys Cys Arg Pro
945                 950                 955                 960

His Arg His Arg His Val Arg Cys Ala Leu Ala Pro Ser Leu Thr Asn
                965                 970                 975

Val Pro Thr Arg Leu Val Gly Pro Cys Trp Pro Ala Val Phe Ala Ala
            980                 985                 990

Ile Gly Ser Ala Val Thr Asp Thr  Gly Glu Pro Val Val  Glu Gly Leu
        995                 1000                1005

Leu Ser  Leu Val His Leu Asp  Thr Arg Pro Arg Val  Val Gly Gln
    1010                1015                1020

Leu Pro  Thr Val Pro Ala Gln  Leu Thr Val Thr Gln  Arg Leu Pro
    1025                1030                1035

Thr Gln  Pro Ile Arg Thr Trp  Ala Ala Ser Cys Arg  Ser Arg Ser
    1040                1045                1050

Ser Phe  Thr Ala Trp Arg Arg  Asp Arg His Ser Arg  Gly Ala Ile
    1055                1060                1065

Arg Asp  Pro Gly Ser His Arg  Phe Ala Glu Leu Asp  Arg Arg Glu
    1070                1075                1080

Pro Val  Ala Arg Cys Arg Glu  Arg His Arg His Pro  Ala Arg Arg
    1085                1090                1095

Arg Arg  Asp Val Thr Ile Thr  Ala Pro Val Asp Met  Arg Pro Phe
    1100                1105                1110

Ala Val  Val Ser Gly Asp His  Asn Pro Ile His Thr  Asp Arg Ala
    1115                1120                1125

Ala Ala  Ala Cys Arg Pro Gly  Val Ala Asp Arg Ala  Arg His Val
    1130                1135                1140

Ala Val  Gly Arg Gly Ala Thr  Arg Gly Asp Arg His  Arg Arg Ala
    1145                1150                1155

Gly Pro  Pro Pro Ala Arg Leu  Val Gly Trp Thr Ala  Arg Phe Leu
    1160                1165                1170

Gly Met  Val Ala Pro Ala Thr  Arg Trp Thr Ser Gly  Arg Ala Arg
    1175                1180                1185

Arg Ile  Asp Gln Gly Ala Glu  Ile Val Asp Val Ala  Ala Arg Val
    1190                1195                1200

Gly Ser  Asp Leu Val Met Ser  Ala Ser Ala Arg Leu  Ala Ala Pro
    1205                1210                1215

Lys Thr  Val Tyr Ala Phe Pro  Gly Gln Gly Ile Gln  His Lys Gly
    1220                1225                1230

Met Gly  Met Glu Val Arg Ala  Ala Pro Arg Arg Pro  Ala Arg Cys
    1235                1240                1245
```

-continued

```
Gly Thr  Pro Arg Thr Ser Ser  Pro Ala Thr Pro Trp  Ala Ser Arg
    1250                 1255                 1260

Tyr Cys  Thr Trp Ser Ala Thr  Thr Arg Pro Ala Ser  Ser Pro Ala
    1265                 1270                 1275

Val Cys  Thr Thr Thr Thr Asp  Gly Val Leu Tyr Leu  Thr Gln Phe
    1280                 1285                 1290

Thr Gln  Val Ala Met Ala Thr  Val Ala Ala Gly Gln  Val Ala Glu
    1295                 1300                 1305

Met Arg  Glu Gln Gly Ala Phe  Val Glu Gly Ala Ile  Ala Cys Gly
    1310                 1315                 1320

His Ser  Val Gly Glu Tyr Thr  Ala Leu Ala Cys Val  Thr Gly Ile
    1325                 1330                 1335

Tyr Gln  Leu Glu Ala Leu Leu  Glu Met Val Phe His  Arg Gly Ser
    1340                 1345                 1350

Lys Met  His Asp Ile Val Pro  Arg Asp Glu Leu Gly  Arg Ser Asn
    1355                 1360                 1365

Tyr Arg  Leu Ser Ala Ile Arg  Pro Ser Gln Ile Asp  Leu Asp Asp
    1370                 1375                 1380

Ala Asp  Val Pro Ala Phe Val  Ala Gly Ile Ala Glu  Ser Thr Gly
    1385                 1390                 1395

Glu Phe  Leu Glu Ile Glu Asn  Phe Asn Leu Gly Gly  Ser Gln Tyr
    1400                 1405                 1410

Ala Ile  Ala Gly Thr Val Arg  Gly Leu Glu Ala Leu  Glu Ala Glu
    1415                 1420                 1425

Val Glu  Arg Arg Arg Glu Leu  Thr Gly Gly Arg Arg  Ser Phe Ile
    1430                 1435                 1440

Leu Val  Pro Gly Ile Asp Val  Pro Phe His Ser Arg  Val Leu Arg
    1445                 1450                 1455

Val Gly  Val Ala Glu Phe Arg  Arg Ser Leu Asp Arg  Val Met Arg
    1460                 1465                 1470

Pro Thr  Arg Thr Arg Pro Asp  His Arg Ala Leu His  Ser Gln Pro
    1475                 1480                 1485

Gly Ala  Ala Glu Val Gln Pro  Trp Thr Ala Thr Ser  Ser Arg Lys
    1490                 1495                 1500

Ser Gly  Ile Trp Cys Pro Ala  Glu Pro Leu Asp Glu  Ile Leu Ala
    1505                 1510                 1515

Asp Tyr  Asp Thr Trp Leu Arg  Asp Asp Arg Arg Asp  Gly Ala His
    1520                 1525                 1530

Gly Val  His Arg Ala Ala Gly  Met Ala Ile Arg Gln  Pro Gly Ala
    1535                 1540                 1545

Leu Asp  Arg Asp Ala Gly Ser  Ala Val His Arg Gly  Gly Ala Gly
    1550                 1555                 1560

Gly Leu  Gly Val Glu Arg Phe  Val Glu Ile Gly Val  Lys Ser Ser
    1565                 1570                 1575

Pro Thr  Val Ala Gly Ser Cys  His Gln His Pro Gln  Thr Ala Arg
    1580                 1585                 1590

Ile Arg  Pro Gln His Ser Glu  Val Leu Asn Ala Glu  Arg Asp Ala
    1595                 1600                 1605

Arg Cys  Cys Ser Pro Pro Thr  Pro Thr Arg Ser Arg  Ser Arg Arg
    1610                 1615                 1620

Lys Thr  Ser Arg Ser Arg Asn  Arg Pro Arg Arg Thr  Ser Ser Arg
    1625                 1630                 1635

Lys Pro  Pro Pro Ser Arg Arg  Pro Leu Arg Arg Arg  Ala Arg Val
```

-continued

```
    1640                1645                1650

Pro Thr  Ile Trp Phe Ser Thr  Pro Pro Met Pro Arg  Cys Val Ile
    1655                1660                1665

Ala Leu  Ser Ala Lys Met Arg  Ile Asp Gln Ile Glu  Glu Leu Asp
    1670                1675                1680

Ser Ile  Glu Ser Ile Thr Asp  Gly Ala Ser Ser Arg  Arg Asn Gln
    1685                1690                1695

Leu Leu  Val Asp Leu Gly Ser  Glu Leu Asn Leu Gly  Ala Ile Glu
    1700                1705                1710

Arg Arg  Arg Arg Ile Gly Pro  Gly Arg Ser Ala Leu  Thr Gly Asp
    1715                1720                1725

Gln Thr  Gly Ala His Leu Gln  Arg Tyr Gly Pro Val  Leu Ser Asp
    1730                1735                1740

Ala Ile  Asn Asp His Val Arg  Thr Val Leu Gly Pro  Ser Gly Lys
    1745                1750                1755

Arg Pro  Gly Ala Ile Ala Glu  Arg Val Lys Lys Thr  Trp Glu Leu
    1760                1765                1770

Gly Glu  Ala Gly Pro Ser Met  Ser Pro Ser Arg Ser  Arg Trp Ala
    1775                1780                1785

Pro Ala  Arg Ala Ala Ala Phe  Ala Ala Ala Pro Trp  Ala Thr Cys
    1790                1795                1800

Thr Arg  Ala Arg Trp Pro Met  Pro Pro Pro Ser Thr  Arg Ser Ser
    1805                1810                1815

Thr Arg  Arg Ser His Arg Trp  Pro Arg Pro Gly Arg  Phe Gly Ser
    1820                1825                1830

Ala Ala  Ser Ala Gly Ser Gly  Gly Ala Thr Ile Asp  Ala Ala Ala
    1835                1840                1845

Leu Ser  Glu Phe Thr Asp Gln  Ile Thr Gly Arg Glu  Gly Val Leu
    1850                1855                1860

Pro Pro  Arg Pro Ala Trp Cys  Trp Gly Ser Trp Asp  Trp Thr Thr
    1865                1870                1875

Pro Ser  Thr Val Ala Gly Arg  Pro Asp Ser Glu Leu  Ile Asp Leu
    1880                1885                1890

Val Thr  Ala Glu Leu Gly Arg  Thr Gly Arg Gly Trp  Trp His Arg
    1895                1900                1905

Cys Ser  Thr Pro Arg Arg Pro  Ser Tyr Ser Thr Thr  Ala Gly Gln
    1910                1915                1920

Arg Pro  Arg Gly Pro Gly Glu  Ala Val Ala Asp Arg  Arg Lys Asp
    1925                1930                1935

Arg Arg  Arg His Arg Arg Arg  Leu Ala Ala Leu Ala  Glu Arg Phe
    1940                1945                1950

Glu Gly  Ala Ala Thr Ser Trp  Arg Pro Arg Leu Pro  Gly Gly Lys
    1955                1960                1965

Val Ser  Arg Ser Arg Gly Pro  Ala Asp Pro Cys Ile  Ala Val Arg
    1970                1975                1980

Pro His  Ala Ala Gly Ala Glu  Asn Pro Glu Pro Arg  Val Arg Arg
    1985                1990                1995

Arg Ser  Cys Arg Gly Asp Arg  Arg Phe Glu Gly Phe  Asp Arg Arg
    2000                2005                2010

Val Gly  Gly Gly Ser Ala Ala  Arg Arg Gly Ala Thr  Val Ile Ala
    2015                2020                2025

Thr Thr  Ser Lys Leu Asp Glu  Glu Arg Leu Arg Phe  Tyr Arg Thr
    2030                2035                2040
```

-continued

```
Leu Tyr  Arg Asp His Ala Arg  Tyr Gly Ala Ala Leu  Trp Leu Val
    2045                 2050                 2055

Ala Ala  Asn Met Ala Ser Tyr  Ser Asp Val Asp Ala  Leu Val Glu
    2060                 2065                 2070

Trp Ile  Gly Thr Glu Gln Thr  Glu Ser Leu Gly Pro  Gln Ser Ile
    2075                 2080                 2085

His Ile  Lys Asp Ala Gln Thr  Pro Thr Leu Leu Phe  Arg Ser Arg
    2090                 2095                 2100

Arg Thr  Arg Val Gly Thr Val  Gly Gly Arg Phe Ala  Arg Arg Asp
    2105                 2110                 2115

Gly Asp  Glu Ser Ala Ala Val  Ala Val Gln Arg Leu  Ile Gly Gly
    2120                 2125                 2130

Leu Ser  Thr Ile Gly Ala Glu  Arg Asp Met Pro Ser  Arg Leu Glu
    2135                 2140                 2145

Arg Gly  Ala Ala Arg Leu Ala  Gln Pro Trp His Val  Arg Arg Arg
    2150                 2155                 2160

Arg Ala  Leu Arg Arg Ser Gln  Val Arg Ala Gly Cys  Arg Gly Asp
    2165                 2170                 2175

Ala Leu  Ala Arg Arg Val Val  Leu Gly Gly Thr Gly  Gln Pro Gly
    2180                 2185                 2190

Ala Arg  Ala His Arg Leu Asp  Pro Arg His Arg Ala  Asp Gly Pro
    2195                 2200                 2205

Gln Arg  Cys His Arg Gly Arg  Arg Arg Arg Gly Arg  Gly His His
    2210                 2215                 2220

Leu Leu  Asp Arg Arg Asp Gly  Ala Ala Ala Ala Arg  Pro Val Ser
    2225                 2230                 2235

Cys Gly  Ile Gln Gly Gly Cys  Gly Arg Ser Pro Ile  Lys Ala Asp
    2240                 2245                 2250

Leu Thr  Gly Gly Leu Pro Arg  Pro Thr Ser Thr Trp  Pro Ser Trp
    2255                 2260                 2265

Arg Pro  Arg Arg Ala Ser Arg  Cys Arg Gln Arg Arg  Pro Ser Thr
    2270                 2275                 2280

Arg Thr  Pro Arg Pro Leu Ala  Pro Ser Pro Arg Cys  Arg Arg Arg
    2285                 2290                 2295

Pro Gly  Phe Thr Pro Ala Pro  Pro Pro Gln Trp Asp  Asp Leu Asp
    2300                 2305                 2310

Val Asp  Pro Ala Asp Leu Val  Val Ile Val Gly Gly  Arg Glu Ile
    2315                 2320                 2325

Gly Pro  Tyr Gly Ser Ser Arg  Thr Arg Phe Glu Met  Glu Val Glu
    2330                 2335                 2340

Asn Glu  Leu Ser Ala Ala Gly  Val Leu Glu Leu Ala  Trp Thr Thr
    2345                 2350                 2355

Gly Leu  Ile Ala Gly Arg Arg  Pro Ala Thr Arg Leu  Val Arg His
    2360                 2365                 2370

Arg Ile  Arg Arg Asn Gly Arg  Arg Ile Arg Val Gly  Ala Ala Leu
    2375                 2380                 2385

His Asp  Ala Val Val Gln Arg  Val Gly Ile Arg Glu  Phe Val Asp
    2390                 2395                 2400

Asp Gly  Ala Ile Asp Pro Asp  His Ala Ser Pro Leu  Leu Val Ser
    2405                 2410                 2415

Val Phe  Leu Glu Lys Asp Phe  Ala Phe Val Val Ser  Ser Glu Ala
    2420                 2425                 2430
```

-continued

```
Asp Ala  Arg Ala Phe Val Glu  Phe Asp Pro Glu His  Thr Val Ile
    2435                 2440                 2445

Arg Pro  Val Pro Asp Ser Thr  Asp Trp Gln Val Ile  Arg Lys Ala
    2450                 2455                 2460

Gly Thr  Glu Ile Arg Val Pro  Arg Lys Thr Lys Leu  Ser Arg Val
    2465                 2470                 2475

Val Gly  Gly Gln Ile Pro Thr  Gly Phe Asp Pro Thr  Val Trp Gly
    2480                 2485                 2490

Ile Ser  Ala Asp Met Ala Gly  Ser Ile Asp Arg Leu  Ala Val Trp
    2495                 2500                 2505

Asn Met  Trp Arg Thr Val Asp  Arg Phe Leu Ser Ser  Gly Phe Ser
    2510                 2515                 2520

Pro Ala  Glu Val Met Arg Tyr  Val His Pro Ser Leu  Val Ala Asn
    2525                 2530                 2535

Thr Gln  Gly Thr Gly Met Gly  Gly Gly Thr Ser Met  Gln Thr Met
    2540                 2545                 2550

Tyr His  Gly Asn Leu Leu Gly  Arg Asn Lys Pro Asn  Asp Ile Phe
    2555                 2560                 2565

Gln Glu  Val Leu Pro Ile Ser  Phe Ala Ala His Val  Val Gln Ser
    2570                 2575                 2580

Tyr Val  Gly Ser Tyr Gly Ala  Met Ile His Pro Val  Ala Ala Cys
    2585                 2590                 2595

Ala Thr  Ala Ala Val Ser Val  Glu Glu Gly Val Asp  Lys Ile Arg
    2600                 2605                 2610

Leu Gly  Arg Leu Asn Trp Trp  Ser Ala Ala Val Asp  Asp Leu Thr
    2615                 2620                 2625

Leu Glu  Gly Ile Ile Gly Phe  Gly Asp Met Ala Ala  Thr Ala Asp
    2630                 2635                 2640

Thr Ser  Met Met Arg Gly Arg  Gly Ile His Asp Ser  Lys Phe Ser
    2645                 2650                 2655

Arg Pro  Asn Asp Arg Arg Arg  Leu Ala Ser Ser Lys  Pro Lys Ala
    2660                 2665                 2670

Ala Gly  Arg Ser Cys Trp Ala  Arg Gly Pro Gly Ala  Ala Asp Gly
    2675                 2680                 2685

Ala Ala  Gly Ala Gly Gly Gly  Gly Phe Ala Gln Ser  Phe Gly Asp
    2690                 2695                 2700

Gly Val  His Thr Ser Ile Arg  Pro Gly Pro Gly Arg  Ala Gly Gly
    2705                 2710                 2715

Gly Ala  Arg Arg Gln Gly Phe  Ser Cys Gly Gly Arg  Trp Pro Ser
    2720                 2725                 2730

Cys Val  Ala Ala Asp Asp Val  Ala Val Ile Ser Lys  His Asp Thr
    2735                 2740                 2745

Ser Thr  Leu Ala Asn Asp Pro  Asn Glu Thr Glu Leu  His Glu Arg
    2750                 2755                 2760

Leu Ala  Asp Ala Leu Gly Arg  Ser Glu Gly Ala Pro  Leu Phe Val
    2765                 2770                 2775

Val Ser  Gln Lys Ser Leu Thr  Gly Gln Pro Arg Ala  Ala Arg Arg
    2780                 2785                 2790

Ser Ser  Arg
    2795
```

<210> SEQ ID NO 32
<211> LENGTH: 675
<212> TYPE: DNA

-continued

<213> ORGANISM: Bacillus subtilis

<400> SEQUENCE: 32

```
atgaagattt acggaattta tatggaccgc ccgctttcac aggaagaaaa tgaacggttc     60

atgactttca tatcacctga aaaacgggag aaatgccgga gattttatca taaagaagat    120

gctcaccgca ccctgctggg agatgtgctc gttcgctcag tcataagcag gcagtatcag    180

ttggacaaat ccgatatccg ctttagcacg caggaatacg ggaagccgtg catccctgat    240

cttcccgacg ctcatttcaa catttctcac tccggccgct gggtcattgg tgcgtttgat    300

tcacagccga tcggcataga tatcgaaaaa acgaaaccga tcagccttga gatcgccaag    360

cgcttctttt caaaaacaga gtacagcgac cttttagcaa aagacaagga cgagcagaca    420

gactattttt atcatctatg gtcaatgaaa gaaagcttta tcaaacagga aggcaaaggc    480

ttatcgcttc cgcttgattc cttttcagtg cgcctgcatc aggacggaca agtatccatt    540

gagcttccgg acagccattc cccatgctat atcaaaacgt atgaggtcga tcccggctac    600

aaaatggctg tatgcgccgc acaccctgat ttccccgagg atatcacaat ggtctcgtac    660

gaagagcttt tataa                                                     675
```

<210> SEQ ID NO 33
<211> LENGTH: 224
<212> TYPE: PRT
<213> ORGANISM: Bacillus subtilis

<400> SEQUENCE: 33

```
Met Lys Ile Tyr Gly Ile Tyr Met Asp Arg Pro Leu Ser Gln Glu Glu
1               5                   10                  15

Asn Glu Arg Phe Met Thr Phe Ile Ser Pro Glu Lys Arg Glu Lys Cys
            20                  25                  30

Arg Arg Phe Tyr His Lys Glu Asp Ala His Arg Thr Leu Leu Gly Asp
        35                  40                  45

Val Leu Val Arg Ser Val Ile Ser Arg Gln Tyr Gln Leu Asp Lys Ser
    50                  55                  60

Asp Ile Arg Phe Ser Thr Gln Glu Tyr Gly Lys Pro Cys Ile Pro Asp
65                  70                  75                  80

Leu Pro Asp Ala His Phe Asn Ile Ser His Ser Gly Arg Trp Val Ile
                85                  90                  95

Gly Ala Phe Asp Ser Gln Pro Ile Gly Ile Asp Ile Glu Lys Thr Lys
            100                 105                 110

Pro Ile Ser Leu Glu Ile Ala Lys Arg Phe Phe Ser Lys Thr Glu Tyr
        115                 120                 125

Ser Asp Leu Leu Ala Lys Asp Lys Asp Glu Gln Thr Asp Tyr Phe Tyr
    130                 135                 140

His Leu Trp Ser Met Lys Glu Ser Phe Ile Lys Gln Glu Gly Lys Gly
145                 150                 155                 160

Leu Ser Leu Pro Leu Asp Ser Phe Ser Val Arg Leu His Gln Asp Gly
                165                 170                 175

Gln Val Ser Ile Glu Leu Pro Asp Ser His Ser Pro Cys Tyr Ile Lys
            180                 185                 190

Thr Tyr Glu Val Asp Pro Gly Tyr Lys Met Ala Val Cys Ala Ala His
        195                 200                 205

Pro Asp Phe Pro Glu Asp Ile Thr Met Val Ser Tyr Glu Glu Leu Leu
    210                 215                 220
```

-continued

<210> SEQ ID NO 34
<211> LENGTH: 714
<212> TYPE: DNA
<213> ORGANISM: Brevibacillus brevis

<400> SEQUENCE: 34

```
atgatagaaa tgttatttgt aaaggttcca aacgaaatcg ataggcatgt gtttaacttc      60

ttgtcatcaa atgtgagtaa ggaaaaacag caggcgtttg ttcgatacgt taatgtgaaa     120

gatgcttatc gttctctttt aggggaattg cttattagaa aatatttgat acaagtatta     180

aacattccta atgaaaacat tctatttagg aaaaatgaat atggaaaacc ttttgttgat     240

ttcgatattc attttaatat ttcccactct gatgaatggg ttgtatgtgc aatttcaaat     300

catcctgttg gaattgatat cgagcgtatt tcggagatag acattaaaat agcagaacaa     360

ttttttcatg aaaatgaata tatatggttg cagtctaaag cccaaaatag tcaagtttct     420

tctttttttg agctttggac tattaaagaa agttatataa aagctattgg taaaggtatg     480

tacataccga ttaattcatt ttggattgat aagaatcaaa cacaaactgt aatttacaaa     540

cagaataaaa aagaacctgt tactatttat gaaccagagt tgtttgaggg ctacaagtgt     600

tcttgttgtt ctttgttttc ttctgtaacg aacttgtcta ttactaaatt gcaagtgcaa     660

gagttatgta atttgtttct agattctaca ttttctgaaa ataataactt ttag           714
```

<210> SEQ ID NO 35
<211> LENGTH: 237
<212> TYPE: PRT
<213> ORGANISM: Brevibacillus brevis

<400> SEQUENCE: 35

```
Met Ile Glu Met Leu Phe Val Lys Val Pro Asn Glu Ile Asp Arg His
1               5                   10                  15

Val Phe Asn Phe Leu Ser Ser Asn Val Ser Lys Glu Lys Gln Gln Ala
            20                  25                  30

Phe Val Arg Tyr Val Asn Val Lys Asp Ala Tyr Arg Ser Leu Leu Gly
        35                  40                  45

Glu Leu Leu Ile Arg Lys Tyr Leu Ile Gln Val Leu Asn Ile Pro Asn
    50                  55                  60

Glu Asn Ile Leu Phe Arg Lys Asn Glu Tyr Gly Lys Pro Phe Val Asp
65                  70                  75                  80

Phe Asp Ile His Phe Asn Ile Ser His Ser Asp Glu Trp Val Val Cys
                85                  90                  95

Ala Ile Ser Asn His Pro Val Gly Ile Asp Ile Glu Arg Ile Ser Glu
            100                 105                 110

Ile Asp Ile Lys Ile Ala Glu Gln Phe Phe His Glu Asn Glu Tyr Ile
        115                 120                 125

Trp Leu Gln Ser Lys Ala Gln Asn Ser Gln Val Ser Ser Phe Phe Glu
    130                 135                 140

Leu Trp Thr Ile Lys Glu Ser Tyr Ile Lys Ala Ile Gly Lys Gly Met
145                 150                 155                 160

Tyr Ile Pro Ile Asn Ser Phe Trp Ile Asp Lys Asn Gln Thr Gln Thr
                165                 170                 175

Val Ile Tyr Lys Gln Asn Lys Lys Glu Pro Val Thr Ile Tyr Glu Pro
            180                 185                 190

Glu Leu Phe Glu Gly Tyr Lys Cys Ser Cys Cys Ser Leu Phe Ser Ser
        195                 200                 205

Val Thr Asn Leu Ser Ile Thr Lys Leu Gln Val Gln Glu Leu Cys Asn
```

-continued

```
                210                 215                 220

Leu Phe Leu Asp Ser Thr Phe Ser Glu Asn Asn Asn Phe
225                 230                 235


<210> SEQ ID NO 36
<211> LENGTH: 648
<212> TYPE: DNA
<213> ORGANISM: Escherichia coli

<400> SEQUENCE: 36

ttgtcatcag tctcgaatat ggtcgatatg aaaactacgc atacctccct cccctttgcc      60

ggacatacgc tgcattttgt tgagttcgat ccggcgaatt tttgtgagca ggatttactc     120

tggctgccgc actacgcaca actgcaacac gctggacgta aacgtaaaac agagcattta     180

gccggacgga tcgctgctgt ttatgctttg cgggaatatg gctataaatg tgtgcccgca     240

atcggcgagc tacgccaacc tgtctggcct gcggaggtat acggcagtat tagccactgt     300

gggactacgg cattagccgt ggtatctcgt caaccgattg gcattgatat agaagaaatt     360

ttttctgtac aaaccgcaag agaattgaca gacaacatta ttacaccagc ggaacacgag     420

cgactcgcag actgcggttt agccttttct ctggcgctga cactggcatt ttccgccaaa     480

gagagcgcat ttaaggcaag tgagatccaa actgatgcag gttttctgga ctatcagata     540

attagctgga ataaacagca ggtcatcatt catcgtgaga atgagatgtt tgctgtgcac     600

tggcagataa aagaaaagat agtcataacg ctgtgccaac acgattaa                 648


<210> SEQ ID NO 37
<211> LENGTH: 215
<212> TYPE: PRT
<213> ORGANISM: Escherichia coli

<400> SEQUENCE: 37

Met Ser Ser Val Ser Asn Met Val Asp Met Lys Thr Thr His Thr Ser
1               5                   10                  15

Leu Pro Phe Ala Gly His Thr Leu His Phe Val Glu Phe Asp Pro Ala
            20                  25                  30

Asn Phe Cys Glu Gln Asp Leu Leu Trp Leu Pro His Tyr Ala Gln Leu
        35                  40                  45

Gln His Ala Gly Arg Lys Arg Lys Thr Glu His Leu Ala Gly Arg Ile
    50                  55                  60

Ala Ala Val Tyr Ala Leu Arg Glu Tyr Gly Tyr Lys Cys Val Pro Ala
65                  70                  75                  80

Ile Gly Glu Leu Arg Gln Pro Val Trp Pro Ala Glu Val Tyr Gly Ser
                85                  90                  95

Ile Ser His Cys Gly Thr Thr Ala Leu Ala Val Val Ser Arg Gln Pro
            100                 105                 110

Ile Gly Ile Asp Ile Glu Glu Ile Phe Ser Val Gln Thr Ala Arg Glu
        115                 120                 125

Leu Thr Asp Asn Ile Ile Thr Pro Ala Glu His Glu Arg Leu Ala Asp
    130                 135                 140

Cys Gly Leu Ala Phe Ser Leu Ala Leu Thr Leu Ala Phe Ser Ala Lys
145                 150                 155                 160

Glu Ser Ala Phe Lys Ala Ser Glu Ile Gln Thr Asp Ala Gly Phe Leu
                165                 170                 175

Asp Tyr Gln Ile Ile Ser Trp Asn Lys Gln Gln Val Ile Ile His Arg
            180                 185                 190
```

-continued

```
Glu Asn Glu Met Phe Ala Val His Trp Gln Ile Lys Glu Lys Ile Val
        195                 200                 205

Ile Thr Leu Cys Gln His Asp
    210                 215


<210> SEQ ID NO 38
<211> LENGTH: 741
<212> TYPE: DNA
<213> ORGANISM: Streptomyces verticillus

<400> SEQUENCE: 38

gtgatcgccg ccctcctgcc ctcctgggcc gtcaccgaac acgccttcac cgacgccccg      60

gacgacccgg tgagcctcct cttccccgag gaggccgccc acgtcgcccg cgccgtcccc     120

aagcgcctgc acgagttcgc caccgtccgg gtgtgcgccc gcgccgccct cggccggctg     180

ggcctcccgc ccggtccgct gctgcccggc cgacggggcg cgccgagctg gccggacggg     240

gtggtgggga gcatgacgca ctgtcagggc ttccggggcg ccgcggtcgc ccgggccgcc     300

gacgccgcgt cgctcgggat agacgccgag ccgaacgggc cgctcccgga cggcgtcctc     360

gccatggtct cgctgccgtc cgagcgcgag tggctcgccg gactggcggc ccgccggccg     420

gacgtgcact gggaccggct gctgttcagc gccaaggaga gcgtcttcaa ggcgtggtac     480

ccgctgaccg gcctggagct ggacttcgac gaggccgagc tggccgtcga tccggacgcc     540

gggacgttca cggcccggct gctggtgccg ggaccggtgg tcggcggccg tcggctggac     600

gggttcgagg ggcgctgggc ggcgggcgag ggcctcgtcg tcacggccat cgccgtcgcg     660

gcgccggccg gtaccgcgga ggaatcggcg gaaggggccg ggaaggaagc gactgcggac     720

gaccggaccg ccgtcccgta a                                                741


<210> SEQ ID NO 39
<211> LENGTH: 246
<212> TYPE: PRT
<213> ORGANISM: Streptomyces verticillus

<400> SEQUENCE: 39

Met Ile Ala Ala Leu Leu Pro Ser Trp Ala Val Thr Glu His Ala Phe
1               5                   10                  15

Thr Asp Ala Pro Asp Asp Pro Val Ser Leu Leu Phe Pro Glu Glu Ala
            20                  25                  30

Ala His Val Ala Arg Ala Val Pro Lys Arg Leu His Glu Phe Ala Thr
        35                  40                  45

Val Arg Val Cys Ala Arg Ala Ala Leu Gly Arg Leu Gly Leu Pro Pro
    50                  55                  60

Gly Pro Leu Leu Pro Gly Arg Arg Gly Ala Pro Ser Trp Pro Asp Gly
65                  70                  75                  80

Val Val Gly Ser Met Thr His Cys Gln Gly Phe Arg Gly Ala Ala Val
                85                  90                  95

Ala Arg Ala Ala Asp Ala Ala Ser Leu Gly Ile Asp Ala Glu Pro Asn
            100                 105                 110

Gly Pro Leu Pro Asp Gly Val Leu Ala Met Val Ser Leu Pro Ser Glu
        115                 120                 125

Arg Glu Trp Leu Ala Gly Leu Ala Ala Arg Arg Pro Asp Val His Trp
    130                 135                 140

Asp Arg Leu Leu Phe Ser Ala Lys Glu Ser Val Phe Lys Ala Trp Tyr
145                 150                 155                 160

Pro Leu Thr Gly Leu Glu Leu Asp Phe Asp Glu Ala Glu Leu Ala Val
```

-continued

```
                165                 170                 175

Asp Pro Asp Ala Gly Thr Phe Thr Ala Arg Leu Leu Val Pro Gly Pro
            180                 185                 190

Val Val Gly Gly Arg Arg Leu Asp Gly Phe Glu Gly Arg Trp Ala Ala
        195                 200                 205

Gly Glu Gly Leu Val Val Thr Ala Ile Ala Val Ala Ala Pro Ala Gly
    210                 215                 220

Thr Ala Glu Glu Ser Ala Glu Gly Ala Gly Lys Glu Ala Thr Ala Asp
225                 230                 235                 240

Asp Arg Thr Ala Val Pro
                245


<210> SEQ ID NO 40
<211> LENGTH: 819
<212> TYPE: DNA
<213> ORGANISM: Saccharomyces cerevisiae

<400> SEQUENCE: 40

atggttaaaa cgactgaagt agtaagcgaa gtttcaaagg tggcaggtgt aagaccatgg     60

gcaggtatat tcgttgttga aattcaagag gatatactcg cggatgagtt tacgttcgag    120

gcattaatga gaactttgcc attggcgtct caagccagaa tcctcaataa aaaatcgttt    180

cacgatagat gttcaaatct atgcagccag ctgctgcagt tgtttggctg ctctatagta    240

acgggcttaa attttcaaga gctgaaattt gacaagggca gcttcggtaa gccattctta    300

gacaacaatc gttttcttcc atttagcatg accatcggtg aacaatatgt agctatgttc    360

ctcgtaaaat gtgtaagtac agatgaatac caggatgtcg gaattgatat cgcttctccg    420

tgcaattatg gcgggaggga agagttggag ctatttaaag aagtttttag tgaaagagaa    480

tttaacggtt tactgaaagc gtctgatcca tgcacaatat ttacttactt atggtccttg    540

aaggagtcgt atacaaaatt tactggaact ggccttaaca cagacttgtc actaatagat    600

tttggcgcta tcagcttttt tccggctgag ggagcttcta tgtgcataac tctggatgaa    660

gttccattga ttttccattc tcaatggttc aataacgaaa ttgtcactat ctgtatgcca    720

aagtccatca gtgataaaat caacacgaac agaccaaaat tatataatat cagcttatct    780

acgttgattg attatttcat cgaaaatgat ggtttataa                           819


<210> SEQ ID NO 41
<211> LENGTH: 272
<212> TYPE: PRT
<213> ORGANISM: Saccharomyces cerevisiae

<400> SEQUENCE: 41

Met Val Lys Thr Thr Glu Val Val Ser Glu Val Ser Lys Val Ala Gly
1               5                   10                  15

Val Arg Pro Trp Ala Gly Ile Phe Val Val Glu Ile Gln Glu Asp Ile
            20                  25                  30

Leu Ala Asp Glu Phe Thr Phe Glu Ala Leu Met Arg Thr Leu Pro Leu
        35                  40                  45

Ala Ser Gln Ala Arg Ile Leu Asn Lys Lys Ser Phe His Asp Arg Cys
    50                  55                  60

Ser Asn Leu Cys Ser Gln Leu Leu Gln Leu Phe Gly Cys Ser Ile Val
65                  70                  75                  80

Thr Gly Leu Asn Phe Gln Glu Leu Lys Phe Asp Lys Gly Ser Phe Gly
                85                  90                  95
```

-continued

```
Lys Pro Phe Leu Asp Asn Asn Arg Phe Leu Pro Phe Ser Met Thr Ile
            100                 105                 110

Gly Glu Gln Tyr Val Ala Met Phe Leu Val Lys Cys Val Ser Thr Asp
        115                 120                 125

Glu Tyr Gln Asp Val Gly Ile Asp Ile Ala Ser Pro Cys Asn Tyr Gly
    130                 135                 140

Gly Arg Glu Glu Leu Glu Leu Phe Lys Glu Val Phe Ser Glu Arg Glu
145                 150                 155                 160

Phe Asn Gly Leu Leu Lys Ala Ser Asp Pro Cys Thr Ile Phe Thr Tyr
                165                 170                 175

Leu Trp Ser Leu Lys Glu Ser Tyr Thr Lys Phe Thr Gly Thr Gly Leu
            180                 185                 190

Asn Thr Asp Leu Ser Leu Ile Asp Phe Gly Ala Ile Ser Phe Phe Pro
        195                 200                 205

Ala Glu Gly Ala Ser Met Cys Ile Thr Leu Asp Glu Val Pro Leu Ile
    210                 215                 220

Phe His Ser Gln Trp Phe Asn Asn Glu Ile Val Thr Ile Cys Met Pro
225                 230                 235                 240

Lys Ser Ile Ser Asp Lys Ile Asn Thr Asn Arg Pro Lys Leu Tyr Asn
                245                 250                 255

Ile Ser Leu Ser Thr Leu Ile Asp Tyr Phe Ile Glu Asn Asp Gly Leu
            260                 265                 270


<210> SEQ ID NO 42
<211> LENGTH: 588
<212> TYPE: DNA
<213> ORGANISM: Escherichia coli

<400> SEQUENCE: 42

atggtggacc aggcgcagga caccctgcgc ccgaataaca gattgtcaga tatgcaggca      60

acaatggaac aaacccaggc ctttgaaaac cgtgtgcttg agcgtctgaa tgctggcaaa     120

accgtgcgaa gctttctgat caccgccgtc gagctcctga ccgaggcggt aaatcttctg     180

gtgcttcagg tattccgcaa agacgattac gcggtgaagt atgctgtaga accgttactc     240

gacggcgatg gtccgctggg cgatctttct gtgcgtttaa aactcattta cgggttgggc     300

gtcattaacc gccaggaata cgaagatgcg gaactgctga tggcattgcg tgaagagcta     360

aatcacgacg gcaacgagta cgcctttacc gacgacgaaa tccttggacc ctttggtgaa     420

ctgcactgcg tggcggcgtt accaccgccg ccacagtttg aaccagcaga ctccagtttg     480

tatgcaatgc aaattcagcg ctatcaacag gctgtgcgat caacaatggt cctttcactg     540

actgagctga tttccaaaat cagcttaaaa aaagcctttc aaaagtaa                  588


<210> SEQ ID NO 43
<211> LENGTH: 195
<212> TYPE: PRT
<213> ORGANISM: Escherichia coli

<400> SEQUENCE: 43

Met Val Asp Gln Ala Gln Asp Thr Leu Arg Pro Asn Asn Arg Leu Ser
1               5                   10                  15

Asp Met Gln Ala Thr Met Glu Gln Thr Gln Ala Phe Glu Asn Arg Val
            20                  25                  30

Leu Glu Arg Leu Asn Ala Gly Lys Thr Val Arg Ser Phe Leu Ile Thr
        35                  40                  45

Ala Val Glu Leu Leu Thr Glu Ala Val Asn Leu Leu Val Leu Gln Val
```

-continued

```
    50                  55                  60

Phe Arg Lys Asp Asp Tyr Ala Val Lys Tyr Ala Val Glu Pro Leu Leu
65                  70                  75                  80

Asp Gly Asp Gly Pro Leu Gly Asp Leu Ser Val Arg Leu Lys Leu Ile
                85                  90                  95

Tyr Gly Leu Gly Val Ile Asn Arg Gln Glu Tyr Glu Asp Ala Glu Leu
            100                 105                 110

Leu Met Ala Leu Arg Glu Glu Leu Asn His Asp Gly Asn Glu Tyr Ala
        115                 120                 125

Phe Thr Asp Asp Glu Ile Leu Gly Pro Phe Gly Glu Leu His Cys Val
    130                 135                 140

Ala Ala Leu Pro Pro Pro Pro Gln Phe Glu Pro Ala Asp Ser Ser Leu
145                 150                 155                 160

Tyr Ala Met Gln Ile Gln Arg Tyr Gln Gln Ala Val Arg Ser Thr Met
                165                 170                 175

Val Leu Ser Leu Thr Glu Leu Ile Ser Lys Ile Ser Leu Lys Lys Ala
            180                 185                 190

Phe Gln Lys
        195
```

ELEVATION OF FATTY ACID SYNTHASE LEVELS IN PLANTS

The patent application claims the benefit of U.S. Provisional Patent Application No. 60/435,197, filed Dec. 19, 2002, which is incorporated by reference herein.

The present invention relates to the fields of nucleic acid chemistry and agricultural biotechnology. In particular, the present invention is directed at the identification of nucleic acids that encode proteins useful for increasing fatty acid synthesis in plants and creating plants that include such nucleic acids.

Higher plants synthesize fatty acids via a common metabolic pathway involving the acyl carrier protein co-factor (ACP) and the fatty acid synthase (FAS) enzyme complex. The FAS complex consists of about eight separate enzymes that catalyze thirty or more individual reaction steps, all of which, in plants, are located in the plastids. In developing seeds, for example, where fatty acids are stored, the FAS enzyme complex is located in the plastids, synthesizes the fatty acids therein, and then the fatty acids are transported to the cytosol in accordance with energy needs there. It would be more energy efficient to provide the plant with a capability to synthesize fatty acids in the cytosol directly.

Obtaining nucleic acid sequences capable of producing increased fatty acid content in plants is problematic because many non-associated, monofunctional enzymes are used to make fatty acids in plants. Accordingly, cloning and genetic manipulation of plant fatty acid synthases ("FASs") would require isolation and coordinated expression of at least eight separate genes. In particular, plant fatty acid synthesis depends on availability of the following plastid-localized FAS enzymes: Malonyl-CoA:ACP transacylase, β-ketoacyl-ACP synthase III, β-ketoacyl-ACP synthase I, β-ketoacyl-ACP synthase II, β-ketoacyl-ACP reductase, β-hydroxyacyl-ACP dehydratase, enoyl-ACP reductase, and stearoyl-ACP desaturase. For movement of the end-product, acyl-ACP, from the plastid to the cytosol of the cell, two more enzymatic activities are required: acyl-ACP thioesterase and acyl-CoA synthase.

A need therefore exists for an efficient method to provide increased capability for the synthesis of fatty acids in plants.

SUMMARY OF THE INVENTION

This present invention provides a method for increasing fatty acid synthase activity in plant tissues by expressing a gene encoding a multifunctional fatty acid synthase (mfFAS) on either a single or multiple polypeptide chain, with the proviso that the plant not be of the *Brassica* species. In one preferred embodiment of this present invention, the gene encodes a cytosol-targeted mfFAS. Alternatively, the mfFAS gene product is targeted to accumulate and be active in a plastid. Preferably, the source of the mfFAS is selected from the group consisting of bacteria, fungae, planta, mycoplasma, and the like; more preferably, the source of the mfFAS is bacteria or fungae. In another embodiment of this present invention, the expression of the mfFAS gene is in the seed tissue of a plant species, preferably resulting in the increase in fatty acid synthase activity in the seed, with the proviso that the plant species not be *Brassica.*

In another embodiment, the present invention provides an isolated sequence of a mfFAS gene from a bacterium, for example, the fasA gene from *Brevibacterium ammoniagenes*. Plant transformation vectors containing a mfFAS gene, as well as transformed plants and seeds are also provided, the plants and seeds not being of the *Brassica* species.

The present invention further provides a method of increasing oil content in a corn plant, comprising expressing a gene encoding a mfFAS, wherein the mfFAS comprises either a single or multiple polypeptide chain. In a preferred embodiment the mfFAS of said method comprises a double polypeptide chain. In a more preferred embodiment the mfFAS of said method is from *Lipomyces starkeyi.*

DESCRIPTION OF THE FIGURES

FIG. 2 provides an alignment of the fasA *Brevibacterium ammoniagenes* nucleic acid sequence (SEQ ID NO: 1) provided herein with a published fasA *Brevibacterium ammoniagenes* nucleic acid sequence (Stuible et al., *J. Bacteriol.,* 178:4787, 1996). A number of differences at the DNA level were observed.

FIG. 3 provides an alignment of the fasA *Brevibacterium ammoniagenes* amino acid sequence [SEQ ID NO: 2]) provided herein with a published fasA *Brevibacterium ammoniagenes* amino acid sequence (Stuible et al., *J. Bacteriol.,*178:4787, 1996). A number of differences at the protein level were observed.

BRIEF DESCRIPTION OF THE SEQUENCES

Figure 1:
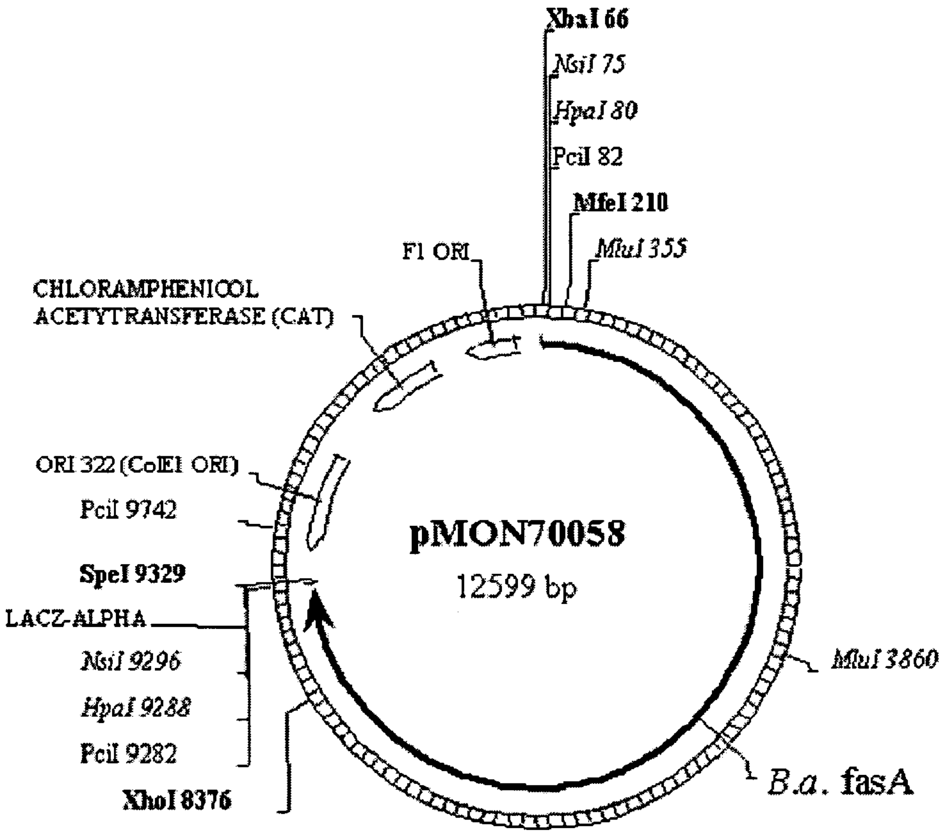
FIG. 1 provides a map of the plasmid pMON70058 that contains the 8 KB fasA gene from *Brevibacterium ammoniagenes.*

SEQ ID NO: 1 is a DNA encoding FasA from *Brevibacterium ammoniagenes.*

SEQ ID NO: 2 is a protein known as FasA from *Brevibacterium ammoniagenes.*

SEQ ID NO: 3 is a DNA encoding a phosphopantetheine: protein transferase (PPT1) enzyme from *Brevibacterium ammoniagenes.*

SEQ ID NO: 4 is a protein known as phosphopantetheine: protein transferase (PPT1) enzyme from *Brevibacterium ammoniagenes.*

SEQ ID NO: 5 is a nucleic acid used as a PCR primer.

SEQ ID NO: 6 is a nucleic acid used as a PCR primer.

SEQ ID NO: 7 is a nucleic acid used as a PCR primer.

SEQ ID NO: 8 is a nucleic acid used as a PCR primer.

SEQ ID NO: 9 is a nucleic acid used as a PCR primer.

SEQ ID NO: 10 is a nucleic acid used as a PCR primer.

SEQ ID NO: 11 is a nucleic acid used as a PCR primer.

SEQ ID NO: 12 is a nucleic acid used as a PCR primer.

SEQ ID NO: 13 is a nucleic acid used as a PCR primer.

SEQ ID NO: 14 is a nucleic acid used as a PCR primer.

SEQ ID NO: 15 is a protein known as fatty acid synthase 1 of *Schizosaccharomyces pombe*; NCBI Accession No. CAB54157.

SEQ ID NO: 16 is a DNA encoding fatty acid synthase subunit beta of *Schizosaccharomyces pombe.*

SEQ ID NO: 17 is a protein known as fatty acid synthase subunit alpha of *Schizosaccharomyces pombe*; NCBI Accession No. D83412.

SEQ ID NO: 18 is a protein known as fatty acid synthase subunit beta of *Saccharomyces cerevisiae*; NCBI Accession No. CAA82025.

SEQ ID NO: 19 is a protein known as fatty acid synthase subunit alpha of *Saccharomyces cerevisiae*; NCBI Accession No. CAA97948.

SEQ ID NO: 20 is a protein known as fatty acid synthase subunit beta of *Candida albicans*; NCBI Accession No. CAA52907.

SEQ ID NO: 21 is a DNA encoding fatty acid synthase subunit alpha of *Candida albicans*; NCBI Accession No. L29063.

SEQ ID NO: 22 is a protein known as fatty acid synthase subunit alpha of *Candida albicans*; NCBI Accession No. L29063.

SEQ ID NO: 23 is a protein known as fatty acid synthase of *Mycobacterium tuberculosis* H37Rv; NCBI Accession No. CAB06201.

SEQ ID NO: 24 is a protein known as fatty acid synthase of *Mycobacterium leprae*; NCBI Accession No. CAB39571.

SEQ ID NO: 25 is a protein known as fatty acid synthase of *Caenorhabditis elegans*; NCBI Accession No. NP492417.

SEQ ID NO: 26 is a DNA encoding fatty acid synthase (FAS) of *Rattus norvegicus*; NCBI Accession No. X13415.

SEQ ID NO: 27 is a protein known as fatty acid synthase (FAS) of *Rattus norvegicus*; NCBI Accession No. X13415.

SEQ ID NO: 28 is a DNA encoding fatty acid synthase (FAS) of chicken (*Gallus gallus*); NCBI Accession No. J03860 M22987.

SEQ ID NO: 29 is a protein known as fatty acid synthase (FAS) of chicken (*Gallus gallus*); NCBI Accession No. J03860 M22987.

SEQ ID NO: 30 is a DNA encoding fatty acid synthase (FAS) of *Mycobacterium bovis*; NCBI Accession No. U36763.

SEQ ID NO: 31 is a protein known as fatty acid synthase (FAS) of *Mycobacterium bovis*; NCBI Accession No. U36763.

SEQ ID NO: 32 is a DNA encoding a phosphopantetheine:protein transferase (sfp gene product) enzyme from *Bacillus subtilis*; NCBI Accession No. X63158.

SEQ ID NO: 33 is a protein known as phosphopantetheine:protein transferase (sfp gene product) enzyme from *Bacillus subtilis*; NCBI Accession No. X63158.

SEQ ID NO: 34 is a DNA encoding a phosphopantetheine:protein transferase (gsp gene product) enzyme from *Brevibacillus brevis* (ATCC 9999); NCBI Accession No. X76434.

SEQ ID NO: 35 is a protein known as phosphopantetheine:protein transferase (gsp gene product) enzyme from *Brevibacillus brevis* (ATCC 9999); NCBI Accession No. X76434.

SEQ ID NO: 36 is a DNA encoding a phosphopantetheine:protein transferase (entD gene product) enzyme from *Escherichia coli*; NCBI Accession No. D90700.

SEQ ID NO: 37 is a protein known as phosphopantetheine:protein transferase (entD gene product) enzyme from *Escherichia coli*; NCBI Accession No. D90700.

SEQ ID NO: 38 is a DNA encoding a phosphopantetheine:protein transferase (pptA gene product) enzyme from *Streptomyces verticillus*; NCBI Accession No. AF210311.

SEQ ID NO: 39 is a protein known as phosphopantetheine:protein transferase (pptA gene product) enzyme from *Streptomyces verticillus*; NCBI Accession No. AF210311.

SEQ ID NO: 40 is a DNA encoding an α-aminoadipate reductase small subunit (lys5 gene product) enzyme from *Saccharomyces cerevisiae*; NCBI Accession No. U32586.

SEQ ID NO: 41 is a protein known as the small subunit (lys5 gene product) of an α-aminoadipate reductase from *Saccharomyces cerevisiae*; NCBI Accession No. U32586.

SEQ ID NO: 42 is a DNA encoding an open reading frame o195 from *Escherichia coli*; NCBI Accession No. U00039.

SEQ ID NO: 43 is a protein encoded by open reading frame o195 from *Escherichia coli*; NCBI Accession No. U00039.

DEFINITIONS

The following definitions are provided as an aid to understanding the detailed description of the present invention.

The phrases "coding sequence," "coding region," "structural sequence," and "structural nucleic acid sequence" refer to a physical structure comprising an orderly arrangement of nucleotides. The nucleotides are arranged in a series of triplets that each form a codon. Each codon encodes a specific amino acid. Thus, the coding sequence, coding region, structural sequence, and structural nucleic acid sequence encode a series of amino acids forming a protein, polypeptide, or peptide sequence. The coding sequence, coding region, structural sequence, and structural nucleic acid sequence may be contained within a larger nucleic acid molecule, vector, or the like. In addition, the orderly arrangement of nucleotides in these sequences may be depicted in the form of a sequence listing, figure, table, electronic medium, or the like.

The phrases "DNA sequence," "nucleic acid sequence," and "nucleic acid molecule" refer to a physical structure comprising an orderly arrangement of nucleotides. The DNA sequence or nucleotide sequence may be contained within a larger nucleotide molecule, vector, or the like. In addition, the orderly arrangement of nucleic acids in these sequences may be depicted in the form of a sequence listing, figure, table, electronic medium, or the like.

The term "expression" refers to the transcription of a gene to produce the corresponding mRNA and translation of this mRNA to produce the corresponding gene product (i.e., a peptide, polypeptide, or protein).

The phrase "expression of antisense RNA" refers to the transcription of a DNA to produce a first RNA molecule capable of hybridizing to a second RNA molecule, said second RNA molecule encodes a gene product that is desirably down-regulated.

The term "homology" refers to the level of similarity between two or more nucleic acid or amino acid sequences in terms of percent of positional identity (i.e., sequence similarity or identity). Homology also refers to the concept of similar functional properties among different nucleic acids or proteins.

The term "heterologous" refers to the relationship between two or more nucleic acid or protein sequences that are derived from different sources. For example, a promoter is heterologous with respect to a coding sequence if such a combination is not normally found in nature. In addition, a particular sequence may be heterologous with respect to a cell or organism into which it is inserted (i.e., does not naturally occur in that particular cell or organism).

The term "hybridization" refers to the ability of a first strand of nucleic acid to join with a second strand via hydrogen bond base pairing when the two nucleic acid strands have sufficient sequence complementarity. Hybridization occurs when the two nucleic acid molecules anneal to one another under appropriate conditions.

The terms "plants" and "plant", in the context of the present invention, refer to higher plants other than those of the *Brassica* species.

The phrase "operably linked" refers to the functional spatial arrangement of two or more nucleic acid regions or nucleic acid sequences. For example, a promoter region may be positioned relative to a nucleic acid sequence such that transcription of the nucleic acid sequence is directed by the promoter region. Thus, a promoter region is operably linked to the nucleic acid sequence.

The terms "promoter" or "promoter region" refers to a nucleic acid sequence, usually found upstream (5') to a coding sequence, which is capable of directing transcription of a nucleic acid sequence into mRNA. The promoter or promoter region typically provides a recognition site for RNA polymerase and the other factors necessary for proper initiation of transcription. As contemplated herein, a promoter or promoter region includes variations of promoters derived by inserting or deleting regulatory regions, subjecting the promoter to random or site-directed mutagenesis, and the like. The activity or strength of a promoter may be measured in terms of the amounts of RNA it produces, or the amount of protein accumulation in a cell or tissue, relative to a second promoter that is similarly measured.

The term "5'-UTR" refers to the untranslated region of DNA upstream, or 5', of the coding region of a gene.

The term "3'-UTR" refers to the untranslated region of DNA downstream, or 3', of the coding region of a gene.

The phrase "recombinant vector" refers to any agent by or in which a nucleic acid of interest is amplified, expressed, or stored, such as a plasmid, cosmid, virus, autonomously replicating sequence, phage, or linear single-stranded, circular single-stranded, linear double-stranded, or circular double-stranded DNA or RNA nucleotide sequence. The recombinant vector may be derived from any source and is capable of genomic integration or autonomous replication.

The phrase "regulatory sequence" refers to a nucleotide sequence located upstream (5'), within, or downstream (3') with respect to a coding sequence. Transcription and expression of the coding sequence is typically impacted by the presence or absence of the regulatory sequence.

The phrase "substantially homologous" refers to two sequences that are at least about 90% identical in sequence, as measured by the CLUSTAL W method in the Omiga program, using default parameters (Version 2.0; Accelrys, San Diego, Calif.).

The term "transformation" refers to the introduction of nucleic acid into a recipient host. The term "host" refers to bacteria cells, fungi, animals or animal cells, plants or seeds, or any plant parts or tissues including plant cells, protoplasts, calli, roots, tubers, seeds, stems, leaves, seedlings, embryos, and pollen.

As used herein, the phrase "transgenic plant" refers to a plant having an introduced nucleic acid stably introduced into a genome of the plant, for example, the nuclear or plastid genomes.

As used herein, the phrase "substantially purified" refers to a molecule separated from substantially all other molecules normally associated with it in its native state. More preferably, a substantially purified molecule is the predominant species present in a preparation. A substantially purified molecule may be greater than about 60% free, preferably about 75% free, more preferably about 90% free, and most preferably about 95% free from the other molecules (exclusive of solvent) present in the natural mixture. The phrase "substantially purified" is not intended to encompass molecules present in their native state.

DETAILED DESCRIPTION OF THE INVENTION

The present invention provides a multifunctional fatty acid synthase ("mfFAS") that encodes the enzymatic functions required to synthesize palmitoyl (16:0) CoA, stearoyl (18:0) CoA, and oleoyl (18:1) CoA, the fatty acids used as precursors for other long chain saturated and unsaturated fatty acids. Furthermore, this present invention provides a multifunctional fatty acid synthase that encodes all of the fatty acid synthase ("FAS") enzymatic functions in a single, long polypeptide chain or in two chains that combine together, which may be employed in the cytosol or plastid, preferably in both, more preferably in the cytosol. Such a multifunctional fatty acid synthase is surprisingly effective in plants even though its structure is so dissimilar from plant fatty acid synthases. Most preferably, the mfFAS of the present invention is employed in the cytosol of a plant, and in this way the need for an acyl carrier protein ("ACP") in fatty acid synthesis and the enzymes acyl-ACP thioesterase and acyl-CoA synthase is removed. Accordingly, not only does the present invention remove the need to clone at least eight different genes to accomplish altered fatty acid synthesis in a plant, but when the mfFAS is employed in the cytosol, it replaces the function of 11 different plant gene products.

Fatty Acid Synthases: Fatty acid synthases are among the functionally most complex multienzyme systems known, which can be formed from a single polypeptide or multiple polypeptides. For mfFASs formed of a single polypeptide, there are multiple regions included thereon that perform the various enzymatic activities; such regions are referred to as "domains". Multifunctional fatty acid synthases formed of multiple polypeptides include various FAS domains as well, which require the interaction of the constituent polypeptides to function. Such polypeptides, whether a multi-domain or single-domain polypeptide, can be isolated from an organism, or can be generated by combining domains or parts of domains together at the nucleic acid level using conventional recombinant technology. Accordingly, recombinant chimeric nucleic acids that combine some mfFAS domains from one source with the remainder of the mfFAS domains from one or more second sources are preferred embodiments of the present invention. In the same fashion, the nucleic acid sequences in a mfFAS gene that encodes a particular domain can be replaced with a homologous nucleic acid sequence from a second source that encodes the same domain.

Fatty acid synthases usually comprise a set of 8 different functional domains and catalyze more than about 30 individual reaction steps. Two structurally distinct classes of fatty acid synthases exist. Type I fatty acid synthases are multifunctional synthases, commonly found in non-plant eukaryotes and in a few bacterial species. Type II fatty acid synthases constitute a set of separate, monofunctional polypeptides that are found in most bacteria and in the plastids of higher plants. These polypeptides must properly interact for the synthase to be active. The fatty acid synthase from some bacteria, such as *Brevibacterium ammoniagenes*, is unlike plant and animal synthases in that it has a ninth catalytic activity (Seyama and Kawaguchi (1987), in Dolthin et al., (eds.), Pyridine Nucleotide Coenzymes: Chemical, Biochemical and Medical Aspects, vol. 2B, Wiley, NY, pp. 381-431), the 3-hydroxydecanoyl β,γ-dehydratase, which enables synthesis of both saturated and unsaturated fatty acids.

For transgenic purposes, type I multifunctional fatty acid synthases may have certain advantages over the type II "monofunctional" fatty acid synthases. For example, the type I multifunctional fatty acid synthases may have greater stability and/or better-coordinated expression. Addition of a single polypeptide specific for one of the enzymatic fatty acid synthase activities to a plant by transgenic means may not provide overproduction of the entire fatty acid synthase complex because there may not be sufficient endogenous amounts of the other non-transgenic FAS polypeptides to substantially increase levels of the functional complex. In contrast, nucleic acids encoding a type I multifunctional fatty acid synthase can reliably be used to overproduce all of the enzymatic functions of fatty acid synthase.

According to the present invention, nucleic acids encoding one or more of the separate domains from a type II monofunctional fatty acid synthase can be fused or linked to provide a synthetic multifunctional fatty acid synthase that can generate higher fatty acid synthase levels when expressed within a host, such as, for example, a plant cell, plant tissue, or seed. Such a fused, synthetic multifunctional fatty acid synthase can be made by fusing or linking the separate enzymatic functions associated with the various polypeptides of type II fatty acid synthases by chemically linking the nucleic acids that encode the various polypeptides. The overall sequence of such a synthetic gene generally aligns with that of a type I multifunctional fatty acid synthase. Using such sequence alignments, the spacing and orientation of polypeptides that contain the various fatty acid synthase activities can be adjusted or modified by altering the lengths of linking DNA between coding regions to generate a synthetic multifunctional fatty acid synthase DNA construct that optimally aligns with a natural type I multifunctional fatty acid synthase gene.

According to the present invention, nucleic acids encoding one or more of the separate domains from a type II monofunctional fatty acid synthase can be fused or linked to provide a synthetic multifunctional fatty acid synthase that can generate higher oil levels when expressed within a host, such as, for example, a plant cell, plant tissue, or seed. Such a fused, synthetic multifunctional fatty acid synthase can be made by fusing or linking the separate enzymatic functions associated with the various polypeptides of type II fatty acid synthases by chemically linking the nucleic acids that encode the various polypeptides. The overall sequence of such a synthetic gene generally aligns with that of a type I multifunctional fatty acid synthase. Using such sequence alignments, the spacing and orientation of polypeptides that contain the various fatty acid synthase activities can be adjusted or modified by altering the lengths of linking DNA between coding regions to generate a synthetic multifunctional fatty acid synthase DNA construct that optimally aligns with a natural type I multifunctional fatty acid synthase gene.

The fatty acid synthase polypeptides of the present invention can therefore encode more than one of the enzymes associated with fatty acid synthase, such as, for example, two through and including nine, thereby enabling up to the same nine catalytic activities as are found in the mfFAS of *Brevibacterium ammoniagenes*. Any of the enzymes involved in the various steps of fatty acid synthesis can be joined. The first step in initiation stage of fatty acid synthesis is the carboxylation of the 2 carbon acetyl-CoA to form the 3-carbon β-ketoacid malonyl-CoA by acetyl-CoA carboxylase (ACCase). The ACCase step is irreversible, so once this step is accomplished, the resultant carbon compound is committed to fatty acid synthesis. All subsequent steps are catalyzed by the FAS. Malonyl-ACP is synthesized from malonyl-CoA and ACP by the enzyme malonyl-CoA:ACP transacylase. An acetyl moiety from acetyl-CoA is joined to a malonyl-ACP in a condensation reaction catalyzed by β-ketoacyl-ACP synthase III. Elongation of acetyl-ACP to 16- and 18-carbon fatty acids involves the cyclical action of the following sequence of reactions. After acetyl-CoA is condensed with malonyl-ACP using β-ketoacyl-ACP synthase, a β-ketoacyl-ACP is formed. The keto group on the β-ketoacyl-ACP is then reduced to an alcohol by β-ketoacyl-ACP reductase. The alcohol is removed in a dehydration reaction to form an enoyl-ACP by β-hydroxyacyl-ACP dehydratase. Finally, the enoyl-ACP is reduced to form the elongated saturated acyl-ACP by enoyl-ACP reductase.

The enzyme β-ketoacyl-ACP synthase I catalyzes elongation up to palmitoyl-ACP (C16:0), which is generally the end product from which other types of fatty acids are made. The enzyme β-ketoacyl-ACP synthase II catalyzes the final elongation of palmitoyl-ACP to stearoyl-ACP (C18:0).

Common plant unsaturated fatty acids, such as oleic, linoleic, and α-linolenic acids, originate from the desaturation of stearoyl-ACP to form oleoyl-ACP (C18:1) in a reaction catalyzed by a soluble plastid enzyme, Δ-9 desaturase (also often referred to as "stearoyl-ACP desaturase"). Molecular oxygen is required for desaturation and reduced ferredoxin serves as an electron co-donor.

Hence, the present invention contemplates polypeptides encoding several functions, for example, those relating to acyl carrier protein, malonyl CoA-ACP acyltransferase, β-ketoayl-ACP synthase III, β-ketoayl-ACP reductase, β-hydroxyacyl-ACP dehydratase, enoyl-ACP reductase, β-ketoacyl-ACP synthase I, β-ketoacyl-ACP synthase II, and Δ-9 desaturase.

In one embodiment, the present invention provides an isolated mfFAS polypeptide from a species of the group consisting of *Brevibacterium ammoniagenes, Schizosaccharomyces pombe, Saccharomyces cerevesiae, Candida albicans, Mycobacterium tuberculosis, Caenorhabditis elegans, Rattus norvegicus, Gallus gallus, Lipomyces starkeyi, Rhodosporidium toruloides*, and *Mycobacterium bovis*. Preferably, the mfFAS polypeptide is isolated from *Brevibacterium ammoniagenes, Schizosaccharomyces pombe, Saccharomyces cerevesiae, Candida albicans*; more preferably, the mfFAS polypeptides is isolated from *Brevibacterium ammoniagenes*. Such mfFAS polypeptides include one of the group consisting of SEQ ID NOS: 2, 15, 17, 18, 19, 20, 22, 23, 24, 25, 27, 29, and 31. Preferably, the mfFAS polypeptide used in the context of the present invention is one of the group consisting of SEQ ID NOS: 2, 15, 17, 18, 19, 20, and 22; more preferably, the mfFAS is SEQ ID NO: 2. Any of the aforementioned mfFAS polypeptides function to increase the fatty acid synthase activity of plant tissues. Additionally, any of the aforementioned mfFAS polypeptides function to increase oil levels in the tissues of plants, wherein the plant is not *Brassica*, and additionally not soybean when the mfFAS polypeptide is isolated from *Brevibacterium ammoniagenes.* mfFAS Nucleic Acids: The present invention provides nucleic acids that encode multifunctional fatty acid synthases, which are used in the context of the present invention for increasing the fatty acid synthase activity of plant tissues. Such nucleic acids can encode a type I multifunctional fatty acid synthase that has been isolated from an organism. Preferred organisms from which nucleic acids encoding mfFAS can be isolated include, without limitation: bacteria, preferably *Brevibacteria* and *Bacilli*; fungae, preferably *Saccharomycetes, Schizosaccharomycetes, Lipomyces starkeyi, Rhodosporidium toruloides*, or *Candidae*; mycobacteria; nematodes, preferably *Caenorhabdites*; and mammals, preferably rat or chicken. Alternatively, the nucleic acids can encode a multifunctional fatty acid synthase that has been recombinantly generated to contain a fusion of two or more regions that encode monofunctional enzymatic domains that facilitate two or more of the steps required to make a fatty acid.

Additionally, the present invention provides nucleic acids that encode multifunctional fatty acid synthases, which are used in the context of the present invention for increasing the oil content of a plant, provided that the plant is not *Brassica*. Such nucleic acids can encode a type I multifunctional fatty acid synthase that has been isolated from an organism. Preferred organisms from which nucleic acids encoding mfFAS can be isolated include, without limitation: fungae, preferably *Saccharomycetes, Schizosaccharomycetes, Lipomyces starkeyi, Rhodosporidium toruloides*, or *Candidae*; mycobacteria; nematodes, preferably *Caenorhabdites*; mammals, preferably rat or chicken; and bacteria, preferably *Bacilli*, and preferably *Brevibacteria*, provided that the plant is not soybean. Alternatively, the nucleic acids can encode a multifunctional fatty acid synthase that has been recombinantly generated to contain a fusion of two or more regions that encode monofunctional enzymatic domains that facilitate two or more of the steps required to make a fatty acid.

In one embodiment, the present invention provides an isolated nucleic acid that encodes a protein having mfFAS activity, which nucleic acid is selected from the group consisting of SEQ ID NOS: 1, 16, 21, 26, 28, and 30, and complements thereof, and nucleic acids having at least about 70% sequence identity thereof. Preferred nucleic acid is SEQ ID NO: 1, 16, 21, 26, 28, or 30; more preferred is SEQ ID NO: 1. The percent sequence identity of included nucleic acids in the group is preferably at least about 75%, more preferably at least about 80%, yet more preferably at least about 85%, and yet more preferably at least about 90%; even more preferably at least about 95%; and most preferably at least about 98%. The nucleic acids of the present invention can be isolated from any species that has a multifunctional fatty acid synthase, including without limitation *Brevibacterium ammoniagenes* (source of SEQ ID NO: 1), *Schizosaccharomyces pombe* (source of SEQ ID NO: 16), *Saccharomyces cerevesiae* (source of SEQ ID NO: 19), *Candida albicans* (source of SEQ ID NO: 21), *Mycobacterium tuberculosis* (source of SEQ ID NO: 23), *Mycobacterium leprae* (source of SEQ ID NO: 24), *Mycobacterium bovis* (source of SEQ ID NO: 30), *Caenorhabditis elegans* (source of SEQ ID NO: 25), rat (source of SEQ ID NO: 26), and chicken (source of SEQ ID NO: 28). In a preferred embodiment, the present invention provides a nucleic acid that encodes mfFAS from *Brevibacterium ammoniagenes, Schizosaccharomyces pombe, Saccharomyces cerevesiae*, or *Candida albicans*; more preferably, the mfFAS polypeptides are isolated from *Brevibacterium ammoniagenes.*

In yet another embodiment, the present invention provides a nucleic acid that encodes a multifunctional fatty acid synthase having an amino acid sequence comprising a protein selected from the group consisting of SEQ ID NOS: 2, 15, 17, 18, 19, 20, 22, 23, 24, 25, 27, 29, and 31. Preferably, the protein is SEQ ID NO: 2. The present invention also provides the set of nucleic acids that includes those nucleic acids that are at least about 80% identical to those that encode SEQ ID NOS: 2, 15, 17, 18, 19, 20, 22, 23, 24, 25, 27, 29, or 31; more preferably, the set of nucleic acids are at least about 85% identical to one or more of the nucleic acids that encode one or more of the identified SEQ ID NOS; yet more preferably, at least about 90% identical; even more preferably, at least about 95% identical; and most preferably, at least about 98% identical.

The present invention also provides vectors containing such multifunctional fatty acid synthase nucleic acids. As set forth in further detail hereinbelow, preferred nucleic acids include appropriate regulatory elements operably linked thereto that facilitate efficient expression of the inventive nucleic acids in a host, including without limitation bacterial, fungal, or plant hosts. Vectors useful in the context of the present invention can include such regulatory elements.

In a preferred embodiment of the present invention, the nucleic acid molecules of the present invention encode enzymes that are allelic to those defined. As used herein, a mutant enzyme is any enzyme that contains an amino acid that is different from the amino acid in the same position of an enzyme of the same type.

The nucleic acids and vectors described herein need not have the exact nucleic acid sequences described herein. Instead, the sequences of these nucleic acids and vectors can vary, so long as the nucleic acid either performs the function for which it is intended or has some other utility, for example, as a nucleic acid probe for complementary nucleic acids. For example, some sequence variability in any part of a multifunctional fatty acid synthase nucleic acid is permitted so long as the mutant or variant polypeptide or polypeptides retains at least about 10% of the fatty acid synthase activity observed under similar conditions for an analogous wild type fatty acid synthase enzyme (FasA), more preferably, the polypeptide(s) retain at least about 25% of the FasA activity; more preferably at least about 50% of the FasA activity; even more preferably, at least about 75% of the FasA activity; and yet more preferably, at least about 90% of the FasA activity. Most preferably, the aforementioned sequence variability results in increased FasA activity. In a preferred embodiment, the comparison of enzymatic activity is with the wild type *Brevibacterium ammoniagenes* fatty acid synthase (SEQ ID NO: 2).

Fragment and variant nucleic acids, for example, of SEQ ID NO: 1, are also encompassed by the present invention. Nucleic acid "fragments" encompassed by the present invention are of three general types. First, fragment nucleic acids that are not full length but do perform their intended function (fatty acid synthesis) are encompassed within the present invention. Second, fragments of nucleic acids identified herein that are useful as hybridization probes, but generally are not functional for fatty acid synthesis, are also included in the present invention. And, third, fragments of nucleic acids identified herein can be used in suppression technologies known in the art, such as, for example, antisense technology or RNA inhibition (RNAi), which provides for reducing carbon flow in a plant into oil, making more carbon available for protein or starch accumulation, for example. Thus, fragments of a nucleotide sequence, such as SEQ ID NO: 1, 16, 21, 26, 28, or 30, without limitation, may range from at least about 15 nucleotides, at least about 17 nucleotides, at least about 18 nucleotides, at least about 20 nucleotides, at least about 50 nucleotides, at least about 100 nucleotides or more. In general, a fragment nucleic acid of the present invention can have any upper size limit so long as it is related in sequence to the nucleic acids of the present invention but does not include the full length.

In another embodiment, the present invention provides DNA molecules comprising a sequence encoding a consensus amino acid sequence, and complements thereof. In another aspect, the present invention provides DNA molecules comprising a sequence encoding a polypeptide comprising a conserved fragment of an amino acid consensus sequence. The present invention includes the use of consensus sequence and fragments thereof in transgenic plants, other organisms, and for other uses including those described below.

As used herein, "variants" have substantially similar or substantially homologous sequences when compared to reference or wild type sequence. For nucleotide sequences that encode proteins, "variants" also include those sequences that, because of the degeneracy of the genetic code, encode the identical amino acid sequence of the reference protein. Variant nucleic acids also include those that encode polypeptides that do not have amino acid sequences identical to that of the proteins identified herein, but which encode an active protein with conservative changes in the amino acid sequence.

As is known by one of skill in the art, the genetic code is "degenerate," meaning that several trinucleotide codons can encode the same amino acid. This degeneracy is apparent from Table 1.

TABLE 1

| 1st Position | 2nd Position | | | | 3rd Position |
|---|---|---|---|---|---|
| | T | C | A | G | |
| T | TTT = Phe | TCT = Ser | TAT = Tyr | TGT = Cys | T |
| T | TTC = Phe | TCC = Ser | TAC = Tyr | TGC = Cys | C |
| T | TTA = Leu | TCA = Ser | TAA = Stop | TGA = Stop | A |
| T | TTG = Leu | TCG = Ser | TAG = Stop | TGG = Trp | G |
| C | CTT = Leu | CCT = Pro | CAT = His | CGT = Arg | T |
| C | CTC = Leu | CCC = Pro | CAC = His | CGC = Arg | C |
| C | CTA = Leu | CCA = Pro | CAA = Gln | CGA = Arg | A |
| C | CTG = Leu | CCG = Pro | CAG = Gln | CGG = Arg | G |
| A | ATT = Ile | ACT = Thr | AAT = Asn | AGT = Ser | T |
| A | ATC = Ile | ACC = Thr | AAC = Asn | AGC = Ser | C |
| A | ATA = Ile | ACA = Thr | AAA = Lys | AGA = Arg | A |
| A | ATG = Met | ACG = Thr | AAG = Lys | AGG = Arg | G |
| G | GTT = Val | GCT = Ala | GAT = Asp | GGT = Gly | T |
| G | GTC = Val | GCC = Ala | GAC = Asp | GGC = Gly | C |
| G | GTA = Val | GCA = Ala | GAA = Gln | GGA = Gly | A |
| G | GTG = Val | GCG = Ala | GAG = Gln | GGG = Gly | G |

Hence, many changes in the nucleotide sequence of the variant may be silent and may not alter the amino acid sequence encoded by the nucleic acid. Where nucleic acid sequence alterations are silent, a variant nucleic acid will encode a polypeptide with the same amino acid sequence as the reference nucleic acid. Therefore, a particular nucleic acid of the present invention also encompasses variants with degenerate codon substitutions, and complementary sequences thereof, as well as the sequence explicitly specified by a SEQ ID NO as set forth herein. Specifically, degenerate codon substitutions may be achieved by generating sequences in which the reference codon is replaced by any of the codons for the amino acid specified by the reference codon. In general, the third position of one or more selected codons can be substituted with mixed-base and/or deoxyinosine residues as disclosed by Batzer et al., *Nucleic Acid Res.*, 19:5081 (1991) and/or Ohtsuka et al., *J. Biol. Chem.*, 260:2605 (1985); Rossolini et al., *Mol. Cell. Probes*, 8:91 (1994).

A host cell often displays a preferred pattern of codon usage. Structural nucleic acid sequences are preferably constructed to utilize the codon usage pattern of the particular host cell. This generally enhances the expression of the structural nucleic acid sequence in a transformed host cell. Any disclosed nucleic acid or amino acid sequence may be modified to reflect the preferred codon usage of a host cell or organism in which they are contained. Modification of a structural nucleic acid sequence for optimal codon usage in plants is described in U.S. Pat. No. 5,689,052, which is incorporated herein by reference. In a preferred embodiment, the present invention includes nucleic acids that encode mfFAS and that are codon-optimized in a plant, more preferable for maize, or soybean.

However, the present invention is not limited to silent changes in the present nucleotide sequences but also includes variant nucleic acid sequences that conservatively alter the amino acid sequence of a polypeptide of the present invention. Because it is the interactive capacity and nature of a protein that defines that protein's biological functional activity, certain amino acid sequence substitutions can be made in a protein sequence and, of course, its underlying DNA coding sequence and, nevertheless, a protein with like properties can still be obtained. It is thus contemplated by the inventors that various changes may be made in the peptide sequences of the proteins or fragments of the present invention, or corresponding DNA sequences that encode the peptides, without appreciable loss of their biological utility or activity. According to the present invention, then, variant and reference nucleic acids of the present invention may differ in the encoded amino acid sequence by one or more substitutions, additions, insertions, deletions, fusions, and truncations, which may be present in any combination, so long as an active mfFAS protein is encoded by the variant nucleic acid. Such variant nucleic acid will not encode exactly the same amino acid sequence as the reference nucleic acid, but have conservative sequence changes. It is known that codons capable of coding for such conservative amino acid substitutions are known in the art.

Another approach to identifying conservative amino acid substitutions require analysis of the hydropathic index of amino acids may be considered. The importance of the hydropathic amino acid index in conferring interactive biological function on a protein is generally understood in the art (Kyte and Doolittle, *J. Mol. Biol.*, 157:105-132, 1982). It is accepted that the relative hydropathic character of the amino acid contributes to the secondary structure of the resultant polypeptide, which in turn defines the interaction of the protein with other molecules, for example, enzymes, substrates, receptors, DNA, antibodies, antigens, and the like.

Each amino acid has been assigned a hydropathic index on the basis of its hydrophobicity and charge characteristics (Kyte and Doolittle, *J. Mol. Biol.*, 157:105-132, 1982); these are isoleucine (+4.5), valine (+4.2), leucine (+3.8), phenylalanine (+2.8), cysteine/cystine (+2.5), methionine (+1.9), alanine (+1.8), glycine (−0.4), threonine (−0.7), serine (−0.8), tryptophan (−0.9), tyrosine (−1.3), proline (−1.6), histidine (−3.2), glutamate (−3.5), glutamine (−3.5), aspartate (−3.5), asparagine (−3.5), lysine (−3.9), and arginine (−4.5).

In making such changes, the substitution of amino acids whose hydropathic indices are within ±2 is preferred, those that are within ±1 are particularly preferred, and those within ±0.5 are even more particularly preferred.

It is also understood in the art that the substitution of like amino acids can be made effectively on the basis of hydrophilicity. U.S. Pat. No. 4,554,101, states that the greatest local average hydrophilicity of a protein, as governed by the hydrophilicity of its adjacent amino acids, correlates with a biological property of the protein.

As detailed in U.S. Pat. No. 4,554,101, the following hydrophilicity values have been assigned to amino acid residues: arginine (+3.0), lysine (+3.0), aspartate (+3.0±1), glutamate (+3.0±1), serine (+0.3), asparagine (+0.2), glutamine (+0.2), glycine (0), threonine (−0.4proline (−0.5±1), alanine (−0.5), histidine (−0.5), cysteine (−1.0), methionine (−1.3), valine (−1.5), leucine (−1.8), isoleucine (−1.8), tyrosine (−2.3), phenylalanine (−2.5), and tryptophan (−3.4).

In making such changes, the substitution of amino acids whose hydrophilicity values are within ±2 is preferred, those that are within ±1 are particularly preferred, and those within ±0.5 are even more particularly preferred.

Variant nucleic acids with silent and conservative changes can be defined and characterized by the degree of homology to the reference nucleic acid. Preferred variant nucleic acids are "substantially homologous" to the reference nucleic acids of the present invention. As recognized by one of skill in the art, such substantially similar nucleic acids can hybridize under stringent conditions with the reference nucleic acids identified by SEQ ID NO herein. These types of substantially homologous nucleic acids are encompassed by this present invention.

Generally, nucleic acid derivatives and variants of the present invention will have at least about 90%, at least about 91%, at least about 92%, at least about 93%, or at least about 94% sequence identity to the reference nucleotide sequence defined herein. Preferably, nucleic acids of the present invention will have at least about 95%, at least about 96%, at least about 97%, or at least about 98% sequence identity to the reference nucleotide sequence defined herein.

Variant nucleic acids can be detected and isolated by standard hybridization procedures. Hybridization to detect or isolate such sequences is generally carried out under "moderately stringent" and preferably under "stringent" conditions. Moderately stringent hybridization conditions and associated moderately stringent and stringent hybridization wash conditions used in the context of nucleic acid hybridization experiments, such as Southern and Northern hybridization, are sequence dependent, and are different under different environmental parameters. Longer sequences hybridize specifically at higher temperatures. An extensive guide to the hybridization of nucleic acids is found in Tijssen, Laboratory Techniques in Biochemistry and Molecular Biology-Hybridization with Nucleic Acid Probes, page 1, Chapter 2 "Overview of principles of hybridization and the strategy of nucleic acid probe assays" Elsevier, NY (1993). See also, J. Sambrook et al., Molecular Cloning: A Laboratory Manual, Cold Spring Harbor Press, NY, pp 9.31-9.58 (1989); J. Sambrook et al., Molecular Cloning: A Laboratory Manual, Cold Spring Harbor Press, NY (3rd ed. 2001).

The present invention also provides methods for detection and isolation of derivative or variant nucleic acids encoding the proteins provided herein. The methods involve hybridizing at least a portion of a nucleic acid comprising any part of SEQ ID NO: 1, 16, 21, 26, 28, or 30, with respect to FAS-related sequences; and any part of SEQ ID NO: 3, 32, 34, 36, 38, 40, or 42, with respect to phosphopantetheine: protein transferase to a sample nucleic acid, thereby forming a hybridization complex; and detecting the hybridization complex. The presence of the complex correlates with the presence of a derivative or variant nucleic acid that can be further characterized by nucleic acid sequencing, expression of RNA and/or protein and testing to determine whether the derivative or variant retains activity. In general, the portion of a nucleic acid comprising any part of the aforementioned DNAs identified by SEQ ID NO used for hybridization is preferably at least about 15 nucleotides, and hybridization is under hybridization conditions that are sufficiently stringent to permit detection and isolation of substantially homologous nucleic acids; preferably, the hybridization conditions are "moderately stringent"; more preferably the hybridization conditions are "stringent", as defined herein and in the context of conventional molecular biological techniques well known in the art.

Generally, highly stringent hybridization and wash conditions are selected to be about 5° C. lower than the thermal melting point ($T_m$) for the specific double-stranded sequence at a defined ionic strength and pH. For example, under "highly stringent conditions" or "highly stringent hybridization conditions" a nucleic acid will hybridize to its complement to a detectably greater degree than to other sequences (e.g., at least 2-fold over background). By controlling the stringency of the hybridization and/or the washing conditions, nucleic acids having 100% complementary can be identified and isolated.

Alternatively, stringency conditions can be adjusted to allow some mismatching in sequences so that lower degrees of similarity are detected (heterologous probing) using, for example, moderately stringent conditions. Appropriate stringency conditions that promote DNA hybridization under moderately stringent conditions are, for example, about 2× sodium chloride/sodium citrate (SSC) at about 65° C., followed by a wash of 2×SSC at 20-25° C., are known to those skilled in the art and can be found in *Current Protocols in Molecular Biology*, John Wiley & Sons, NY, 6.3.1-6.3.6 (1989). Both temperature and salt may be varied, or either the temperature or the salt concentration may be held constant while the other variable is changed.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides), and at least about 60° C. for long probes (e.g., greater than 50 nucleotides). Stringent conditions may also be achieved with the addition of destabilizing agents such as formamide, in which case hybridization temperatures can be decreased. Dextran sulfate and/or Denhardt's solution (50× Denhardt's is 5% Ficoll, 5% polyvinylpyrrolidone, 5% BSA) can also be included in the hybridization reactions.

Exemplary low stringency conditions include hybridization with a buffer solution of 30 to 50% formamide, 5×SSC (20×SSC is 3M NaCl, 0.3 M trisodium citrate), 50 mM sodium phosphate, pH7, 5mM EDTA, 0.1% SDS (sodium dodecyl sulfate), 5× Denhardt's with 100 μg/ml denatured salmon sperm DNA at 37° C., and a wash in 1× to 5×SSC (20×SSC=3.0 M NaCl and 0.3 M trisodium citrate), 0.1% SDS at 37° C. Exemplary moderate stringency conditions include hybridization in 40 to 50% formamide, 5×SSC 50 mM sodium phosphate, pH 7, 5 mM EDTA, 0.1% SDS, 5× Denhardt's with 100 μg/ml denatured salmon sperm DNA at 42° C., and a wash in 0.1× to 2×SSC, 0.1% SDS at 42 to 55°

C. Exemplary high stringency conditions include hybridization in 50% formamide, 5×SSC, 50 mM sodium phosphate, pH 7.0, 5 mM EDTA, 0.1% SDS, 5× Denhardt's with 100 μg/ml denatured salmon sperm DNA at 42° C., and a wash in 0.1×SSC, 0.1% SDS at 60 to 65° C.

The degree of complementarity or homology of hybrids obtained during hybridization is typically a function of post-hybridization washes, the critical factors being the ionic strength and temperature of the final wash solution. The type and length of hybridizing nucleic acids also affects whether hybridization will occur and whether any hybrids formed will be stable under a given set of hybridization and wash conditions. For DNA-DNA hybrids, the $T_m$ can be approximated from the equation of Meinkoth and Wahl, *Anal. Biochem.*, 138:267-284 (1984);

$$T_m=81.5° \text{ C.}+16.6(\log M)+0.41(\%GC)-0.61(\% \text{ form})-500/L$$

where M is the molarity of monovalent cations, % GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. Very stringent conditions are selected for hybridization to derivative and variant nucleic acids having a $T_m$ equal to the exact complement of a particular probe, less stringent conditions are selected for hybridization to derivative and variant nucleic acids having a $T_m$ less than the exact complement of the probe.

In general, $T_m$ is reduced by about 1° C. for each 1% of mismatching. Thus, $T_m$, hybridization, and/or wash conditions can be adjusted to hybridize to sequences of the desired sequence identity. For example, if sequences with greater than about 90% identity are sought, the $T_m$ can be decreased by about 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at about 1, about 2, about 3, or about 4° C. lower than the thermal melting point ($T_m$); moderately stringent conditions can utilize a hybridization and/or wash at about 6, about 7, about 8, about 9, or about 10° C. lower than the thermal melting point ($T_m$); low stringency conditions can utilize a hybridization and/or wash at about 11, about 12, about 13, about 14, about 15, or about 20° C. lower than the thermal melting point ($T_m$).

If the desired degree of mismatching results in a $T_m$ of less than 45° C. (aqueous solution) or 32° C. (formamide solution), it is preferred to increase the SSC concentration so that a higher temperature can be used. An extensive guide to the hybridization of nucleic acids is found in Tijssen (1993) Laboratory Techniques in Biochemistry and Molecular Biology-Hybridization with Nucleic Acid Probes, Part 1, Chapter 2 (Elsevier, NY); Ausubel et al., eds. (1995) Current Protocols in Molecular Biology, Chapter 2 (Greene Publishing and Wiley-Interscience, NY). See, Sambrook et al., (1989) Molecular Cloning: A Laboratory Manual (2d ed., Cold Spring Harbor Laboratory Press, Plainview, N.Y.). Using these references and the teachings herein on the relationship between $T_m$, mismatch, and hybridization and wash conditions, those of ordinary skill can generate variants of the present nucleic acids.

In another preferred embodiment of the present invention, the inventive nucleic acids are defined by the percent identity relationship between particular nucleic acids and other members of the class using analytic protocols well known in the art. Such analytic protocols include, but are not limited to: CLUSTAL in the PC/Gene program (available from Intelligenetics, Mountain View, Calif. or in the Omiga program version 2.0 Accelrys Inc., San Diego, Calif.); the ALIGN program (Version 2.0) and GAP, BESTFIT, BLAST, FASTA, and TFASTA in the Wisconsin Genetics Software Package, Version 8 (available from Genetics Computer Group (GCG), 575 Science Drive, Madison, Wis.). Alignments using these programs can be performed using the default parameters. The CLUSTAL program is well described by Higgins et al., *Gene,* 73:237-244 (1988); Higgins et al., *CABIOS,* 5:151-153 (1989); Corpet et al., *Nucleic Acids Res.,* 16:10881-10890 (1988); Huang et al., *CABIOS,* 8:155-165 (1992); and Pearson et al., *Meth. Mol. Biol.,* 24:307-331 (1994). The ALIGN program is based on the algorithm of Meyers and Miller, *Computer Applic. Biol. Sci.,* 4:11-17 (1988). The BLAST programs of Altschul et al., *J. Mol. Biol.,* 215:403 (1990), are based on the algorithm of Karlin and Altschul, *Proc. Natl. Acad. Sci.* (*U.S.A.*), 87:2264-2268 (1990). To obtain gapped alignments for comparison purposes, Gapped BLAST (in BLAST 2.0) can be utilized as described in Altschul et al., *Nucleic Acids Res.,* 25:3389 (1997). Alternatively, PSI-BLAST (in BLAST 2.0) can be used to perform an iterated search that detects distant relationships between molecules. See, Altschul et al., supra. When utilizing BLAST, Gapped BLAST, PSI-BLAST, the default parameters of the respective programs (e.g., BLASTN for nucleotide sequences, BLASTX for proteins) can be used. The BLASTN program (for nucleotide sequences) uses as defaults a word length (W) of 11, an expectation (E) of 10, a cutoff of 100, M=5, N=−4, and a comparison of both strands. For amino acid sequences, the BLASTP program uses as defaults a word length (W) of 3, an expectation (E) of 10, and the BLOSUM62 scoring matrix (see Henikoff & Henikoff, *Proc. Natl. Acad. Sci.* (*U.S.A.*), 89:10915, 1989). (See, http://www.ncbi.n1m.nih.gov.) Alignment may also be performed manually by inspection.

For purposes of the present invention, comparison of nucleotide sequences for determination of percent sequence identity to the nucleic acid sequences disclosed herein is preferably made using the BLASTN program (version 1.4.7 or later) with its default parameters or any equivalent program. By "equivalent program" is intended any sequence comparison program that, for any two sequences in question, generates an alignment having identical nucleotide or amino acid residue matches and an identical percent sequence identity when compared to the corresponding alignment generated by the preferred program.

Isolation of Nucleic Acids Encoding Multifunctional Fatty Acid Synthases: Nucleic acids encoding a multifunctional fatty acid synthase can be identified and isolated by standard methods, as described by Sambrook et al., *Molecular Cloning: A Laboratory Manual*, Cold Spring Harbor, N.Y. (1989). For example, a DNA sequence encoding a type I multifunctional fatty acid synthase can be identified by screening of a DNA or cDNA library generated from nucleic acid derived from a particular cell type, cell line, primary cells, or tissue. Examples of libraries useful for identifying and isolating a multifunctional fatty acid synthase include libraries made from the genomic DNA or cDNA of any organism encoding a type I fatty acid synthase, preferably a bacteria or non-plant eukaryote.

Screening for DNA fragments that encode a multifunctional fatty acid synthase can be accomplished by screening colonies or plaques from a genomic or cDNA library for hybridization to a probe of an available multifunctional fatty acid synthase from other organisms or by screening colonies or plaques from a cDNA expression library for binding to antibodies that specifically recognize a multifunctional fatty acid synthase. DNA fragments that hybridize to multifunctional fatty acid synthase probes from other organisms and/or colonies or plaques carrying DNA fragments that are immunoreactive with antibodies to multifunctional fatty acid synthase can be subcloned into a vector and sequenced and/or used as probes to identify other cDNA or genomic sequences encoding all or a portion of the desired multifunctional fatty acid synthase gene. Probes for isolation of multifunctional fatty acid synthase genes can also include DNA fragments of type II fatty acid synthase genes or antibodies to the type II proteins, as noted herein above.

A cDNA library can be prepared, for example, by random oligo priming or oligo dT priming. Plaques containing DNA fragments can be screened with probes or antibodies specific for multifunctional fatty acid synthase. DNA fragments encoding a portion of a multifunctional fatty acid synthase gene can be subcloned and sequenced and used as probes to identify a genomic multifunctional fatty acid synthase gene. DNA fragments encoding a portion of a multifunctional fatty acid synthase can be verified by determining sequence homology with other known multifunctional fatty acid synthase genes or by hybridization to multifunctional fatty acid synthase-specific messenger RNA. Once cDNA fragments encoding portions of the 5', middle and 3' ends of a multifunctional fatty acid synthase are obtained, they can be used as probes to identify and clone a complete genomic copy of the multifunctional fatty acid synthase gene from a genomic library.

Portions of the genomic copy or copies of a multifunctional fatty acid synthase gene can be sequenced and the 5' end of the gene identified by standard methods, including either DNA sequence homology to other multifunctional fatty acid synthase genes or by RNAase protection analysis, as described by Sambrook et al., *Molecular Cloning: A Laboratory Manual*, Cold Spring Harbor Press, Cold Spring Harbor, N.Y. (1989). The 3' and 5' ends of the target gene can also be located by computer searches of genomic sequence databases using known fatty acid synthase coding regions. Once portions of the 5' end of the gene are identified, complete copies of the multifunctional fatty acid synthase gene can be obtained by standard methods, including cloning or polymerase chain reaction (PCR) synthesis using oligonucleotide primers complementary to the DNA sequence at the 5' end of the gene. The presence of an isolated full-length copy of the multifunctional fatty acid synthase gene can be verified by hybridization, partial sequence analysis, or by expression of the multifunctional fatty acid synthase enzyme.

Phosphopantetheine Protein Transferases: During the process of fatty acid synthesis, the growing acyl chain is preferably covalently linked by a thioester bond to the cysteamine thiol of a phosphopantetheinyl (P-Pan) moiety, which is preferably attached at the other end to a specific serine residue of acyl carrier protein (ACP), in the case of type II FAS systems, or the ACP-domain of a type I FAS. This P-Pan moiety acts as a "swinging arm," carrying the growing acyl chain between the active sites of the different enzymes or domains of the FAS complex. Accordingly, the transgenic mfFAS used in the context of the present invention is preferably phosphopantetheinylated, which phosphopantetheinylation is accomplished by a co-transformed gene that encodes a suitable phosphopantetheinyl transferase (PPTase) or by a host PPTase that has sufficient substrate range of activity for the purpose of modifying the transgenic mfFAS.

The enzymatic post-translational attachment of the P-Pan group to an ACP protein or domain is carried out by a PPTase. Any suitable PPTase can be used in the context of the present invention, the suitability of which is determined by the ability of the PPTase to phosphopantetheinylate a mfFAS used herein. For example, the *Brevibacterium ammoniagenes* FasA protein (SEQ ID NO: 2) can be suitably combined with the PPTase from the same species, which is identified herein as SEQ ID NO: 4. In another embodiment of the present invention, the gene encoding the mfFAS includes its own PPTase activity, such as the mfFAS derived from yeast (e.g., SEQ ID NOS: 15-19), and thus the transgenic mfFAS is suitably modified to be active upon expression in the host. Particularly preferred PPTases have broad specificity, such as, for example, those referred to as being of the sfp-type, as further discussed hereinbelow. More preferred, the mfFAS employed in the context of the present invention is pantethenylated by an enzyme having PPTase activity that is native to the host plant into which the mfFAS transgene has been inserted.

A PPTase from *Bacillus subtillis*, the sfp gene product, has a remarkably broad range of substrate specificity, being able to phosphopantetheinylate non-native substrates both in vitro (Lambalot et al., *Chem. Biol.,* 3:923-936, 1996) and in vivo (Mootz et al., *J. Biol. Chem.,* 276:37389-37298, 2001); see, SEQ ID NOS: 34 and 35 for the recital of the sequences of the sfp gene and its product, respectively. Mootz and co-workers have shown that the sfp gene product not only complements heterologous PPTases, such as *E. coli* ACPS, but it in vivo phosphopantetheinylates all the different acceptor domains in natural host cells (e.g., *Bacillus subtillis*) that include ACP and PCP (peptide carrier protein) of type I polyketide synthases (PKS) and non-ribosomal peptide synthetases (NRPS) involved in secondary metabolism as well as the type II ACP protein required for fatty acid synthesis (primary metabolism). Indeed, this broad range of specificity appears to be a general feature of many sfp-type PPTases. *Streptomyces verticullus* svp PPTase (see, SEQ ID NO: 38), another sfp-type enzyme, was also found to be able to phosphopantetheinylate a broad range of substrates, including type I and II ACP and PCP domains from various *Streptomyces* species (Sánchez et al., *Chem. Biol.,* 8:725-728, 2001). Other useful sfp-type PPTases include those found in *Brevibacillus brevis* (SEQ ID NO: 36), and *Escherichia coli* (SEQ ID NO: 37), which are listed here without any intention to limit the sfp-type PPTases that are usefully employed in the context of the present invention. The sfp gene, which is the gene that encodes the *Bacillus subtilis* PPTase, is a preferred embodiment.

In the case of the multifunctional FasA and FasB proteins from *Brevibacterium ammoniagenes*, Stuible and co-workers found that the *E. coli* ACPS was unable to phosphopantetheinylate these type I FAS proteins either in vivo when the genes were introduced into *E. coli*, or in vitro when mixed with the proteins. The *B. ammoniagenes* PPT1 protein was required to phosphopantetheinylate both of these type I FAS proteins (Stuible et al., *Eur. J. Biochem.,* 248:481-487, 1997).

A preferred embodiment of the present invention relates to the use of a mfFAS that can be phosphopantetheinylated by a PPTase that is innate to a plant of interest. An alternative preferred embodiment relates to the use of a PPTase specific for the introduced multifunctional FAS that is inserted in a plant, such as ppt1 in the case of the *B.*

*ammoniagenes* fasA and fasB genes, which specific PPTase could be co-expressed in order to engineer functional multifunctional FAS expression in plants. As a further embodiment of the present invention, a PPTase of broad specificity, such as a sfp-type PPTase, may be co-expressed with a type II FAS gene in order to engineer functional multifunctional FAS expression in plants.

Expression Vectors and Cassettes: The expression vectors and cassettes of the present invention include nucleic acids encoding multifunctional fatty acid synthases. When inclusion of an exogenous phosphopantetheine protein transferase enzyme (PPTase) is desired, such expression vectors and cassettes can also include a nucleic acid encoding a PPTase that can post-translationally activate the multifunctional fatty acid synthase polypeptide. Alternatively, a separate expression vector or cassette can encode a phosphopantetheine protein transferase enzyme. One such PPTase is encoded by the *B. ammoniagenes* ppt1 gene. Other sources of PPTase having broad spectrum activity include: *Bacillus subtilis, Brevibacillus brevis, Escherichia coli, Streptomyces verticullus*, and *Saccharomyces cerevisiae.*

A transgene comprising a multifunctional fatty acid synthase can be subcloned into an expression vector or cassette, and fatty acid synthase expression can be detected and/or quantified. This method of screening is useful to identify transgenes providing for an expression of a multifunctional fatty acid synthase, and expression of a multifunctional fatty acid synthase in a transformed plant cell.

Plasmid vectors that provide for easy selection, amplification, and transformation of the transgene in prokaryotic and eukaryotic cells include, for example, pUC-derived vectors, pSK-derived vectors, pGEM-derived vectors, pSP-derived vectors, pBS-derived vectors, pFastBac (Invitrogen) for baculovirus expression and pYES2 (Invitrogen) for yeast expression. Additional elements may be present in such vectors, including origins of replication to provide for autonomous replication of the vector, selectable marker genes, preferably encoding antibiotic or herbicide resistance, unique multiple cloning sites providing for multiple sites to insert DNA sequences or genes encoded in the transgene, and sequences that enhance transformation of prokaryotic and eukaryotic cells. One vector that is useful for expression in both plant and prokaryotic cells is the binary Ti plasmid (as disclosed in Schilperoot et al., U.S. Pat. No. 4,940,838), as exemplified by vector pGA582. This binary Ti plasmid vector has been previously characterized by An, *Methods in Enzymology,* 153:292 (1987). This binary Ti vector can be replicated in prokaryotic bacteria, such as *E. coli* and *Agrobacterium*. The *Agrobacterium* plasmid vectors can also be used to transfer the transgene to plant cells. The binary Ti vectors preferably include the nopaline T DNA right and left borders to provide for efficient plant cell transformation, a selectable marker gene, unique multiple cloning sites in the T border regions, the colE1 replication of origin and a wide host range replicon. The binary Ti vectors carrying a transgene of the present invention can be used to transform both prokaryotic and eukaryotic cells, but is preferably used to transform plant cells. See, for example, Glassman et al., U.S. Pat. No. 5,258,300.

In general, the expression vectors and cassettes of the present invention contain at least a promoter capable of expressing RNA in a plant cell and a terminator, in addition to a nucleic acid encoding a multifunctional fatty acid synthase. Other elements may also be present in the expression cassettes of the present invention. For example, expression cassettes can also contain enhancers, introns, untranslated leader sequences, cloning sites, matrix attachment regions for silencing the effects of chromosomal control elements, and other elements known to one of skill in the art.

Nucleic acids encoding fatty acid synthases are operably linked to regulatory elements, such as a promoter, termination signals, and the like. Operably linking a nucleic acid under the regulatory control of a promoter or a regulatory element means positioning the nucleic acid such that the expression of the nucleic acid is controlled by these sequences. In general, promoters are found positioned 5' (upstream) to the nucleic acid that they control. Thus, in the construction of heterologous promoter/nucleic acid combinations, the promoter is preferably positioned upstream to the nucleic acid and at a distance from the transcription start site of the nucleic acid that the distance between the promoter and the transcription start site approximates the distance observed in the natural setting. As is known in the art, some variation in this distance can be tolerated without loss of promoter function. Similarly, the preferred positioning of a regulatory element with respect to a heterologous nucleic acid placed under its control is the natural position of the regulatory element relative to the structural gene it naturally regulates. Again, as is known in the art, some variation in this distance can be accommodated.

Expression cassettes have promoters that can regulate gene expression. Promoter regions are typically found in the flanking DNA sequence upstream from coding regions in both prokaryotic and eukaryotic cells. A promoter sequence provides for regulation of transcription of the downstream gene sequence and typically includes from about 50 to about 2,000 nucleotide base pairs. Promoter sequences also contain regulatory sequences, such as enhancer sequences that can influence the level of gene expression. Some isolated promoter sequences can provide for gene expression of heterologous genes, that is, a gene different from the native or homologous gene. Promoter sequences are also known to be strong, or weak, or inducible. A strong promoter provides for a high level of gene expression, whereas a weak promoter provides for a very low level of gene expression. An inducible promoter is a promoter that provides for turning on and off of gene expression in response to an exogenously added agent or to an environmental or developmental stimulus. Promoters can also provide for tissue specific or developmental regulation. An isolated promoter sequence that is a strong promoter for heterologous genes is advantageous because it provides for a sufficient level of gene expression to allow for easy detection and selection of transformed cells and provides for a high level of gene expression when desired. Transcription initiation regions that are preferentially expressed in seed tissue, and that are undetectable in other plant parts, are considered desirable for seed oil modifications in order to minimize any disruptive or adverse effects of the gene product.

Promoters of the present invention will generally include, but are not limited to, promoters that function in bacteria, bacteriophage, plastids, or plant cells. Useful promoters include the globulin promoter (see, for example, Belanger and Kriz, *Genet.,* 129:863-872, 1991), gamma zein Z27 promoter (see, for example, U.S. Ser. No. 08/763,705; also Lopes et al., *Mol Gen Genet.,* 247:603-613, 1995), L3 oleosin promoter (U.S. Pat. No. 6,433,252), USP promoter and 7Sα promoter (U.S. Ser. No. 10/235,618), 7Sα' promoter (see, for example, Beachy et al., *EMBO J.,* 4:3047, 1985; Schuler et al., *Nucleic Acid Res.,* 10(24):8225-8244, 1982), CaMV 35S promoter (Odell et al., *Nature,* 313:810, 1985), the CaMV 19S (Lawton et al., *Plant Mol. Biol.,* 9:31F, 1987), nos (Ebert et al., *Proc. Natl. Acad. Sci. (U.S.A.*), 84:5745, 1987), Adh (Walker et al., *Proc. Natl.*

*Acad. Sci.* (*U.S.A.*), 84:6624, 1987), sucrose synthase (Yang et al., *Proc. Natl. Acad. Sci.* (*U.S.A.*), 87:4144, 1990), tubulin, actin (Wang et al., *Mol. Cell. Biol.,* 12:3399, 1992), cab (Sullivan et al., *Mol. Gen. Genet.,* 215:431, 1989), PEPCase promoter (Hudspeth et al., *Plant Mol. Biol.,* 12:579, 1989), or those associated with the R gene complex (Chandler et al., *The Plant Cell,* 1, 1175, 1989). Other useful promoters include the Figwort Mosaic Virus (FMV) promoter (Richins et al., *Nucleic Acids Res.,* 20:8451, 1987), arcelin, tomato E8, patatin, ubiquitin, mannopine synthase (mas), soybean seed protein glycinin (Gly), soybean vegetative storage protein (vsp), bacteriophage SP6, T3, and T7 promoters.

Indeed, in a preferred embodiment, the promoter used is a seed-specific promoter. Examples of seed regulated genes and transcriptional regions are disclosed in U.S. Pat. Nos. 5,420,034; 5,608,152; and 5,530,194. Examples of such promoters include the 5' regulatory regions from such genes as napin (Kridl et al., *Seed Sci. Res.,* 1:209-219, 1991), phaseolin (Bustos et al., *Plant Cell,* 1(9):839-853, 1989), soybean trypsin inhibitor (Riggs et al., *Plant Cell,* 1(6):609-621, 1989), ACP (Baerson et al., *Plant Mol. Biol.,* 22(2): 255-267, 1993), stearoyl-ACP desaturase (Slocombe et al., *Plant Physiol.,* 104(4):167-176, 1994), soybean a' subunit of β-conglycinin (Chen et al., *Proc. Natl. Acad. Sci.,* 83:8560-8564, 1986), *Lesquerella* hydroxylase promoter (described in Broun et al., *Plant Journal,* 12(2):201-210, 1998; and in U.S. Pat. No. 5,965,793), delta 12 desaturase and oleosin (Hong et al., *Plant Mol. Biol.,* 34(3):549-555, 1997). Further examples include the promoter for β-conglycinin (Chen et al., *Dev. Genet.,* 10:112-122, 1989), the GL2 promoter (Szymanski et al., *Development,* 125:1161-1171, 1998), the tt2 promoter (Nesi et al., *The Plant Cell,* 13:2099-114, 2001), the LDOX promoter (Pelletier et al., *Plant Physiology,* 113:1437-1445, 1997), the CPC promoter (Wada et al., *Science,* 277:1113-1116, 1997).

Also included are the zeins, which are a group of storage proteins found in maize endosperm. Genomic clones for zein genes have been isolated (Pedersen et al., *Cell,* 29:1015-1026, 1982; Russell et al., *Transgenic Res.,* 6(2): 157-168, 1997) and the promoters from these clones, including the 15 kD, 16 kD, 19 kD, 22 kD, and 27 kD genes, can also be used. Other preferred promoters, known to function in maize, and in other plants, include the promoters for the following genes: waxy (granule bound starch synthase), Brittle and Shrunken 2 (ADP glucose pryophosphorylase), Shrunken 1 (sucrose synthase), branching enzymes I and II, starch synthases, debranching enzymes, oleosins, glutelins, sucrose synthases (Yang et al., *Proc. Natl. Acad. Sci.* (*U.S.A.*), 87:4144-4148, 1990), BetlI (basal endosperm transfer layer), and globulin1. Other promoters useful in the practice of the present invention that are known by one of skill in the art are also contemplated by the present invention.

Plastid promoters can also be used. Most plastid genes contain a promoter for the multi-subunit plastid-encoded RNA polymerase (PEP) as well as the single-subunit nuclear-encoded RNA polymerase. A consensus sequence for the nuclear-encoded polymerase (NEP) promoters and listing of specific promoter sequences for several native plastid genes can be found in Hajdukiewicz et al., *EMBO J.,* 16:4041-4048, 1997, which is hereby in its entirety incorporated by reference.

Examples of plastid promoters that can be used include the *Zea mays* plastid RRN (ZMRRN) promoter. The ZMRRN promoter can drive expression of a gene when the *Arabidopsis thaliana* plastid RNA polymerase is present. Similar promoters that can be used in the present invention are the Glycine max plastid RRN (SOYRRN) and the *Nicotiana tabacum* plastid RRN (NTRRN) promoters. All three promoters can be recognized by the *Arabidopsis* plastid RNA polymerase. The general features of RRN promoters are described by Hajdukiewicz et al., supra, and U.S. Pat. No. 6,218,145.

Moreover, transcription enhancers or duplications of enhancers can be used to increase expression from a particular promoter. Examples of such enhancers include, but are not limited to, elements from the CaMV 35S promoter and octopine synthase genes (Last et al., U.S. Pat. No. 5,290,924). As the DNA sequence between the transcription initiation site and the start of the coding sequence, i.e., the untranslated leader sequence, can influence gene expression, one may also wish to employ a particular leader sequence. Any leader sequence available to one of skill in the art may be employed. Preferred leader sequences direct optimum levels of expression of the attached gene, for example, by increasing or maintaining mRNA stability and/or by preventing inappropriate initiation of translation (Joshi, *Nucl. Acid Res.,* 15:6643, 1987). The choice of such sequences is at the discretion of those of skill in the art. Sequences that are derived from genes that are highly expressed in higher plants, and in soybean and corn in particular, are contemplated.

An inducible promoter can be turned on or off by an exogenously added agent so that expression of an operably linked nucleic acid is also turned on or off. For example, a bacterial promoter, such as the $P_{tac}$, promoter can be induced to varying levels of gene expression depending on the level of isothiopropylgalactoside added to the transformed bacterial cells. It may also be preferable to combine the nucleic acid encoding the polypeptide of interest with a promoter that provides tissue specific expression or developmentally regulated gene expression in plants.

Expression cassettes of the present invention will also include a sequence near the 3' end of the cassette that acts as a signal to terminate transcription from a heterologous nucleic acid and that directs polyadenylation of the resultant mRNA. Some 3' elements that can act as termination signals include those from the nopaline synthase gene of *Agrobacterium tumefaciens* (Bevan et al., *Nucl. Acid Res.,* 11:369, 1983), a napin 3' untranslated region (Kridl et al., *Seed Sci. Res.,* 1:209-219, 1991), a globulin 3' untranslated region (Belanger and Kriz, *Genetics,* 129:863-872, 1991), or one from a zein gene, such as Z27 (Lopes et al., *Mol. Gen. Genet.,* 247:603-613, 1995). Other 3' elements known by one of skill in the art also can be used in the vectors of the present invention.

Regulatory elements, such as Adh intron 1 (Callis et al., *Genes Develop.,* 1:1183, 1987), a rice actin intron (McElroy et al., *Mol. Gen. Genet.,* 231(1):150-160, 1991), sucrose synthase intron (Vasil et al., *Plant Physiol.,* 91:5175, 1989), the maize HSP70 intron (Rochester et al., *EMBO J.,* 5:451-458, 1986), or TMV omega element (Gallie et al., *The Plant Cell,* 1:301, 1989) may further be included where desired. These 3' nontranslated regulatory sequences can be obtained as described in An, *Methods in Enzymology,* 153:292, 1987, or are already present in plasmids available from commercial sources, such as Clontech, Palo Alto, Calif. The 3' nontranslated regulatory sequences can be operably linked to the 3' terminus of any heterologous nucleic acid to be expressed by the expression cassettes contained within the present vectors. Other such regulatory elements useful in the practice of the present invention are known by one of skill in the art and can also be placed in the vectors of the present invention.

The vectors of the present invention, as well as the coding regions claimed herein, can be optimized for expression in plants by having one or more codons replaced by other codons encoding the same amino acids so that the polypeptide is optimally translated by the translation machinery of the plant species in which the vector is used.

Selectable Markers: Selectable marker genes or reporter genes are also useful in the present invention. Such genes can impart a distinct phenotype to cells expressing the marker gene and thus allow such transformed cells to be distinguished from cells that do not have the marker. Selectable marker genes confer a trait that one can 'select' for by chemical means, i.e., through the use of a selective agent (e.g., a herbicide, antibiotic, or the like). Reporter genes, or screenable genes, confer a trait that one can identify through observation or testing, i.e., by 'screening' (e.g., the R-locus trait). Of course, many examples of suitable marker genes are known to the art and can be employed in the practice of the present invention.

Possible selectable markers for use in connection with the present invention include, but are not limited to, a neo gene (Potrykus et al., *Mol. Gen. Genet.,* 199:183, 1985) which codes for kanamycin resistance and can be selected for by applying kanamycin, a kanamycin analog such as geneticin (Sigma Chemical Company, St. Louis, Mo.), and the like; a bar gene that codes for bialaphos resistance; a gene that encodes an altered EPSP synthase protein (Hinchee et al., *Biotech.,* 6:915, 1988) thus conferring glyphosate resistance; a nitrilase gene, such as bxn from *Klebsiella ozaenae*, which confers resistance to bromoxynil (Stalker et al., *Science,* 242:419, 1988); a mutant acetolactate synthase gene (ALS) that confers resistance to imidazolinone, sulfonylurea or other ALS-inhibiting chemicals (EP 154 204A1, 1985); a methotrexate-resistant DHFR gene (Thillet et al., *J. Biol. Chem.,* 263:12500, 1988); a dalapon dehalogenase gene that confers resistance to the herbicide dalapon. Where a mutant EPSP synthase gene is employed, additional benefit may be realized through the incorporation of a suitable plastid transit peptide (CTP).

An illustrative embodiment of a selectable marker gene capable of being used in systems to select transformants is the genes that encode the enzyme phosphinothricin acetyltransferase, such as the bar gene from *Streptomyces hygroscopicus* or the pat gene from *Streptomyces viridochromogenes* (U.S. Pat. No. 5,550,318, which is incorporated by reference herein). The enzyme phosphinothricin acetyl transferase (PAT) inactivates the active ingredient in the herbicide bialaphos, phosphinothricin that inhibits glutamine synthetase (Murakami et al., *Mol. Gen. Genet.,* 205:42, 1986); Twell et al., *Plant Physiol.,* 91:1270, 1989) causing rapid accumulation of ammonia and cell death.

Screenable markers that may be employed include, but are not limited to, a β-glucuronidase or uidA gene (GUS), which encodes an enzyme for which various chromogenic substrates are known; an R-locus gene, which encodes a product that regulates the production of anthocyanin pigments (red color) in plant tissues (Dellaporta et al., in *Chromosome Structure and Function*, pp. 263-282, 1988); a β-lactamase gene (Sutcliffe, *Proc. Natl. Acad. Sci.* (*U.S.A.*), 75:3737, 1978), which encodes an enzyme for which various chromogenic substrates are known (e.g., PADAC, a chromogenic cephalosporin); a xylE gene (Zukowsky et al., *Proc. Natl. Acad. Sci.* (*U.S.A.*), 80:1101, 1983) that encodes a catechol dioxygenase that can convert chromogenic catechols; an α-amylase gene (Ikuta et al., *Biotech.,* 8:241, 1990); a tyrosinase gene (Katz et al., *J. Gen. Microbiol.,* 129:2703, 1983) that encodes an enzyme capable of oxidizing tyrosine to DOPA and dopaquinone, which in turn condenses to form the easily detectable compound melanin; a α-galactosidase gene, which encodes an enzyme for which there are chromogenic substrates; a luciferase (lux) gene (Ow et al., *Science,* 234:856, 1986), which allows for bioluminescence detection; or an aequorin gene (Prasher et al., *Biochem. Biophys. Res. Comm.,* 126:1259, 1985), which may be employed in calcium-sensitive bioluminescence detection, or a green fluorescent protein gene (Niedz et al., *Plant Cell Reports,* 14:403, 1995). The presence of the lux gene in transformed cells may be detected using, for example, X-ray film, scintillation counting, fluorescent spectrophotometry, low-light video cameras, photon-counting cameras, or multiwell luminometry. It is also envisioned that this system may be developed for populational screening for bioluminescence, such as on tissue culture plates, or even for whole plant screening.

Transit Peptides: Additionally, transgenes may be constructed and employed to provide targeting of the gene product to an intracellular compartment within plant cells or in directing a protein to the extracellular environment. This will generally be achieved by joining a DNA sequence encoding a transit or signal peptide sequence to the coding sequence of a particular gene. The resultant transit or signal peptide will transport the protein to a particular intracellular or extracellular destination, respectively, and may then be post-translationally removed. Transit or signal peptides act by facilitating the transport of proteins through intracellular membranes, e.g., vacuole, vesicle, plastid, and mitochondrial membranes, whereas signal peptides direct proteins through the extracellular membrane. By facilitating transport of the protein into compartments inside or outside the cell, these sequences may increase the accumulation of gene product.

An example of such a use concerns the direction of a fatty acid synthase to a particular organelle, such as to a plastid rather than to the cytoplasm. This is exemplified by the use of the *Arabidopsis* SSU1A transit peptide that confers plastid-specific targeting of proteins. Alternatively, the transgene can comprise a plastid transit peptide-encoding DNA sequence or a DNA sequence encoding the rbcS (RuBISCO) transit peptide operably linked between a promoter and the DNA sequence encoding a fatty acid synthase (for a review of plastid targeting peptides, see, Heijne et al., *Eur. J. Biochem.,* 180:535, 1989; Keegstra et al., *Ann. Rev. Plant Physiol. Plant Mol. Biol.,* 40:471, 1989). If the transgene is to be introduced into a plant cell, the transgene can also contain plant transcriptional termination and polyadenylation signals and translational signals linked to the 3' terminus of a plant fatty acid synthase gene.

An exogenous plastid transit peptide can be linked to a multifunctional fatty acid synthase gene. A plastid transit peptide is typically 40 to 70 amino acids in length and functions post-translationally to direct a protein to the plastid. The transit peptide is cleaved either during or just after import into the plastid to yield the mature protein.

Exogenous plastid transit peptide encoding sequences can be obtained from a variety of plant nuclear genes, so long as the products of the genes are expressed as preproteins comprising an amino terminal transit peptide and transported into plastid. Examples of plant gene products known to include such transit peptide sequences include, but are not limited to, the small subunit of ribulose biphosphate carboxylase, chlorophyll a/b binding protein, plastid ribosomal proteins encoded by nuclear genes, certain heat shock proteins, amino acid biosynthetic enzymes, (such as acetolactate acid synthase, 3-enolpyruvylphosphoshikimate synthase, dihydrodipicolinate synthase), fatty acid synthase, and the like. In some instances, a plastid transit peptide already may be encoded in the fatty acid synthase gene of interest, in which case there may be no need to add such plastid transit sequences. Alternatively, the DNA fragment coding for the transit peptide may be chemically synthesized either wholly or in part from the known sequences of transit peptides such as those listed above.

Regardless of the source of the DNA fragment coding for the transit peptide, it should include a translation initiation codon, for example, an ATG codon, and be expressed as an amino acid sequence that is recognized by and will function properly in plastids of the host plant. Attention should also be given to the amino acid sequence at the junction between the transit peptide and the fatty acid synthase enzyme, where it is cleaved to yield the mature enzyme. Certain conserved amino acid sequences have been identified and may serve as a guideline. Precise fusion of the transit peptide coding sequence with the fatty acid synthase coding sequence may require manipulation of one or both DNA sequences to introduce, for example, a convenient restriction site. This may be accomplished by methods including site-directed mutagenesis, insertion of chemically synthesized oligonucleotide linkers, and the like.

Precise fusion of the nucleic acids encoding the plastid transport protein may not be necessary so long as the coding sequence of the plastid transport protein is in-frame with that of the fatty acid synthase. For example, additional peptidyl or amino acids can often be included without adversely affecting the expression or localization of the protein of interest.

Once obtained, and when desired, the plastid transit peptide sequence can be appropriately linked to the promoter and a fatty acid synthase coding region in a transgene using standard methods. A plasmid containing a promoter functional in plant cells and having multiple cloning sites downstream can be constructed or obtained from commercial sources. The plastid transit peptide sequence can be inserted downstream from the promoter using restriction enzymes. A fatty acid synthase coding region can then be translationally fused or inserted immediately downstream from and in frame with the 3' terminus of the plastid transit peptide sequence. Hence, the plastid transit peptide is preferably linked to the amino terminus of the fatty acid synthase. Once formed, the transgene can be subcloned into other plasmids or vectors.

In addition to nuclear plant transformation, the present invention also extends to direct transformation of the plastid genome of plants. Hence, targeting of the gene product to an intracellular compartment within plant cells may also be achieved by direct delivery of a gene to the intracellular compartment. In some embodiments, direct transformation of plastid genome may provide additional benefits over nuclear transformation. For example, direct plastid transformation of fatty acid synthase eliminates the requirement for a plastid targeting peptide and post-translational transport and processing of the pre-protein derived from the corresponding nuclear transformants. Plastid transformation of plants has been described by Maliga, *Current Opinion in Plant Biology,* 5:164-172, 2002; Heifetz, *Biochimie,* 82:655-666, 2000; Bock, *J. Mol. Biol.,* 312:425-438, 2001; Daniell et al., *Trends in Plant Science,* 7:84-91, 2002; and references cited therein.

After constructing a transgene containing a multifunctional fatty acid synthase, the expression vector or cassette can then be introduced into a plant cell. Depending on the type of plant cell, the level of gene expression, and the activity of the enzyme encoded by the gene, introduction of DNA encoding a multifunctional fatty acid synthase into the plant cell can lead to increased fatty acid synthase activity in plant tissues.

Plant Transformation: There are many methods for introducing transforming nucleic acid molecules into plant cells. Suitable methods are believed to include virtually any method by which nucleic acid molecules may be introduced into a cell, such as by *Agrobacterium* infection or direct delivery of nucleic acid molecules, such as, for example, by PEG-mediated transformation, by electroporation or by acceleration of DNA coated particles, and the like. (Potrykus, *Ann. Rev. Plant Physiol. Plant Mol. Biol.,* 42:205-225, 1991; and Vasil, *Plant Mol. Biol.,* 25:925-937, 1994). For example, electroporation has been used to transform maize protoplasts (Fromm et al., *Nature,* 312:791-793, 1986).

Other vector systems suitable for introducing transforming DNA into a host plant cell include but are not limited to binary artificial chromosome (BIBAC) vectors (Hamilton et al., *Gene,* 200:107-116, 1997); and transfection with RNA viral vectors (Della-Cioppa et al., *Ann. N.Y. Acad. Sci.,* 1996), 792 (Engineering Plants for Commercial Products and Applications, 57-61). Additional vector systems also include plant selectable YAC vectors, such as those described in Mullen et al., *Molecular Breeding,* 4:449-457, 1988.

Technology for introduction of DNA into cells is well known by one of skill in the art. Four general methods for delivering a gene into cells have been described: (1) chemical methods (Graham and van der Eb, *Virology,* 54:536-539, 1973); (2) physical methods, such as microinjection (Capecchi, *Cell,* 22:479-488, 1980), electroporation (Wong and Neumann, *Biochem. Biophys. Res. Commun.,* 107:584-587, 1982; Fromm et al., *Proc. Natl. Acad. Sci.* (*U.S.A.*), 82:5824-5828, 1985; U.S. Pat. No. 5,384,253), the gene gun (Johnston and Tang, *Methods Cell Biol.,* 43:353-365, 1994), and vacuum infiltration (Bechtold et al., *C.R. Acad. Sci. Paris, Life Sci.,* 316:1194-1199, 1993); (3) viral vectors (Clapp, *Clin. Perinatol.,* 20:155-168, 1993; Lu et al., *J. Exp. Med.,* 178:2089-2096, 1993; Eglitis and Anderson, *Biotechniques,* 6:608-614, 1988); and (4) receptor-mediated mechanisms (Curiel et al., *Hum. Gen. Ther.,* 3:147-154, 1992; Wagner et al., *Proc. Natl. Acad. Sci.* (*U.S.A.*), 89:6099-6103, 1992).

Acceleration methods that may be used include, for example, microprojectile bombardment and the like. One example of a method for delivering transforming nucleic acid molecules into plant cells is microprojectile bombardment. This method has been reviewed by Yang and Christou (eds.), *Particle Bombardment Technology for Gene Transfer*, Oxford Press, Oxford, England (1994). Non-biological particles (microprojectiles) may be coated with nucleic acids and delivered into cells by a propelling force. Exemplary particles include those comprised of tungsten, gold, platinum, and the like.

A particular advantage of microprojectile bombardment, in addition to it being an effective means of reproducibly transforming monocots, is that neither the isolation of protoplasts (Cristou et al., *Plant Physiol.,* 87:671-674, 1988) nor the susceptibility to *Agrobacterium* infection is required. An illustrative embodiment of a method for delivering DNA into maize cells by acceleration is a biolistics α-particle delivery system, which can be used to propel particles coated with DNA through a screen, such as a stainless steel or Nytex screen, onto a filter surface covered with maize cells cultured in suspension. Gordon-Kamm et al., describes the basic procedure for coating tungsten particles with DNA (Gordon-Kamm et al., *Plant Cell,* 2:603-618, 1990). The screen disperses the tungsten nucleic acid particles so that they are not delivered to the recipient cells in large aggregates. A particle delivery system suitable for use with the present invention is the helium acceleration PDS-1000/He gun, which is available from Bio-Rad Laboratories (Bio-Rad, Hercules, Calif.) (also, see, Sanford et al., *Technique,* 3:3-16, 1991).

For the bombardment, cells in suspension may be concentrated on filters. Filters containing the cells to be bombarded are positioned at an appropriate distance below the microprojectile stopping plate. If desired, one or more screens are also positioned between the gun and the cells to be bombarded.

Alternatively, immature embryos or other target cells may be arranged on solid culture medium. The cells to be bombarded are positioned at an appropriate distance below the microprojectile stopping plate. If desired, one or more screens are also positioned between the acceleration device and the cells to be bombarded. Through the use of techniques set forth herein one may obtain 1000 or more loci of cells transiently expressing a marker gene. The number of cells in a focus that express the exogenous gene product 48 hours post-bombardment often ranges from 1 to 10, and average 1 to 3.

In bombardment transformation, one may optimize the pre-bombardment culturing conditions and the bombardment parameters to yield the maximum numbers of stable transformants. Both the physical and biological parameters for bombardment are important in this technology. Physical factors are those that involve manipulating the DNA/microprojectile precipitate or those that affect the flight and velocity of the microprojectiles. Biological factors include all steps involved in manipulation of cells before and immediately after bombardment, the osmotic adjustment of target cells to help alleviate the trauma associated with bombardment and, also, the nature of the transforming DNA, such as linearized DNA or intact supercoiled plasmids. It is believed that pre-bombardment manipulations are especially important for successful transformation of immature embryos.

In another alternative embodiment, plastids can be stably transformed. Methods disclosed for plastid transformation in higher plants include the particle gun delivery of DNA containing a selectable marker and targeting of the DNA to the plastid genome through homologous recombination (Svab et al., *Proc. Natl. Acad. Sci.* (*U.S.A.*), 87:8526-8530, 1990; Svab and Maliga, *Proc. Natl. Acad. Sci.* (*U.S.A.*), 90:913-917, 1993; Staub and Maliga, *EMBO J.,* 12:601-606, 1993; U.S. Pat. Nos. 5,451,513 and 5,545,818).

Accordingly, it is contemplated that one may wish to adjust various aspects of the bombardment parameters in small scale studies to fully optimize the conditions. One may particularly wish to adjust physical parameters such as gap distance, flight distance, tissue distance, and helium pressure. One may also minimize the trauma reduction factors by modifying conditions that influence the physiological state of the recipient cells and which may therefore influence transformation and integration efficiencies. For example, the osmotic state, tissue hydration, and the subculture stage or cell cycle of the recipient cells may be adjusted for optimum transformation. The execution of other routine adjustments will be known by one of skill in the art in light of the present disclosure.

*Agrobacterium*-mediated transfer is a widely applicable system for introducing genes into plant cells because the DNA can be introduced into whole plant tissues, thereby bypassing the need for regeneration of an intact plant from a protoplast. The use of *Agrobacterium*-mediated plant integrating vectors to introduce DNA into plant cells is well known in the art. See, for example the methods described by Fraley et al., *Bio/Technology,* 3:629-635, 1985 and Rogers et al., *Methods Enzymol.,* 153:253-277, 1987. Further, the integration of the Ti-DNA is a relatively precise process resulting in few rearrangements. The region of DNA to be transferred is defined by the border sequences and intervening DNA is usually inserted into the plant genome as described (Spielmann et al., *Mol. Gen. Genet.,* 205:34. 1986).

Modern *Agrobacterium* transformation vectors are capable of replication in *E. coli* as well as *Agrobacterium*, allowing for convenient manipulations as described (Klee et al., In: *Plant DNA Infectious Agents*, Hohn and Schell (eds.), Springer-Verlag, NY, pp. 179-203, 1985). Moreover, technological advances in vectors for *Agrobacterium*-mediated gene transfer have improved the arrangement of genes and restriction sites in the vectors to facilitate construction of vectors capable of expressing various polypeptide coding genes. The vectors described have convenient multi-linker regions flanked by a promoter and a polyadenylation site for direct expression of inserted polypeptide coding genes and are suitable for present purposes (Rogers et al., *Methods Enzymol.,* 153:253-277, 1987). In addition, *Agrobacterium* containing both armed and disarmed Ti genes can be used for the transformations. In those plant strains where *Agrobacterium*-mediated transformation is efficient, it is the method of choice because of the facile and defined nature of the gene transfer.

A transgenic plant formed using *Agrobacterium* transformation methods typically contains a single gene on one chromosome. Such transgenic plants can be referred to as being heterozygous for the added gene. More preferred is a transgenic plant that is homozygous for the added structural gene; i.e., a transgenic plant that contains two added genes, one gene at the same locus on each chromosome of a chromosome pair. A homozygous transgenic plant can be obtained by sexually mating (selfing) an independent segregant, transgenic plant that contains a single added gene, germinating some of the seed produced and analyzing the resulting plants produced for the gene of interest.

It is also to be understood that 2 different transgenic plants can also be mated to produce offspring that contain 2 independently segregating, exogenous genes. Selfing of appropriate progeny can produce plants that are homozygous for both added, exogenous genes that encode a polypeptide of interest. Back-crossing to a parental plant and out-crossing with a non-transgenic plant are also contemplated, as is vegetative propagation.

Transformation of plant protoplasts can be achieved using methods based on calcium phosphate precipitation, polyethylene glycol treatment, electroporation, and combinations of these treatments (see, for example, Potrykus et al., *Mol. Gen. Genet.,* 205:193-200, 1986; Lorz et al., *Mol. Gen. Genet.,* 199:178, 1985; Fromm et al., *Nature,* 319:791, 1986; Uchimiya et al., *Mol. Gen. Genet.,* 204:204, 1986; Marcotte et al., *Nature,* 335:454-457, 1988).

Application of these systems to different plant strains depends upon the ability to regenerate that particular plant strain from protoplasts. Illustrative methods for the regeneration of cereals from protoplasts are described (Fujimura et al., *Plant Tissue Culture Letters,* 2:74, 1985; Toriyama et al., *Theor. Appl. Genet.,* 205:34, 1986; Yamada et al., *Plant Cell Rep.,* 4:85, 1986; Abdullah et al., *Biotechnology,* 4:1087, 1986).

To transform plant strains that cannot be successfully regenerated from protoplasts, other ways to introduce DNA into intact cells or tissues can be utilized. For example, regeneration of cereals from immature embryos or explants can be effected as described (Vasil, *Biotechnology,* 6:397, 1988). In addition, "particle gun" or high-velocity microprojectile technology can be utilized (Vasil et al., *Bio/Technology,* 10:667, 1992).

Using the latter technology, DNA is carried through the cell wall and into the cytoplasm on the surface of small metal particles as described (Klein et al., *Nature,* 328:70, 1987; Klein et al., *Proc. Natl. Acad. Sci.* (*U.S.A.*), 85:8502-8505, 1988; McCabe et al., *Bio/Technology,* 6:923, 1988). The metal particles penetrate through several layers of cells and thus allow the transformation of cells within tissue explants.

Other methods of cell transformation can also be used and include but are not limited to introduction of DNA into plants by direct DNA transfer into pollen (Hess et al., *Intern Rev. Cytol.,* 107:367, 1987; Luo et al., *Plant Mol Biol. Reporter,* 6:165, 1988), by direct injection of DNA into reproductive organs of a plant (Pena et al., *Nature,* 325:274, 1987), or by direct injection of DNA into the cells of immature embryos followed by the rehydration of desiccated embryos (Neuhaus et al., *Theor. Appl. Genet.,* 75:30, 1987).

The regeneration, development and cultivation of plants from single plant protoplast transformants or from various transformed explants is well known in the art (Weissbach and Weissbach, In: *Methods for Plant Molecular Biology*, Academic Press, San Diego, Calif., 1988). This regeneration and growth process typically includes the steps of selection of transformed cells, culturing those individualized cells through the usual stages of embryonic development through the rooted plantlet stage. Transgenic embryos and seeds are similarly regenerated. The resulting transgenic rooted shoots are thereafter planted in an appropriate plant growth medium such as soil.

The development or regeneration of plants containing the foreign, exogenous gene that encodes a protein of interest is well known in the art. Preferably, the regenerated plants are self-pollinated to provide homozygous transgenic plants. Otherwise, pollen obtained from the regenerated plants is crossed to seed-grown plants of agronomically important lines. Conversely, pollen from plants of these important lines is used to pollinate regenerated plants. A transgenic plant of the present invention containing a desired polypeptide is cultivated using methods well known to one skilled in the art.

There are a variety of methods for the regeneration of plants from plant tissue. The particular method of regeneration will depend on the starting plant tissue and the particular plant species to be regenerated.

Methods for transforming dicots, primarily by use of *Agrobacterium tumefaciens* and obtaining transgenic plants have been published for cotton (U.S. Pat. Nos. 5,004,863; 5,159,135; and 5,518,908); soybean (U.S. Pat. Nos. 6,384,301; 5,569,834; and 5,416,011; McCabe et al., *Biotechnology,* 6:923, 1988; Christou et al., *Plant Physiol.,* 87:671-674, 1988); *Brassica* (U.S. Pat. No. 5,463,174); peanut (Cheng et al., *Plant Cell Rep.,* 15:653-657, 1996; McKently et al., *Plant Cell Rep.,* 14:699-703, 1995); papaya; pea (Grant et al., *Plant Cell Rep.,* 15:254-258, 1995); and *Arabidopsis thaliana* (Bechtold et al., *C.R. Acad. Sci. Paris, Life Sci.,* 316:1194-1199, 1993). The latter method for transforming *Arabidopsis thaliana* is commonly called "dipping" or vacuum infiltration or germplasm transformation.

Transformation of monocotyledons using electroporation, particle bombardment and *Agrobacterium* have also been reported. Transformation and plant regeneration have been achieved in asparagus (Bytebier et al., *Proc. Natl. Acad. Sci.* (*U.S.A.*), 84:5354, 1987); barley (Wan and Lemaux, *Plant Physiol.,* 104:37, 1994); maize (Rhodes et al., *Science,* 240:204, 1988; Gordon-Kamm et al., *Plant Cell,* 2:603-618, 1990; Fromm et al., *Bio/Technology,* 8:833, 1990; Koziel et al., *Bio/Technology,* 11: 194, 1993; Armstrong et al., *Crop Science,* 35:550-557, 1995); oat (Somers et al., *Bio/Technology,* 10: 1589, 1992); orchard grass (Horn et al., *Plant Cell Rep.,* 7:469, 1988); rice (Toriyama et al., *Theor Appl. Genet.,* 205:34, 1986; Part et al., *Plant Mol. Biol.,* 32:1135-1148, 1996; Abedinia et al., *Aust. J. Plant Physiol.,* 24:133-141, 1997; Zhang and Wu, *Theor. Appl. Genet.,* 76:835, 1988; Zhang et al., *Plant Cell Rep.,* 7:379, 1988; Battraw and Hall, *Plant Sci.,* 86:191-202, 1992; Christou et al., *Bio/Technology,* 9:957, 1991); rye (DelaPena et al., *Nature,* 325:274, 1987); sugarcane (Bower and Birch, *Plant J.,* 2:409, 1992); tall fescue (Wang et al., *Bio/Technology,* 10:691, 1992); and wheat (Vasil et al., *Bio/Technology,* 10:667, 1992; U.S. Pat. No. 5,631,152).

Assays for gene expression based on the transient expression of cloned nucleic acid constructs have been developed by introducing the nucleic acid molecules into plant cells by polyethylene glycol treatment, electroporation, or particle bombardment (Marcotte et al., *Nature,* 335:454-457, 1988; Marcotte et al., *Plant Cell,* 1:523-532, 1989; McCarty et al., *Cell,* 66:895-905, 1991; Hattori et al., *Genes Dev.,* 6:609-618, 1992; Goff et al., *EMBO J.,* 9:2517-2522, 1990). Transient expression systems may be used to functionally dissect gene constructs (see, Maliga et al., *Methods in Plant Molecular Biology*, Cold Spring Harbor Press, 1995).

Any of the nucleic acid molecules of the present invention may be introduced into a plant cell in a permanent or transient manner in combination with other genetic elements such as vectors, promoters, enhancers, etc. Further, any of the nucleic acid molecules of the present invention may be introduced into a plant cell in a manner that allows for expression or overexpression of the protein or fragment thereof encoded by the nucleic acid molecule.

It is also to be understood that 2 different transgenic plants can also be mated to produce offspring that contain 2 independently segregating added, exogenous genes. Selfing of appropriate progeny can produce plants that are homozygous for both added, exogenous genes that encode a polypeptide of interest. Backcrossing to a parental plant and out-crossing with a non-transgenic plant are also contemplated, as is vegetative propagation.

Transgenic plants may find use in the commercial manufacture of proteins or other molecules, where the molecule of interest is extracted or purified from plant parts, seeds, and the like. Cells or tissue from the plants may also be cultured, grown in vitro, or fermented to manufacture such molecules.

The transgenic plants may also be used in commercial breeding programs, or may be crossed or bred to plants of related crop species. Improvements encoded by the recombinant DNA may be transferred, e.g., from cells of one species to cells of other species, e.g., by protoplast fusion.

The present invention also provides for a method of stably expressing a fatty acid synthase of interest in a plant, which includes, contacting the plant cell with a vector of the present invention that has a selectable marker gene and a nucleic acid encoding the fatty acid synthase of interest, under conditions effective to transform the plant cell. A promoter within the expression cassette can be any of the promoters provided herein, for example, a constitutive promoter, an inducible promoter, a tissue-specific promoter, or a seed specific promoter. Such promoters can provide expression of an encoded fatty acid synthase at a desired time, or at a desired developmental stage, or in a desired tissue.

The present invention also provides for a method of stably expressing a fatty acid synthase of interest in a plant, which includes, contacting the plant cell with a vector of the present invention that has a nucleic acid encoding the fatty acid synthase of interest, under conditions effective to transfer and integrate the vector into the nuclear genome of the cell. The vector can also include a selectable marker gene. When using the vector with *Agrobacterium tumefaciens*, the vector can have an *Agrobacterium tumefaciens* origin of replication.

Plants: Plants for use with the vectors of the present invention include dicots and monocots, especially oil producing species including but not limited to, corn (*Zea mays*) and soybean (*Glycine max*).

The following examples are provided to illustrate the present invention and are not intended to limit the present invention in any way.

EXAMPLE 1

This example describes the isolation of the fasA and ppt1 genes from *Brevibacterium ammoniagenes.*

Genomic DNA was isolated from *B. ammoniagenes* (ATCC 6871) using standard methodologies. A genomic library was prepared by partially digesting *B. ammoniagenes* genomic DNA with the restriction enzyme Sau3A, isolating DNA fragments ranging from 30-42 kb in size and generating the library using the SuperCos 1 Cosmid Vector kit from Stratagene, Inc. (La Jolla, Calif.). The genomic library was screened by hybridization and washing under stringent conditions with a 32P-labelled 1.1 kb fasA PCR fragment generated from isolated genomic DNA using the following PCR primers:

14713 (forward):

5'-CCAGCTCAACGATGAAGTAG-3' [SEQ ID NO:5] and 14714 (reverse):

5'-TCGATGATCTGGTCTACTTC-3' [SEQ ID NO:6]

```
14713 (forward):
5'-CCAGCTCAACGATGAAGTAG-3'    [SEQ ID NO: 5]
and

14714 (reverse):
5'-TCGATGATCTGGTCTACTTC-3'    [SEQ ID NO: 6]
```

Rehybridization was in a solution of 40% formamide, 5× SSC, 50 mM sodium phosphate, pH 7.0, 5× Denhardt's, 0.1% SDS, 5 mM EDTA, 0.1 μg/ml salmon sperm DNA, and 5% Dextran sulfate for 2 hrs at 42° C. The filters were rinsed briefly in 0.1× SSC, 0.1% SDS at RT and then washed 2 times for 20 mm each in 0.1× SSC, 0.1% SDS at 50° C. FasA-containing clones were identified by autoradiography and restriction mapping. Selected cosmid clones were analyzed in more detail and one clone was confinned to have the full-length fasA gene by restriction mapping and comparison with the restriction sites in the published sequence (Stuible et al., *J Bacteriol.,* 178:4787-4793, 1996).

The full-length fasA gene was assembled so as to introduce convenient flanking restriction sites for sub-cloning by using the following basic steps: a) PCR amplification of the 5' and 3' ends; b) assembling the 5' and 3' ends of the gene together by an overlapping PCR strategy resulting in deletion of the fasA sequence between the internal MfeI and XhoI sites; c) cloning the "5'-3' fused" PCR fragment; d) insertion of the 8166 bp fasA MfeI/XhoI fragment between the MfeI and XhoI sites in the "5'-3' fused" PCR fragment so as to re-generate the full-length fasA gene with convenient flanking cloning sites. The details for each of these steps are outlined below.

A 5' 280 bp fasA PCR fragment was generated using the following primers:

```
16393 (forward)
5'-TCTAGATGCATAGTTAACATGTCGTTGACCCCCTTGC-3'  [SEQ ID NO: 9]
and

14873 (reverse)
5'-GGTACGCGTCATATTCCTTG-3'                   [SEQ ID NO: 10]
```

The forward primer, 16393, introduced XbaI, NsiI, HpaI, and PciI flanking restriction sites.

A 3' 946 bp fasA PCR fragment was generated using the following primers:

```
16385 (forward) 5'-CAAGGAATATGACGCGTACCCTCGAGGCAGAAGGCGGCGG-3'  [SEQ ID NO: 11]
and

16394 (reverse) 5'-ATGCATGTTAACATGTCTACTTTGTCCTACTTCGCCG-3'     [SEQ ID NO: 12]
```

The reverse primer, 16394, introduced 3' flanking NsiI, HpaI, and PciI restriction sites. The forward primer, 16385, contained 20 bp of sequence matching the 3'-end of the 5' 280bp restriction fragment described above to allow the 2 fragments to anneal together. The 5' 280 bp fasA PCR fragment and the 3' 946 bp fasA PCR fragment were fused together by annealing the 2 fragments and PCR amplifying the full length (1206 bp) overlapped fragment using the external primers 16393 (forward) and 16394 (reverse). The 1206 bp 5'-3'-fused PCR fragment was cloned into pCR-Blunt II-TOPO (Invitrogen Corporation, Carlsbad, Calif.) and the correct DNA sequence was confirmed by sequencing. The 1206 bp 5'-3'-fused PCR fragment was then subcloned as an SpeI/XbaI fragment into a Bluescript pBC KS+ (Stratagene Inc., La Jolla, Calif.) vector which contained a modified multiple cloning sequence (pCGN3686). The full-length fasA gene was then obtained by ligation of the 3505 bp MluI/MluI and 4516 bp MluI/XhoI internal fasA fragments isolated from the full-length cosmid clone between the MluI and XhoI sites in the 5'-3' fused PCR fragment to make pMON70058 (FIG. 1).

Figure 4:
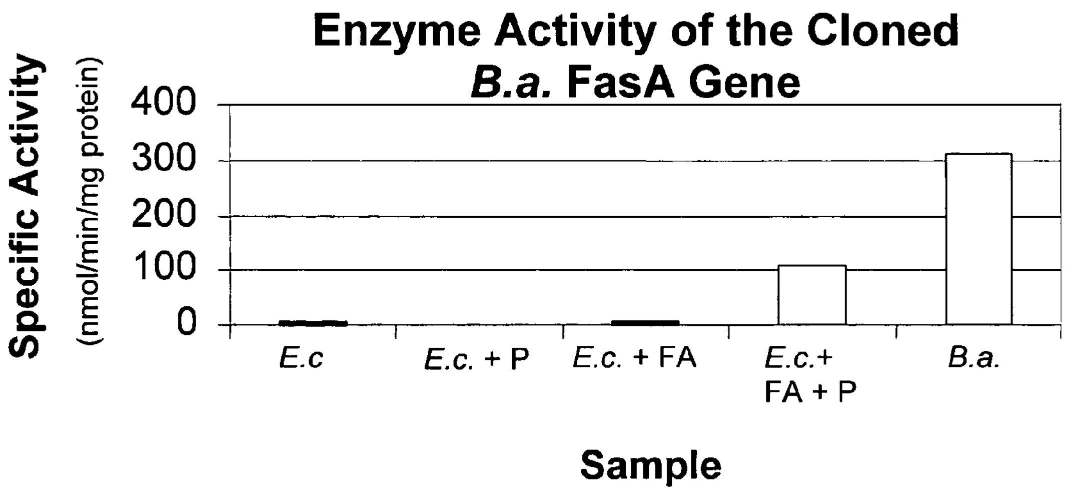
FIG. 4 illustrates FasA enzyme activity of the cloned fasA gene from *Brevibacterium ammoniagenes*. The FasA enzyme activity was determined as outlined in Kawaguchi et al., *Methods in Enzymology,* 71:120-127 (1981) for partially purified enzyme preparations from *Brevibacterium ammoniagenes* (B.a.), for an untransformed *E. coli* strain VCS257 (E.c.), and for the same strain transformed with either the ppt1 expressing plasmid (E.c.+P), the fasA cosmid (E.c.+FA), or the ppt1 expressing plasmid and the fasA cosmid (E.c.+P+FA).

The complete double-stranded sequence of the full-length fasA gene open reading frame in pMON70058 was determined using a Perkin Elmer ABI 377 DNA sequencer (SEQ ID NO: 1). The corresponding protein sequence (SEQ ID NO: 2) was predicted based on standard genetic code using the program Omiga (Accelrys, Inc., Cambridge, UK) and compared with the published fasA sequence (FIG. 4). Alignment of both the nucleic acid and predicted amino acid sequences to the published sequences (Stuible et al., *J. Bacteriol.,* 178:4787, 1996) revealed a number of differences both at the DNA and protein levels (FIGS. 2 and 3).

The *B. ammoniagenes* ppt1 gene was PCR amplified from isolated genomic DNA using the following primers:

```
16117 (forward): 5'-GTCGACATGCTCGACAACCGTGAAGCG-3'      [SEQ ID NO: 7]
and

16118 (reverse): 5'-AGATCTTCACTGGTGGCTTGCCGTAGATCGC-3' [SEQ ID NO: 8]
```

The PCR-amplified fragment was then cloned into the commercially available cloning vector pCR-Blunt II TOPO (Invitrogen Corporation, Carlsbad, Calif.). The complete double stranded sequence of the full-length ppt1 gene (SEQ ID NO: 3) was determined using a Perkin Elmer ABI 377 DNA sequencer. The corresponding protein sequence (SEQ ID NO: 4) was predicted based on standard genetic code using the program Omiga and compared with the published ppt1 sequence. Alignment of both the nucleic acid and predicted amino acid sequences to the published sequences (Stuible et al., *J. Bacteriol.,* 178:4787, 1996) revealed that the cloned ppt1 gene was identical to the published sequence.

EXAMPLE 2

This example describes the transformation of *E. coli* with the fasA gene constructs, described in Example 1, for functional testing.

The full-length, sequence-confirmed *B. ammoniagenes* ppt1 gene in the pCR-Blunt II TOPO vector described in Example 1 was cut out of the pCR-Blunt II TOPO backbone as a Sal I/Bgl II fragment, and ligated into the Sal I/BamHI sites, respectively, of pSU19 (Bartolome et al., *Gene,* 102 (1):75-78, 1991). The Sal I sites of both the ppt1 and the pSU19 fragments were blunt-ended with the Klenow fragment of DNA polymerase I prior to ligation to enable inframe insertion of the ppt1 coding sequence into the lacZ coding sequence of pSU19. The PPT1 protein was thus expressed in *E. coli* as a lacZ fusion protein upon induction of the lacZ promoter in pSU19 by the use of isopropyl-1-thio-β-D-galactopyranoside (IPTG). This ppt1-containing vector was then transformed into *E. coli* strain VCS257 from Stratagene (cat#200256-51), along with the mfFAS cosmid clone, described in Example 1, for functional testing.

Because the plasmid pSU19 has a pACYC184 origin of replication and conveys chloramphenicol resistance, the ppt1 expressing plasmid could be stably maintained along with the cosmid (ampicillin resistance) expressing the fasA gene.

Based on the published report of Stuible et al., *Eur. J. Biochem.,* 248:481-487, 1997, the endogenous fasA promoter was used to express the mfFAS polypeptide encoded by fasA in *E. coli.* As a result, *E. coli* transformants containing the fasA cosmid alone, the pSU19/ppt1 construct alone, and both the fasA cosmid and the pSU19/ppt1 construct were made for functional testing. The full-length fasA gene was also subcloned as a PciI fragment from pMON70058 into the *E. coli* expression vector pQE60 (QIAGEN, Inc., Valencia, Calif.) to enable inducible expression from an *E. coli* promoter (pMON70081).

EXAMPLE 3

This example sets forth the functional testing of transgene activity in *E. coli* using enzymatic assays.

In order to assay the *E. coli* strains containing the fasA cosmid and ppt1 gene construct the fasA gene product was partially purified essentially as outlined in Kawaguchi et al., *Methods in Enzymology,* 71:120-127, 1981. Frozen cells from the strain containing either the fasA cosmid alone, the pSU19/ppt1 construct alone, both the fasA cosmid and the pSU19/ppt1 construct, or the untransformed cell line alone were thawed in 0.1M potassium phosphate buffer (~1 ml/1 gm) and cells lysed by high speed mixing with glass beads. The supernatant was centrifuged at 105,000×g for 60 minutes and removed. Ammonium sulfate was slowly added to the supernatant to give a final concentration of 30% w/v followed by 30 minutes of stirring. A second centrifugation step (25,000×g) was performed and the precipitate was re-suspended in 0.5M potassium phosphate buffer before passing through a Sephadex G-25 column.

The fasA activity in each of the extracts was determined by a radiochemical assay at 37° C. for 15 minutes using the conditions outlined in Kawaguchi et al., 1981. The results of these assays demonstrated that only when the fasA cosmid (FA) and the pSU19/ppt1 (P) construct were both present was there any measurable fasA activity (FIG. 4). Furthermore, they demonstrated that the fasA gene that was cloned and used for preparation of plant transformation constructs did encode a functional fasA enzyme.

EXAMPLE 4

This example describes the construction of a plant binary vector for seed-specific expression of the fasA gene in plants. The construction is shown graphically in FIGS. 5-8. The vector pMON75201 was designed to produce seed-specific expression of the *B. ammoniagenes* fasA and ppt1 genes in soybean.

Figure 5:
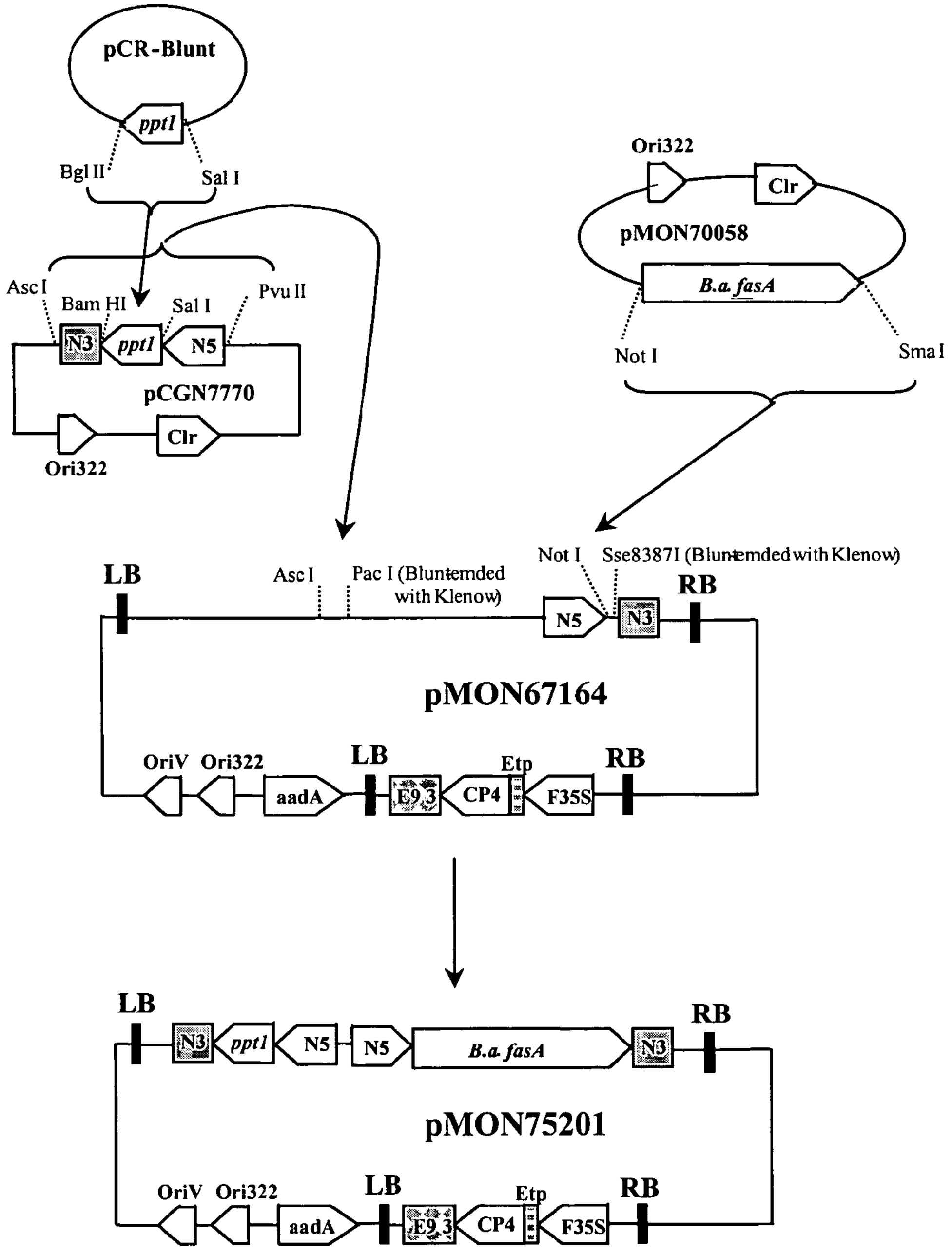
FIG. 5 provides a schematic representation of the preparation of pMON75201 as well as a map of pMON75201.

The full-length, sequence-confirmed *B. ammoniagenes* ppt1 gene in the pCR-Blunt II TOPO vector described in Example 1 was cut out of the pCR-Blunt II TOPO backbone using the SalI and BglII sites engineered into the PCR primers 16117 and 16118 (SEQ ID NOS: 7 and 8, respectively) used in the cloning and ligated to the SalI and BamHI sites between the napin promoter (base pairs 407-2151 of the *Brassica campestris* napin gene, N5, GenBank Accession Number M64632) and the napin 3' untranslated region (UTR), N3, (base pairs 2728-3982 of the *Brassica campestris* napin gene, GenBank Accession Number M64632) found in the plant/*E. coli* binary vector pCGN7770 (FIG. 5). The napin promoter/*B. ammoniagenes* ppt1/napin 3' UTR cassette was combined with the *B. ammoniagenes* fasA gene for simultaneous expression in plants as described below.

The full-length, sequence-confirmed *B. ammoniagenes* fasA gene was removed from pMON70058 (described in Example 1 and FIG. 1) using the restriction enzymes NotI and SmaI and was ligated into the NotI and blunted Sse8387I restriction sites between a napin promoter and napin 3' UTR (as described above) contained in a 2 T-DNA binary vector pMON67164. The Sse8387I site was blunt-ended by the action of Klenow fragment of DNA polymerase I. The resultant vector, containing the pMON67164 backbone and the *B. ammoniagenes* fasA gene flanked by the napin expression sequences, was digested with PacI, blunt-ended by the action of Klenow fragment of DNA polymerase I, and then digested with AscI. The AscI/PvuII fragment containing the napin promoter/*B. ammoniagenes* ppt1 gene/napin 3' UTR cassette in pCGN7770 (described above) was then inserted into the PacI blunt/AscI sites to form pMON75201 (See FIG. 5). pMON75201 is a 2 T-DNA vector containing both the *B. ammoniagenes* fasA gene and the *B. ammoniagenes* ppt1 gene each under the control of seed-specific napin expression sequences (napin promoter and 3' UTR) and located within one set of T-DNA left and right borders. A selectable marker for plant transformation, containing the FMV 35S promoter, F35S (base pairs 6927-6474 of the FMV which is the promoter for ORF VII, GenBank Accession Number X06166) driving a CP4 selectable marker gene (a chloroplast targeting sequence from the *Arabidopsis* EPSP gene linked to a synthetic EPSP synthase coding region as described in U.S. Pat. No. 5,633,435), and a E9 3' UTR (Coruzzi et al., *EMBO J.,* 3(8):1671-1679, 1984) is located within a second set of T-DNA left and right borders.

EXAMPLE 5

This example describes the transformation of soybean plants with fasA and ppt1 genes.

Soybean plants were transformed using an *Agrobacterium*-mediated transformation method, as described by Martinell (U.S. Pat. No. 6,384,301). For this method, overnight cultures of *Agrobacterium tumefaciens* containing the plasmid that includes a gene of interest, such as pMON75201, were grown to log phase and then diluted to a final optical density of 0.3 to 0.6 using standard methods known to one skilled in the art. These cultures were used to inoculate the soybean embryo explants prepared as described below.

Briefly, the method is a direct germline transformation into individual soybean cells in the meristem of an excised soybean embryo. The soybean embryo is removed after surface sterilization and germination of the seed. The explants are then plated on OR media, a standard MS medium as modified by Barwale et al., *Plants,* 167:473-481, 1986; plus 3 mg/L BAP, 200 mg/L Carbenicillin, 62.5 mg/L Cefotaxime, and 60 mg/L Benomyl, and stored at 15° C. overnight in the dark. The following day the explants are wounded with a scalpel blade and inoculated with the *Agrobacterium* culture prepared as described above. The inoculated explants are then cultured for 3 days at room temperature.

Following the post-transformation culture, the meristemac region is then cultured on standard plant tissue culture media in the presence of the herbicide glyphosate (Monsanto Company, St. Louis, Mo.), which acts as both a selection agent and a shoot inducing hormone. Media compositions and culture lengths are detailed in the aforementioned Martinell patent (U.S. Pat. No. 6,384,301).

After 5 to 6 weeks, the surviving explants that have a positive phenotype are transferred to soil and grown under greenhouse conditions until maturity. The fasA activity of the plant extracts at various stages of growth is determined by a radiochemical assay at 37° C. for 15 minutes using the conditions outlined in Kawaguchi et al., *Methods in Enzymology,* 71:120-127, 1981.

EXAMPLE 6

This example describes the construction of a plant binary vector for constitutive expression of the fasA gene and the *B. ammoniagenes* ppt1 gene in plants (pMON75202).

The full-length sequence-confirmed *B. ammoniagenes* ppt1 gene in the pCR-Blunt II TOPO vector described in Example 1 was cut out of the pCR-Blunt II TOPO backbone using the SalI and BglII sites engineered into the PCR primers, 16117 (SEQ ID NO: 7) and 16118 (SEQ ID NO: 8) used in its construction. The resulting fragment was cloned between the SalI and BamHI sites, respectively, in between an enhanced CaMV 35S promoter (fusion between base pairs 6493-7340 and 7189-7429 of the CaMV 35S protein sequence, GenBank Accession Number V00140, denoted as d35S in FIG. 6) and a tml 3' UTR (base pairs 10301-9203 of the *Agrobacterium tumefaciens* octopine-type Ti plasmid, GenBank Accession Number AF242881) in the plant/*E. coli* binary vector pCGN7787. The cloning is shown diagramatically in FIG. 6. The CaMV double 35S promoter/*B. ammoniagenes* ppt1 gene/tml expression cassette was then cut out of pCGN7787 with the restriction enzymes AscI and PvuII.

Figure 6:
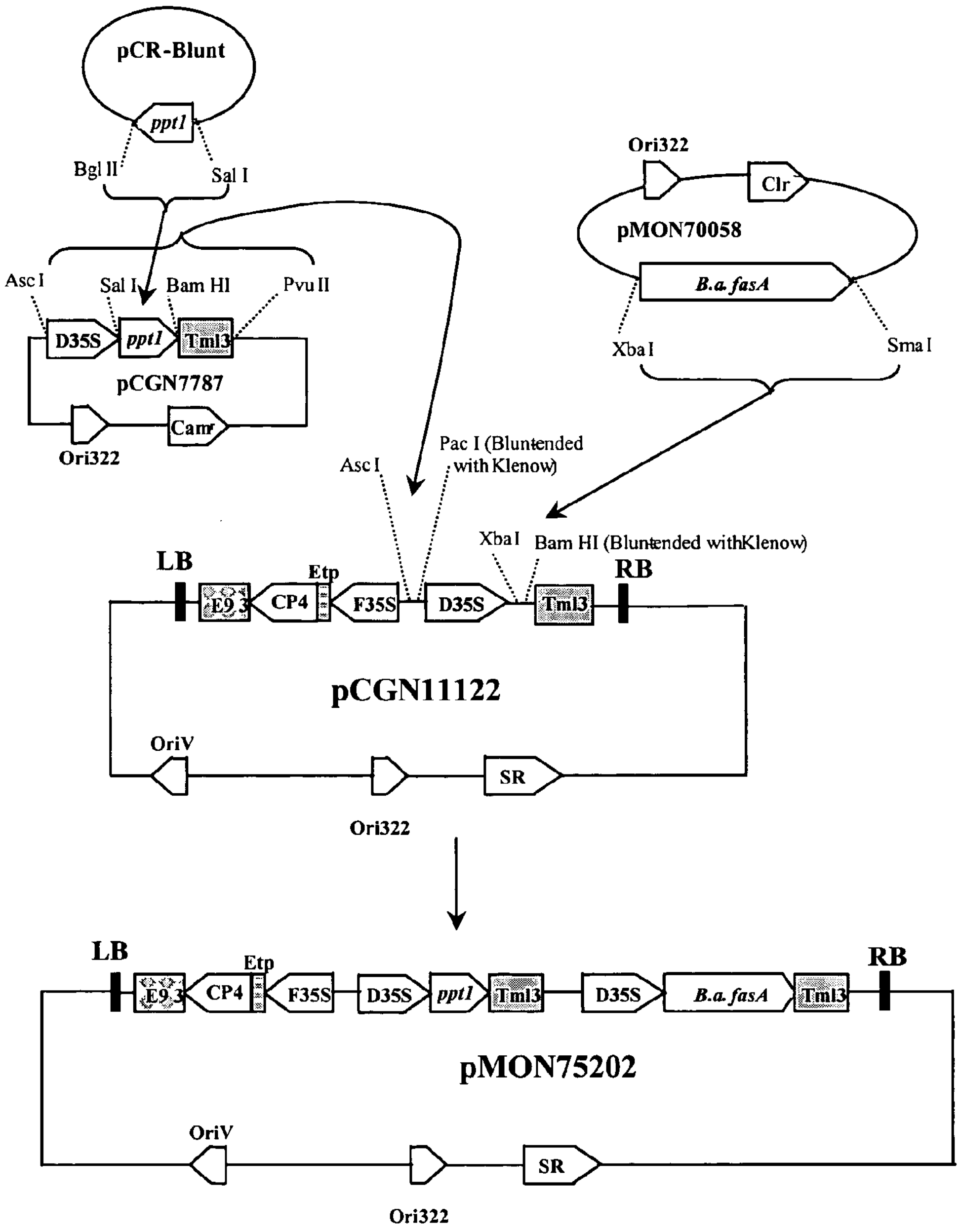
FIG. 6 provides a schematic representation of the preparation of pMON75202 as well as a map of pMON75202.

The full-length sequence-confirmed *B. ammoniagenes* fasA gene was removed from pMON70058 (FIG. 1) using the restriction enzymes XbaI and SmaI. The resulting fragment was then inserted into a one T-DNA plant binary vector, pCGN11122, between the XbaI and BamHI sites following blunt-ending of the BamHI site by the action of Klenow fragment of DNA polymerase I. The resultant T-DNA binary vector contains the pCGN11122 backbone, the *B. ammoniagenes* fasA gene behind an enhanced CaMV 35S promoter and a plant selectable marker, FMV 35s/CP4/E9 3'. This vector was digested with PacI, blunt-ended by the action of Klenow fragment of DNA polymerase I, and then digested with AscI. The AscI/PvuII fragment containing the enhanced CaMV 35S promoter/*B. ammoniagenes* ppt1 gene/tml 3' cassette described above was then ligated to this fragment to form pMON75202 (FIG. 6).

EXAMPLE 7

This example describes the transformation and regeneration of transgenic *Arabidopsis* plants expressing a fasA gene.

*Arabidopsis* plants were grown by sowing seeds onto 4 inch pots containing reverse osmosis water (ROW) saturated MetroMix 200 (The Scotts Company, Columbus, Ohio). The plants were vernalized by placing the pots in a flat, covered with a humidity dome, in a growth chamber at 4-7° C., 8 hours light/day for 4-7 days. The flats were transferred to a growth chamber at 22° C., 55% relative humidity, and 16 hours light/day at an average intensity of 160-200 μEinstein/sec-$m^2$. After germination the dome was lifted and slid back 1 inch to allow for mild air circulation without desiccation. The humidity dome was removed when the true leaves had formed. The plants were bottom watered, as needed, with ROW until 2-3 weeks after germination. Plants were then bottom watered, as needed, with Plantex 15-15-18 solution (Plantex Corporation Ottawa, Canada) at 50 ppm $N_2$. Plants were thinned so that 1 plant remained per pot at 2-3 weeks after germination. Once the plants began to bolt, the primary inflorescence was trimmed to encourage the growth of axillary bolts.

The transformation vector pMON75202 was introduced into *Agrobacterium tumefaciens* strain ABI in accordance with the method set forth at Example 5 hereof. Transgenic *Arabidopsis thaliana* plants were obtained as described by Bent et al., *Science,* 265:1856-1860 (1994) or Bechtold et al., *C.R. Acad. Sci., Life Sciences,* 316:1194-1199 (1993). Briefly, cultures of Agrobacterium containing pMON75202 were grown overnight in LB (10% bacto-tryptone, 5% yeast extract, and 10% NaCl with kanamycin (75 mg/L), chloramphenicol (25 mg/L), and spectinomycin (100 mg/L)). The bacterial culture was centrifuged and resuspended in 5% sucrose+0.05% Silwet 77. The aerial portion of whole *Arabidopsis thaliana* plants (at ~5-7 weeks of age) were immersed in the resulting solution for 2-3 seconds. The excess solution was removed by blotting the plants on paper towels. The dipped plants were placed on their side in a covered flat and transferred to a growth chamber at 19° C. After 16 to 24 hours the dome was removed and the plants were set upright. When plants had reached maturity, water was withheld for 2-7 days prior to seed harvest. Harvested seed was passed through a stainless steel mesh screen (40 holes/inch) to remove debris. The harvested seed was stored in paper coin envelopes at room temperature until further analysis.

EXAMPLE 8

This example describes the construction of plant binary vectors for expression of *B. ammoniagenes* fasA and ppt1 genes in corn kernel tissues.

Embryo Expression Vector (pMON70098; see FIG. 7): The *B. ammoniagenes* ppt1 gene was PCR amplified from the sequence-confirmed full-length pCR-Blunt II TOPO clone described in Example 1 using the PCR primers:

```
16395 (forward): 5'-GTCGACATGCATATGCTCGACAACCGTGAAGCG-3' [SEQ ID NO: 13]
and

16396 (reverse): 5'-AGATCTATGCATTACCGCTGGTACCGCAGC-3'    [SEQ ID NO: 14]
```

in order to introduce SalI, NsiI, and NedI sites 5' of the ppt1 gene, and BglII and NsiI sites 3' of the ppt1 gene to facilitate cloning the ppt1 gene into plant transformation binary vectors. The resultant PCR product was re-cloned into pCR-Blunt II TOPO (Invitrogen). The ppt1 gene was then cut out of the pCR-Blunt II TOPO vector with NsiI and ligated into the PstI site in the lacZ multiple cloning site of the commercial E.coli expression vector pBC SK+ (Stratagene) to form pMON70092. The XbaI site in the multiple cloning site of pMON70092 was then cut and filled-in with the Klenow fragment of DNA polymerase I to form pMON70096. The ppt1 gene was cut out of pMON70096 using NotI and EcoRV and cloned into the Bsp120I and StuI sites, respectively, in between a 1 kb L3 maize oleosin promoter (U.S. Pat. No. 6,433,252) and rice actin intron (base pairs 572-121 of the *O. sativa* Act 1 gene, GenBank Accession Number X63830) and a globulin-1 3' UTR sequence (base pairs 2546-3120 of the *Zea mays* G1b1-S gene for vicilin-like embryo storage protein, GenBank Accession Number X59084) of the plant binary vector pMON72021 to make pMON70097.

Figure 7:
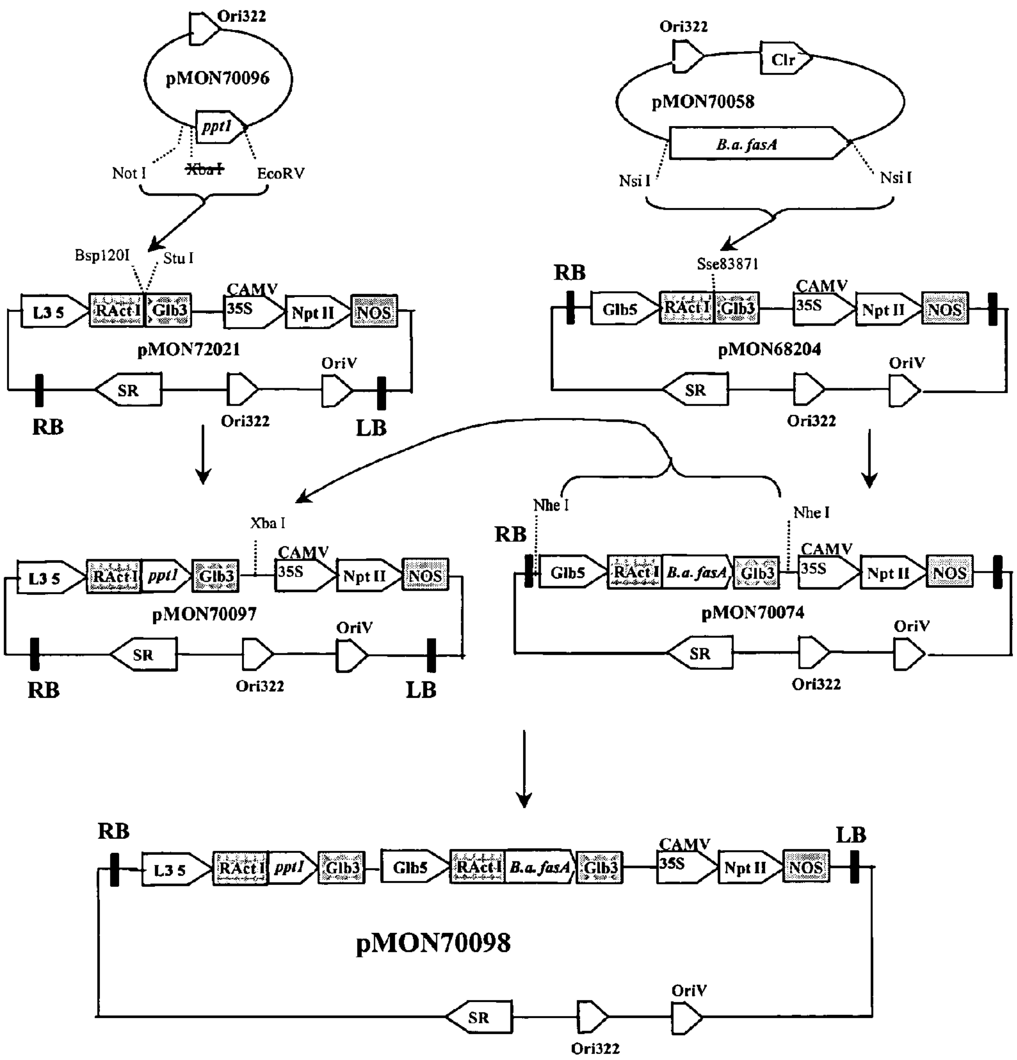
FIG. 7 provides a schematic representation of the preparation of pMON70098 as well as a map of pMON70098.
Figure 8:
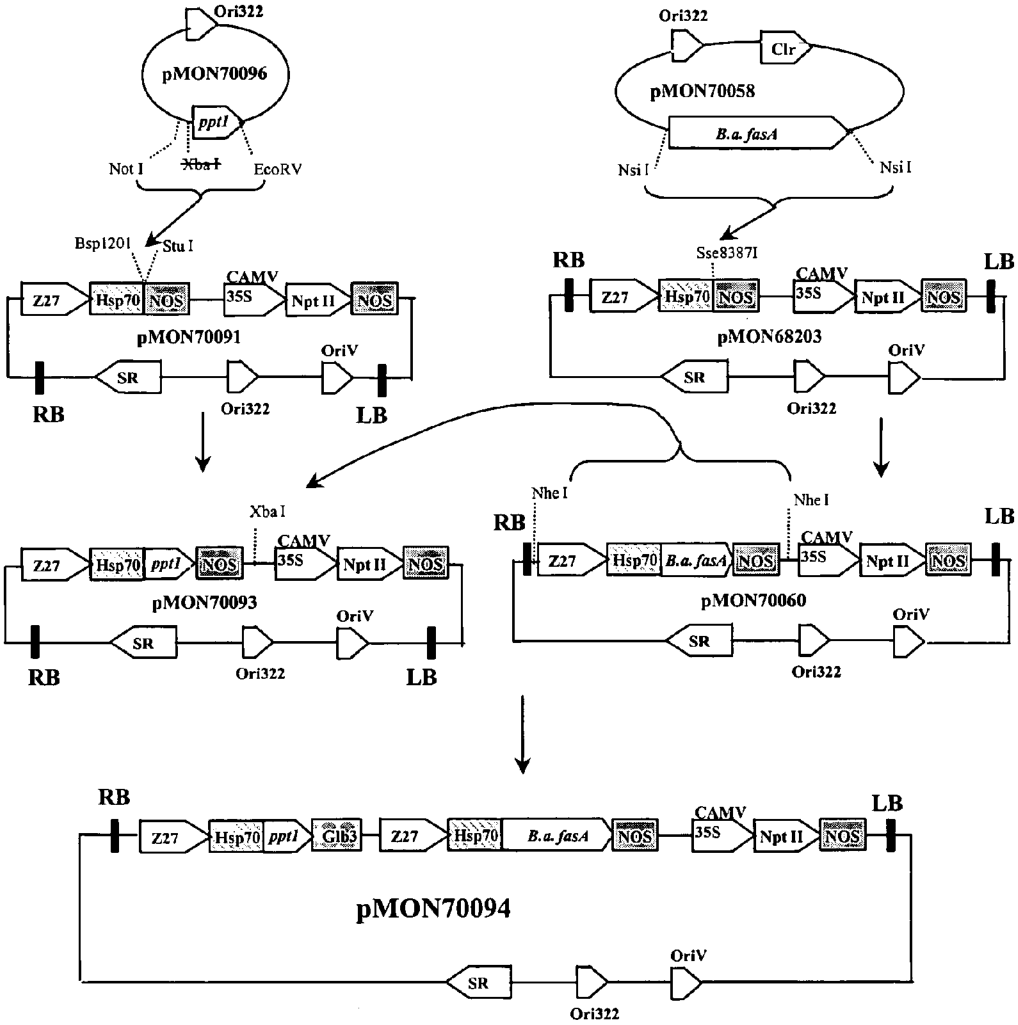
FIG. 8 provides a schematic representation of the preparation of pMON70094 as well as a map of pMON70094.

The full-length sequence-confirmed *B. ammoniagenes* fasA gene was removed from pMON70058 (FIG. 1) using the NsiI sites in the PCR primer sequences flanking the gene and the resultant NsiI fragment was then ligated into the Sse8387I site between the 1.4 kb globulin 1 promoter (base pairs 7-1401 of the *Zea mays* globulin-1 gene promoter region; NCBI GenBank Accession Number L22344) and the rice actin intron (as above) and a globulin-1 3' UTR (as above) in the plant binary vector pMON68204 to form pMON70074. The resultant expression cassette containing the globulin 1 promoter/rice actin intron/B.a. fasA gene/globulin 3' UTR was then cut out of pMON70074 using the flanking NheI sites and cloned into the XbaI site of pMON70097 to form the final plant transformation construct pMON70098 (FIG. 7). This construct contains 3 expression cassettes between the one set of T-DNA borders: 1) the L3 oleosin promoter/rice actin intron driving expression of the *B. ammoniagenes* ppt1 gene; 2) the globulin 1 promoter/rice actin intron driving expression of the *B. ammoniagenes* fasA gene; and 3) a CaMV 35S/npt II/nos 3' UTR selectable marker (as described in U.S. Pat. No. 6,255,560).

Endosperm Expression Vector (pMON70094; see FIG. 8): The ppt1 gene was cut out of pMON70096 (described above) using NotI and EcoRV and cloned into the Bsp120I and StuI sites, respectively, in between the 1.1 kb Zein 27 promoter (gamma-zeinA sequence (GenBank Accession Number S78780)) and corn hsp70 intron (base pairs 4-153 of the Maize gene for heat shock protein 70 exon 2 (GenBank Accession Number X03697)) and a nos 3' UTR (base pairs 2924-2671 of the *Agrobacterium tumefaciens* strain C58 Ti plasmid (GenBank Accession Number AE009420)) in the plant binary vector pMON70091 to form pMON70093.

The full-length sequence-confirmed *B. ammoniagenes* fasA gene was removed from pMON70058 (FIG. 1) using the NsiI sites in the PCR primer sequences flanking the gene and the resultant NsiI fragment was then ligated into the Sse83871 site in between the Zein 27 promoter, corn hsp70 intron and a nos 3' UTR in the plant binary vector pMON68203 to form pMON70060. The resultant expression cassette containing the Zein 27 promoter/corn hsp70 intron/B.a. fasA gene/nos 3' UTR was then cut out of pMON70060 using the flanking NheI sites and cloned into the XbaI site of pMON70093 to form the final plant transformation construct pMON70094. This construct contains 3 expression cassettes between the one set of T-DNA borders: a) the Zein 27 promoter/corn hsp70 intron driving expression of the *B. ammoniagenes* ppt1 gene; b) the Zein 27 promoter/corn hsp70 intron/driving expression of the *B. ammoniagenes* fasA gene; and c) a CaMV 35s/npt II/nos 3' UTR selectable marker (as described in U.S. Pat. No. 6,255,560).

EXAMPLE 9

The transformation vectors pMON70094 and pMON70098 are used to transform maize plants using the following procedure.

Maize plants are grown in a greenhouse under standard practices. Controlled pollinations are made. The ears of the plants are harvested when the resulting hybrid embryos are 1.5 to 2.0 mm in length, usually 10-15 days after pollination. After removing the husks, the kernels on the ears are surface-sterilized by spraying with or soaking in 80% ethanol.

The *Agrobacterium* strain ABI, and an *Agrobacterium tumefaciens* binary vector system are used for the transformations. Prior to inoculation of maize cells the *Agrobacterium* cells are grown overnight at room temperature in AB medium (Chilton et al., *Proc. Nat. Acad. Sci.* (*U.S.A.*), 71:3672-3676, 1974) comprising appropriate antibiotics for plasmid maintenance and 200 μM acetosyringone. Immediately prior to inoculation the *Agrobacterium* cells are pelleted by centrifugation, and resuspended in either CRN122 medium (2.2 g/L GIBCO MS (Murashige and Skoog, *Physiol. Plant,* 15:473-497, 1962) basal salts, 2 mg/L glycine, 0.5 g/L niacin, 0.5 g/L L-pyridoxine-HCl, 0.1 g/L thiamine, 115 mg/L L-proline, 36 g/L glucose, and 68.5 g/L sucrose, pH 5.4) or CRN347 medium (CRN122 medium except with 0.44 g/L MS salts, 10 g/L glucose, 20 g/L sucrose and 100 mg/L ascorbic acid) containing 200 μM acetosyringone and 20 μM Ag $NO_3$.

The immature maize embryos are excised from individual kernels using methods known to those of skill in the art, immersed in an *Agrobacterium* suspension, and incubated at room temperature for 5-15 minutes. The *Agrobacterium* solution is then removed, and the inoculated immature embryos are transferred scutellum-side up from innoculation CRN122 medium to co-cultivation CRN123 medium (CRN122 medium except with 0.5 mg/L additional thiamine HCl, 20 g/L sucrose, 10 g/L glucose and 3 mg/L 2,4 D) containing 200 μM acetosyringone and 20 μM silver nitrate and incubate at 23° C. for 1 day. Alternatively, excised embryos are cultured for 8-11 days in 211V medium (3.98 g/L Chu N6 salts (Chu, C.C., The N6 medium and its application to anther culture of cereal crops, in *Plant Tissue Culture Plant Tissue Culture. Proceedings of the Peking Symposium*, Boston, Mass. (1981), 43-50), 0.5 mg/L thiamine HCl, 0.5 mg/L nicotinic acid, 1.0 mg/L 2,4 D, 20 g/L sucrose, 0.69 g/L L-proline, 0.91 g/L L-asparagine monohydrate, 1.6 g/L $MgCl_2$ hexahydrate, 0.1 g/L casein hydrolysate, 0.5 g/L MES, 0.1 g/L myo-inositol, and 16.9 mg/L silver nitrate, pH 5.8 solidified with 2 g/L Gelgro) and calli are inoculated with *Agrobacterium* CRN347 medium suspensions at 23° C. for 3 days without adding additional media.

The embryos are then transferred to CRN220 selection medium (4.4 g/L MS salts, 1.3 mg/L nicotinic acid, 0.25 mg/L pyridoxine HCl, 0.25 mg/L thiamine HCl, 0.25 mg/L calcium pantothenate, 30 g/L sucrose, 12 mM proline, 0.05 g/L casamino acids, 500 mg/L carbenicillin, 200 mg/L paromomycin, 2.2 mg/L picloram, 0.5 mg/L 2,4 D and 3.4 mg/L silver nitrate, pH 5.6 solidified with 7 g/L Phytagar), or calli are transferred to CRN344 selection medium (3.98 g/L Chu N6 salts, 1.0 mg/L thiamine HCl, 0.5 mg/L nicotinic acid, 1.0 mg/L 2,4 D, 20 g/L sucrose, 0.69 g/L L-proline, 0.91 g/L L-asparagine monohydrate, 1.6 g/L $MgCl_2$ hexahydrate, 0.1 g/L casein hydrolysate, 0.5 g/L MES, 0.1 g/L myo-inositol, 500 mg/L carbenicillin, 200 mg/L paromomycin and 16.9 mg/L silver nitrate, pH 5.8 solidified with 6 g/L Phytagar). After 2-3 weeks at 27° C. in the dark, surviving tissues are transferred to the same selection medium and cultured for up to an additional 2 weeks or transferred to regeneration medium as described below.

Plant regeneration is achieved by transferring the putative transgenic callus from CRN220 to CRN232 medium (CRN220 medium lacking picloram, 2,4 D, and silver nitrate, and containing 3.52 mg/L BAP and 250 mg/L carbenicillin) or from CRN344 medium to 217A medium (211RTTV lacking silver nitrate, 2,4 D, and paromomycin and containing 3.52 mg/L BAP and 250 mg/L carbenicillin) and incubating for 5-7 days at 27° C. Tissue is then transferred from CRN232 medium to CRN264 medium (4.4 g/L MS salts, 1.3 g/L nicotinic acid, 0.25 mg/L pyridoxine HCl, 0.25 mg/L thiamine HCl, 0.25 mg/L calcium pantothenate, 10 g/L glucose, 20 g/L maltose, 1 mM L-asparagine, 0.1 g/L myo-inositol, 250 mg/L carbenicillin and 100 mg/L paromomycin, pH 5.8 solidified with 6 g/L Phytagar) or from 217A medium to CRN346 medium (4.4 g/L MS salts, MS vitamins, 60 g/L sucrose, 0.05 g/L myo-inositol, 250 mg/L carbenicillin, 75 mg/L paromomycin, pH 5.8 solidified with 6 g/L KOH) in Phytatrays, and incubated in the light at 28° C. until shoots with well-developed roots are produced (typically 2-3 weeks). These developing plantlets are then transferred to soil, hardened off in a growth chamber at 27° C., 80% humidity, and low light intensity for approximately 1 week, and then transferred to a greenhouse and grown under standard greenhouse conditions.

The fasA activity of the plant extracts at various stages of growth is determined by a radiochemical assay at 37° C. for 15 minutes using the conditions outlined in Kawaguchi et al., *Methods in Enzymology,* 71:120-127, 1981.

EXAMPLE 10

This example provides the analytical procedures to determine oil and protein content of transgenic corn plants containing a mfFAS gene.

Oil levels in corn kernels are analyzed by low-resolution $^1H$ nuclear magnetic resonance (NMR) (Tiwari et al., *JAOCS* 51:104-109 (1974) or Rubel, *JAOCS* 71:1057-1062 (1994)), whereby NMR relaxation times of single kernel samples are measured, and oil levels are calculated based on regression analysis using a standard curve generated from analysis of corn kernels with varying oil levels as determined gravimetrically following accelerated solvent extraction. Oil levels in endosperm and germ from individual kernels are established by hand dissecting the kernel tissues from individual kernels, then analysis of the dissected tissue by $^1H$ nuclear magnetic resonance as described above.

For seed protein analysis, small bulk samples consisting of 50-100 kernels for each treatment are measured using near infrared reflectance spectroscopy (InfraTec model 1221, Teccator, Hogannas, Sweden). This procedure is based upon the observation that a linear relation exists between the absorption of near infrared radiation and the quantity of chemical constituents comprised in a typical grain sample. Prior to analyzing unknown samples, spectral data is collected with calibration samples that are subsequently analyzed using a nitrogen combustion analysis technique (Murray, I., and P. C. Williams, 1987, Chemical Principles of Near-infrared Technology, in "Near-Infrared Technology in the Agricultural and Food Industries", P. Williams and K. Norris eds.). A multivariate model is developed using the spectral data from the spectrometer and the primary data. In the present case a PLS-1 (Partial Least Squares Regression Type I) multivariate model is constructed using 152 calibration samples. Each unknown sample is scanned on the spectrometer at least 5 times and its protein content predicted with each scan. Each time the sample is scanned it is added back to the sample cuvette to minimize multiplicative scattering effects, which are not correlated to chemical property of interest. The predicted protein is averaged for the multiple scans and then reported for each sample.

The present invention is not limited to the precise details shown and set forth hereinabove, for it should be understood that many variations and modifications may be made while still remaining within the spirit and scope of the present invention defined by the claims.

What is claimed:

1. A DNA vector comprising a nucleic acid encoding a multifunctional fatty acid synthase, wherein the nucleic acid encodes SEQ ID NO:2.

2. The vector of claim 1, wherein the nucleic acid encoding a multifunctional fatty acid synthase comprises SEQ ID NO: 1.

3. A method for expressing a heterologous multifunctional fatty acid synthase in a plant comprising transforming a plant with the vector of claim 1, resulting in expression of the heterologous multifunctional fatty acid synthase in the plant.

4. A plant comprising the DNA vector of claim 1 encoding a multifunctional fatty acid synthase].

* * * * *

UNITED STATES PATENT AND TRADEMARK OFFICE

CERTIFICATE OF CORRECTION

PATENT NO. : 7,273,966 B2
APPLICATION NO. : 10/741191
DATED : September 25, 2007
INVENTOR(S) : Voelker et al.

It is certified that error appears in the above-identified patent and that said Letters Patent is hereby corrected as shown below:

On Title page, item [73] under ASSIGNEE, delete "MI" and insert --MO--.

In claim 4, column 258, line 6, delete "encoding a multifunctional fatty acid synthase]." and insert --.--.

Signed and Sealed this

Thirteenth Day of May, 2008

JON W. DUDAS
*Director of the United States Patent and Trademark Office*